US009064045B2

(12) United States Patent
Von Hoff et al.

(10) Patent No.: US 9,064,045 B2
(45) Date of Patent: Jun. 23, 2015

(54) MOLECULAR PROFILING OF TUMORS

(71) Applicant: Caris MPI, Inc., Irving, TX (US)

(72) Inventors: Daniel D. Von Hoff, Scottsdale, AZ (US); David M. Loesch, Greenwood, IN (US); Arlet Alarcon, Phoenix, AZ (US); Robert J. Penny, Lebanon, IN (US); Alan Wright, Irving, TX (US); Matthew J. McGinniss, San Diego, CA (US); Ryan P. Bender, Phoenix, AZ (US); Traci Pawlowski, Laguna Hills, CA (US)

(73) Assignee: Caris MPI, Inc., Irving, TX (US)

( * ) Notice: Subject to any disclaimer, the term of this patent is extended or adjusted under 35 U.S.C. 154(b) by 0 days.

(21) Appl. No.: 14/175,800

(22) Filed: Feb. 7, 2014

(65) Prior Publication Data

US 2014/0156199 A1     Jun. 5, 2014

Related U.S. Application Data

(63) Continuation of application No. 12/658,770, filed on Feb. 12, 2010, now Pat. No. 8,768,629, which is a continuation-in-part of application No. 13/188,350, application No. 14/175,800, which is a continuation of application No. 12/579,241, filed on Oct. 14, 2009, now abandoned, which is a continuation-in-part of application No. 11/750,721, filed on May 18, 2007, now Pat. No. 8,700,335.

(60) Provisional application No. 61/151,758, filed on Feb. 11, 2009, provisional application No. 61/170,565, filed on Apr. 17, 2009, provisional application No. 61/217,289, filed on May 28, 2009, provisional application No. 61/229,686, filed on Jul. 29, 2009, provisional application No. 61/279,970, filed on Oct. 27, 2009, provisional application No. 61/261,709, filed on Nov. 16, 2009, provisional application No. 61/294,440, filed on Jan. 12, 2010, provisional application No. 61/105,335, filed on Oct. 14, 2008, provisional application No. 61/106,921, filed on Oct. 20, 2008, provisional application No. 60/747,645, filed on May 18, 2006.

(51) Int. Cl.
| | |
|---|---|
| *G01N 33/48* | (2006.01) |
| *G06F 19/00* | (2011.01) |
| *G01N 33/574* | (2006.01) |
| *G06F 19/24* | (2011.01) |
| *G06F 19/10* | (2011.01) |
| *G06F 19/18* | (2011.01) |
| *C40B 30/02* | (2006.01) |
| *C40B 60/12* | (2006.01) |
| *C12Q 1/68* | (2006.01) |

(52) U.S. Cl.
CPC .......... *G06F 19/3487* (2013.01); *C12Q 1/6841* (2013.01); *C12Q 1/6886* (2013.01); *C12Q 2600/106* (2013.01); *C12Q 2600/156* (2013.01); *C12Q 2600/158* (2013.01); *G01N 33/57484* (2013.01); *G01N 2800/52* (2013.01); *G06F 19/24* (2013.01); *G06F 19/34* (2013.01); *G06F 19/3418* (2013.01); *G06F 19/10* (2013.01); *G06F 19/18* (2013.01); *C40B 30/02* (2013.01); *C40B 60/12* (2013.01)

(58) Field of Classification Search
CPC ....................................................... G06F 19/18
USPC ........................................................ 702/19
See application file for complete search history.

(56) References Cited

U.S. PATENT DOCUMENTS

| | | | |
|---|---|---|---|
| 7,711,580 B1 | 5/2010 | Hudson | |
| 8,700,335 B2 | 4/2014 | Von Hoff et al. | |
| 8,831,890 B2 | 9/2014 | Von Hoff et al. | |
| 8,880,350 B2 | 11/2014 | Von Hoff et al. | |
| 8,914,239 B2 | 12/2014 | Von Hoff et al. | |
| 2005/0026194 A1 | 2/2005 | Mu | |
| 2005/0181385 A1 | 8/2005 | Linsley et al. | |
| 2005/0222163 A1 | 10/2005 | Eck et al. | |
| 2006/0008807 A1 | 1/2006 | O'Hara et al. | |
| 2006/0019256 A1* | 1/2006 | Clarke et al. ........... | 435/6 |
| 2006/0127928 A1 | 6/2006 | Bacus et al. | |
| 2007/0172844 A1 | 7/2007 | Lancaster et al. | |
| 2007/0212721 A1 | 9/2007 | Fischer et al. | |
| 2007/0231797 A1* | 10/2007 | Fan et al. .............. | 435/6 |
| 2008/0090232 A1 | 4/2008 | Engelhard | |
| 2008/0118576 A1 | 5/2008 | Theodorescu et al. | |
| 2009/0226443 A1 | 9/2009 | Filvaroff et al. | |
| 2009/0291434 A1 | 11/2009 | Cowens et al. | |
| 2010/0304989 A1 | 12/2010 | Von Hoff et al. | |
| 2011/0118298 A1 | 5/2011 | Fritz et al. | |

OTHER PUBLICATIONS

Adlard et al. Prediction of the response of colorectal cancer to systemic therapy. Lancet Oncology. 2002; 3: 75-82.
Bild et al. Oncogenic pathway signatures in human cancers as a guide to targeted therapies. Nature. 2006; 439(19): 353-357.
Brueckner et al. DNA methyltransferase inhibitors: old and new drugs for an epigenetic cancer therapy. Trends in Pharmacol Sciences. 2004; 25: 551-554.
Chappuis et al. A significant response to neoadjuvant chemotherapy in BRCA 1/2 related breast cancer. J Med Genet. 2002; 39: 608-610.
Chekerov et al. Altered expression pattern of topoisomerase IIα in ovarian tumor epithelial and stromal cells after platinum-based chemotherapy. Neoplasia. 2006; 1: 38-45.

(Continued)

*Primary Examiner* — Jerry Lin
(74) *Attorney, Agent, or Firm* — Ramin Akhavan

(57) ABSTRACT

Provided herein are methods and systems of molecular profiling of diseases, such as cancer. In some embodiments, the molecular profiling can be used to identify treatments for a disease, such as treatments that were not initially identified as a treatment for the disease or not expected to be a treatment for a particular disease.

20 Claims, 94 Drawing Sheets

(56) References Cited

OTHER PUBLICATIONS

Duxbury et al. RNA interference targeting the M2 subunit of ribonucleotide reductase enhances pancreatic adenocarcinoma chemosensitivity to gemcitabine. Oncogene. 2004; 23: 1539-1548.
Giovannetti et al. Transcription analysis of human equilibrative nucleoside transporter-1 predicts survival in pancreas cancer patients treated with gemcitabine. Cancer Res. 2006; 66: 3928-3935.
Hernandez-Vargas et al. Transcriptional profiling of MCF7 breast cancer cells in response to 5-Fluorouracil: Relationship with cell cycle changes and apoptosis, and identification of novel targets of p53. Int. J. Cancer. 2006; 119: 1164-1175.
Kabbinavar et al. Phase II, randomized trial comparing bevacizumab plus fluorouracil (FU)/leucovorin (LV) with FU/LV alone in patients with metastatic colorectal cancer. Journal of Clinical Oncology. 2003; 21: 60-65.
Kubota et al. Identification of somatostatin receptor subtypes and an implication for the efficacy of somatostatin analogue SMS 201-995 in treatment of human endocrine tumors. J. Clin. Invest. 1994; 93: 1321-1325.
Lin et al. Epha2 overexpression is associated with angiogenesis in ovarian cancer. Cancer. 2007; 109: 332-340.
Lundin et al. Cellular immune reconstitution after subcutaneous alemtuzumab (anti-CD52 monoclonal antibody, CAMPATH-1 H) treatment as first-line therapy for B-cell chronic lymphocytic leukaemia. Leukemia. 2004; 18: 484-490.
Nagata et al. PTEN activation contributes to tumor inhibition by trastuzumab, and loss of PTEN predicts trastuzumab resistance in patients. Cancer Cell. 2004; 6: 117-127.
Notice of Allowance dated Dec. 19, 2013 for U.S. Appl. No. 11/750,721.
Notice of Allowance dated Mar. 18, 2014 for U.S. Appl. No. 12/658,770.
Office Action dated Apr. 10, 2013 for Australian application No. 2007253740.
Office Action dated Nov. 5, 2013 for Japanese application No. 2009-511252 (translation at pp. 4-8).
Office Action dated Dec. 17, 2013 for Canadian application No. 2,651,995.
Office Action dated Jan. 28, 2014 for U.S. Appl. No. 13/188,350.
Office Action dated Mar. 25, 2014 for U.S. Appl. No. 14/150,624.
Office Action dated Mar. 26, 2014 for U.S. Appl. No. 14/170,466.
Office Action dated Apr. 4, 2014 for Chinese application No. 201080016438.9 (translation at pp. 6-12).
Office Action dated Jun. 9, 2014 for U.S. Appl. No. 14/170,370.
Sidransky. Emerging molecular markers of cancer. Nature. 2002; 2: 210-219.
Taron et al. BRCA1 mRNA expression levels as an indicator of chemoresistance in lung cancer. Human Mol Genet. 2004; 13: 2443-2449.
Zent et al. The distinct gene expression profiles of chronic lymphocytic leukemia and multiple myeloma suggest different anti-apoptotic mechanisms but predict only some differences in phenotype. Leukemia Research. 2003; 27: 765-774.
Advisory Action dated Jan. 29, 2015 for U.S. Appl. No. 14/187,020.
Advisory Action dated Jan. 29, 2015 for U.S. Appl. No. 14/187,028.
Bandyopadhyay et al. The tumor metastasis suppressor gene Drg-1 downregulates the expression of activating transcription factor 3 in prostate cancer. Cancer Research. 2006; 66: 11983-11990.
Debiec-Rychter et al. Use of c-KIT/PDGFRA mutational analysis to predict the clinical response to imatinib in patients with advanced gastrointestinal stromal tumours entered on phase I and II studies of the EORTC soft tissue and bone sarcoma group. European Journal of Cancer. 2004; 40(5): 689-695.
Gautam et al. RRM1-induced metastasis suppression through PTEN-regulated pathways. Oncogene. 2003; 22: 2135-2142.
Lievre et al. KRAS mutation status is predictive of response to cetuximab therapy in colorectal cancer. Cancer Research. 2006; 66(8): 3992-3995.
Lukashova-V.Zangen et al. Ependymoma gene expression profiles associated with histological subtype, proliferation, and patient survival. Acta Neuropathol. 2007; 113: 325-337.
Notice of Allowance dated Jul. 15, 2014 for U.S. Appl. No. 14/052,503, now issued as U.S. patent No. 8,831,890.
Notice of Allowance dated Sep. 23, 2014 for U.S. Appl. No. 14/170,466, now issused as U.S. patent No. 8,880,350.
Notice of Allowance dated Oct. 27, 2014 for U.S. Appl. No. 14/143,959, now issued as U.S. patent No. 8,914,239.
Notice of Allowance dated Jan. 29, 2015 for Chinese application No. 201080016438.9 (translation at p. 1).
Office Action dated Apr. 23, 2014 for Israeli application No. 214400 (English translation only).
Office Action dated Jun. 17, 2014 for U.S. Appl. No. 14/143,959.
Office Action dated Jul. 23, 2014 for U.S. Appl. No. 14/170,450.
Office Action dated Jul. 29, 2014 for U.S. Appl. No. 14/150,624.
Office Action dated Jul. 29, 2014 for U.S. Appl. No. 14/170,466.
Office Action dated Aug. 4, 2014 for U.S. Appl. No. 14/187,028.
Office Action dated Aug. 12, 2014 for U.S. Appl. No. 14/187,020.
Office Action dated Aug. 26, 2014 for Chinese application No. 201080016438.9 (translation).
Office Action dated Oct. 21, 2014 for U.S. Appl. No. 14/175,781.
Office Action dated Oct. 23, 2014 for U.S. Appl. No. 14/170,450.
Office Action dated Oct. 24, 2014 for U.S. Appl. No. 14/187,008.
Office Action dated Oct. 27, 2014 for U.S. Appl. No. 14/175,728.
Office Action dated Nov. 5, 2014 for U.S. Appl. No. 14/170,370.
Office Action dated Nov. 12, 2014 for U.S. Appl. No. 14/187,028.
Office Action dated Nov. 13, 2014 for U.S. Appl. No. 14/187,020.
Office Action dated Nov. 19, 2014 for Israeli application No. 195266 (translation at pp. 4-9).
Office Action dated Dec. 14, 2014 for Israeli application No. 214400 (translation at pp. 2-3).
Press Release "Personalized Medicine Helps Cancer Patients Survive," EurekAlert, published online Apr. 19, 2009.
Randall-Whitis et al. cDNA microarray analysis of gene expression in ovarian cancer cells after treatment with carboplatin and paclitaxel. Cancer Genomics & Proteomics. 2006; 3: 289-294.
Smith, "AACR: Molecular Profile Improves Outcome in Advanced Cancer" Medpage Today, published online Apr. 24, 2009.
Zhu et al., Role of KRAS and EGFR as Biomarkers of Response to Erlotinib in National Cancer Institute of Canada Clinical Trials Group Study BR.21. J Clin Oncol. 2008; 26:4268-4275.

* cited by examiner

| MOLECULAR PROFILING INSTITUTE | PATIENT INFORMATION<br>NAME: SAMPLE PATIENT<br>SEX: FEMALE<br>DOB: 6/1/1974<br>SSN#: 123-45-6789 | PHYSICIAN INFORMATION<br>SOME DOCTOR, M.D.<br>1234 E. SOUTH ST.<br>TUCSON, AX 12345<br>480-123-4567 |
|---|---|---|
| | REPORT INFORMATION | VER 1.6.2:4-25-06 |
| | DATE SPECIMEN RECEIVED: 02/01/2006  DATE REPORTED: 02/09/2006  CASE NO. MP-TN06-05040 | |
| | DATE SPECIMEN COLLECTED AT HOST MEDICAL CENTER: 01/24/2006 | |

SPECIAL STUDIES
RESULTS AND INTERPRETATION

ADVANCED IMMUNOHISTOCHEMICAL ANALYSIS:

| GENE EXPRESSED PROTEIN | CONCLUSION | SPECIFICITY | INTENSITY | % | TARGET STATUS |
|---|---|---|---|---|---|
| HER2/NEU | NEGATIVE | | | | |
| ER | NEGATIVE | | | | |
| PR | NEGATIVE | | | | |
| C-KIT | POSITIVE | SPECIFIC | 2 | 90 | TARGET |
| EGFR | NEGATIVE | | | | |
| COX-2 | NEGATIVE | | | | |
| ANDROGEN RECEPTOR | NEGATIVE | | | | |
| CD52 | NEGATIVE | | | | |
| PDGFR | NEGATIVE | NON-SPECIFIC | | | |
| CD25 | NEGATIVE | | | | |

*2+ IHC IN GREATER THAN 30% OF THE TUMOR CELLS HAS BEEN CHOSEN AS A CONSERVATIVE DIVIDING POINT TO REPORT A POTENTIAL TARGET AS POSITIVE TO HELP INCREASE PHARMACOLOGIC EFFECTIVENESS.

IMMUNOHISTOCHEMICAL TESTS NOT PERFORMED

| | | |
|---|---|---|
| IL-2 | TOPOISOMERASE I | MLH1 |
| NF-KAPPA BETA | TOPOISOMERASE II | MSH2 |
| THYMIDYLATE SYNTHASE | RETINOIC ACID RECEPTOR | CD20 |
| ERCC3 (HELICASE) | RXR | P53 |
| THYMIDINE PHOSPHORYLASE | ORNITHINE DECARBOXYLASE | CYCLIN D1 |
| NGF | SOMATOSTATIN | BCL-2 |
| MTAP | RAS (MUTATED) | VEGF |
| MAP KINASE PROTEIN | ASPARAGINE SYNTHETASE | |
| XANTHINE OXIDASE | | |

FIG.3B

MOLECULAR PROFILING INSTITUTE

PATIENT INFORMATION
NAME: SAMPLE PATIENT
SEX: FEMALE
DOB: 6/1/1974
SSN#: 123-45-6789

PHYSICIAN INFORMATION
SOME DOCTOR, M.D.
1234 E. SOUTH ST.
TUCSON, AX 12345
480-123-4567

REPORT INFORMATION VER 1.6.2:4-25-06
DATE SPECIMEN RECEIVED: 02/01/2006  DATE REPORTED: 02/09/2006  CASE NO. MP-TN06-05040
DATE SPECIMEN COLLECTED AT HOST MEDICAL CENTER: 01/24/2006

SPECIAL STUDIES
MICROARRAY RESULTS

MICROARRAY ANALYSIS:

| GENE | RATIO | EXPRESSION* ANALYSIS |
|---|---|---|
| AR | 0.02 | UNDER EXPRESSED |
| ESR1 | 0.09 | UNDER EXPRESSED |
| PGR | 0.10 | UNDER EXPRESSED |
| VEGF | 0.33 | UNDER EXPRESSED |
| KIT | 0.51 | UNDER EXPRESSED |
| PDGFC | 0.53 | UNDER EXPRESSED |
| RXRB | 0.62 | NO CHANGE |
| TOP2B | 0.62 | UNDER EXPRESSED |
| RAF1 | 0.68 | NO CHANGE |
| ERBB2 | 0.69 | NO CHANGE |
| ERCC3 | 0.71 | NO CHANGE |
| BCL2 | 0.71 | NO CHANGE |
| PDGFRB | 0.78 | NO CHANGE |
| BCL2 | 0.80 | NO CHANGE |
| GSTP1 | 0.85 | NO CHANGE |
| SPARC | 0.92 | NO CHANGE |
| HDAC1 | 0.95 | NO CHANGE |
| POLA | 0.98 | NO CHANGE |
| MSH2 | 0.98 | NO CHANGE |
| CES2 | 1.05 | NO CHANGE |
| VEGF | 1.09 | NO CHANGE |
| SSTR1 | 1.11 | NO CHANGE |
| PTEN | 1.11 | NO CHANGE |

| GENE | RATIO | EXPRESSION* ANALYSIS |
|---|---|---|
| EGFR | 1.16 | NO CHANGE |
| OGFR | 1.17 | NO CHANGE |
| MLH1 | 1.19 | NO CHANGE |
| VHL | 1.22 | NO CHANGE |
| TNF | 1.29 | NO CHANGE |
| RARA | 1.38 | NO CHANGE |
| HSPCA | 1.42 | NO CHANGE |
| TXNRD1 | 1.42 | NO CHANGE |
| ASNS | 1.44 | NO CHANGE |
| DNMT1 | 1.51 | OVER EXPRESSED |
| NFKB2 | 1.74 | NO CHANGE |
| NFKBIA | 1.78 | OVER EXPRESSED |
| PTGS2 | 1.81 | NO CHANGE |
| BRCA2 | 1.83 | NO CHANGE |
| GART | 1.90 | OVER EXPRESSED |
| CDW52 | 2.15 | OVER EXPRESSED |
| ZAP70 | 2.18 | NO CHANGE |
| FOLR2 | 2.21 | OVER EXPRESSED |
| ZAP70 | 2.76 | NO CHANGE |
| TOP1 | 2.78 | OVER EXPRESSED |
| MS4A1 | 2.86 | NO CHANGE |
| ZAP70 | 2.86 | NO CHANGE |
| ZAP70 | 2.92 | NO CHANGE |

| GENE | RATIO | EXPRESSION* ANALYSIS |
|---|---|---|
| ZAP70 | 3.00 | NO CHANGE |
| ZAP70 | 3.02 | NO CHANGE |
| CD33 | 3.05 | OVER EXPRESSED |
| ZAP70 | 3.06 | NO CHANGE |
| ZAP70 | 3.13 | NO CHANGE |
| ZAP70 | 3.18 | NO CHANGE |
| ZAP70 | 3.40 | NO CHANGE |
| CD33 | 3.52 | OVER EXPRESSED |
| HIF1A | 3.84 | OVER EXPRESSED |
| HIF1A | 3.85 | OVER EXPRESSED |
| HIF1A | 3.88 | OVER EXPRESSED |
| HIF1A | 3.90 | OVER EXPRESSED |
| HIF1A | 3.90 | OVER EXPRESSED |
| HIF1A | 3.91 | OVER EXPRESSED |
| HIF1A | 3.94 | OVER EXPRESSED |
| HIF1A | 3.97 | OVER EXPRESSED |
| HIF1A | 4.01 | OVER EXPRESSED |
| HIF1A | 4.03 | OVER EXPRESSED |
| PDGFRA | 4.74 | OVER EXPRESSED |
| TK1 | 4.94 | OVER EXPRESSED |
| IL2RA | 5.07 | NO CHANGE |
| ADA | 5.26 | OVER EXPRESSED |
| TOP2A | 9.34 | NO CHANGE |
| TYMS | 22.95 | OVER EXPRESSED |
| VDR | 37.30 | OVER EXPRESSED |

*"NO CHANGE" INDICATES THAT THERE IS NO DIFFERENCE IN EXPRESSION FOR THIS GENE BETWEEN THE TUMOR AND CONTROL TISSUES AT A SIGNIFICANCE LEVEL OF P<=0.001. A SIGNIFICANCE LEVEL OF P<=0.001 HAS BEEN CHOSEN SINCE GENES PASSING THIS THRESHOLD CAN BE VALIDATED AS DIFFERENTIALLY EXPRESSED BY ALTERNATIVE METHODS APPROXIMATELY 95% OF THE TIME.

FIG.3C

PATIENT: SAMPLE PATIENT        CASE NO. MP-TN06-05040        DATE REPORTED: 2/9/2006

CLINICAL INFORMATION

CLINICAL HISTORY

THE PATIENT WAS DIAGNOSED WITH INFLAMATORY MYOFIBROBLASTIC TUMOR IN FEB, 2004. AT THAT TIME A LARGE MASS WAS REMOVED FROM HER ABDOMEN. THE PATIENT NOW HAS RECURRENT MASSES ON HER LEFT UPPER QUADRANT AND IN THE PELVIS. PER THE PATIENT CHART, DR SOME REVIEWED THIS CASE WITH DR VON HOFF AND IT WAS AGREED THAT PERFORMING DNA MICROARRAY AND IHC TESTING ON THIS PATIENT MAY PROVIDE INSIGHT INTO FURTHER TREATMENT OPTIONS.

SPECIMENS SUBMITTED

RECEIVED FROM MAIN HOSPITAL, TUCSON, AZ, ONE PARAFFIN BLOCK LABELED M01-123 AND FROZEN TISSUE WITH THE ACCOMPANYING SURGICAL PATHOLOGY REPORT.

DISCLAIMER

THESE TESTS WERE DEVELOPED BY MOLECULAR PROFILING AND THEIR PERFORMANCE CHARACTERISTICS DETERMINED BY MOLECULAR PROFILING. IT HAS NOT BEEN CLEARED OR APPROVED BY THE U.S. FOOD AND DRUG ADMINISTRATION (FDA). THESE TESTS ARE PERMITTED FOR CLINICAL PURPOSES AND SHOULD NOT BE REGARDED AS PURELY INVESTIGATIONAL OR FOR RESEARCH. MOLECULAR PROFILING IS CERTIFIED UNDER THE CLINICAL LABORATORY IMPROVEMENT AMENDMENTS OF 1988 (CLIA) AS QUALIFIED TO PERFORM HIGH-COMPLEXITY CLINICAL TESTING.

DECISIONS REGARDING CARE AND TREATMENT SHOULD NOT BE BASED ON A SINGLE TEST SUCH AS THIS TEST. RATHER DECISIONS ON CARE AND TREATMENT SHOULD BE BASED ON THE INDEPENDENT MEDICAL JUDGMENT OF THE TREATING PHYSICIAN TAKING INTO CONSIDERATION ALL AVAILABLE INFORMATION CONCERNING THE PATIENT'S CONDITION, INCLUDING OTHER LABORATORY TESTS, IN ACCORDANCE WITH THE STANDARD OF CARE IN A GIVEN COMMUNITY.

THE FINDING OF A TARGET DOES NOT NECESSARILY INDICATE PHARMACOLOGIC EFFECTIVENESS.

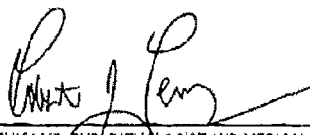

ROBERT J. PENNY, MD, PHD, PATHOLOGIST AND MEDICAL DIRECTOR    2/9/2006    DATE

| GENE EXPRESSED PROTEIN | SPECIFICITY | INTENSITY | % | CONCLUSION | GENE EXPRESSED PROTEIN |
|---|---|---|---|---|---|
| HER2/NEU | SPECIFIC NON-SPECIFIC | 0 1 2 3 4 | | NEGATIVE | HER2/NEU |
| ER | SPECIFIC NON-SPECIFIC | 0 1 2 3 4 | | NEGATIVE | ER |
| PR | SPECIFIC NON-SPECIFIC | 0 1 2 3 4 | | NEGATIVE | PR |
| C-KIT | SPECIFIC NON-SPECIFIC | 0 1 2 3 4 | 70 | POSITIVE | C-KIT |
| EGFR | SPECIFIC NON-SPECIFIC | 0 1 2 3 4 | | NEGATIVE | EGFR |
| COX-2 | SPECIFIC NON-SPECIFIC | 0 1 2 3 4 | 90 | POSITIVE | COX-2 |
| ANDROGEN RECEPTOR | SPECIFIC NON-SPECIFIC | 0 1 2 3 4 | | NEGATIVE | ANDROGEN RECEPTOR |
| CD52 | SPECIFIC NON-SPECIFIC | 0 1 2 3 4 | 90 | POSITIVE | CD52 |
| PDGFR | SPECIFIC NON-SPECIFIC | 0 1 2 3 4 | 90 | POSITIVE | PDGFR |
| CD25 | SPECIFIC NON-SPECIFIC | 0 1 2 3 4 | | NEGATIVE | CD25 |

FIG. 26A

| IHC | Tumor Type | | | | | | | | | | | |
|---|---|---|---|---|---|---|---|---|---|---|---|---|
| | Adipose (13) | | Adipose tissue, if not available use fibroblast (1) | | Adrenal Cortex (18) | | Adrenal Gland (1) | | Adrenal Gland -- Medulla (15) | | Appendix (5) | |
| | biomarker flagged as target | tumor type | biomarker flagged as target | tumor type | biomarker flagged as target | tumor type | biomarker flagged as target | tumor type | biomarker flagged as target | % in tumor type | biomarker flagged as target | tumor type |
| Androgen Receptor | | 0.0% | | 0.0% | 1 | 1.79% | | 0.00% | 1 | 2.22% | | 0.00% |
| c-kit | 3 | 10.0% | | 0.0% | 4 | 7.14% | | 0.00% | 7 | 15.56% | 1 | 8.33% |
| CD25 | | 0.0% | | 0.0% | | 0.00% | | 0.00% | | 0.00% | | 0.00% |
| CD52 | | 0.0% | | 0.0% | 1 | 1.79% | | 0.00% | | 0.00% | | 0.00% |
| COX-2 | | 0.0% | | 0.0% | | 0.00% | | 0.00% | | 0.00% | | 0.00% |
| Cyclin D1 | | 0.0% | | 0.0% | | 0.00% | | 0.00% | | 0.00% | | 0.00% |
| EGFR | 5 | 16.7% | 1 | 25.0% | 9 | 16.07% | 1 | 33.33% | 3 | 67.67% | 2 | 16.67 |
| ER | | 0.0% | | 0.0% | | 0.00% | | 0.00% | | 0.00% | | 0.00% |
| Her2/Neu | | 0.0% | | 0.0% | | 0.00% | | 0.00% | 2 | 4.44% | | 0.00% |
| HSP90 | 7 | 23.3% | | 0.0% | 8 | 14.29% | | 0.00% | 10 | 22.22% | 4 | 33.33% |
| MLH1 | | 0.0% | | 0.0% | | 0.00% | | 0.00% | 1 | 2.22% | | 0.00% |
| MSH2 | 1 | 3.3% | 1 | 25.0% | 2 | 3.57% | | 0.00% | 2 | 4.44% | | 0.00% |
| PDGFR | 7 | 0.0% | | 0.0% | 1 | 1.79% | | 0.00% | 8 | 17.78% | 3 | 25.00% |
| PR | | 0.0% | | 0.0% | 8 | 14.29% | 1 | 33.33% | 1 | 2.22% | | 0.00% |
| PTEN | | 0.0% | | 0.0% | 1 | 1.79% | | 0.00% | | 0.00% | | 0.00% |
| RRM1 | | 0.0% | | 0.0% | | 0.00% | | 0.00% | | 0.00% | | 0.00% |
| SPARC | 7 | 23.3% | 1 | 25.0% | 17 | 30.38% | 1 | 33.33% | 3 | 6.67% | 1 | 8.33% |
| Survivin | | 0.0% | | 0.0% | | 0.00% | | 0.00% | | 0.00% | | 0.00% |
| TOP2A | | 0.0% | 1 | 25.0% | 4 | 7.14% | | 0.00% | 7 | 15.56% | 1 | 8.33% |
| Topoisomerase II alpha | | 0.0% | | 0.0% | | 0.00% | | 0.00% | | 0.00% | | 0.00% |
| Total Number of ICH Biomarkers Flagged as Target for Tumor Type Samples | 30 | 100.00% | 4 | 100.00% | 56 | 100.00% | 3 | 100.00% | 45 | 100.00% | 12 | 100.00% |

FIG. 26B

| Bladder (7) | | Blood Vessel Vain (4) | | Bone (2) | | Bone if you have it if not Cartilage (1) | | Brain (2) | | Breast (99) | | Cartilage (5) | |
|---|---|---|---|---|---|---|---|---|---|---|---|---|---|
| biomarker flagged as | tumor type | biomarker flagged as target | % in tumor type | biomarker flagged as target | % in tumor type | # of times biomarker flagged as target | % in tumor type | biomarker flagged as target | % in tumor type | biomarker flagged as target | tumor type | biomarker flagged as | tumor type |
| 1 | 5.26% | | 0.00% | | 0.00% | | 0.00% | | 0.00% | 36 | 9.81% | | 0.00% |
| | 0.00% | | 0.00% | | 0.00% | | 0.00% | | 0.00% | 34 | 9.26% | 2 | 10.53% |
| | 0.00% | | 0.00% | | 0.00% | | 0.00% | | 0.00% | 1 | 0.27% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| 5 | 26.32% | 1 | 16.67% | | 0.00% | 1 | 50.00% | 2 | 33.33% | 36 | 9.81% | 2 | 10.53% |
| | 0.00% | | 0.00% | | 0.00% | | 0.00% | | 0.00% | 27 | 7.36% | | 0.00% |
| | 0.00% | | 0.00% | | 0.00% | | 0.00% | | 0.00% | 28 | 7.83% | | 0.00% |
| 3 | 15.79% | | 0.00% | | 0.00% | | 0.00% | | 0.00% | 60 | 16.35% | 3 | 15.79% |
| | 0.00% | | 0.00% | 1 | 33.33% | | 0.00% | | 0.00% | 1 | 0.27% | | 0.00% |
| | 0.00% | | 0.00% | | 0.00% | | 0.00% | | 0.00% | 6 | 1.63% | | 0.00% |
| 1 | 5.26% | 1 | 16.67% | | 0.00% | | 0.00% | 2 | 33.33% | 35 | 9.54% | 4 | 21.05% |
| | 0.00% | | 0.00% | | 0.00% | | 0.00% | | 0.00% | 15 | 4.09% | 2 | 10.53% |
| 2 | 10.53% | | 0.00% | | 0.00% | | 0.00% | | 0.00% | 1 | 0.27% | | 0.00% |
| | 0.00% | | 0.00% | | 0.00% | | 0.00% | | 0.00% | | 0.00% | | 0.00% |
| 2 | 10.53% | 3 | 50.00% | 2 | 66.67% | 1 | 50.00% | 2 | 33.33% | 41 | 11.17% | 5 | 26.32% |
| | 0.00% | | 0.00% | | 0.00% | | 0.00% | | 0.00% | | 0.00% | | 0.00% |
| 5 | 26.32% | 1 | 16.67% | | 0.00% | | 0.00% | | 0.00% | 46 | 12.53% | 1 | 5.26% |
| | 0.00% | | 0.00% | | 0.00% | | 0.00% | | 0.00% | | 0.00% | | 0.00% |
| 19 | 100.00% | | 100.00% | | 100.00% | 2 | 100.00% | 6 | 100.00% | 367 | 100.00% | | 100.00% |

FIG. 26C

| Cervix (10) | | Colon (67) | | Colon Sigmoid (1) | | Dendritic cells can be found in skin, the spleen, lymph node. Let's get Mike Bittner's take on site of origin (1) | | Difficult origin to define. Try skeletal muscle (1) | | Endometrium (3) | | Esophagus |
|---|---|---|---|---|---|---|---|---|---|---|---|---|
| biomarker flagged as target | tumor type | biomarker flagged as target | % in tumor type | # of times biomarker flagged as target | % in tumor type | # of times biomarker flagged as target | % in tumor type | biomarker flagged as target | % in tumor type | # of times biomarker flagged as target | % in tumor type | biomarker flagged as target |
|  | 0.00% |  | 0.47% |  | 0.00% |  | 0.00% |  | 0.00% |  | 0.00% |  |
| 3 | 9.38% | 32 | 15.09% | 1 | 20.00% |  | 0.00% |  | 0.00% |  | 0.00% |  |
| 1 | 3.13% | 1 | 0.47% |  | 0.00% |  | 0.00% |  | 0.00% |  | 0.00% |  |
|  | 0.00% |  | 0.00% |  | 0.00% |  | 0.00% |  | 0.00% |  | 0.00% |  |
|  | 0.00% | 1 | 0.47% |  | 0.00% |  | 0.00% |  | 0.00% |  | 0.00% |  |
|  | 0.00% |  | 0.00% |  | 0.00% |  | 0.00% |  | 0.00% |  | 0.00% |  |
| 4 | 12.50% | 38 | 17.92% | 1 | 20.00% | 1 | 33.33% |  | 0.00% | 1 | 11.11% | 6 |
|  | 0.00% | 1 | 0.47% |  | 0.00% |  | 0.00% |  | 0.00% | 1 | 11.11% |  |
| 2 | 6.25% | 5 | 2.36% |  | 0.00% |  | 0.00% |  | 0.00% |  | 0.00% | 3 |
| 7 | 21.88% | 40 | 18.87% | 1 | 20.00% |  | 0.00% | 1 | 25.00% | 3 | 33.33% | 5 |
| 1 | 3.13% |  | 0.00% |  | 0.00% |  | 0.00% |  | 0.00% |  | 0.00% |  |
| 1 | 3.13% | 3 | 1.42% |  | 0.00% |  | 0.00% |  | 0.00% |  | 0.00% |  |
| 2 | 6.25% | 26 | 12.26% | 1 | 20.00% |  | 0.00% | 1 | 25.00% |  | 0.00% | 1 |
| 2 | 6.25% | 2 | 0.00% |  | 0.00% |  | 0.00% |  | 0.00% |  | 0.00% |  |
|  | 0.00% | 3 | 1.42% |  | 0.00% |  | 0.00% |  | 0.00% | 2 | 22.22% |  |
|  | 0.00% |  | 0.00% |  | 0.00% |  | 0.00% |  | 0.00% |  | 0.00% |  |
| 2 | 6.25% | 20 | 9.43% |  | 0.00% | 1 | 33.33% | 1 | 25.00% |  | 0.00% | 5 |
|  | 0.00% |  | 0.00% |  | 0.00% |  | 0.00% |  | 0.00% |  | 0.00% |  |
| 7 | 21.88% | 39 | 18.40% | 1 | 20.00% | 1 | 33.33% | 1 | 25.00% | 2 | 22.22% | 8 |
|  | 0.00% |  | 0.00% |  | 0.00% |  | 0.00% |  | 0.00% |  | 0.00% |  |
| 32 | 100.00% | 212 | 100.00% | 5 | 100.00% | 3 | 100.00% | 4 | 100.00% | 9 | 100.00% | 28 |

FIG. 26D

| S (9) | | Fallopian Tube (3) | | Fibroblast (7) | | Gallbladder (5) | | Kidney (14) | | Larynx (3) | | Liver (1) | | Lung (74) | | Lymph Node (9) | |
|---|---|---|---|---|---|---|---|---|---|---|---|---|---|---|---|---|---|
| biomarker flagged as target | % in tumor type | biomarker flagged as target | % in tumor type | biomarker flagged as target | % in tumor type | biomarker flagged as target | % in tumor type | biomarker flagged as target | tumor type | biomarker flagged as target | tumor type | biomarker flagged as target | tumor type | times biomark | tumor type | biomarker flagged as | % in tumor type |
| | 0.00% | | 0.00% | | 0.00% | | 0.00% | 5 | 11.90% | | 0.00% | | 0.00% | 4 | 1.79% | | 0.00% |
| | 0.00% | | 0.00% | | 0.00% | 1 | 5.88% | 3 | 7.14% | | 0.00% | | 0.00% | 26 | 11.81% | | 0.00% |
| | 0.00% | 1 | 11.11% | | 0.00% | | 0.00% | | 0.00% | | 0.00% | | 0.00% | 1 | 0.45% | 2 | 27.27% |
| | 0.00% | | 0.00% | | 0.00% | | 0.00% | | 0.00% | | 0.00% | | 0.00% | 2 | 0.89% | 6 | % |
| | 0.00% | | 0.00% | | 0.00% | | 0.00% | | 0.00% | | 0.00% | | 0.00% | 4 | 1.79% | | 0.00% |
| | 0.00% | | 0.00% | | 0.00% | | 0.00% | | 0.00% | | 0.00% | | 0.00% | | 0.00% | | 0.00% |
| 21.43% | | 1 | 11.11% | 1 | 6.25% | 5 | 29.41% | 13 | 30.95% | 3 | 25.00% | | 0.00% | 55 | 24.55% | | 0.00% |
| 0.00% | | | 0.00% | | 0.00% | | 0.00% | | 0.00% | | 0.00% | | 0.00% | | 0.00% | | 0.00% |
| 10.71% | | | 0.00% | | 0.00% | 1 | 5.88% | | 0.00% | | 0.00% | | 0.00% | 7 | 3.13% | | 0.00% |
| 17.86% | | 1 | 11.11% | 2 | 12.50% | 3 | 17.65% | 7 | 16.67% | 3 | 25.00% | | 0.00% | 30 | 13.39% | 5 | 22.73% |
| 0.00% | | | 0.00% | | 0.00% | | 0.00% | 1 | 2.38% | 1 | 8.33% | | 0.00% | 3 | 1.34% | | 0.00% |
| 0.00% | | 1 | 11.11% | | 0.00% | 1 | 5.88% | 1 | 2.38% | 1 | 8.33% | | 0.00% | 4 | 1.79% | 1 | 4.55% |
| 3.57% | | 1 | 11.11% | 2 | 12.50% | 1 | 5.88% | 3 | 7.14% | | 0.00% | 1 | 50.00% | 28 | 12.50% | 2 | 9.09% |
| 0.00% | | | 0.00% | 2 | 12.50% | | 0.00% | 1 | 2.38% | | 0.00% | | 0.00% | 5 | 2.23% | | 0.00% |
| 0.00% | | | 0.00% | 1 | 6.25% | | 0.00% | | 0.00% | | 0.00% | | 0.00% | 2 | 0.89% | | 0.00% |
| 0.00% | | | 0.00% | | 0.00% | | 0.00% | | 0.00% | | 0.00% | | 0.00% | | 0.00% | | 0.00% |
| 17.86% | | | 0.00% | 5 | 31.25% | 3 | 17.65% | 8 | 19.05% | 1 | 8.33% | 1 | 50.00% | 25 | 11.16% | 1 | 4.55% |
| 0.00% | | | 0.00% | | 0.00% | | 0.00% | | 0.00% | | 0.00% | | 0.00% | | 0.00% | | 0.00% |
| 28.57% | | 3 | 33.33% | 3 | 18.75% | 2 | 11.76% | | 0.00% | 3 | 25.00% | | 0.00% | 28 | 12.50% | 5 | 22.73% |
| 0.00% | | | 0.00% | | 0.00% | | 0.00% | | 0.00% | | 0.00% | | 0.00% | | 0.00% | | 0.00% |
| 100.00% | | 9 | 100.00% | 16 | 100.00% | 17 | 100.00% | 42 | 100.00% | 12 | 100.00% | 2 | 100.00% | 224 | 100.00% | 22 | 100.00% |

FIG. 26E

| Melanocytes (22) | | Mesothelial Lining (6) | | Myoepithilial cells (1) | | Osteoblasts (2) | | Ovary (40) | | Pancreas (35) | | Parotid (2) | | Prostate (6) |
|---|---|---|---|---|---|---|---|---|---|---|---|---|---|---|
| biomarker flagged as target | % in tumor type | biomarker flagged as target | % in tumor type | biomarker flagged as target | % in tumor type | biomarker flagged as target | % in tumor type | biomarker flagged as target | tumor type | biomarker flagged as target | tumor type | biomarker flagged as target | tumor type | biomarker flagged as target |
|  | 0.00% |  | 0.00% |  | 0.00% |  | 0.00% | 14 | 10.14% | 2 | 0.00% | 2 | 40.00% | 5 |
| 9 | 20.45% | 1 | 4.76% | 1 | 25.00% |  | 0.00% | 6 | 4.35% |  | 2.35% |  | 0.00% | 2 |
|  | 0.00% | 2 | 9.52% |  | 0.00% |  | 0.00% | 2 | 1.45% |  | 0.00% |  | 0.00% |  |
|  | 0.00% |  | 0.00% |  | 0.00% |  | 0.00% |  | 0.00% |  | 0.00% |  | 0.00% |  |
|  | 0.00% |  | 0.00% |  | 0.00% |  | 0.00% |  | 0.00% |  | 0.00% |  | 0.00% |  |
|  | 0.00% |  | 0.00% |  | 0.00% |  | 11.11% |  | 0.00% |  | 0.00% |  | 0.00% |  |
|  | 0.00% | 5 | 23.81% | 1 | 25.00% | 1 | 0.00% | 16 | 11.59% | 28 | 32.94% |  | 0.00% | 3 |
|  | 0.00% | 1 | 4.76% |  | 0.00% |  | 0.00% | 22 | 15.94% |  | 0.00% |  | 0.00% |  |
|  | 0.00% |  | 0.00% |  | 0.00% |  | 11.11% | 7 | 5.07% |  | 0.00% | 1 | 20.00% | 1 |
| 11 | 25.00% | 2 | 9.52% |  | 0.00% | 1 | 0.00% | 22 | 15.94% | 16 | 18.82% |  | 0.00% | 4 |
|  | 0.00% | 1 | 4.76% |  | 0.00% |  | 0.00% |  | 0.00% |  | 0.00% |  | 0.00% |  |
| 1 | 2.27% | 1 | 4.76% |  | 0.00% | 2 | 22.22% | 2 | 1.45% | 3 | 3.53% |  | 0.00% | 1 |
| 5 | 11.36% | 2 | 9.52% |  | 0.00% | 2 | 11.11% | 7 | 5.07% | 10 | 11.76% |  | 0.00% | 4 |
|  | 0.00% |  | 0.00% | 1 | 25.00% | 1 | 0.00% | 9 | 6.52% | 2 | 2.35% |  | 0.00% |  |
|  | 0.00% |  | 0.00% |  | 0.00% |  | 0.00% | 1 | 0.72% | 1 | 1.18% |  | 0.00% |  |
|  | 0.00% |  | 0.00% |  | 0.00% | 2 | 22.22% |  | 0.00% | 1 | 1.18% |  | 0.00% |  |
| 15 | 34.09% | 5 | 23.81% | 1 | 25.00% | 2 | 0.00% | 12 | 8.70% | 14 | 16.47% | 1 | 20.00% | 3 |
|  | 0.00% |  | 0.00% |  | 0.00% | 2 | 22.22% |  | 0.00% |  | 0.00% |  | 0.00% |  |
| 3 | 6.82% | 1 | 4.76% |  | 0.00% |  | 0.00% | 18 | 13.04% | 8 | 9.41% | 1 | 20.00% | 2 |
|  | 0.00% |  | 0.00% |  | 0.00% |  | 0.00% |  | 0.00% |  | 0.00% |  | 0.00% |  |
| 44 | 100.00% | 21 | 100.00% | 4 | 100.00% | 9 | 100.00% | 138 | 100.00% | 85 | 100.00% | 5 | 100.00% | 25 |

FIG. 26F

| (6) | Salivary Gland (5) | | Sinus tissue (1) | | Skeletal Muscles (2) | | Skin (5) | | Small Intestine (4) | | smooth muscle (3) | | Smooth Muscle such as smooth muscle from the intestine without the epithelium, ditto for the uterus ie no endometrium (1) | |
|---|---|---|---|---|---|---|---|---|---|---|---|---|---|---|
| tumor type | biomarker flagged as | tumor type | biomarker flagged as target | % in tumor type | biomarker flagged as target | tumor type | biomarker flagged as | tumor type | biomarker flagged as target | tumor type | biomarker flagged as target | tumor type | # of times biomarker flagged as target | % in tumor type |
| 20.00% | | 0.00% | | 0.00% | | 0.00% | 1 | 6.25% | 1 | 9.09% | 1 | 7.14% | | 0.00% |
| 8.00% | 3 | 13.64% | 1 | 20.00% | 1 | 12.50% | | 0.00% | 3 | 27.27% | 1 | 7.14% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 12.00% | 3 | 13.64% | 1 | 20.00% | | 0.00% | 5 | 31.25% | 3 | 27.27% | 2 | 14.29% | 1 | 50.00% |
| 0.00% | | 0.00% | | 0.00% | | 0.00% | | 0.00% | | 0.00% | | 0.00% | | 0.00% |
| 4.00% | 1 | 4.55% | | 0.00% | | 0.00% | 1 | 6.25% | | 0.00% | | 0.00% | | 0.00% |
| 16.00% | 4 | 18.18% | 1 | 20.00% | 2 | 25.00% | 1 | 6.25% | 1 | 9.09% | 1 | 7.14% | | 0.00% |
| 0.00% | | 0.00% | | 0.00% | | 0.00% | | 0.00% | | 0.00% | 1 | 7.14% | | 0.00% |
| 4.00% | | 0.00% | | 0.00% | | 0.00% | 1 | 6.25% | | 0.00% | 1 | 7.14% | | 0.00% |
| 16.00% | 3 | 13.64% | 1 | 20.00% | 1 | 12.50% | 1 | 6.25% | 1 | 9.09% | 1 | 7.14% | | 0.00% |
| 0.00% | 1 | 4.55% | | 0.00% | 1 | 12.50% | | 0.00% | | 0.00% | 1 | 7.14% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 12.00% | 5 | 22.73% | 1 | 20.00% | 2 | 25.00% | 4 | 25.00% | | 0.00% | 3 | 21.43% | 1 | 50.00% |
| 0.00% | | 0.00% | | 0.00% | | 0.00% | | 0.00% | | 0.00% | | 0.00% | | 0.00% |
| 8.00% | 2 | 9.09% | | 0.00% | 1 | 12.50% | 2 | 12.50% | 2 | 18.18% | 2 | 14.29% | | 0.00% |
| 0.00% | | 0.00 | | 0.00% | | 0.00% | | 0.00% | | 0.00% | | 0.00% | | 0.00% |
| 100.00% | 22 | 100.00% | 5 | 100.00% | 8 | 100.00% | 16 | 100.00% | 11 | 100.00% | 14 | 100.00% | 2 | 100.00% |

FIG. 26G

| Smooth muscle such as Uterine wall but not uterine lining i.e., not endometrium (1) | | Stomach (6) | | Synovium (1) | | Synovium or joint lining tissue (1) | | Tendon (1) | | Testis (1) | | Thymus (2) | |
|---|---|---|---|---|---|---|---|---|---|---|---|---|---|
| # of times biomarker flagged as target | % in tumor type | biomarker flagged as | % in tumor type | biomarker flagged as | % in tumor type | # of times biomarker flagged as target | % in tumor type | biomarker flagged as | % in tumor type | biomarker flagged as | tumor type | biomarker flagged as | tumor type |
|  | 0.00% |  | 0.00% |  | 0.00% |  | 0.00% |  | 0.00% |  | 0.00% | 2 | 40.00% |
|  | 0.00% | 1 | 5.88% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
|  | 0.00% | 4 | 23.53% | 1 | 20.00% | 1 | 100.00% |  | 0.00% | 1 | 50.00% | 2 | 40.00% |
| 1 | 20.00% |  | 0.00% |  | 0.00% |  | 0.00% |  | 0.00% |  | 0.00% |  | 0.00% |
| 1 | 20.00% | 1 | 5.88% | 1 | 20.00% |  | 0.00% |  | 0.00% | 1 | 50.00% |  | 0.00% |
|  | 0.00% | 3 | 17.65% | 1 | 20.00% |  | 0.00% |  | 0.00% |  | 0.00% | 1 | 20.00% |
|  | 0.00% |  | 0.00% |  | 0.00% |  | 0.00% |  | 0.00% |  | 0.00% |  | 0.00% |
| 1 | 20.00% | 1 | 5.88% |  | 0.00% |  | 0.00% |  | 0.00% |  | 0.00% |  | 0.00% |
|  | 0.00% | 4 | 23.53% | 1 | 20.00% |  | 0.00% |  | 0.00% |  | 0.00% |  | 0.00% |
| 1 | 20.00% | 1 | 5.88% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
| 1 | 20.00% |  | 0.00% | 1 | 20.00% |  | 0.00% | 1 | 100.00% |  | 0.00% |  | 0.00% |
|  | 0.00% |  | 0.00% |  | 0.00% |  | 0.00% |  | 0.00% |  | 0.00% |  | 0.00% |
|  | 0.00% | 2 | 11.76% |  | 0.00% |  | 0.00% |  | 0.00% |  | 0.00% |  | 0.00% |
|  | 0.00% |  | 0.00% |  | 0.00% |  | 0.00% |  | 0.00% |  | 0.00% |  | 0.00% |
| 5 | 100.00% | 17 | 100.00% | 5 | 100.00% | 1 | 100.00% | 1 | 100.00% | 2 | 100.00% | 5 | 100.00% |

FIG. 26H

| Thyroid (4) | | Uterus (3) | | Uterus:corpus (10) | | Overall | | |
|---|---|---|---|---|---|---|---|---|
| biomarker flagged as | tumor type | biomarker flagged as | tumor type | # of times biomarker flagged as target | % in tumor type | | | |
| | 0.00% | | 0.00% | 3 | 6.67% | 78 | 4.5% | Androgen Receptor |
| | 0.00% | | 0.00% | | 0.00% | 148 | 8.6% | c-kit |
| | 0.00% | | 0.00% | | 0.00% | 11 | 0.6% | CD25 |
| | 0.00% | | 0.00% | | 0.00% | 9 | 0.5% | CD52 |
| | 0.00% | | 0.00% | | 0.00% | 5 | 0.3% | COX-2 |
| | 0.00% | | 0.00% | | 0.00% | 0 | 0.0% | Cyclin D1 |
| 2 | 25.00% | 1 | 12.50% | 6 | 13.33% | 284 | 16.6% | EGFR |
| 1 | 12.50% | 1 | 12.50% | 4 | 8.89% | 60 | 3.5% | ER |
| 1 | 12.50% | | 0.00% | | 0.00% | 64 | 3.7% | Her2/Neu |
| 2 | 25.00% | 1 | 12.50% | 8 | 17.78% | 285 | 16.6% | HSP90 |
| | 0.00% | | 0.00% | | 0.00% | 11 | 0.6% | MLH1 |
| | 0.00% | | 0.00% | | 0.00% | 37 | 2.2% | MSH2 |
| | 0.00% | 1 | 12.50% | 4 | 8.89% | 179 | 10.4% | PDGFR |
| 1 | 12.50% | 1 | 12.50% | 2 | 4.44% | 61 | 3.6% | PR |
| | 0.00% | | 0.00% | | 0.00% | 14 | 0.8% | PTEN |
| | 0.00% | | 0.00% | | 0.00% | 1 | 0.1% | PRM1 |
| 1 | 12.50% | 2 | 25.00% | 10 | 22.22% | 244 | 14.2% | SPARC |
| | 0.00% | | 0.00% | | 0.00% | 0 | 0.0% | Survivin |
| | 0.00% | 1 | 12.50% | 8 | 17.78% | 224 | 13.1% | TOP2A |
| | 0.00% | | 0.00% | | 0.00% | 0 | 0.0% | Topoisomerase II alpha |
| 8 | 100.00% | 8 | 100.00% | 45 | 100.00% | 1715 | | |
| | | | | | | 0 | | |

FIG. 27A

| Gene Name (Microarray) | Tumor Type | | | | | | | | | | | |
|---|---|---|---|---|---|---|---|---|---|---|---|---|
| | Adipose (13) | | Adipose tissue, if not available use fibroblast (1) | | Adrenal Cortex (18) | | Adrenal Gland (1) | | Adrenal Gland – Medulla (15) | | Appendix (5) | |
| Gene | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type |
| ADA | 3 | 2.75% | 1 | 11.11% | 4 | 3.28% | | 0.00% | 9 | 5.59% | 2 | 3.23% |
| AR | | 0.00% | | 0.00% | 1 | 0.82% | | 0.00% | 1 | 0.62% | | 0.00% |
| ASNS | 4 | 3.67% | | 0.00% | 6 | 4.92% | | 0.00% | | 0.00% | 1 | 1.61% |
| ASNS | | 0.00% | | 0.00% | | 0.00% | | 0.00% | | 0.00% | | 0.00% |
| BRCA1 | 1 | 0.92% | | 0.00% | | 0.00% | | 0.00% | | 0.00% | 4 | 6.45% |
| BRCA2 | | 0.00% | | 0.00% | | 0.00% | | 0.00% | | 0.00% | 3 | 4.84% |
| CD52 | | 0.00% | | 0.00% | 1 | 0.82% | | 0.00% | | 0.00% | | 0.00% |
| CDW52 | | 0.00% | | 0.00% | | 0.00% | | 0.00% | | 0.00% | | 0.00% |
| CES2 | 2 | 1.83% | | 0.00% | 1 | 0.82% | | 0.00% | 1 | 0.62% | 1 | 1.61% |
| CES2* | | 0.00% | | 0.00% | | 0.00% | | 0.00% | | 0.00% | | 0.00% |
| DCK | 5 | 4.59% | 1 | 11.11% | 7 | 5.74% | 1 | 10.00% | 9 | 5.59% | | 0.00% |
| DHFR | | 0.00% | | 0.00% | | 0.00% | | 0.00% | | 0.00% | 1 | 1.61% |
| DMNT1 | 4 | 3.67% | | 0.00% | 2 | 1.64% | | 0.00% | 8 | 4.97% | | 0.00% |
| DMNT3A | 5 | 4.59% | 1 | 11.11% | 7 | 5.74% | | 0.00% | 9 | 5.59% | | 0.00% |
| DMNT3B | 11 | 10.09% | 1 | 11.11% | 10 | 8.20% | | 0.00% | 14 | 8.70% | | 0.00% |
| EGFR | 1 | 0.92% | | 0.00% | 6 | 4.92% | | 0.00% | 1 | 0.62% | 1 | 1.61% |
| EPHA2 | 2 | 1.83% | | 0.00% | 1 | 0.82% | | 0.00% | 1 | 0.62% | 2 | 3.23% |
| ERBB2 | | 0.00% | | 0.00% | | 0.00% | | 0.00% | 1 | 0.62% | | 0.00% |
| ESR1 | | 0.00% | | 0.00% | | 0.00% | | 0.00% | | 0.00% | | 0.00% |
| FLT1 | | 0.00% | | 0.00% | | 0.00% | 1 | 10.00% | 1 | 0.62% | 1 | 1.61% |
| GART | 10 | 9.17% | | 0.00% | 1 | 0.82% | | 0.00% | 4 | 2.48% | 2 | 3.23% |
| GNRH1 | | 0.00% | | 0.00% | | 0.00% | | 0.00% | | 0.00% | | 0.00% |
| HIF1A | 3 | 2.75% | | 0.00% | 7 | 5.74% | | 0.00% | | 0.00% | 3 | 4.84% |
| HSP90AA1 | | 0.00% | | 0.00% | | 0.00% | | 0.00% | | 0.00% | 1 | 1.61% |
| HSPCA | | 0.00% | | 0.00% | | 0.00% | | 0.00% | | 0.00% | | 0.00% |
| IL2RA | | 0.00% | | 0.00% | | 0.00% | | 0.00% | | 0.00% | | 0.00% |
| KDR | | 0.00% | | 0.00% | 1 | 0.82% | | 0.00% | 2 | 1.24% | 1 | 1.61% |
| KIT | | 0.00% | | 0.00% | 4 | 3.28% | | 0.00% | 6 | 3.73% | | 0.00% |
| LCK | | 0.00% | | 0.00% | | 0.00% | | 0.00% | | 0.00% | | 0.00% |
| MGMT | 3 | 2.75% | | 0.00% | 4 | 3.28% | 1 | 10.00% | 3 | 1.86% | 1 | 1.61% |
| M1H1 | | 0.00% | | 0.00% | | 0.00% | | 0.00% | | 0.00% | | 0.00% |
| MSI2 | 1 | 0.92% | | 0.00% | | 0.00% | | 0.00% | | 0.00% | | 0.00% |
| NFKB1 | 4 | 3.67% | 1 | 11.11% | 3 | 2.46% | 1 | 10.00% | 9 | 5.59% | 3 | 4.84% |
| NFKB2 | 4 | 3.67% | | 0.00% | | 0.00% | 1 | 10.00% | 3 | 1.86% | 2 | 3.23% |
| NFKBIA | 2 | 1.83% | | 0.00% | 4 | 3.28% | | 0.00% | 14 | 8.70% | 1 | 1.61% |
| PDGFC | | 0.00% | | 0.00% | | 0.00% | | 0.00% | | 0.00% | | 0.00% |
| PDGFRA | 2 | 1.83% | | 0.00% | | 0.00% | | 0.00% | | 0.00% | 1 | 1.61% |
| PDGFRB | 1 | 0.92% | 1 | 11.11% | 1 | 0.82% | 1 | 10.00% | 5 | 3.11% | 4 | 6.45% |
| PGR | | 0.00% | | 0.00% | 4 | 3.28% | | 0.00% | | 0.00% | | 0.00% |
| PTEN | 1 | 0.92% | | 0.00% | | 0.00% | | 0.00% | | 0.00% | | 0.00% |
| PTGS2 | 6 | 5.50% | | 0.00% | | 0.00% | | 0.00% | | 0.00% | 1 | 1.61% |
| RARA | | 0.00% | | 0.00% | | 0.00% | | 0.00% | | 0.00% | | 0.00% |
| RRM1 | 2 | 1.83% | | 0.00% | | 0.00% | | 0.00% | | 0.00% | 2 | 3.23% |
| RRM2 | | 0.00% | | 0.00% | | 0.00% | | 0.00% | | 0.00% | 4 | 6.45% |
| RRM2B | 1 | 0.92% | | 0.00% | 2 | 1.64% | | 0.00% | 7 | 4.35% | 1 | 1.61% |
| RXRG | 1 | 0.92% | | 0.00% | | 0.00% | | 0.00% | 2 | 1.24% | | 0.00% |
| SPARC | 8 | 7.34% | 1 | 11.11% | 14 | 11.48% | 1 | 10.00% | 2 | 1.24% | 1 | 1.61% |
| SPARC* | | 0.00% | | 0.00% | | 0.00% | | 0.00% | | 0.00% | | 0.00% |
| SRC | 2 | 1.83% | | 0.00% | 1 | 0.82% | | 0.00% | 1 | 0.62% | 1 | 1.61% |
| SSTR1 | 1 | 0.92% | | 0.00% | 2 | 1.64% | | 0.00% | 4 | 2.48% | 2 | 3.23% |
| SSTR2 | | 0.00% | | 0.00% | | 0.00% | | 0.00% | 3 | 1.86% | | 0.00% |
| SSTR3 | 2 | 1.83% | | 0.00% | 2 | 1.64% | | 0.00% | 8 | 4.97% | 3 | 4.84% |
| SSTR4 | 1 | 0.92% | | 0.00% | 1 | 0.82% | | 0.00% | 4 | 2.48% | 1 | 1.61% |
| SSTR5 | 1 | 0.92% | | 0.00% | 4 | 3.28% | | 0.00% | 4 | 2.48% | | 0.00% |
| TOP1 | 4 | 3.67% | 1 | 11.11% | 4 | 3.28% | 1 | 10.00% | 4 | 2.48% | 1 | 1.61% |
| TOP2A | 1 | 0.92% | 1 | 11.11% | 4 | 3.28% | 1 | 10.00% | 7 | 4.35% | 3 | 4.84% |
| TOP2B | 4 | 3.67% | | 0.00% | 1 | 0.82% | | 0.00% | 12 | 7.45% | | 0.00% |
| TYMS | 1 | 0.92% | | 0.00% | | 0.00% | | 0.00% | | 0.00% | 3 | 4.84% |
| VDR | 2 | 1.83% | | 0.00% | | 0.00% | 1 | 10.00% | 1 | 0.62% | 1 | 1.61% |
| VEGF | 1 | 0.92% | | 0.00% | | 0.00% | | 0.00% | | 0.00% | | 0.00% |
| VEGFA | 1 | 0.92% | | 0.00% | 3 | 2.46% | | 0.00% | | 0.00% | 2 | 3.23% |
| VHL | 1 | 0.92% | | 0.00% | 5 | 4.10% | | 0.00% | | 0.00% | 1 | 1.61% |
| YES1 | | 0.00% | | 0.00% | 3 | 2.46% | | 0.00% | 1 | 0.62% | | 0.00% |
| ZAP70 | | 0.00% | | 0.00% | | 0.00% | | 0.00% | | 0.00% | | 0.00% |
| Total Number of DMA Biomarkers Flagged as Target for Tumor Type Samples | 109 | 100.00% | 9 | 100.00% | 122 | 99.18% | 10 | 100.00% | 161 | 100.00% | 82 | 100.00% |

FIG. 27B

| Bladder (7) | | Blood Vessel Vain (4) | | Bone (2) | | Bone if you have it if not Cartilage (1) | | Brain (2) | | Breast (100) | | Cartilage (5) | |
|---|---|---|---|---|---|---|---|---|---|---|---|---|---|
| # of times biomarker flagged as | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as | % in tumor type |
| 4 | 4.94% | 2 | 4.35% | 2 | 7.41% | | 0.00% | | 0.00% | 42 | 3.63% | 3 | 4.84% |
| 1 | 1.23% | | 0.00% | | 0.00% | | 0.00% | | 0.00% | 27 | 2.33% | | 0.00% |
| | 0.00% | 1 | 2.17% | 1 | 3.70% | 1 | 9.09% | 2 | 6.67% | 5 | 0.43% | 1 | 1.61% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | 9 | 0.78% | 1 | 1.61% |
| | 0.00% | | 0.00% | | 0.00% | | 0.00% | | 0.00% | 62 | 5.35% | | 0.00% |
| | 0.00% | | 0.00% | | 0.00% | | 0.00% | | 0.00% | 1 | 0.09% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | 21 | 1.81% | 1 | 1.61% |
| 1 | 1.23% | 3 | 6.52% | | 0.00% | | 0.00% | | 0.00% | | 0.00% | | 0.00% |
| | 0.00% | | 0.00% | | 0.00% | | 0.00% | | 0.00% | 30 | 2.59% | 3 | 4.84% |
| 5 | 6.17% | | 0.00% | | 0.00% | | 0.00% | | 0.00% | 18 | 1.55% | 1 | 1.61% |
| | 0.00% | | 0.00% | | 0.00% | | 0.00% | | 0.00% | 2 | 0.17% | 1 | 1.61% |
| 1 | 1.23% | | 0.00% | | 0.00% | 1 | 9.09% | | 0.00% | | 0.00% | | 0.00% |
| 4 | 4.94% | | 0.00% | 1 | 3.70% | 1 | 9.09% | 2 | 6.67% | 8 | 0.69% | | 0.00% |
| 3 | 3.70% | 3 | 6.52% | 2 | 7.41% | | 0.00% | 1 | 3.33% | 13 | 1.12% | 2 | 3.23% |
| 1 | 1.23% | | 0.00% | | 0.00% | | 0.00% | 1 | 3.33% | 4 | 0.35% | 1 | 1.61% |
| 2 | 2.47% | | 0.00% | | 0.00% | | 0.00% | 1 | 3.33% | | 0.00% | | 0.00% |
| | 0.00% | | 0.00% | | 0.00% | | 0.00% | | 0.00% | 10 | 0.86% | | 0.00% |
| | 0.00% | | 0.00% | | 0.00% | | 0.00% | | 0.00% | 29 | 2.50% | | 0.00% |
| | 0.00% | | 0.00% | 2 | 7.41% | | 0.00% | 2 | 6.67% | 18 | 1.55% | | 0.00% |
| 4 | 4.94% | 1 | 2.17% | | 0.00% | 1 | 9.09% | 2 | 6.67% | 22 | 1.90% | 2 | 3.23% |
| | 0.00% | | 0.00% | | 0.00% | | 0.00% | | 0.00% | | 0.00% | | 0.00% |
| 6 | 7.41% | 1 | 2.17% | | 0.00% | 1 | 9.09% | 2 | 6.67% | 15 | 1.30% | 4 | 6.45% |
| 2 | 2.47% | | 0.00% | | 0.00% | | 0.00% | | 0.00% | 7 | 0.60% | 1 | 1.61% |
| | 0.00% | | 0.00% | | 0.00% | | 0.00% | | 0.00% | 7 | 0.60% | 1 | 1.61% |
| | 0.00% | | 0.00% | | 0.00% | | 0.00% | | 0.00% | | 0.00% | | 0.00% |
| | 0.00% | 1 | 2.17% | 1 | 3.70 | | 0.00% | | 0.00% | 12 | 1.04% | | 0.00% |
| | 0.00% | | 0.00% | | 0.00% | | 0.00% | | 0.00% | 23 | 1.99% | 2 | 3.23% |
| | 0.00% | | 0.00% | | 0.00% | | 0.00% | | 0.00% | | 0.00% | | 0.00% |
| 6 | 7.41% | | 0.00% | 2 | 7.41% | 1 | 9.09% | 1 | 3.33% | 56 | 4.84% | 3 | 4.84% |
| 1 | 1.23% | | 0.00% | | 0.00% | | 0.00% | | 0.00% | 1 | 0.09% | | 0.00% |
| | 0.00% | | 0.00% | | 0.00% | | 0.00% | | 0.00% | 31 | 2.68% | | 0.00% |
| 2 | 2.47% | 4 | 8.70% | | 0.00% | | 0.00% | 1 | 3.33% | 33 | 2.85% | 1 | 1.61% |
| | 0.00% | 3 | 6.52% | 2 | 7.41% | | 0.00% | 1 | 3.33% | 21 | 1.81% | 2 | 3.23% |
| 2 | 2.47% | 3 | 6.52% | 2 | 7.41% | 1 | 9.09% | 1 | 3.33% | 55 | 4.75% | 3 | 4.84% |
| | 0.00% | | 0.00% | | 0.00% | | 0.00% | | 0.00% | 1 | 0.09% | | 0.00% |
| | 0.00% | 1 | 2.17% | | 0.00% | | 0.00% | 2 | 6.67% | 5 | 0.43% | 1 | 1.61% |
| | 0.00% | 2 | 4.35% | | 0.00% | 1 | 9.09% | 2 | 6.67% | 48 | 4.15% | 3 | 4.84% |
| | 0.00% | | 0.00% | | 0.00% | | 0.00% | | 0.00% | 10 | 0.86% | | 0.00% |
| | 0.00% | | 0.00% | | 0.00% | | 0.00% | | 0.00% | 1 | 0.09% | | 0.00% |
| 1 | 1.23% | | 00.0% | | 0.00% | | 0.00% | | 0.00% | | 0.00% | | 0.00% |
| 2 | 2.47% | 1 | 2.17% | 2 | 7.41% | | 0.00% | | 0.00% | 15 | 1.30% | 3 | 4.84% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | 4 | 0.35% | | 0.00% |
| | 0.00% | 1 | 2.17% | | 0.00% | | 0.00% | | 0.00% | 48 | 4.15% | | 0.00% |
| | 0.00% | | 0.00% | | 0.00% | | 0.00% | | 0.00% | 15 | 1.30% | | 0.00% |
| | 0.00% | | 0.00% | 1 | 3.70% | | 0.00% | | 0.00% | 2 | 0.17% | | 0.00% |
| | 0.00% | | 0.00% | | 0.00% | | 0.00% | | 0.00% | | 0.00% | | 0.00% |
| 2 | 2.47% | 3 | 6.52% | 1 | 3.70% | 1 | 9.09% | 2 | 6.67% | 16 | 1.38% | 3 | 4.84% |
| | 0.00% | | 0.00% | | 0.00% | | 0.00% | | 0.00% | | 0.00% | | 0.00% |
| | 0.00% | 3 | 6.52% | | 0.00% | | 0.00% | | 0.00% | 32 | 2.76% | 1 | 1.61% |
| 2 | 2.47% | | 0.00% | | 0.00% | | 0.00% | | 0.00% | 42 | 3.63% | 1 | 1.61% |
| | 0.00% | 2 | 4.35% | 2 | 7.41% | | 0.00% | | 0.00% | 12 | 1.04% | | 0.00% |
| 5 | 6.17% | 3 | 6.52% | 1 | 3.70% | | 0.00% | | 0.00% | 74 | 6.39% | 3 | 4.84 |
| 2 | 2.47% | | 0.00% | | 0.00% | | 0.00% | | 0.00% | 27 | 2.33% | 1 | 1.61% |
| | 0.00% | | 0.00% | | 0.00% | | 0.00% | 1 | 3.33% | 23 | 1.99% | 3 | 4.84% |
| | 0.00% | | 0.00% | | 0.00% | | 0.00% | 1 | 3.33% | 26 | 2.25% | | 0.00% |
| 7 | 8.64% | 2 | 4.35% | 1 | 3.70% | | 0.00% | | 0.00% | 34 | 2.94% | 1 | 1.61% |
| 6 | 7.41% | 1 | 2.17% | | 0.00% | | 0.00% | | 0.00% | 18 | 1.55% | 2 | 3.23% |
| 2 | 2.47% | | 0.00% | 2 | 7.41% | 1 | 9.09% | 1 | 3.33% | 29 | 2.50% | | 0.00% |
| | 0.00% | | 0.00% | | 0.00% | | 0.00% | | 0.00% | 67 | 5.79% | 5 | 8.06% |
| 4 | 4.94% | | 0.00% | | 0.00% | 1 | 9.09% | 2 | 6.67% | 1 | 0.09% | | 0.00% |
| | 0.00% | | 0.00% | | 0.00% | | 0.00% | | 0.00% | 15 | 1.30% | 1 | 1.61% |
| 1 | 1.23% | 3 | 6.52% | 2 | 7.41% | | 0.00% | 2 | 6.67% | | 0.00% | 1 | 1.61% |
| 1 | 1.23% | | 0.00% | | 0.00% | | 0.00% | | 0.00% | 11 | 0.95% | | 0.00% |
| 1 | 1.23% | 2 | 4.35% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| 81 | 100.00% | 46 | 100.00% | 27 | 100.00% | 11 | 100.00% | 30 | 100.00% | 1158 | 100.00% | 82 | 100.00% |

FIG. 27C

| Cervix (10) | | Colon (66) | | Colon Sigmoid (1) | | Dendritic cells can be found in skin, the spleen, lymph node. Let's get Mike Bittner's take on site of origin (1) | | Difficult origin to define. Try skeletal muscle (1) | | Endometrium (3) | | Esophagus |
|---|---|---|---|---|---|---|---|---|---|---|---|---|
| # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target |
| 5 | 4.46% | 20 | 3.08% | | 0.00% | 1 | 12.50% | | 0.00% | 2 | 4.88% | 5 |
| | 0.00% | 1 | 0.15% | | 0.00% | | 0.00% | | 0.00% | | 0.00% | |
| | 0.00% | 3 | 0.46% | | 0.00% | | 0.00% | | 0.00% | 1 | 2.44% | 1 |
| | 0.00% | | 0.00% | | 0.00% | | 0.00% | | 0.00% | | 0.00% | |
| | 0.00% | 10 | 1.54% | | 0.00% | | 0.00% | | 0.00% | | 0.00% | |
| | 0.00% | 12 | 1.85% | | 0.00% | | 0.00% | | 0.00% | | 0.00% | |
| | 0.00% | | 0.00% | | 0.00% | | 0.00% | | 0.00% | | 0.00% | |
| | 0.00% | | 0.00% | | 0.00% | | 0.00% | | 0.00% | | 0.00% | |
| | 0.00% | | 0.00% | | 0.00% | | 0.00% | | 0.00% | | 0.00% | |
| | 0.00% | | 0.00% | | 0.00% | | 0.00% | | 0.00% | | 0.00% | |
| 5 | 4.46% | 3 | 0.46% | | 0.00% | | 0.00% | | 0.00% | 2 | 4.88% | 5 |
| | 0.00% | 3 | 0.46% | 1 | 7.14% | | 0.00% | | 0.00% | | 0.00% | |
| 3 | 2.68% | 2 | 0.31% | | 0.00% | | 0.00% | 1 | 6.25% | 1 | 2.44% | 1 |
| 5 | 4.46% | 27 | 4.16% | | 0.00% | | 0.00% | | 0.00% | 2 | 4.88% | 6 |
| 9 | 8.04% | 32 | 4.93% | 1 | 7.14% | 1 | 12.50% | 1 | 6.25% | 3 | 7.32% | 8 |
| 1 | 0.89% | 9 | 1.39% | 1 | 7.14% | 1 | 12.50% | | 0.00% | 1 | 2.44% | 4 |
| | 0.00% | 3 | 0.46% | | 0.00% | | 0.00% | | 0.00% | 2 | 4.88% | |
| 2 | 1.79% | 1 | 0.15% | | 0.00% | | 0.00% | | 0.00% | | 0.00% | 3 |
| | 0.00% | 1 | 0.15% | | 0.00% | | 0.00% | | 0.00% | | 0.00% | |
| | 0.00% | 24 | 3.70% | | 0.00% | | 0.00% | | 0.00% | | 0.00% | 2 |
| 10 | 8.93% | 30 | 4.62% | | 0.00% | 1 | 12.50% | 1 | 6.25% | 2 | 4.88% | 3 |
| | 0.00% | | 0.00% | | 0.00% | | 0.00% | | 0.00% | | 0.00% | |
| 3 | 2.68% | 29 | 4.47% | | 0.00% | | 0.00% | 1 | 6.25% | 2 | 4.88% | 7 |
| 4 | 3.57% | 15 | 2.31% | | 0.00% | | 0.00% | 1 | 6.25% | 2 | 4.88% | 4 |
| 1 | 0.89% | | 0.00% | | 0.00% | | 0.00% | | 0.00% | | 0.00% | |
| | 0.00% | | 0.00% | | 0.00% | | 0.00% | | 0.00% | | 0.00% | |
| | 0.00% | 6 | 0.92% | | 0.00% | | 0.00% | | 0.00% | | 0.00% | |
| | 0.00% | 3 | 0.46% | | 0.00% | | 0.00% | | 0.00% | | 0.00% | |
| | 0.00% | | 0.00% | | 0.00% | | 0.00% | | 0.00% | | 0.00% | |
| 4 | 3.57% | 21 | 3.24% | 1 | 7.14% | 1 | 12.50% | 1 | 6.25% | | 0.00% | 6 |
| | 0.00% | 2 | 0.31% | | 0.00% | | 0.00% | 1 | 6.25% | 1 | 2.44% | |
| | 0.00% | 2 | 0.31% | | 0.00% | | 0.00% | | 0.00% | | 0.00% | |
| 3 | 2.68% | 22 | 3.39% | 1 | 7.14% | | 0.00% | | 0.00% | 1 | 2.44% | 3 |
| | 0.00% | 9 | 1.39% | | 0.00% | | 0.00% | | 0.00% | 1 | 2.44% | 2 |
| 5 | 4.46% | 26 | 4.01% | 1 | 7.14% | | 0.00% | 1 | 6.25% | 3 | 7.32% | 1 |
| | 0.00% | 1 | 0.15% | | 0.00% | | 0.00% | | 0.00% | | 0.00% | |
| | 0.00% | 3 | 0.46% | | 0.00% | | 0.00% | | 0.00% | | 0.00% | |
| | 0.00% | 29 | 4.47% | 1 | 7.14% | | 0.00% | | 0.00% | | 0.00% | 2 |
| | 0.00% | | 0.00% | | 0.00% | | 0.00% | | 0.00% | | 0.00% | |
| | 0.00% | 1 | 0.15% | | 0.00% | | 0.00% | | 0.00% | 3 | 7.32% | |
| | 0.00% | 3 | 0.46% | 1 | 7.14% | | 0.00% | | 0.00% | 3 | 7.32% | 4 |
| | 0.00% | | 0.00% | | 0.00% | | 0.00% | | 0.00% | | 0.00% | |
| | 0.00% | 3 | 0.46% | | 0.00% | | 0.00% | | 0.00% | | 0.00% | 1 |
| | 0.00% | 20 | 3.08% | 1 | 7.14% | | 0.00% | | 0.00% | | 0.00% | |
| | 0.00% | 7 | 1.08% | | 0.00% | | 0.00% | 1 | 6.25% | | 0.00% | 3 |
| | 0.00% | 3 | 0.46% | | 0.00% | | 0.00% | | 0.00% | | 0.00% | |
| 2 | 1.79% | 18 | 2.77% | | 0.00% | | 0.00% | 1 | 6.25% | | 0.00% | 5 |
| | 0.00% | | 0.00% | | 0.00% | | 0.00% | | 0.00% | | 0.00% | |
| | 0.00% | 4 | 0.62% | | 0.00% | | 0.00% | 1 | 6.25% | | 0.00% | 7 |
| 4 | 3.57% | 24 | 3.70% | 1 | 7.14% | | 0.00% | | 0.00% | | 0.00% | 3 |
| 1 | 0.89% | 5 | 0.77% | | 0.00% | | 0.00% | | 0.00% | | 0.00% | 2 |
| 9 | 8.04% | 48 | 7.40% | 1 | 7.14% | 1 | 12.50% | | 0.00% | | 0.00% | 7 |
| 3 | 2.68% | 30 | 4.62% | 1 | 7.14% | | 0.00% | | 0.00% | | 0.00% | 2 |
| 1 | 0.89% | 16 | 2.47% | | 0.00% | | 0.00% | | 0.00% | | 0.00% | 1 |
| 6 | 5.36% | 18 | 2.77% | | 0.00% | 1 | 12.50% | 1 | 6.25% | | 0.00% | 7 |
| 10 | 8.93% | 32 | 4.93% | | 0.00% | 1 | 12.50% | 1 | 6.25% | 2 | 4.88% | 8 |
| 1 | 0.89% | 15 | 2.31% | | 0.00% | | 0.00% | 1 | 6.25% | | 0.00% | 4 |
| | 0.00% | 7 | 1.08% | 1 | 7.14% | | 0.00% | | 0.00% | | 0.00% | 1 |
| 6 | 5.36% | | 0.00% | | 0.00% | | 0.00% | 1 | 6.25% | 3 | 7.32% | 1 |
| 1 | 0.89% | 2 | 0.31% | | 0.00% | | 0.00% | | 0.00% | | 0.00% | |
| 5 | 4.46% | 39 | 6.01% | 1 | 7.14% | | 0.00% | | 0.00% | 3 | 7.32% | 3 |
| | 0.00% | 2 | 0.31% | | 0.00% | | 0.00% | | 0.00% | 1 | 2.44% | |
| 3 | 2.68% | 3 | 0.46% | | 0.00% | | 0.00% | 1 | 6.25% | | 0.00% | 3 |
| | 0.00% | | 0.00% | | 0.00% | | 0.00% | | 0.00% | | 0.00% | |
| 112 | 100.00% | 649 | 100.00% | 14 | 100.00% | 8 | 100.00% | 16 | 100.00% | 41 | 100.00% | 128 |

FIG. 27D

| S (9) | Fallopian Tube (3) | | Fibroblast (7) | | Gallbladder (5) | | Kidney (14) | | Larynx (3) | | Liver (1) | | Lung (74) | | Lymph Node (9) | |
|---|---|---|---|---|---|---|---|---|---|---|---|---|---|---|---|---|
| % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomark | % in tumor type | # of times biomarker flagged as | % in tumor type |
| 3.91% | 2 | 4.88% | 5 | 5.88% | 4 | 6.45% | 12 | 9.45% | 1 | 2.27% | 1 | 6.25% | 29 | 3.63% | 5 | 4.81% |
| 0.00% | | 0.00% | | 0.00% | | 0.00% | 1 | 0.79% | | 0.00% | | 0.00% | | 0.00% | | 0.00% |
| 0.78% | | 0.00% | 3 | 3.53% | 1 | 1.61% | | 0.00% | | 0.00% | | 0.00% | 1 | 0.13% | 1 | 0.96% |
| 0.00% | | 0.00% | | 0.00% | | 0.00% | | 0.00% | | 0.00% | | 0.00% | | 0.00% | | 0.00% |
| 0.00% | | 0.00% | 6 | 7.06% | | 0.00% | | 0.00% | | 0.00% | 1 | 6.25% | 1 | 0.13% | 1 | 0.96% |
| 0.00% | | 0.00% | 5 | 5.88% | 2 | 3.23% | | 0.00% | | 0.00% | | 0.00% | | 0.00% | 2 | 1.92% |
| 0.00% | | 0.00% | | 0.00% | | 0.00% | | 0.00% | | 0.00% | | 0.00% | | 0.00% | 2 | 1.92% |
| 0.00% | | 0.00% | | 0.00% | | 0.00% | | 0.00% | | 0.00% | | 0.00% | | 0.00% | | 0.00% |
| 0.00% | | 0.00% | 1 | 1.18% | 1 | 1.61% | | 0.00% | | 0.00% | | 0.00% | 17 | 2.13% | | 0.00% |
| 0.00% | | 0.00% | | 0.00% | | 0.00% | | 0.00% | | 0.00% | | 0.00% | | 0.00% | | 0.00% |
| 3.91% | 3 | 7.32% | | 0.00% | | 0.00% | 7 | 5.51% | 2 | 4.55% | | 0.00% | 8 | 1.00% | 5 | 4.81% |
| 0.00% | | 0.00% | 3 | 3.53% | | 0.00% | 3 | 2.36% | | 0.00% | 1 | 6.25% | | 0.00% | 2 | 1.92% |
| 0.78% | 1 | 2.44% | | 0.00% | | 0.00% | | 0.00% | | 0.00% | | 0.00% | 5 | 0.63% | | 0.00% |
| 4.69% | 3 | 7.32% | 5 | 5.88% | 1 | 1.61% | 11 | 8.66% | 3 | 6.82% | 1 | 6.25% | 36 | 4.51% | 5 | 4.81% |
| 6.25% | 3 | 7.32% | 2 | 2.35% | 1 | 1.61% | 9 | 7.09% | 2 | 4.55% | | 0.00% | 42 | 5.26% | 2 | 1.92% |
| 3.13% | | 0.00% | | 0.00% | 3 | 4.84% | 4 | 3.15% | 3 | 6.82% | | 0.00% | 18 | 2.25% | | 0.00% |
| 0.00% | | 0.00% | 1 | 1.18% | 4 | 6.45% | | 0.00% | | 0.00% | | 0.00% | 2 | 0.25% | | 0.00% |
| 2.34% | | 0.00% | | 0.00% | | 0.00% | | 0.00% | | 0.00% | | 0.00% | 3 | 0.38% | | 0.00% |
| 0.00% | 1 | 2.44% | | 0.00% | | 0.00% | | 0.00% | | 0.00% | | 0.00% | | 0.00% | | 0.00% |
| 1.56% | | 0.00% | | 0.00% | | 0.00% | 2 | 1.57% | | 0.00% | | 0.00% | 3 | 0.38% | 1 | 0.96% |
| 2.34% | 3 | 7.32% | 4 | 4.71% | 3 | 4.84% | 7 | 5.51% | 3 | 6.82% | | 0.00% | 44 | 5.51% | 5 | 4.81% |
| 0.00% | | 0.00% | | 0.00% | | 0.00% | | 0.00% | | 0.00% | | 0.00% | | 0.00% | | 0.00% |
| 5.47% | 3 | 7.32% | | 0.00% | | 0.00% | 3 | 2.36% | 3 | 6.82% | 1 | 6.25% | 37 | 4.63% | 3 | 2.88% |
| 3.13% | 1 | 2.44% | | 0.00% | | 0.00% | 1 | 0.79% | 3 | 6.82% | | 0.00% | 15 | 1.88% | 5 | 4.81% |
| 0.00% | | 0.00% | | 0.00% | | 0.00% | | 0.00% | | 0.00% | | 0.00% | 1 | 0.13% | | 0.00% |
| 0.00% | | 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | 1 | 0.13% | 1 | 0.96% |
| 0.00% | | 0.00% | | 0.00% | | 0.00% | 2 | 1.57% | | 0.00% | | 0.00% | 5 | 0.63% | | 0.00% |
| 0.00% | | 0.00% | | 0.00% | | 0.00% | | 0.00% | | 0.00% | | 0.00% | | 0.00% | | 0.00% |
| 7.03% | 2 | 4.88% | 2 | 2.35% | 2 | 3.23% | 10 | 7.87% | 3 | 6.82% | 1 | 6.25% | 46 | 5.76% | 3 | 2.88% |
| 0.00% | | 0.00% | | 0.00% | 1 | 1.61% | | 0.00% | | 0.00% | | 0.00% | | 0.00% | | 0.00% |
| 0.00% | | 0.00% | 1 | 1.18% | 1 | 1.61% | 1 | 0.79% | | 0.00% | | 0.00% | | 0.00% | | 0.00% |
| 2.34% | 1 | 2.44% | 3 | 3.53% | | 0.00% | 1 | 0.79% | 1 | 2.27% | | 0.00% | 47 | 5.88% | 1 | 0.96% |
| 1.56% | 3 | 7.32% | 1 | 1.18% | 3 | 4.84% | 2 | 1.57% | 3 | 6.82% | | 0.00% | 33 | 4.13% | 2 | 1.92% |
| 0.78% | 1 | 2.44% | 5 | 5.88% | 2 | 3.23% | 4 | 3.15% | 1 | 2.27% | | 0.00% | 42 | 5.26% | 4 | 3.85% |
| 0.00% | | 0.00% | | 0.00% | | 0.00% | | 0.00% | | 0.00% | | 0.00% | 4 | 0.50% | | 0.00% |
| 0.00% | | 0.00% | 1 | 1.18% | | 0.00% | 2 | 1.57% | | 0.00% | | 0.00% | 3 | 0.38% | | 0.00% |
| 1.56% | | 0.00% | 1 | 1.18% | | 0.00% | 5 | 3.94% | | 0.00% | 1 | 6.25% | 3 | 0.38% | | 0.00% |
| 0.00% | | 0.00% | 1 | 1.18% | | 0.00% | | 0.00% | | 0.00% | | 0.00% | | 0.00% | | 0.00% |
| 0.00% | | 0.00% | | 0.00% | 1 | 1.61% | | 0.00% | | 0.00% | | 0.00% | 1 | 0.13% | | 0.00% |
| 3.13% | | 0.00% | | 0.00% | | 0.00% | | 0.00% | | 0.00% | | 0.00% | 4 | 0.50% | | 0.00% |
| 0.00% | | 0.00% | | 0.00% | | 0.00% | | 0.00% | | 0.00% | | 0.00% | | 0.00% | 2 | 1.92% |
| 0.78% | | 0.00% | 4 | 4.71% | | 0.00% | | 0.00% | | 0.00% | | 0.00% | 1 | 0.13% | 1 | 0.96% |
| 0.00% | | 0.00% | 4 | 4.71% | 1 | 1.61% | | 0.00% | | 0.00% | 1 | 6.25% | 1 | 0.13% | 5 | 4.81% |
| 2.34% | | 0.00% | 2 | 2.35% | 3 | 4.84% | 2 | 1.57% | | 0.00% | | 0.00% | 19 | 2.38% | | 0.00% |
| 0.00% | | 0.00% | | 0.00% | 2 | 3.23% | | 0.00% | | 0.00% | | 0.00% | 4 | 0.50% | 1 | 0.96% |
| 3.91% | | 0.00% | 1 | 1.18% | | 0.00% | 7 | 5.51% | 1 | 2.27% | 1 | 6.25% | 10 | 1.25% | 1 | 0.96% |
| 0.00% | | 0.00% | | 0.00% | | 0.00% | | 0.00% | | 0.00% | | 0.00% | | 0.00% | | 0.00% |
| 5.47% | | 0.00% | | 0.00% | 2 | 3.23% | 1 | 0.79% | | 0.00% | | 0.00% | 8 | 1.00% | 4 | 3.85% |
| 2.34% | | 0.00% | | 0.00% | 3 | 4.84% | 2 | 1.57% | 1 | 2.27% | 1 | 6.25% | 20 | 2.50% | 3 | 2.88% |
| 1.56% | | 0.00% | 5 | 5.88% | | 0.00% | | 0.00% | | 0.00% | | 0.00% | 13 | 1.63% | 2 | 1.92% |
| 5.47% | | 0.00% | 4 | 4.17% | 3 | 4.84% | 11 | 8.66% | 1 | 2.27% | 1 | 6.25% | 42 | 5.26% | 9 | 8.65% |
| 1.56% | | 0.00% | 1 | 1.18% | 3 | 4.84% | 2 | 1.57% | 1 | 2.27% | 1 | 6.25% | 17 | 2.13% | 6 | 5.77% |
| 0.78% | | 0.00% | 1 | 1.18% | 2 | 3.23% | | 0.00% | | 0.00% | 1 | 6.25% | 15 | 1.88% | 4 | 3.85% |
| 5.47% | 3 | 7.32% | 2 | 2.35% | 5 | 6.66% | 1 | 0.79% | 3 | 6.82% | 1 | 6.25% | 34 | 4.26% | 4 | 3.85% |
| 6.25% | 3 | 7.32% | 4 | 4.71% | 1 | 1.61% | 1 | 0.79% | 3 | 6.82% | 1 | 6.25% | 41 | 5.13% | 3 | 2.88% |
| 3.13% | 3 | 7.32% | 1 | 1.18% | 3 | 4.84% | 2 | 1.57% | | 0.00% | 1 | 6.25% | 55 | 6.88% | 3 | 2.88% |
| 0.78% | | 0.00% | 4 | 4.71% | 1 | 1.61% | | 0.00% | | 0.00% | | 0.00% | | 0.00% | 1 | 0.96% |
| 0.78% | 2 | 4.88% | | 0.00% | | 0.00% | 1 | 0.79% | 3 | 6.82% | 1 | 6.25% | 32 | 4.01% | 3 | 2.88% |
| 0.00% | | 0.00% | | 0.00% | | 0.00% | 2 | 1.57% | | 0.00% | | 0.00% | 6 | 0.75% | | 0.00% |
| 2.34% | 1 | 2.44% | 2 | 2.35% | 3 | 4.84% | 2 | 1.57% | 1 | 2.27% | | 0.00% | 13 | 1.63% | 2 | 1.92% |
| 0.00% | | 0.00% | | 0.00% | | 0.00% | 6 | 4.72% | | 0.00% | | 0.00% | 11 | 1.38% | | 0.00% |
| 2.34% | 2 | 4.88% | | 0.00% | | 0.00% | | 0.00% | 2 | 4.55% | | 0.00% | 6 | 0.75% | | 0.00% |
| 0.00% | | 0.00% | | 0.00% | | 0.00% | | 0.00% | | 0.00% | | 0.00% | | 0.00% | | 0.00% |
| 100.00% | 41 | 100.00% | 85 | 100.00% | 62 | 100.00% | 127 | 100.00% | 44 | 100.00% | 16 | 100.00% | 799 | 100.00% | 104 | 100.00% |

FIG. 27E

| Melanocytes (22) | | Mesothelial Lining (6) | | Myoepithilial cells (1) | | Osteoblasts (2) | | Ovary (39) | | Pancreas (31) | | Parotid (2) | | Prostate (6) |
|---|---|---|---|---|---|---|---|---|---|---|---|---|---|---|
| # of biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as target |
| 15 | 4.37% | 2 | 2.82% | 1 | 8.33% | 2 | 5.88% | 13 | 2.69% | 12 | 3.48% | 2 | 5.71% | 2 |
|  | 0.00% |  | 0.00% |  | 0.00% |  | 0.00% |  | 0.00% |  | 0.00% | 2 | 5.71% | 2 |
| 6 | 1.75% |  | 0.00% |  | 0.00% | 2 | 5.88% | 1 | 0.21% | 22 | 6.38% | 2 | 5.71% |  |
|  | 0.00% |  | 0.00% |  | 0.00% |  | 0.00% |  | 0.00% |  | 0.00% |  | 0.00% |  |
| 18 | 5.25% | 4 | 5.63% |  | 0.00% |  | 0.00% | 1 | 0.21% | 1 | 0.29% |  | 0.00% |  |
| 16 | 4.66% | 4 | 5.63% |  | 0.00% |  | 0.00% | 1 | 0.00% | 1 | 0.29% |  | 0.00% |  |
|  | 0.00% |  | 0.00% |  | 0.00% |  | 0.00% |  | 0.00% |  | 0.00% |  | 0.00% |  |
|  | 0.00% |  | 0.00% |  | 0.00% |  | 0.00% |  | 0.00% |  | 0.00% |  | 0.00% |  |
| 2 | 0.58% |  | 0.00% |  | 0.00% |  | 0.00% | 2 | 0.41% | 3 | 0.87% |  | 0.00% |  |
|  | 0.00% |  | 0.00% |  | 0.00% |  | 0.00% |  | 0.00% |  | 0.00% |  | 0.00% |  |
| 1 | 0.29% |  | 0.00% |  | 0.00% |  | 0.00% | 19 | 3.93% | 12 | 3.48% | 1 | 2.86% | 3 |
| 10 | 2.92% | 5 | 7.04% |  | 0.00% |  | 0.00% | 1 | 0.21% | 1 | 0.29% |  | 0.00% |  |
| 1 | 0.29% |  | 0.00% |  | 0.00% |  | 0.00% | 2 | 0.41% | 2 | 0.58% | 1 | 2.86% |  |
| 4 | 1.17% | 2 | 2.82% | 1 | 8.33% | 1 | 2.94% | 10 | 2.07% | 4 | 1.16% | 2 | 5.71% | 2 |
| 3 | 0.87% |  | 0.00% | 1 | 8.33% | 2 | 5.88% | 32 | 6.61% | 1 | 0.29% | 2 | 5.71% | 4 |
|  | 0.00% |  | 0.00% |  | 0.00% |  | 0.00% |  | 0.00% | 7 | 2.03% |  | 0.00% |  |
| 8 | 2.33% |  | 0.00% |  | 0.00% |  | 0.00% | 1 | 0.21% | 2 | 0.58% |  | 0.00% |  |
|  | 0.00% |  | 0.00% |  | 0.00% |  | 0.00% | 3 | 0.62% |  | 0.00% | 1 | 2.86% |  |
|  | 0.00% | 1 | 1.41% |  | 0.00% |  | 0.00% | 10 | 2.07% |  | 0.00% |  | 0.00% |  |
| 19 | 5.54% | 5 | 7.04% |  | 0.00% | 2 | 5.88% | 2 | 0.41% | 2 | 0.58% |  | 0.00% |  |
| 7 | 2.04% | 1 | 1.41% |  | 0.00% | 2 | 5.88% | 29 | 5.99% | 24 | 6.96% | 2 | 5.71% | 3 |
|  | 0.00% |  | 0.00% |  | 0.00% |  | 0.00% |  | 0.00% |  | 0.00% |  | 0.00% |  |
| 5 | 1.46% |  | 0.00% |  | 0.00% |  | 0.00% | 29 | 5.99% | 27 | 7.83% | 2 | 5.71% | 1 |
| 3 | 0.87% |  | 0.00% |  | 0.00% | 1 | 2.94% | 19 | 3.93% | 11 | 3.19% |  | 0.00% |  |
|  | 0.00% |  | 0.00% |  | 0.00% |  | 0.00% | 3 | 0.62% | 1 | 0.29% |  | 0.00% |  |
|  | 0.00% |  | 0.00% |  | 0.00% |  | 0.00% |  | 0.00% |  | 0.00% |  | 0.00% |  |
| 3 | 0.87% |  | 0.00% |  | 0.00% |  | 0.00% | 2 | 0.41% |  | 0.00% |  | 0.00% |  |
|  | 0.00% |  | 0.00% | 1 | 8.33% |  | 0.00% | 1 | 0.21% | 1 | 0.29% |  | 0.00% |  |
|  | 0.00% |  | 0.00% |  | 0.00% |  | 0.00% |  | 0.00% |  | 0.00% |  | 0.00% |  |
| 16 | 4.66% | 2 | 2.82% | 1 | 8.33% | 2 | 5.88% | 30 | 6.20% | 23 | 6.67% | 1 | 2.86% | 3 |
| 1 | 0.29% |  | 0.00% |  | 0.00% |  | 0.00% | 2 | 0.41% |  | 0.00% |  | 0.00% |  |
| 3 | 0.87% |  | 0.00% |  | 0.00% |  | 0.00% | 1 | 0.21% |  | 0.00% |  | 0.00% |  |
| 6 | 1.75% |  | 0.00% |  | 0.00% | 1 | 2.94% | 25 | 5.17% | 1 | 0.29% | 1 | 2.86% | 1 |
| 5 | 1.46% | 3 | 4.23% |  | 0.00% | 2 | 5.88% | 23 | 4.75% | 12 | 3.48% |  | 0.00% | 1 |
| 19 | 5.54% | 2 | 2.82% |  | 0.00% | 2 | 5.88% | 12 | 2.48% | 15 | 4.35% | 2 | 5.71% | 2 |
|  | 0.00% |  | 0.00% |  | 0.00% |  | 0.00% |  | 0.00% |  | 0.00% |  | 0.00% |  |
| 4 | 1.17% |  | 0.00% |  | 0.00% |  | 0.00% |  | 0.00% | 6 | 1.74% |  | 0.00% |  |
| 14 | 4.08% | 4 | 5.63% |  | 0.00% |  | 0.00% | 1 | 0.21% | 13 | 3.77% | 1 | 2.86% |  |
|  | 0.00% |  | 0.00% |  | 0.00% | 1 | 2.94% | 1 | 0.21% |  | 0.00% |  | 0.00% |  |
| 2 | 0.58% |  | 0.00% |  | 0.00% |  | 0.00% | 1 | 0.21% | 2 | 0.58% |  | 0.00% |  |
| 2 | 0.58% | 3 | 4.23% |  | 0.00% | 2 | 5.88% | 2 | 0.41% | 23 | 6.67% | 1 | 2.86% |  |
|  | 0.00% |  | 0.00% |  | 0.00% |  | 0.00% |  | 0.00% |  | 0.00% |  | 0.00% |  |
| 14 | 4.08% | 5 | 7.04% |  | 0.00% |  | 0.00% | 1 | 0.21% |  | 0.00% |  | 0.00% |  |
| 20 | 5.83% | 5 | 7.04% | 1 | 8.33% |  | 0.00% |  | 0.00% | 3 | 0.87% |  | 0.00% |  |
| 8 | 2.33% | 4 | 5.63% | 1 | 8.33% |  | 0.00% | 3 | 0.62% | 3 | 0.87% |  | 0.00% | 1 |
| 5 | 1.46% |  | 0.00% |  | 0.00% |  | 0.00% | 1 | 0.21% |  | 0.00% |  | 0.00% | 1 |
| 6 | 1.75% | 1 | 1.41% |  | 0.00% |  | 0.00% | 6 | 1.24% | 14 | 4.06% | 1 | 2.86% | 1 |
|  | 0.00% |  | 0.00% |  | 0.00% |  | 0.00% |  | 0.00% |  | 0.00% |  | 0.00% |  |
| 11 | 3.21% |  | 0.00% |  | 0.00% |  | 0.00% | 1 | 0.21% | 2 | 0.58% |  | 0.00% |  |
| 2 | 0.58% | 1 | 1.41% |  | 0.00% | 1 | 2.94% | 5 | 1.03% | 4 | 1.16% | 1 | 2.86% | 3 |
| 16 | 4.66% | 5 | 7.04% | 1 | 8.33% | 1 | 2.94% | 1 | 0.21% | 4 | 1.16% | 1 | 2.86% |  |
| 10 | 2.92% | 4 | 5.63% |  | 0.00% | 1 | 2.94% | 19 | 3.93% | 2 | 0.58% | 1 | 2.86% | 4 |
| 5 | 1.46% | 2 | 2.82% | 1 | 8.33% | 1 | 2.94% | 6 | 1.24% | 1 | 0.29% | 1 | 2.86% | 2 |
| 3 | 0.87% |  | 0.00% |  | 0.00% | 1 | 2.94% | 2 | 0.41% | 1 | 0.29% |  | 0.00% | 1 |
| 5 | 1.46% |  | 0.00% |  | 0.00% | 1 | 8.33% | 1 | 2.94% | 31 | 6.40% | 27 | 7.83% | 2 | 5.71% | 2 |
| 5 | 1.46% | 1 | 1.41% |  | 0.00% | 2 | 5.88% | 23 | 4.75% | 8 | 2.32% | 1 | 2.86% | 2 |
| 3 | 0.87% | 1 | 1.41% | 1 | 8.33% | 1 | 2.94% | 34 | 7.02% | 21 | 6.09% |  | 0.00% | 4 |
| 10 | 2.92% | 3 | 4.23% |  | 0.00% |  | 0.00% | 1 | 0.21% |  | 0.00% |  | 0.00% |  |
| 8 | 2.33% |  | 0.00% |  | 0.00% | 1 | 2.94% | 28 | 5.79% | 18 | 5.22% | 2 | 5.71% | 1 |
|  | 0.00% |  | 0.00% |  | 0.00% |  | 0.00% | 3 | 0.62% |  | 0.00% |  | 0.00% |  |
| 15 | 4.37% | 1 | 1.41% |  | 0.00% | 2 | 5.88% | 23 | 4.75% | 1 | 0.29% | 1 | 2.86% |  |
|  | 0.00% |  | 0.00% |  | 0.00% |  | 0.00% |  | 0.00% |  | 0.00% |  | 0.00% |  |
| 4 | 1.17% |  | 0.00% |  | 0.00% |  | 0.00% | 18 | 3.72% | 7 | 2.03% | 1 | 2.86% |  |
|  | 0.00% |  | 0.00% |  | 0.00% |  | 0.00% |  | 0.00% |  | 0.00% |  | 0.00% |  |
| 343 | 100.00% | 71 | 100.00% | 12 | 100.00% | 34 | 100.00% | 484 | 100.00% | 345 | 100.00% | 35 | 100.00% | 46 |

FIG. 27F

| (6) | Salivary Gland (5) | | Sinus tissue (1) | | Skeletal Muscles (2) | | Skin (5) | | Small Intestine (4) | | smooth muscle (3) | | Smooth Muscle such as smooth muscle from the intestine without the epithelium, ditto for the uterus ie no endometrium (1) | |
|---|---|---|---|---|---|---|---|---|---|---|---|---|---|---|
| % in tumor type | # of times biomarker flagged as | % in tumor type | # of times biomarker flagged as target | % in tumor type | # of times biomarker flagged as target | % in tumor type | # of times biomarker flagged as | % in tumor type | # of times biomarker flagged as target | % in tumor type | # of times biomarker flagged as target | % in tumor type | # of times biomarker flagged as target | % in tumor type |
| 4.35% | 3 | 3.85% | | 0.00% | 1 | 3.23% | 4 | 9.76% | 3 | 9.68% | 2 | 5.56% | | 0.00% |
| 4.35% | | 0.00% | | 0.00% | | 0.00% | | 0.00% | 1 | 3.23% | | 0.00% | | 0.00% |
| 0.00% | | 0.00% | | 0.00% | | 0.00% | | 0.00% | | 0.00% | | 0.00% | 1 | 10.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | 1 | 2.78% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | 1 | 2.44% | | 0.00% | | 0.00% | | 0.00% |
| 0.00% | | 0.00% | | 0.00% | | 0.00% | | 0.00% | | 0.00% | | 0.00% | | 0.00% |
| 6.52% | 3 | 3.85% | | 0.00% | | 0.00% | 1 | 2.44% | 1 | 3.23% | 1 | 2.78% | 1 | 10.00% |
| 0.00% | 1 | 1.28% | | 0.00% | | 0.00% | | 0.00% | | 0.00% | | 0.00% | | 0.00% |
| 0.00% | 1 | 1.28% | | 0.00% | | 0.00% | 1 | 2.44% | | 0.00% | | 0.00% | | 0.00% |
| 4.35% | 3 | 3.85% | | 0.00% | 1 | 3.23% | 5 | 12.20% | | 0.00% | 2 | 5.56% | | 0.00% |
| 8.70% | 2 | 2.56% | 1 | 7.14% | 2 | 6.45% | 3 | 7.32% | | 0.00% | 2 | 5.56% | | 0.00% |
| 0.00% | 1 | 1.28% | | 0.00% | | 0.00% | | 0.00% | 1 | 3.23% | | 0.00% | | 0.00% |
| 0.00% | | 0.00% | | 0.00% | 1 | 3.23% | | 0.00% | | 0.00% | | 0.00% | | 0.00% |
| 0.00% | | 0.00% | | 0.00% | | 0.00% | 1 | 2.44% | | 0.00% | | 0.00% | | 0.00% |
| 0.00% | | 0.00% | | 0.00% | | 0.00% | | 0.00% | | 0.00% | | 0.00% | | 0.00% |
| 0.00% | 2 | 2.56% | | 0.00% | | 0.00% | | 0.00% | | 0.00% | 1 | 2.78% | | 0.00% |
| 6.52% | 4 | 5.13% | 1 | 7.14% | 1 | 3.23% | | 0.00% | | 0.00% | 1 | 2.78% | | 0.00% |
| 0.00% | | 0.00% | | 0.00% | | 0.00% | | 0.00% | | 0.00% | | 0.00% | | 0.00% |
| 2.17% | 5 | 6.41% | 1 | 7.14% | 2 | 6.45% | 1 | 2.44% | 2 | 6.45% | 3 | 8.33% | 1 | 10.00% |
| 0.00% | 3 | 3.85% | | 0.00% | | 0.00% | | 0.00% | 1 | 3.23% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | 2 | 2.56% | | 0.00% | 1 | 3.23% | | 0.00% | 1 | 3.23% | | 0.00% | | 0.00% |
| 0.00% | | 0.00% | | 0.00% | | 0.00% | | 0.00% | | 0.00% | | 0.00% | | 0.00% |
| 6.52% | 4 | 5.13% | 1 | 7.14% | 2 | 6.45% | 1 | 2.44% | 2 | 6.45% | 3 | 8.33% | 1 | 10.00% |
| 0.00% | | 0.00% | | 0.00% | 1 | 3.23% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 2.17% | 3 | 3.85% | | 0.00% | 1 | 3.23% | 4 | 9.76% | | 0.00% | 2 | 5.56% | | 0.00% |
| 2.17% | 2 | 2.56% | 1 | 7.14% | | 0.00% | 2 | 4.88% | | 0.00% | | 0.00% | | 0.00% |
| 4.35% | 1 | 1.28% | 1 | 7.14% | | 0.00% | 2 | 4.88% | | 0.00% | 2 | 5.56% | 1 | 10.00% |
| 0.00% | | 0.00% | | 0.00% | | 0.00% | | 0.00% | | 0.00% | | 0.00% | | 0.00% |
| 0.00% | 2 | 2.56% | 1 | 7.14% | 1 | 3.23% | | 0.00% | 1 | 3.23% | 1 | 2.78% | | 0.00% |
| 0.00% | 2 | 2.56% | 1 | 7.14% | 1 | 3.23% | | 0.00% | | 0.00% | 2 | 5.56% | 1 | 10.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | 2 | 2.56% | | 0.00% | | 0.00% | 2 | 4.88% | | 0.00% | 1 | 2.78% | 1 | 10.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | | 0.00% | | 0.00% | | 0.00% |
| 0.00% | | 0.00% | | 0.00% | | 0.00% | | 0.00% | 2 | 6.45% | | 0.00% | | 0.00% |
| 2.17% | | 0.00% | | 0.00% | 1 | 3.23% | | 0.00% | | 0.00% | | 0.00% | | 0.00% |
| 2.17% | | 0.00% | | 0.00% | | 0.00% | | 0.00% | | 0.00% | | 0.00% | | 0.00% |
| 2.17% | 5 | 6.41% | 1 | 7.14% | 2 | 6.45% | | 0.00% | | 0.00% | 1 | 2.78% | | 0.00% |
| 0.00% | | 0.00% | | 0.00% | | 0.00% | | 0.00% | | 0.00% | | 0.00% | | 0.00% |
| 0.00% | 1 | 1.28% | | 0.00% | 2 | 6.45% | 1 | 2.44% | | 0.00% | | 0.00% | | 0.00% |
| 6.52% | 1 | 1.28% | | 0.00% | | 0.00% | | 0.00% | | 0.00% | | 0.00% | | 0.00% |
| 0.00% | | 0.00% | | 0.00% | 1 | 3.23% | | 0.00% | | 0.00% | 1 | 2.78% | 1 | 10.00% |
| 8.70% | 3 | 3.85% | 1 | 7.14% | 1 | 3.23% | 4 | 9.76% | 3 | 9.68% | 3 | 8.33% | | 0.00% |
| 4.35% | 1 | 1.28% | | 0.00% | | 0.00% | 2 | 4.88% | 1 | 3.23% | | 0.00% | | 0.00% |
| 2.17% | | 0.00% | | 0.00% | 1 | 3.23% | | 0.00% | 1 | 3.23% | | 0.00% | | 0.00% |
| 4.35% | 5 | 6.41% | 1 | 7.14% | 2 | 6.45% | 1 | 2.44% | 3 | 9.68% | 1 | 2.78% | 1 | 10.00% |
| 4.35% | 3 | 3.85% | 1 | 7.14% | 1 | 3.23% | 2 | 4.88% | 2 | 6.45% | 2 | 5.56% | | 0.00% |
| 8.70% | 5 | 6.41% | 1 | 7.14% | 2 | 6.45% | 2 | 4.88% | 3 | 9.68% | 2 | 5.56% | | 0.00% |
| 0.00% | | 0.00% | | 0.00% | | 0.00% | | 0.00% | 1 | 3.23% | | 0.00% | | 0.00% |
| 2.17% | 4 | 5.13% | 1 | 7.14% | 1 | 3.23% | 1 | 2.44% | | 0.00% | 1 | 2.78% | 1 | 10.00% |
| 0.00% | | 0.00% | | 0.00% | | 0.00% | | 0.00% | | 0.00% | | 0.00% | | 0.00% |
| 0.00% | 1 | 1.28% | | 0.00% | | 0.00% | | 0.00% | 1 | 3.23% | 1 | 2.78% | | 0.00% |
| 0.00% | | 0.00% | | 0.00% | | 0.00% | | 0.00% | | 0.00% | | 0.00% | | 0.00% |
| 0.00% | 3 | 3.85% | | 0.00% | 2 | 6.45% | | 0.00% | 1 | 3.23% | | 0.00% | | 0.00% |
| 0.00% | | 0.00% | | 0.00% | | 0.00% | | 0.00% | | 0.00% | | 0.00% | | 0.00% |
| 100.00% | 78 | 100.00% | 14 | 100.00% | 31 | 100.00% | 41 | 100.00% | 31 | 100.0% | 36 | 100.00% | 10 | 100.00% |

FIG. 27G

| Smooth muscle such as Uterine wall but not uterine lining i.e., not endometrium (1) | | Stomach (5) | | Synovium (1) | | Synovium or joint lining tissue (1) | | Tendon (1) | | Testis (1) | | Thymus (2) | |
|---|---|---|---|---|---|---|---|---|---|---|---|---|---|
| # of times biomarker flagged as target | % in tumor type | # of times biomarker flagged as | % in tumor type | # of times biomarker flagged as target | % in tumor type | # of times biomarker flagged as target | % in tumor type | # of times biomarker flagged as target | % in tumor type | # of times biomarker flagged as target | % in tumor type | # of times biomarker flagged as | % in tumor type |
| 1 | 10.00% | 5 | 8.62% | | 0.00% | 1 | 6.67% | 1 | 10.00% | 1 | 4.55% | 2 | 6.45% |
| | 0.00% | | 0.00% | | 0.00% | | 0.00% | | 0.00% | | 0.00% | 1 | 3.23% |
| | 0.00% | 1 | 1.72% | | 0.00% | | 0.00% | | 0.00% | 1 | 4.55% | | 0.00% |
| | 0.00% | | 0.00% | | 0.00% | | 0.00% | | 0.00% | | 0.00% | | 0.00% |
| | 0.00% | | 0.00% | | 0.00% | 1 | 6.67% | | 0.00% | 1 | 4.55% | | 0.00% |
| | 0.00% | 2 | 3.45% | | 0.00% | | 0.00% | | 0.00% | 1 | 4.55% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | 2 | 6.45% |
| | 0.00% | | 0.00% | | 0.00% | | 0.00% | | 0.00% | | 0.00% | | 0.00% |
| | 0.00% | 2 | 3.45% | 1 | 6.25% | 1 | 6.67% | | 0.00% | 1 | 4.55% | | 0.00% |
| 1 | 10.00% | 4 | 6.90% | 1 | 6.25% | 1 | 6.67% | 1 | 10.00% | 1 | 4.55% | | 0.00% |
| | 0.00% | 1 | 1.72% | 1 | 6.25% | | 0.00% | | 0.00% | 1 | 4.55% | 1 | 3.23% |
| | 0.00% | | 0.00% | 1 | 6.25% | | 0.00% | | 0.00% | 1 | 4.55% | | 0.00% |
| | 0.00% | | 0.00% | 1 | 6.25% | | 0.00% | | 0.00% | 1 | 4.55% | | 0.00% |
| 1 | 10.00% | | 0.00% | | 0.00% | | 0.00% | | 0.00% | | 0.00% | | 0.00% |
| | 0.00% | | 0.00% | | 0.00% | | 0.00% | | 0.00% | 1 | 4.55% | | 0.00% |
| 1 | 10.00% | | 0.00% | 1 | 6.25% | 1 | 6.67% | 1 | 10.00% | | 0.00% | | 0.00% |
| 1 | 10.00% | | 0.00% | | 0.00% | | 0.00% | | 0.00% | | 0.00% | | 0.00% |
| 1 | 10.00% | 2 | 3.45% | 1 | 6.25% | 1 | 6.67% | 1 | 10.00% | 1 | 4.55% | 2 | 6.45% |
| | 0.00% | 1 | 1.72% | 1 | 6.25% | | 0.00% | | 0.00% | | 0.00% | 1 | 3.23% |
| | 0.00% | 1 | 1.72% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | 1 | 1.72% | | 0.00% | | 0.00% | | 0.00% | 1 | 4.55% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | 3 | 5.17% | 1 | 6.25% | 1 | 6.67% | 1 | 10.00% | 1 | 4.55% | 1 | 3.23% |
| | 0.00% | 1 | 1.72% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | 3 | 5.17% | | 0.00% | | 0.00% | | 0.00% | | 0.00% | 2 | 6.45% |
| | 0.00% | 2 | 3.45% | | 0.00% | | 0.00% | | 0.00% | | 0.00% | 2 | 6.45% |
| | 0.00% | 3 | 5.17% | | 0.00% | | 0.00% | | 0.00% | 1 | 4.55% | 1 | 3.23% |
| | 0.00% | | 0.00% | | 0.00% | | 0.00% | | 0.00% | | 0.00% | | 0.00% |
| | 0.00% | | 0.00% | 1 | 6.25% | | 0.00% | | 0.00% | | 0.00% | | 0.00% |
| | 0.00% | 2 | 3.45% | | 0.00% | | 0.00% | | 0.00% | 1 | 4.55% | 1 | 3.23% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | 1 | 1.72% | | 0.00% | | 0.00% | | 0.00% | 1 | 4.55% | | 0.00% |
| | 0.00% | | 0.00% | | 0.00% | | 0.00% | | 0.00% | | 0.00% | | 0.00% |
| | 0.00% | | 0.00% | | 0.00% | | 0.00% | | 0.00% | | 0.00% | | 0.00% |
| | 0.00% | 2 | 3.45% | | 0.00% | 1 | 6.67% | | 0.00% | | 0.00% | 2 | 6.45% |
| | 0.00% | 1 | 1.72% | 1 | 6.25% | 1 | 6.67% | 1 | 10.00% | | 0.00% | | 0.00% |
| | 0.00% | 1 | 1.72% | | 0.00% | | 0.00% | | 0.00% | | 0.00% | | 0.00% |
| | 0.00% | | 0.00% | 1 | 6.25% | | 0.00% | 1 | 10.00% | | 0.00% | | 0.00% |
| | 0.00% | | 0.00% | | 0.00% | | 0.00% | | 0.00% | | 0.00% | | 0.00% |
| 1 | 10.00% | 1 | 1.72% | | 0.00% | | 0.00% | | 0.00% | | 0.00% | | 0.00% |
| | 0.00% | 1 | 1.72% | | 0.00% | 1 | 6.67% | | 0.00% | 1 | 4.55% | 2 | 6.45% |
| | 0.00% | 1 | 1.72% | 1 | 6.25% | 1 | 6.67% | | 0.00% | | 0.00% | | 0.00% |
| | 0.00% | 4 | 6.90% | | 0.00% | 1 | 6.67% | | 0.00% | 1 | 4.55% | 2 | 6.45% |
| | 0.00% | 3 | 5.17% | | 0.00% | | 0.00% | | 0.00% | | 0.00% | | 0.00% |
| | 0.00% | 1 | 1.72% | 1 | 6.25% | 1 | 6.67% | | 0.00% | | 0.00% | | 0.00% |
| 1 | 10.00% | 2 | 3.45% | | 0.00% | | 0.00% | 1 | 10.00% | 1 | 4.55% | 2 | 6.45% |
| | 0.00% | 3 | 5.17% | | 0.00% | | 0.00% | | 0.00% | | 0.00% | | 0.00% |
| 1 | 10.00% | | 0.00% | 1 | 6.25% | 1 | 6.67% | 1 | 10.00% | | 0.00% | 2 | 6.45% |
| | 0.00% | | 0.00% | | 0.00% | | 0.00% | | 0.00% | 1 | 4.55% | 2 | 6.45% |
| 1 | 10.00% | | 0.00% | | 0.00% | | 0.00% | 1 | 10.00% | 1 | 4.55% | 2 | 6.45% |
| | 0.00% | | 0.00% | | 0.00% | | 0.00% | | 0.00% | | 0.00% | | 0.00% |
| | 0.00% | 3 | 5.17% | | 0.00% | | 0.00% | | 0.00% | 1 | 4.55% | | 0.00% |
| | 0.00% | | 0.00% | | 0.00% | | 0.00% | | 0.00% | | 0.00% | | 0.00% |
| | 0.00% | | 0.00% | 1 | 6.25% | 1 | 6.67% | | 0.00% | | 0.00% | 1 | 3.23% |
| | 0.00% | | 0.00% | | 0.00% | | 0.00% | | 0.00% | | 0.00% | | 0.00% |
| 10 | 100.00% | 58 | 100.00% | 16 | 100.00% | 15 | 100.00% | 10 | 100.00% | 22 | 100.00% | 31 | 100.00% |

FIG. 27H

| Thyroid (4) | | Uterus (3) | | Uterus:corpus (10) | | Overall | | |
|---|---|---|---|---|---|---|---|---|
| # of times biomarker flagged as | % in tumor type | # of times biomarker flagged as | % in tumor type | # of times biomarker flagged as target | % in tumor type | | | |
| 3 | 4.11% | 1 | 2.44% | 6 | 4.69% | 247 | 4.0% | ADA |
|  | 0.00% |  | 0.00% |  | 0.00% | 38 | 0.6% | AR |
| 1 | 1.37% | 1 | 2.44% |  | 0.00% | 71 | 1.2% | ASNS |
|  | 0.00% |  | 0.00% |  | 0.00% | 0 | 0.0% | ASNS |
|  | 0.00% |  | 0.00% |  | 0.00% | 61 | 1.0% | BRCA1 |
| 4 | 5.48% |  | 0.00% |  | 0.00% | 114 | 1.9% | BRCA2 |
|  | 0.00% |  | 0.00% |  | 0.00% | 4 | 0.1% | CD52 |
|  | 0.00% |  | 0.00% |  | 0.00% | 0 | 0.00% | CDW52 |
|  | 0.00% | 1 | 2.44% |  | 0.00% | 59 | 1.0% | CES2 |
|  | 0.00% |  | 0.00% |  | 0.00% | 0 | 0.0% | CES2 |
|  | 0.00% |  | 0.00% | 4 | 3.13% | 148 | 2.4% | DCK |
|  | 0.00% |  | 0.00% |  | 0.00% | 54 | 0.9% | DHFR |
|  | 0.00% |  | 0.00% | 4 | 3.13% | 45 | 0.7% | DNMT1 |
| 4 | 5.48% | 2 | 4.88% | 5 | 3.91% | 196 | 3.2% | DNMT3A |
| 4 | 5.48% | 2 | 4.188 | 10 | 7.81% | 256 | 4.2% | DNMT3B |
| 2 | 2.74% |  | 0.00% |  | 0.00% | 76 | 1.2% | EGFR |
|  | 0.00% |  | 0.00% |  | 0.00% | 35 | 0.6% | EPHA2 |
| 1 | 1.37% |  | 0.00% |  | 0.00% | 28 | 0.5% | ERBB2 |
| 1 | 1.37% |  | 0.00% | 2 | 1.56% | 46 | 0.7% | ESR1 |
| 1 | 1.37% |  | 0.00% |  | 0.00% | 92 | 1.5% | FLT1 |
| 1 | 1.37% | 2 | 4.88% | 6 | 4.69% | 253 | 4.1% | GART |
|  | 0.00% |  | 0.00% |  | 0.00% | 1 | 0.0% | GNRH1 |
| 3 | 4.11% | 2 | 4.88% | 7 | 5.47% | 234 | 3.8% | HIF1A |
| 1 | 1.37 | 1 | 2.44% | 6 | 4.69% | 111 | 1.8% | HSP90AA1 |
|  | 0.00% |  | 0.00% |  | 0.00% | 15 | 0.2% | HSPCA |
|  | 0.00% |  | 0.00% |  | 0.00% | 0 | 0.0% | IL2RA |
| 1 | 1.37% |  | 0.00% |  | 0.00% | 34 | 0.6% | KDR |
|  | 0.00% |  | 0.00% |  | 0.00% | 52 | 0.8% | KIT |
|  | 0.00% |  | 0.00% |  | 0.00% | 0 | 0.0% | LCK |
| 4 | 5.48% | 2 | 4.88% | 10 | 7.81% | 303 | 4.9% | MGMT |
| 1 | 1.37% |  | 0.00% | 1 | 0.78% | 14 | 0.2% | MLH1 |
| 1 | 1.37% |  | 0.00% |  | 0.00% | 42 | 0.7% | MSH2 |
| 3 | 4.11% | 3 | 7.32% | 3 | 2.34% | 205 | 3.3% | NFKB1 |
| 1 | 1.37% | 2 | 4.88% | 4 | 3.13% | 160 | 2.6% | NFKB2 |
| 3 | 4.11% | 2 | 4.88% | 6 | 4.69% | 261 | 4.2% | NFKBIA |
|  | 0.00% |  | 0.00% |  | 0.00% | 6 | 0.1% | PDGFC |
|  | 0.00% |  | 0.00% | 1 | 0.78% | 39 | 0.6% | PDGFRA |
| 3 | 4.11% |  | 0.00% | 1 | 0.78% | 159 | 2.6% | PDGFRB |
|  | 0.00% |  | 0.00% |  | 0.00% | 17 | 0.3% | PGR |
|  | 0.00% |  | 0.00% | 2 | 1.56% | 16 | 0.3% | PTEN |
| 1 | 1.37% | 3 | 7.32% |  | 0.00% | 90 | 1.5% | PTGS2 |
|  | 0.00% |  | 0.00% |  | 0.00% | 2 | 0.0% | RARA |
|  | 0.00% | 1 | 2.44% |  | 0.00% | 39 | 0.6% | RRM1 |
| 4 | 5.48% |  | 0.00% |  | 0.00% | 126 | 2.0% | RRM2 |
| 2 | 2.74% | 1 | 2.44% | 1 | 0.78% | 93 | 1.5% | RRM2B |
| 2 | 2.74% |  | 0.00% |  | 0.00% | 25 | 0.4% | RXRG |
| 1 | 1.37% |  | 0.00% |  | 0.00% | 143 | 2.3% | SPARC |
|  | 0.00% |  | 0.00% |  | 0.00% | 0 | 0.0% | SPARC* |
| 3 | 4.11% |  | 0.00% | 4 | 3.13% | 96 | 1.6% | SRC |
| 2 | 2.75% |  | 0.00% | 4 | 3.13% | 145 | 2.4% | SSTR1 |
| 1 | 1.37% | 2 | 4.88% | 2 | 1.56% | 87 | 1.4% | SSTR2 |
| 4 | 5.48% | 2 | 4.88% | 6 | 4.69% | 314 | 5.1% | SSTR3 |
| 2 | 2.74% | 1 | 2.44% | 3 | 2.34% | 136 | 2.2% | SSTR4 |
| 1 | 1.37% | 1 | 2.44% |  | 0.00% | 92 | 1.5% | SSTR5 |
| 2 | 2.74% | 3 | 7.32% | 10 | 7.81% | 242 | 3.9% | TOP1 |
| 1 | 1.37% | 1 | 2.44% | 9 | 7.03% | 236 | 3.8% | TOP2A |
|  | 0.00% | 2 | 4.88% | 2 | 1.56% | 222 | 3.6% | TOP2B |
|  | 0.00% |  | 0.00% |  | 0.00% | 68 | 1.1% | TYMS |
| 1 | 1.37% | 1 | 2.44% | 3 | 2.34% | 214 | 3.5% | VDR |
|  | 0.00% | 1 | 2.44% |  | 0.00% | 17 | 0.3% | VEGF |
| 3 | 4.11% |  | 0.00% | 4 | 3.13% | 162 | 2.6% | VEGFA |
|  | 0.00% | 1 | 2.44% |  | 0.00% | 30 | 0.5% | VHL |
|  | 0.00% |  | 0.00% |  | 0.00% | 77 | 1.3% | YES1 |
|  | 0.00% |  | 0.00% |  | 0.00% | 0 | 0.0% | ZAP70 |
| 73 | 100.00% | 41 | 100.00% | 128 | 98.44% | 6,149 | | |

FIG. 28A

| | Tumor Type | | | |
|---|---|---|---|---|
| | Accessory, Sinuses, Middle & Inner Ear | | Adrenal Glands | |
| Count of Case # | 3 | | 42 | |
| IHC | Number of times biomarker flagged as target | % in tumor type | Number of times biomarker flagged as target | % in tumor type |
| Androgen Receptor | | | 2 | 1.60% |
| c - kit | 2 | 18.18% | 10 | 8.00% |
| CD25 | | 0.00% | | 0.00% |
| CD52 | | 0.00% | 2 | 1.60% |
| COX - 2 | | 0.00% | 5 | 4.00% |
| Cyclin D1 | | 0.00% | | 0.00% |
| EGFR | 2 | 18.18% | 21 | 16.80% |
| ER | | 0.00% | | 0.00% |
| Her2/Neu | | 0.00% | | 0.00% |
| HSP90 | 2 | 18.18% | 13 | 10.40% |
| MLH1 | | 0.00% | | 0.00% |
| MSH2 | | 0.00% | 2 | 1.60% |
| PDGFR | 1 | 9.09% | 6 | 4.80% |
| PR | | 0.00% | 20 | 16.00% |
| PTEN | | 0.00% | 3 | 2.40% |
| RRM1 | | 0.00% | | 0.00% |
| SPARC | 3 | 27.27% | 36 | 28.80% |
| Survivin | | 0.00% | | 0.00% |
| TOP2A | 1 | 9.09% | 5 | 4.00% |
| Grand Total | 11 | 100.00% | 125 | 100.00% |

FIG. 28B

| Appendix | | Hematopoietic Sys | | Bones & Joints | | Spinal Cord, (Excl. | |
|---|---|---|---|---|---|---|---|
| 11 | | 4 | | 25 | | 10 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| | 0 | | 0 | 1 | 1.39% | | 0.00% |
| 4 | 14.81% | | 0.00% | 7 | 9.72% | 1 | 5.00% |
| 1 | 3.70% | | 0.00% | | 0.00% | | 0.00% |
| | 0.00% | 1 | 25.00% | | 0.00% | | 0.00% |
| | 0.00% | | 0.00% | 1 | 1.39% | | 0.00% |
| | 0.00% | | 0.00% | | 0.00% | | 0.00% |
| 7 | 25.93% | | 0.00% | 10 | 13.89% | 5 | 25.00% |
| | 0.00% | | 0.00% | | 0.00% | | 0.00% |
| 2 | 7.41% | | 0.00% | 1 | 1.39% | | 0.00% |
| 5 | 18.52% | | 0.00% | 10 | 13.89% | 1 | 5.00% |
| | 0.00% | | 0.00% | 1 | 1.39% | | 0.00% |
| | 0.00% | | 0.00% | | 0.00% | | 0.00% |
| 3 | 11.11% | | 0.00% | 10 | 13.89% | 6 | 30.00% |
| | 0.00% | | 0.00% | 7 | 9.72% | 1 | 5.00% |
| | 0.00% | 1 | 25.00% | | 0.00% | | 0.00% |
| | 0.00% | | 0.00% | | 0.00% | | 0.00% |
| 4 | 14.81% | 2 | 50.00% | 18 | 25.00% | 6 | 30.00% |
| | 0.00% | | 0.00% | | 0.00% | | 0.00% |
| 1 | 3.70% | | 0.00% | 6 | 8.33% | | 0.00% |
| 27 | 100.00% | 4 | 100.00% | 72 | 100.00% | 20 | 100.00% |

FIG. 28C

| Breast | | Cerebellum | | Cervix Uteri | | Connective & Soft Tissue | |
|---|---|---|---|---|---|---|---|
| 254 | | 2 | | 16 | | 49 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 87 | 11.34% | | 0 | 1 | 2.04% | 6 | 4.51% |
| 94 | 12.26% | 1 | 25.00% | 4 | 8.16% | 8 | 6.02% |
| 4 | 0.52% | | 0.00% | 1 | 2.04% | | 0.00% |
| 2 | 0.26% | | 0.00% | | 0.00% | 1 | 0.75% |
| 10 | 1.30% | | 0.00% | 1 | 2.04% | 2 | 1.50% |
| | 0.00% | | 0.00% | | 0.00% | | 0.00% |
| 88 | 11.47% | | 0.00% | 9 | 18.37% | 26 | 19.55% |
| 53 | 6.91% | | 0.00% | | 0.00% | | 0.00% |
| 46 | 6.00% | | 0.00% | 4 | 8.16% | | 0.00% |
| 85 | 11.08% | 1 | 25.00% | 9 | 18.37% | 22 | 16.54% |
| 1 | 0.13% | | 0.00% | 1 | 2.04% | 1 | 0.75% |
| 6 | 0.78% | | 0.00% | 1 | 2.04% | 3 | 2.26% |
| 80 | 10.43% | | 0.00% | 2 | 4.08% | 17 | 12.78% |
| 31 | 4.04% | 1 | 25.00% | 1 | 2.04% | 4 | 3.01% |
| 4 | 0.52% | | 0.00% | | 0.00% | | 0.00% |
| 1 | 0.13% | | 0.00% | | 0.00% | | 0.00% |
| 103 | 13.43% | 1 | 25.00% | 6 | 12.24% | 32 | 24.06% |
| 3 | 0.39% | | 0.00% | | 0.00% | | 0.00% |
| 69 | 9.00% | | 0.00% | 9 | 18.37% | 11 | 8.27% |
| 767 | 100.00% | 4 | 100.00% | 49 | 100.00% | 133 | 100.00% |

FIG. 28D

| Corpus Uteri | | Esophagus | | Eye, Nos | | Eyeball | |
|---|---|---|---|---|---|---|---|
| 22 | | 24 | | 6 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 5 | 6.94% | 1 | 1.47% | | 0 | | 0 |
| 3 | 4.17% | 7 | 10.29% | 4 | 28.57% | 1 | 33.33% |
| | 0.00% | 2 | 2.94% | | 0.00% | | 0.00% |
| | 0.00% | | 0.00% | | 0.00% | | 0.00% |
| | 0.00% | 2 | 2.94% | | 0.00% | | 0.00% |
| | 0.00% | | 0.00% | | 0.00% | | 0.00% |
| 12 | 16.67% | 19 | 27.94% | 2 | 14.29% | | 0.00% |
| 5 | 6.94% | | 0.00% | | 0.00% | | 0.00% |
| 2 | 2.78% | 7 | 10.29% | | 0.00% | | 0.00% |
| 8 | 11.11% | 7 | 10.29% | 1 | 7.14% | 1 | 33.33% |
| | 0.00% | | 0.00% | | 0.00% | | 0.00% |
| 1 | 1.39% | | 0.00% | | 0.00% | | 0.00% |
| 12 | 16.67% | 7 | 10.29% | 2 | 14.29% | | 0.00% |
| 5 | 6.94% | | 0.00% | | 0.00% | | 0.00% |
| | 0.00% | | 0.00% | | 0.00% | | 0.00% |
| | 0.00% | | 0.00% | | 0.00% | | 0.00% |
| 14 | 19.44% | 6 | 8.82% | 3 | 21.43% | 1 | 33.33% |
| | 0.00% | | 0.00% | | 0.00% | | 0.00% |
| 5 | 6.94% | 10 | 14.71% | 2 | 14.29% | | 0.00% |
| 72 | 100.00% | 68 | 100.00% | 14 | 100.00% | 3 | 100.00% |

FIG. 28E

| Fallopian Tube | | Extrahepatic Bile Ducts | | Other Mouth | | Intrahepatic Bile Ducts | |
|---|---|---|---|---|---|---|---|
| 2 | | 12 | | 2 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
|  | 0 |  | 0 |  | 0 |  | 0 |
| 1 | 33.33% | 1 | 3.57% | 2 | 33.33% | 1 | 25.00% |
| 1 | 33.33% |  | 0.00% |  | 0.00% |  | 0.00% |
|  | 0.00% | 2 | 7.14% |  | 0.00% |  | 0.00% |
|  | 0.00% | 3 | 10.71% |  | 0.00% |  | 0.00% |
|  | 0.00% |  | 0.00% |  | 0.00% |  | 0.00% |
|  | 0.00% | 7 | 25.00% | 1 | 16.67% | 1 | 25.00% |
| 1 | 33.33% |  | 0.00% |  | 0.00% |  | 0.00% |
|  | 0.00% | 3 | 10.71% |  | 0.00% |  | 0.00% |
|  | 0.00% | 4 | 14.29% |  | 0.00% | 1 | 25.00% |
|  | 0.00% |  | 0.00% |  | 0.00% |  | 0.00% |
|  | 0.00% | 1 | 3.57% |  | 0.00% |  | 0.00% |
|  | 0.00% | 6 | 21.43% | 1 | 16.67% |  | 0.00% |
|  | 0.00% |  | 0.00% | 1 | 16.67% |  | 0.00% |
|  | 0.00% |  | 0.00% |  | 0.00% |  | 0.00% |
|  | 0.00% |  | 0.00% |  | 0.00% |  | 0.00% |
|  | 0.00% | 1 | 3.57% | 1 | 16.67% | 1 | 25.00% |
|  | 0.00% |  | 0.00% |  | 0.00% |  | 0.00% |
|  | 0.00% |  | 0.00% |  | 0.00% |  | 0.00% |
| 3 | 100.00% | 28 | 100.00% | 6 | 100.00% | 4 | 100.00% |

FIG. 28F

| Kidney | | Appendix)-Colon | | Larynx | | Lip | |
|---|---|---|---|---|---|---|---|
| 35 | | 138 | | 4 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 10 | 11.36% | 3 | 0.80% | | 0 | | 0 |
| 4 | 4.55% | 63 | 16.71% | 1 | 6.25% | | 0.00% |
| | 0.00% | 2 | 0.53% | | 0.00% | | 0.00% |
| | 0.00% | 2 | 0.53% | | 0.00% | | 0.00% |
| 3 | 3.41% | 12 | 3.18% | | 0.00% | 1 | 33.33% |
| | 0.00% | | 0.00% | | 0.00% | | 0.00% |
| 31 | 35.23% | 62 | 16.45% | 4 | 25.00% | 1 | 33.33% |
| | 0.00% | 1 | 0.27% | | 0.00% | | 0.00% |
| 1 | 1.14% | 9 | 2.39% | | 0.00% | | 0.00% |
| 10 | 11.36% | 65 | 17.24% | 2 | 12.50% | | 0.00% |
| 1 | 1.14% | 1 | 0.27% | 1 | 6.25% | | 0.00% |
| 1 | 1.14% | 4 | 1.06% | 1 | 6.25% | | 0.00% |
| 7 | 7.95% | 57 | 15.12% | 1 | 6.25% | 1 | 33.33% |
| 2 | 2.27% | 1 | 0.27% | | 0.00% | | 0.00% |
| | 0.00% | 5 | 1.33% | | 0.00% | | 0.00% |
| | 0.00% | | 0.00% | | 0.00% | | 0.00% |
| 17 | 19.32% | 32 | 8.49% | 3 | 18.75% | | 0.00% |
| | 0.00% | 1 | 0.27% | | 0.00% | | 0.00% |
| 1 | 1.14% | 57 | 15.12% | 3 | 18.75% | | 0.00% |
| 88 | 100.00% | 377 | 100.00% | 16 | 100.00% | 3 | 100.00% |

FIG. 28G

| Liver | | Lung & Bronchus | | Lymph Nodes | | (Cerebral,Spinal) | |
|---|---|---|---|---|---|---|---|
| 16 | | 121 | | 17 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 2 | 5.56% | 9 | 2.56% | | 0 | | 0 |
| 3 | 8.33% | 46 | 13.11% | | 0.00% | | 0.00% |
| | 0.00% | 5 | 1.42% | 4 | 11.43% | | 0.00% |
| 1 | 2.78% | 4 | 1.14% | 13 | 37.14% | | 0.00% |
| | 0.00% | 9 | 2.56% | | 0.00% | | 0.00% |
| | 0.00% | 1 | 0.28% | | 0.00% | | 0.00% |
| 11 | 30.56% | 81 | 23.08% | | 0.00% | 1 | 33.33% |
| | 0.00% | 3 | 0.85% | | 0.00% | | 0.00% |
| 1 | 2.78% | 12 | 3.42% | | 0.00% | | 0.00% |
| 7 | 19.44% | 41 | 11.68% | 4 | 11.43% | 1 | 33.33% |
| | 0.00% | 2 | 0.57% | | 0.00% | | 0.00% |
| | 0.00% | 5 | 1.42% | 1 | 2.86% | | 0.00% |
| 5 | 13.89% | 42 | 11.97% | 4 | 11.43% | | 0.00% |
| | 0.00% | 8 | 2.28% | | 0.00% | 1 | 33.33% |
| | 0.00% | 4 | 1.14% | | 0.00% | | 0.00% |
| | 0.00% | | 0.00% | | 0.00% | | 0.00% |
| 4 | 11.11% | 41 | 11.68% | 4 | 11.43% | | 0.00% |
| | 0.00% | | 0.00% | | 0.00% | | 0.00% |
| 2 | 5.56% | 38 | 10.83% | 5 | 14.29% | | 0.00% |
| 36 | 100.00% | 351 | 100.00% | 35 | 100.00% | 3 | 100.00% |

FIG. 28H

| Nasal Cartilage) | | (Excl. Retina, Eye, Nos) | | Oropharnyx | | Other Endocrine Glands | |
|---|---|---|---|---|---|---|---|
| 1 | | 1 | | 2 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| | 0 | | 0 | | 0 | | 0 |
| | 0.00% | 1 | 25.00% | 2 | 25.00% | 1 | 33.33% |
| | 0.00% | | 0.00% | 1 | 12.50% | | 0.00% |
| | 0.00% | | 0.00% | | 0.00% | | 0.00% |
| | 0.00% | | 0.00% | | 0.00% | | 0.00% |
| | 0.00% | | 0.00% | | 0.00% | | 0.00% |
| 1 | 100.00% | | 0.00% | 2 | 25.00% | 1 | 33.33% |
| | 0.00% | | 0.00% | | 0.00% | | 0.00% |
| | 0.00% | | 0.00% | | 0.00% | | 0.00% |
| | 0.00% | 1 | 25.00% | 1 | 12.50% | | 0.00% |
| | 0.00% | | 0.00% | | 0.00% | | 0.00% |
| | 0.00% | | 0.00% | | 0.00% | | 0.00% |
| | 0.00% | 1 | 25.00% | | 0.00% | 1 | 33.33% |
| | 0.00% | | 0.00% | | 0.00% | | 0.00% |
| | 0.00% | | 0.00% | | 0.00% | | 0.00% |
| | 0.00% | | 0.00% | | 0.00% | | 0.00% |
| | 0.00% | 1 | 25.00% | | 0.00% | | 0.00% |
| | 0.00% | | 0.00% | | 0.00% | | 0.00% |
| | 0.00% | | 0.00% | 2 | 25.00% | | 0.00% |
| 1 | 100.00% | 4 | 100.00% | 8 | 100.00% | 3 | 100.00% |

FIG. 28I

| Other Female Genital | | Ovary | | Pancreas | | Penis & Scrotum | |
|---|---|---|---|---|---|---|---|
| 3 | | 99 | | 143 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| | 0 | 21 | 6.60% | 1 | 0.30% | | 0 |
| | 0.00% | 16 | 5.03% | 23 | 6.89% | | 0.00% |
| | 0.00% | 8 | 2.52% | 7 | 2.10% | | 0.00% |
| | 0.00% | 3 | 0.94% | 3 | 0.90% | | 0.00% |
| | 0.00% | 6 | 1.89% | 20 | 5.99% | | 0.00% |
| | 0.00% | | 0.00% | | 0.00% | | 0.00% |
| 2 | 20.00% | 46 | 14.47% | 108 | 32.34% | | 0.00% |
| 1 | 10.00% | 56 | 17.61% | 2 | 0.60% | | 0.00% |
| 1 | 10.00% | 19 | 5.97% | 8 | 2.40% | | 0.00% |
| | 0.00% | 31 | 9.75% | 37 | 11.08% | | 0.00% |
| | 0.00% | | 0.00% | 1 | 0.30% | | 0.00% |
| 1 | 10.00% | 2 | 0.63% | 5 | 1.50% | | 0.00% |
| 2 | 20.00% | 28 | 8.81% | 37 | 11.08% | | 0.00% |
| | 0.00% | 24 | 7.55% | 10 | 2.99% | | 0.00% |
| | 0.00% | 2 | 0.63% | 6 | 1.80% | | 0.00% |
| | 0.00% | | 0.00% | 3 | 0.90% | | 0.00% |
| 1 | 10.00% | 29 | 9.12% | 45 | 13.47% | 1 | 50.00% |
| | 0.00% | | 0.00% | 1 | 0.30% | | 0.00% |
| 2 | 20.00% | 27 | 8.49% | 17 | 5.09% | 1 | 50.00% |
| 10 | 100.00% | 318 | 100.00% | 334 | 100.00% | 2 | 100.00% |

FIG. 28J

| Pituitary Gland | | Pleura | | Prostate Gland | | Rectum | |
|---|---|---|---|---|---|---|---|
| 1 | | 1 | | 22 | | 21 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 0 | | 0 | | 18 | 24.66% | 1 | 1.64% |
| | 0.00% | | 0.00% | 6 | 8.22% | 10 | 16.39% |
| | 0.00% | | 0.00% | 1 | 1.37% | | 0.00% |
| | 0.00% | | 0.00% | | 0.00% | 1 | 1.64% |
| | 0.00% | | 0.00% | 2 | 2.74% | 4 | 6.56% |
| | 0.00% | | 0.00% | | 0.00% | | 0.00% |
| | 0.00% | 1 | 50.00% | 13 | 17.81% | 15 | 24.59% |
| 1 | 50.00% | | 0.00% | | 0.00% | | 0.00% |
| | 0.00% | | 0.00% | 3 | 4.11% | 1 | 1.64% |
| | 0.00% | | 0.00% | 10 | 13.70% | 7 | 11.48% |
| | 0.00% | | 0.00% | | 0.00% | | 0.00% |
| | 0.00% | | 0.00% | 1 | 1.37% | | 0.00% |
| | 0.00% | | 0.00% | 7 | 9.59% | 8 | 13.11% |
| 1 | 50.00% | | 0.00% | | 0.00% | 1 | 1.64% |
| | 0.00% | | 0.00% | | 0.00% | | 0.00% |
| | 0.00% | | 0.00% | | 0.00% | | 0.00% |
| | 0.00% | 1 | 50.00% | 10 | 13.70% | 6 | 9.84% |
| | 0.00% | | 0.00% | | 0.00% | | 0.00% |
| | 0.00% | | 0.00% | 2 | 2.74% | 7 | 11.48% |
| 2 | 100.00% | 2 | 100.00% | 73 | 100.00% | 61 | 100.00% |

FIG. 28K

| Renal Pelvis, Ureter | | Peritoneum | | Salivary Gland | | Skin | |
|---|---|---|---|---|---|---|---|
| 3 | | 18 | | 15 | | 58 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 1 | 14.29% | | 0 | 2 | 4.08% | 3 | 2.31% |
| | 0.00% | 4 | 10.53% | 8 | 16.33% | 25 | 19.23% |
| | 0.00% | 1 | 2.63% | 2 | 4.08% | | 0.00% |
| | 0.00% | 1 | 2.63% | 1 | 2.04% | | 0.00% |
| | 0.00% | | 0.00% | 1 | 2.04% | 1 | 0.77% |
| | 0.00% | | 0.00% | | 0.00% | | 0.00% |
| 3 | 42.86% | 6 | 15.79% | 8 | 16.33% | 11 | 8.46% |
| | 0.00% | 2 | 5.26% | | 0.00% | | 0.00% |
| 1 | 14.29% | | 0.00% | 1 | 2.04% | 2 | 1.54% |
| 1 | 14.29% | 5 | 13.16% | 5 | 10.20% | 21 | 16.15% |
| | 0.00% | | 0.00% | | 0.00% | | 0.00% |
| | 0.00% | | 0.00% | | 0.00% | 1 | 0.77% |
| 1 | 14.29% | 7 | 18.42% | 9 | 18.37% | 15 | 11.54% |
| | 0.00% | 2 | 5.26% | 1 | 2.04% | 2 | 1.54% |
| | 0.00% | 1 | 2.63% | 1 | 2.04% | | 0.00% |
| | 0.00% | | 0.00% | | 0.00% | | 0.00% |
| | 0.00% | 7 | 18.42% | 8 | 16.33% | 41 | 31.54% |
| | 0.00% | | 0.00% | | 0.00% | | 0.00% |
| | 0.00% | 2 | 5.26% | 2 | 4.08% | 8 | 6.15% |
| 7 | 100.00% | 38 | 100.00% | 49 | 100.00% | 130 | 100.00% |

FIG. 28L

| Small Intestine | | Stomach | | Testis | | Thymus | |
|---|---|---|---|---|---|---|---|
| 5 | | 23 | | 4 | | 10 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
|  | 0 | 2 | 3.23% |  | 0 | 3 | 0.1 |
| 2 | 15.38% | 7 | 11.29% |  | 0.00% | 7 | 23.33% |
|  | 0.00% |  | 0.00% |  | 0.00% |  | 0.00% |
|  | 0.00% |  | 0.00% |  | 0.00% |  | 0.00% |
|  | 0.00% | 3 | 4.84% |  | 0.00% |  | 0.00% |
|  | 0.00% |  | 0.00% |  | 0.00% |  | 0.00% |
| 3 | 23.08% | 16 | 25.81% | 3 | 27.27% | 8 | 26.67% |
|  | 0.00% | 2 | 3.23% | 1 | 9.09% |  | 0.00% |
|  | 0.00% | 1 | 1.61% | 1 | 9.09% |  | 0.00% |
| 1 | 7.69% | 10 | 16.13% | 1 | 9.09% | 3 | 10.00% |
|  | 0.00% |  | 0.00% |  | 0.00% |  | 0.00% |
|  | 0.00% | 1 | 1.61% |  | 0.00% |  | 0.00% |
| 4 | 30.77% | 6 | 9.68% | 2 | 18.18% | 2 | 6.67% |
|  | 0.00% | 4 | 6.45% | 1 | 9.09% | 3 | 10.00% |
|  | 0.00% |  | 0.00% |  | 0.00% |  | 0.00% |
|  | 0.00% |  | 0.00% |  | 0.00% |  | 0.00% |
| 1 | 7.69% | 4 | 6.45% | 2 | 18.18% | 4 | 13.33% |
|  | 0.00% |  | 0.00% |  | 0.00% |  | 0.00% |
| 2 | 15.38% | 6 | 9.68% |  | 0.00% |  | 0.00% |
| 13 | 100.00% | 62 | 100.00% | 11 | 100.00% | 30 | 100.00% |

FIG. 28M

| Thyroid Gland | | Tongue | | Unknown | | | |
|---|---|---|---|---|---|---|---|
| 10 | | 4 | | 64 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
|  | 0 |  | 0 | 2 | 1.25% |  | 0 |
|  | 0.00% | 2 | 18.18% | 13 | 8.13% | 1 | 33.33% |
|  | 0.00% | 1 | 9.09% | 1 | 0.63% |  | 0.00% |
|  | 0.00% |  | 0.00% | 2 | 1.25% |  | 0.00% |
| 2 | 9.52% |  | 0.00% | 3 | 1.88% |  | 0.00% |
|  | 0.00% |  | 0.00% |  | 0.00% |  | 0.00% |
| 6 | 28.57% | 4 | 36.36% | 35 | 21.88% | 1 | 33.33% |
| 1 | 4.76% |  | 0.00% | 2 | 1.25% |  | 0.00% |
| 2 | 9.52% |  | 0.00% | 5 | 3.13% |  | 0.00% |
| 3 | 14.29% |  | 0.00% | 19 | 11.88% | 1 | 33.33% |
|  | 0.00% |  | 0.00% | 2 | 1.25% |  | 0.00% |
|  | 0.00% |  | 0.00% | 3 | 1.88% |  | 0.00% |
| 2 | 9.52% |  | 0.00% | 17 | 10.63% |  | 0.00% |
| 2 | 9.52% |  | 0.00% | 10 | 6.25% |  | 0.00% |
|  | 0.00% |  | 0.00% | 1 | 0.63% |  | 0.00% |
|  | 0.00% |  | 0.00% |  | 0.00% |  | 0.00% |
| 3 | 14.29% | 3 | 27.27% | 31 | 19.38% |  | 0.00% |
|  | 0.00% |  | 0.00% | 1 | 0.63% |  | 0.00% |
|  | 0.00% | 1 | 9.09% | 13 | 8.13% |  | 0.00% |
| 21 | 100.00% | 11 | 100.00% | 160 | 100.00% | 3 | 100.00% |

FIG. 28N

| Urinary Bladder | | Uterus, Nos | | Vagina & Labia | | Vulva, Nos | |
|---|---|---|---|---|---|---|---|
| 19 | | 14 | | 3 | | 1 | |
| Number of times biomarker flagged as target | % in tumor type | Number of times biomarker flagged as target | % in tumor type | Number of times biomarker flagged as target | % in tumor type | Number of times biomarker flagged as target | % in tumor type |
| 3 | 4.62% | | 0 | | 0 | | 0 |
| 5 | 7.69% | 1 | 2.22% | 1 | 10.00% | 1 | 25.00% |
| | 0.00% | 1 | 2.22% | | 0.00% | | 0.00% |
| | 0.00% | | 0.00% | | 0.00% | | 0.00% |
| | 0.00% | | 0.00% | | 0.00% | | 0.00% |
| | 0.00% | | 0.00% | | 0.00% | | 0.00% |
| 16 | 24.62% | 6 | 13.33% | 1 | 10.00% | | 0.00% |
| | 0.00% | 4 | 8.89% | | 0.00% | | 0.00% |
| 8 | 12.31% | 1 | 2.22% | | 0.00% | | 0.00% |
| 9 | 13.85% | 6 | 13.33% | 1 | 10.00% | 1 | 25.00% |
| 1 | 1.54% | | 0.00% | | 0.00% | | 0.00% |
| 1 | 1.54% | | 0.00% | | 0.00% | | 0.00% |
| 5 | 7.69% | 6 | 13.33% | 2 | 20.00% | 1 | 25.00% |
| | 0.00% | 1 | 2.22% | 2 | 20.00% | | 0.00% |
| 1 | 1.54% | 2 | 4.44% | 1 | 10.00% | | 0.00% |
| | 0.00% | | 0.00% | | 0.00% | | 0.00% |
| 8 | 12.31% | 8 | 17.78% | 2 | 20.00% | | 0.00% |
| | 0.00% | 1 | 2.22% | | 0.00% | | 0.00% |
| 8 | 12.31% | 8 | 17.78% | | 0.00% | 1 | 25.00% |
| | | | | | | | |
| 65 | 100.00% | 45 | 100.00% | 10 | 100.00% | 4 | 100.00% |

FIG. 28O

| (blank) | | Grand Total | | |
|---|---|---|---|---|
| 16 | | 1392 | | |
| Number of times biomarker flagged as target | % in tumor type | Number of times biomarker flagged as target | % in tumor type | IHC |
| 3 | 5.45% | 187 | 4.82% | Androgen Receptor |
| 5 | 9.09% | 411 | 10.60% | c - kit |
| | 0.00% | 45 | 1.16% | CD25 |
| 1 | 1.82% | 40 | 1.03% | CD52 |
| | 0.00% | 91 | 2.35% | COX - 2 |
| | 0.00% | 1 | 0.03% | Cyclin D1 |
| 7 | 12.73% | 731 | 18.85% | EGFR |
| 4 | 7.27% | 139 | 3.58% | ER |
| 1 | 1.82% | 143 | 3.69% | Her2/Neu |
| 8 | 14.55% | 483 | 12.45% | HSP90 |
| | 0.00% | 13 | 0.34% | MLH1 |
| | 0.00% | 41 | 1.06% | MSH2 |
| 4 | 7.27% | 439 | 11.32% | PDGFR |
| 3 | 5.45% | 153 | 3.95% | PR |
| 1 | 1.82% | 33 | 0.85% | PTEN |
| | 0.00% | 4 | 0.10% | RRM1 |
| 10 | 18.18% | 569 | 14.67% | SPARC |
| | 0.00% | 7 | 0.18% | Survivin |
| 8 | 14.55% | 348 | 8.97% | TOP2A |
| 55 | 100.00% | 3878 | 100.00% | Grand Total |

FIG. 29

Biomarkers Tagged as Target in Order of Frequency

| Number of times biomarker flagged as target | % in tumor type | IHC |
|---|---|---|
| 3878 | 100.00% | Grand Total |
| 731 | 18.85% | EGFR |
| 569 | 14.67% | SPARC |
| 483 | 12.45% | HSP90 |
| 439 | 11.32% | PDGFR |
| 411 | 10.60% | c - kit |
| 348 | 8.97% | TOP2A |
| 187 | 4.82% | Androgen Receptor |
| 153 | 3.95% | PR |
| 143 | 3.69% | Her2/Neu |
| 139 | 3.58% | ER |
| 91 | 2.35% | COX - 2 |
| 45 | 1.16% | CD25 |
| 41 | 1.06% | MSH2 |
| 40 | 1.03% | CD52 |
| 33 | 0.85% | PTEN |
| 13 | 0.34% | MLH1 |
| 7 | 0.18% | Survivin |
| 4 | 0.10% | RRM1 |
| 1 | 0.03% | Cyclin D1 |

FIG. 30A

| | Tumor Type | | | | | |
|---|---|---|---|---|---|---|
| | Accessory, Sinuses, Middle & Inner Ear | | Adrenal Glands | | Anal Canal & Anus | |
| Count of Case # | 1 | | 28 | | 5 | |
| Gene | Number of times biomarker flagged as | % in tumor type | Number of times biomarker flagged as | % in tumor type | Number of times biomarker flagged as | % in tumor type |
| ADA | | 0.00% | 9 | 4.97% | 2 | 4.26% |
| AR | | 0.00% | 1 | 0.55% | | 0.00% |
| ASNS | | 0.00% | 6 | 3.31% | 1 | 2.13% |
| ASNS | | 0.00% | | 0.00% | | 0.00% |
| BRCA1 | | 0.00% | | 0.00% | | 0.00% |
| BRCA2 | | 0.00% | | 0.00% | | 0.00% |
| CD52 | | 0.00% | 1 | 0.55% | | 0.00% |
| COW52 | | 0.00% | | 0.00% | | 0.00% |
| CES2 | | 0.00% | 4 | 2.21% | 2 | 4.26% |
| DCK | | 0.00% | 8 | 4.42% | | 0.00% |
| DHFR | | 0.00% | | 0.00% | | 0.00% |
| DNMT1 | | 0.00% | 8 | 4.42% | 1 | 2.13% |
| DNMT3A | | 0.00% | 8 | 4.42% | 3 | 6.38% |
| DNMT3B | 1 | 7.14% | 13 | 7.18% | 2 | 4.26% |
| EGFR | | 0.00% | 7 | 3.87% | 3 | 6.38% |
| EPHA2 | | 0.00% | 1 | 0.55% | | 0.00% |
| ERBB2 | | 0.00% | | 0.00% | | 0.00% |
| ERCC3 | | 0.00% | | 0.00% | | 0.00% |
| ESR1 | | 0.00% | | 0.00% | | 0.00% |
| FLT1 | | 0.00% | 1 | 0.55% | 1 | 2.13% |
| GART | 1 | 7.14% | 1 | 0.55% | 1 | 2.13% |
| GNRH1 | | 0.00% | | 0.00% | | 0.00% |
| HIF1A | 1 | 7.14% | 9 | 4.97% | 1 | 2.13% |
| HSP90AA1 | | 0.00% | | 0.00% | | 0.00% |
| HSPCA | | 0.00% | | 0.00% | | 0.00% |
| IL2RA | | 0.00% | | 0.00% | | 0.00% |
| KDR | | 0.00% | 1 | 0.55% | | 0.00% |
| KIT | | 0.00% | 5 | 2.76% | | 0.00% |
| LCK | | 0.00% | | 0.00% | | 0.00% |
| MGMT | 1 | 7.14% | 5 | 2.76% | 2 | 4.26% |
| MLH1 | | 0.00% | | 0.00% | | 0.00% |
| MSH2 | | 0.00% | | 0.00% | | 0.00% |
| NFKB1 | | 0.00% | 4 | 2.21% | 1 | 2.13% |
| NFKB2 | 1 | 7.14% | 1 | 0.55% | 3 | 6.38% |
| NFKBIA | 1 | 7.14% | 5 | 2.76% | 3 | 6.38% |
| PDGFC | | 0.00% | 2 | 1.10% | | 0.00% |
| PDGFRA | 1 | 7.14% | | 0.00% | | 0.00% |
| PDGFRB | 1 | 7.14% | 5 | 2.76% | 2 | 4.26% |
| PGR | | 0.00% | 5 | 2.76% | | 0.00% |
| PTEN | | 0.00% | | 0.00% | | 0.00% |
| PTGS2 | | 0.00% | | 0.00% | 1 | 2.13% |
| RARA | | 0.00% | | 0.00% | | 0.00% |
| RRM1 | | 0.00% | | 0.00% | | 0.00% |
| RRM2 | | 0.00% | | 0.00% | | 0.00% |
| RRM2B | | 0.00% | 3 | 1.66% | | 0.00% |
| RXRG | | 0.00% | | 0.00% | | 0.00% |
| SPARC | 1 | 7.14% | 23 | 12.71% | 1 | 2.13% |
| SRC | | 0.00% | 1 | 0.55% | 2 | 4.26% |
| SSTR1 | | 0.00% | 2 | 1.10% | 2 | 4.26% |
| SSTR2 | | 0.00% | | 0.00% | | 0.00% |
| SSTR3 | 1 | 7.14% | 3 | 1.66% | 3 | 6.38% |
| SSTR4 | | 0.00% | 1 | 0.55% | 2 | 4.26% |
| SSTR5 | | 0.00% | 4 | 2.21% | | 0.00% |
| TOP1 | 1 | 7.14% | 7 | 3.87% | | 0.00% |
| TOP2A | 1 | 7.14% | 9 | 4.97% | 3 | 6.38% |
| TOP2B | 1 | 7.14% | 4 | 2.21% | 1 | 2.13% |
| TYMS | | 0.00% | | 0.00% | | 0.00% |
| VDR | 1 | 7.14% | 1 | 0.55% | | 0.00% |
| VEGF | | 0.00% | | 0.00% | 2 | 4.26% |
| VEGFA | | 0.00% | 4 | 2.21% | 2 | 4.26% |
| VHL | | 0.00% | 6 | 3.31% | | 0.00% |
| YES1 | | 0.00% | 3 | 1.66% | | 0.00% |
| ZAP70 | | 0.00% | | 0.00% | | 0.00% |
| Grand Total | 14 | 100.00% | 181 | 100.00% | 47 | 100.00% |

FIG. 30B

| Appendix | | Blood, Bone Marrow, & Hematopoietic Sys | | Bones & Joints | | Brain, & Cranial Nervos, & Spinal Cord, (Excl. Ventricle, Cerebellum) | |
|---|---|---|---|---|---|---|---|
| 8 | | 1 | | 19 | | 5 | |
| Number of times biomarker flagged as | % in tumor type | Number of times biomarker flagged as | % in tumor type | Number of times biomarker flagged as | % in tumor type | Number of times biomarker flagged as | % in tumor type |
| 3 | 2.94% | 1 | 12.50% | 11 | 4.78% | 3 | 4.41% |
|  | 0.00% |  | 0.00% |  | 0.00% |  | 0.00% |
| 1 | 0.98% |  | 0.00% | 6 | 2.61% | 3 | 4.41% |
|  | 0.00% |  | 0.00% |  | 0.00% |  | 0.00% |
| 6 | 5.88% |  | 0.00% | 3 | 1.30% |  | 0.00% |
| 3 | 2.94% |  | 0.00% | 1 | 0.43% |  | 0.00% |
|  | 0.00% |  | 0.00% |  | 0.00% |  | 0.00% |
|  | 0.00% |  | 0.00% |  | 0.00% | 1 | 1.47% |
| 2 | 1.96% | 1 | 12.50% | 3 | 1.30% | 2 | 2.94% |
|  | 0.00% |  | 0.00% | 5 | 2.17% | 1 | 1.47% |
| 1 | 0.98% |  | 0.00% | 1 | 0.43% |  | 0.00% |
|  | 0.00% |  | 0.00% | 6 | 2.61% | 2 | 2.94% |
|  | 0.00% |  | 0.00% | 10 | 4.35% | 2 | 2.94% |
|  | 0.00% |  | 0.00% | 10 | 4.35% | 2 | 2.94% |
| 2 | 1.96% |  | 0.00% | 2 | 0.87% | 2 | 2.94% |
| 3 | 2.94% |  | 0.00% | 1 | 0.43% | 1 | 1.47% |
|  | 0.00% |  | 0.00% | 1 | 0.43% |  | 0.00% |
|  | 0.00% |  | 0.00% |  | 0.00% |  | 0.00% |
|  | 0.00% |  | 0.00% |  | 0.00% |  | 0.00% |
| 2 | 1.96% |  | 0.00% | 4 | 1.74% | 2 | 2.94% |
| 3 | 2.94% | 1 | 12.50% | 8 | 3.48% | 3 | 4.41% |
|  | 0.00% |  | 0.00% |  | 0.00% |  | 0.00% |
| 7 | 6.86% |  | 0.00% | 7 | 3.04% | 2 | 2.94% |
| 1 | 0.98% |  | 0.00% | 3 | 1.30% |  | 0.00% |
|  | 0.00% |  | 0.00% | 1 | 0.43% |  | 0.00% |
|  | 0.00% |  | 0.00% |  | 0.00% |  | 0.00% |
| 1 | 0.98% |  | 0.00% | 1 | 0.43% |  | 0.00% |
|  | 0.00% | 1 | 12.50% | 5 | 2.17% | 2 | 2.94% |
|  | 0.00% |  | 0.00% |  | 0.00% |  | 0.00% |
| 2 | 1.96% |  | 0.00% | 9 | 3.91% | 1 | 1.47% |
|  | 0.00% |  | 0.00% |  | 0.00% |  | 0.00% |
|  | 0.00% |  | 0.00% |  | 0.00% |  | 0.00% |
| 1 | 0.98% |  | 0.00% | 4 | 1.74% | 2 | 2.94% |
| 4 | 3.92% |  | 0.00% | 8 | 3.48% | 4 | 5.88% |
| 2 | 1.96% | 1 | 12.50% | 14 | 6.09% | 3 | 4.41% |
| 2 | 1.96% |  | 0.00% | 1 | 0.43% |  | 0.00% |
| 2 | 1.96% |  | 0.00% | 3 | 1.30% | 3 | 4.41% |
| 3 | 2.94% |  | 0.00% | 7 | 3.04% | 3 | 4.41% |
| 7 | 6.86% | 1 | 12.50% | 2 | 0.87% |  | 0.00% |
|  | 0.00% |  | 0.00% |  | 0.00% |  | 0.00% |
|  | 0.00% |  | 0.00% | 6 | 2.61% | 1 | 1.47% |
| 2 | 1.96% | 1 | 12.50% |  | 0.00% |  | 0.00% |
| 3 | 2.94% |  | 0.00% | 1 | 0.43% |  | 0.00% |
| 5 | 4.90% |  | 0.00% | 1 | 0.43% |  | 0.00% |
| 2 | 1.96% |  | 0.00% | 3 | 1.30% | 1 | 1.47% |
|  | 0.00% |  | 0.00% |  | 0.00% |  | 0.00% |
| 3 | 2.94% | 1 | 12.50% | 10 | 4.35% | 3 | 4.41% |
| 2 | 1.96% |  | 0.00% | 1 | 0.43% | 1 | 1.47% |
| 2 | 1.96% |  | 0.00% | 3 | 1.30% |  | 0.00% |
|  | 0.00% |  | 0.00% | 5 | 2.17% | 1 | 1.47% |
| 4 | 3.92% |  | 0.00% | 7 | 3.04% | 1 | 1.47% |
| 1 | 0.98% |  | 0.00% | 4 | 1.74% |  | 0.00% |
|  | 0.00% |  | 0.00% | 4 | 1.74% | 1 | 1.47% |
| 2 | 1.96% |  | 0.00% | 7 | 3.04% | 3 | 4.41% |
| 4 | 3.92% |  | 0.00% | 8 | 3.48% | 2 | 2.94% |
| 2 | 1.96% |  | 0.00% | 12 | 5.22% | 3 | 4.41% |
| 4 | 3.92% |  | 0.00% | 2 | 0.87% |  | 0.00% |
| 3 | 2.94% |  | 0.00% | 7 | 3.04% | 2 | 2.94% |
|  | 0.00% |  | 0.00% | 3 | 1.30% | 1 | 1.47% |
| 3 | 2.94% |  | 0.00% | 5 | 2.17% | 3 | 4.41% |
| 2 | 1.96% |  | 0.00% | 2 | 0.87% |  | 0.00% |
|  | 0.00% |  | 0.00% | 2 | 0.87% | 1 | 1.47% |
|  | 0.00% |  | 0.00% |  | 0.00% |  | 0.00% |
| 102 | 100.00% | 8 | 100.00% | 230 | 100.00% | 68 | 100.00% |

FIG. 30C

| Breast | | Cerebellum | | Cervix Uteri | | Connective & Soft Tissue | |
|---|---|---|---|---|---|---|---|
| 168 | | 1 | | 11 | | 34 | |
| Number of times biomarker flagged as | % in tumor type | Number of times biomarker flagged as | % in tumor type | Number of times biomarker flagged as | % in tumor type | Number of times biomarker flagged as | % in tumor type |
| 78 | 4.19% | 1 | 7.14% | 4 | 4.12% | 15 | 4.34% |
| 41 | 2.20% | | 0.00% | | 0.00% | | 0.00% |
| 10 | 0.54% | | 0.00% | | 0.00% | 6 | 1.73% |
| | 0.00% | | 0.00% | | 0.00% | | 0.00% |
| 9 | 0.48% | | 0.00% | | 0.00% | 6 | 1.73% |
| 64 | 3.44% | | 0.00% | | 0.00% | 3 | 0.87% |
| 1 | 0.05% | | 0.00% | | 0.00% | | 0.00% |
| 4 | 0.21% | | 0.00% | | 0.00% | 2 | 0.58% |
| 74 | 3.97% | | 0.00% | 3 | 3.09% | 10 | 2.89% |
| 36 | 1.93% | 1 | 7.14% | 4 | 4.12% | 7 | 2.02% |
| 20 | 1.07% | | 0.00% | | 0.00% | 2 | 0.58% |
| 25 | 1.34% | | 0.00% | 3 | 3.09% | 14 | 4.05% |
| 25 | 1.34% | 1 | 7.14% | 5 | 5.15% | 9 | 2.60% |
| 37 | 1.99% | 1 | 7.14% | 7 | 7.22% | 19 | 5.49% |
| 11 | 0.59% | | 0.00% | | 0.00% | 3 | 0.87% |
| | 0.00% | | 0.00% | | 0.00% | 2 | 0.58% |
| 27 | 1.45% | | 0.00% | 1 | 1.03% | | 0.00% |
| | 0.00% | | 0.00% | | 0.00% | | 0.00% |
| 55 | 2.95% | | 0.00% | | 0.00% | | 0.00% |
| 19 | 1.02% | | 0.00% | | 0.00% | 3 | 0.87% |
| 46 | 2.47% | | 0.00% | 8 | 8.25% | 17 | 4.91% |
| | 0.00% | | 0.00% | | 0.00% | | 0.00% |
| 37 | 1.99% | | 0.00% | 1 | 1.03% | 17 | 4.91% |
| 8 | 0.43% | | 0.00% | 3 | 3.09% | 1 | 0.29% |
| 25 | 1.34% | | 0.00% | 1 | 1.03% | 3 | 0.87% |
| | 0.00% | | 0.00% | | 0.00% | | 0.00% |
| 12 | 0.64% | | 0.00% | | 0.00% | | 0.00% |
| 30 | 1.61% | 1 | 7.14% | | 0.00% | 2 | 0.58% |
| 1 | 0.05% | | 0.00% | | 0.00% | | 0.00% |
| 81 | 4.35% | | 0.00% | 2 | 2.06% | 17 | 4.91% |
| 2 | 0.11% | | 0.00% | | 0.00% | | 0.00% |
| 35 | 1.88% | | 0.00% | | 0.00% | 1 | 0.29% |
| 49 | 2.63% | | 0.00% | 4 | 4.12% | 9 | 2.60% |
| 56 | 3.01% | 1 | 7.14% | 1 | 1.03% | 10 | 2.89% |
| 90 | 4.83% | 1 | 7.14% | 4 | 4.12% | 13 | 3.76% |
| 3 | 0.16% | | 0.00% | | 0.00% | 2 | 0.58% |
| 9 | 0.48% | | 0.00% | | 0.00% | 3 | 0.87% |
| 51 | 2.74% | | 0.00% | | 0.00% | 9 | 2.60% |
| 12 | 0.64% | | 0.00% | | 0.00% | | 0.00% |
| 2 | 0.11% | | 0.00% | | 0.00% | 1 | 0.29% |
| 14 | 0.75% | | 0.00% | | 0.00% | 6 | 1.73% |
| 1 | 0.05% | | 0.00% | | 0.00% | | 0.00% |
| 7 | 0.38% | | 0.00% | | 0.00% | 4 | 1.16% |
| 57 | 3.06% | | 0.00% | | 0.00% | 2 | 0.58% |
| 17 | 0.91% | 1 | 7.14% | | 0.00% | 5 | 1.45% |
| 3 | 0.16% | | 0.00% | | 0.00% | 2 | 0.58% |
| 38 | 2.04% | | 0.00% | 2 | 2.06% | 16 | 4.62% |
| 47 | 2.52% | 1 | 7.14% | 1 | 1.03% | 5 | 1.45% |
| 47 | 2.52% | 1 | 7.14% | 3 | 3.09% | 5 | 1.45% |
| 17 | 0.91% | | 0.00% | 1 | 1.03% | 5 | 1.45% |
| 94 | 5.05% | 1 | 7.14% | 7 | 7.22% | 13 | 3.76% |
| 38 | 2.04% | 1 | 7.14% | 2 | 2.06% | 4 | 1.16% |
| 25 | 1.34% | 1 | 7.14% | | 0.00% | 4 | 1.16% |
| 58 | 3.11% | | 0.00% | 6 | 6.19% | 18 | 5.20% |
| 71 | 3.81% | | 0.00% | 10 | 10.31% | 15 | 4.34% |
| 56 | 3.01% | 1 | 7.14% | 1 | 1.03% | 12 | 3.47% |
| 38 | 2.04% | | 0.00% | | 0.00% | 1 | 0.29% |
| 86 | 4.62% | | 0.00% | 6 | 6.19% | 11 | 3.18% |
| 28 | 1.50% | | 0.00% | 2 | 2.06% | 2 | 0.58% |
| 19 | 1.02% | | 0.00% | 3 | 3.09% | 4 | 1.16% |
| 3 | 0.16% | | 0.00% | | 0.00% | 3 | 0.87% |
| 13 | 0.70% | | 0.00% | 2 | 2.06% | 3 | 0.87% |
| 1 | 0.05% | | 0.00% | | 0.00% | | 0.00% |
| 1863 | 100.00% | 14 | 100.00% | 97 | 100.00% | 346 | 100.00% |

FIG. 30D

| Corpus Uteri | | Esophagus | | Eye, Nos | | Eyeball | |
|---|---|---|---|---|---|---|---|
| 13 | | 15 | | 4 | | 1 | |
| Number of times biomarker flagged as | % in tumor type | Number of times biomarker flagged as | % in tumor type | Number of times biomarker flagged as | % in tumor type | Number of times biomarker flagged as | % in tumor type |
| 11 | 7.80% | 7 | 4.14% | 2 | 5.00% | 1 | 6.67% |
|  | 0.00% | 2 | 1.18% |  | 0.00% |  | 0.00% |
|  | 0.00% | 2 | 1.18% |  | 0.00% |  | 0.00% |
|  | 0.00% |  | 0.00% |  | 0.00% |  | 0.00% |
|  | 0.00% |  | 0.00% | 1 | 2.50% | 1 | 6.67% |
|  | 0.00% |  | 0.00% |  | 0.00% | 1 | 6.67% |
|  | 0.00% |  | 0.00% |  | 0.00% |  | 0.00% |
|  | 0.00% |  | 0.00% |  | 0.00% |  | 0.00% |
|  | 0.00% | 2 | 1.18% | 1 | 2.50% |  | 0.00% |
| 4 | 2.84% | 6 | 3.55% |  | 0.00% |  | 0.00% |
|  | 0.00% |  | 0.00% | 1 | 2.50% |  | 0.00% |
| 6 | 4.26% | 1 | 0.59% |  | 0.00% |  | 0.00% |
| 6 | 4.26% | 6 | 3.55% | 1 | 2.50% |  | 0.00% |
| 8 | 5.67% | 11 | 6.51% | 2 | 5.00% |  | 0.00% |
|  | 0.00% | 8 | 4.73% |  | 0.00% |  | 0.00% |
|  | 0.00% | 1 | 0.59% |  | 0.00% |  | 0.00% |
| 1 | 0.71% | 3 | 1.78% |  | 0.00% |  | 0.00% |
|  | 0.00% |  | 0.00% |  | 0.00% |  | 0.00% |
| 2 | 1.42% |  | 0.00% |  | 0.00% |  | 0.00% |
|  | 0.00% | 2 | 1.18% |  | 0.00% | 1 | 6.67% |
| 9 | 6.38% | 4 | 2.37% | 1 | 2.50% |  | 0.00% |
| 1 | 0.71% |  | 0.00% |  | 0.00% |  | 0.00% |
| 9 | 6.38% | 9 | 5.33% |  | 0.00% |  | 0.00% |
| 4 | 2.84% | 4 | 2.37% |  | 0.00% | 1 | 6.67% |
| 4 | 2.84% | 2 | 1.18% | 1 | 2.50% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
| 7 | 4.96% | 11 | 6.51% | 2 | 5.00% | 1 | 6.67% |
| 1 | 0.71% |  | 0.00% |  | 0.00% |  | 0.00% |
|  | 0.00% |  | 0.00% |  | 0.00% |  | 0.00% |
| 4 | 2.84% | 3 | 1.78% | 1 | 2.50% | 1 | 6.67% |
| 6 | 4.26% | 5 | 2.96% | 1 | 2.50% |  | 0.00% |
| 9 | 6.38% | 6 | 3.55% | 3 | 7.50% | 1 | 6.67% |
| 1 | 0.71% | 1 | 0.59% | 1 | 2.50% |  | 0.00% |
|  | 0.00% |  | 0.00% |  | 0.00% |  | 0.00% |
|  | 0.00% | 2 | 1.18% | 2 | 5.00% |  | 0.00% |
|  | 0.00% |  | 0.00% |  | 0.00% |  | 0.00% |
|  | 0.00% | 1 | 0.59% |  | 0.00% |  | 0.00% |
|  | 0.00% | 5 | 2.96% |  | 0.00% |  | 0.00% |
|  | 0.00% |  | 0.00% |  | 0.00% |  | 0.00% |
|  | 0.00% | 3 | 1.78% | 2 | 5.00% | 1 | 6.67% |
|  | 0.00% |  | 0.00% | 2 | 5.00% | 1 | 6.67% |
|  | 0.00% | 3 | 1.78% | 1 | 2.50% |  | 0.00% |
|  | 0.00% |  | 0.00% |  | 0.00% |  | 0.00% |
| 2 | 1.42% | 4 | 2.37% | 3 | 7.50% |  | 0.00% |
| 4 | 2.84% | 7 | 4.14% | 3 | 7.50% | 1 | 6.67% |
| 1 | 0.71% | 1 | 0.59% |  | 0.00% |  | 0.00% |
| 2 | 1.42% | 1 | 0.59% | 2 | 5.00% |  | 0.00% |
| 4 | 2.84% | 10 | 5.92% | 1 | 2.50% |  | 0.00% |
| 1 | 0.71% | 1 | 0.59% |  | 0.00% |  | 0.00% |
|  | 0.00% |  | 0.00% |  | 0.00% |  | 0.00% |
| 7 | 4.96% | 9 | 5.33% |  | 0.00% |  | 0.00% |
| 8 | 5.67% | 9 | 5.33% | 3 | 7.50% |  | 0.00% |
| 5 | 3.55% | 5 | 2.96% |  | 0.00% | 1 | 6.67% |
|  | 0.00% | 1 | 0.59% | 2 | 5.00% | 1 | 6.67% |
| 9 | 6.38% | 2 | 1.18% |  | 0.00% |  | 0.00% |
| 1 | 0.71% | 2 | 1.18% |  | 0.00% |  | 0.00% |
| 2 | 1.42% | 4 | 2.37% | 1 | 2.50% | 1 | 6.67% |
| 1 | 0.71% |  | 0.00% |  | 0.00% |  | 0.00% |
| 1 | 0.71% | 3 | 1.78% |  | 0.00% | 1 | 6.67% |
|  | 0.00% |  | 0.00% |  | 0.00% |  | 0.00% |
| 141 | 100.00% | 169 | 100.00% | 40 | 100.00% | 15 | 100.00% |

FIG. 30E

| Fallopian Tube | | Gallbladder & Extrahepatic Bile Ducts | | Gum, Floor Of Mouth, & Other Mouth | | Intrahepatic Bile Ducts | |
|---|---|---|---|---|---|---|---|
| 2 | | 3 | | 1 | | 1 | |
| Number of times biomarker flagged as | % in tumor type | Number of times biomarker flagged as | % in tumor type | Number of times biomarker flagged as | % in tumor type | Number of times biomarker flagged as | % in tumor type |
| 1 | 9.09% | 1 | 6.25% |  | 0.00% | 1 | 6.67% |
|  | 0.00% |  | 0.00% |  | 0.00% |  | 0.00% |
|  | 0.00% | 1 | 6.25% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% | 1 | 6.67% |
|  | 0.00% |  | 0.00% |  | 0.00% |  | 0.00% |
|  | 0.00% |  | 0.00% |  | 0.00% |  | 0.00% |
|  | 0.00% | 3 | 18.75% |  | 0.00% |  | 0.00% |
|  | 0.00% |  | 0.00% | 1 | 7.14% |  | 0.00% |
|  | 0.00% |  | 0.00% |  | 0.00% |  | 0.00% |
| 1 | 9.09% |  | 0.00% |  | 0.00% |  | 0.00% |
|  | 0.00% |  | 0.00% | 1 | 7.14% |  | 0.00% |
|  | 0.00% |  | 0.00% | 1 | 7.14% |  | 0.00% |
|  | 0.00% | 1 | 6.25% |  | 0.00% | 1 | 6.67% |
|  | 0.00% | 1 | 6.25% |  | 0.00% | 1 | 6.67% |
|  | 0.00% |  | 0.00% |  | 0.00% |  | 0.00% |
|  | 0.00% |  | 0.00% |  | 0.00% |  | 0.00% |
| 1 | 9.09% |  | 0.00% |  | 0.00% |  | 0.00% |
|  | 0.00% |  | 0.00% |  | 0.00% |  | 0.00% |
| 1 | 9.09% | 1 | 6.25% | 1 | 7.14% |  | 0.00% |
|  | 0.00% |  | 0.00% |  | 0.00% |  | 0.00% |
|  | 0.00% |  | 0.00% | 1 | 7.14% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% | 1 | 7.14% |  | 0.00% |
|  | 0.00% |  | 0.00% |  | 0.00% |  | 0.00% |
|  | 0.00% |  | 0.00% | 1 | 7.14% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
| 2 | 18.18% | 2 | 12.50% | 1 | 7.14% | 1 | 6.67% |
|  | 0.00% |  | 0.00% | 1 | 7.14% |  | 0.00% |
|  | 0.00% | 1 | 6.25% |  | 0.00% |  | 0.00% |
|  | 0.00% |  | 0.00% |  | 0.00% |  | 0.00% |
|  | 0.00% | 1 | 6.25% | 1 | 7.14% |  | 0.00% |
|  | 0.00% |  | 0.00% |  | 0.00% |  | 0.00% |
|  | 0.00% |  | 0.00% |  | 0.00% | 1 | 6.67% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% | 1 | 6.67% |
|  | 0.00% |  | 0.00% |  | 0.00% | 1 | 6.67% |
| 1 | 9.09% |  | 0.00% | 1 | 7.14% |  | 0.00% |
|  | 0.00% |  | 0.00% |  | 0.00% |  | 0.00% |
|  | 0.00% |  | 0.00% |  | 0.00% | 1 | 6.67% |
|  | 0.00% |  | 0.00% |  | 0.00% |  | 0.00% |
|  | 0.00% |  | 0.00% |  | 0.00% | 1 | 6.67% |
|  | 0.00% |  | 0.00% |  | 0.00% | 1 | 6.67% |
|  | 0.00% |  | 0.00% |  | 0.00% | 1 | 6.67% |
|  | 0.00% | 1 | 6.25% | 1 | 7.14% | 1 | 6.67% |
|  | 0.00% |  | 0.00% |  | 0.00% |  | 0.00% |
| 1 | 9.09% |  | 0.00% | 1 | 7.14% | 1 | 6.67% |
|  | 0.00% |  | 0.00% |  | 0.00% |  | 0.00% |
| 2 | 18.18% |  | 0.00% | 1 | 7.14% |  | 0.00% |
| 1 | 9.09% | 2 | 12.50% |  | 0.00% |  | 0.00% |
|  | 0.00% | 1 | 6.25% |  | 0.00% | 1 | 6.67% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
| 11 | 100.00% | 16 | 100.00% | 14 | 100.00% | 15 | 100.00% |

FIG. 30F

| Kidney | | Large Intestine, (Excl. Appendix)-Colon | | Larynx | | Lip | |
|---|---|---|---|---|---|---|---|
| 20 | | 91 | | 3 | | 0 | |
| Number of times biomarker flagged as | % in tumor type | Number of times biomarker flagged as | % in tumor type | Number of times biomarker flagged as | % in tumor type | Number of times biomarker flagged as | % in tumor type |
| 17 | 9.83% | 23 | 2.72% | 2 | 4.65% | | |
| 2 | 1.16% | 2 | 0.24% | | 0.00% | | |
| | 0.00% | 5 | 0.59% | 1 | 2.33% | | |
| | 0.00% | | 0.00% | | 0.00% | | |
| 1 | 0.58% | 12 | 1.42% | | 0.00% | | |
| | 0.00% | 12 | 1.42% | | 0.00% | | |
| | 0.00% | | 0.00% | | 0.00% | | |
| | 0.00% | 1 | 0.12% | | 0.00% | | |
| 1 | 0.58% | 1 | 0.12% | | 0.00% | | |
| 7 | 4.05% | 5 | 0.59% | | 0.00% | | |
| 4 | 2.31% | 4 | 0.47% | | 0.00% | | |
| | 0.00% | 3 | 0.35% | | 0.00% | | |
| 13 | 7.51% | 29 | 3.43% | 2 | 4.65% | | |
| 10 | 5.78% | 33 | 3.90% | 2 | 4.65% | | |
| 8 | 4.62% | 14 | 1.65% | 3 | 6.98% | | |
| | 0.00% | 3 | 0.35% | | 0.00% | | |
| | 0.00% | 1 | 0.12% | | 0.00% | | |
| | 0.00% | | 0.00% | | 0.00% | | |
| | 0.00% | 1 | 0.12% | | 0.00% | | |
| 2 | 1.16% | 23 | 2.72% | 1 | 2.33% | | |
| 7 | 4.05% | 40 | 4.73% | 3 | 6.98% | | |
| | 0.00% | | 0.00% | | 0.00% | | |
| 4 | 2.31% | 37 | 4.37% | 3 | 6.98% | | |
| 1 | 0.58% | 16 | 1.89% | 1 | 2.33% | | |
| | 0.00% | 5 | 0.59% | | 0.00% | | |
| | 0.00% | 1 | 0.12% | | 0.00% | | |
| | 0.00% | 7 | 0.83% | | 0.00% | | |
| 1 | 0.58% | 4 | 0.47% | | 0.00% | | |
| | 0.00% | 1 | 0.12% | | 0.00% | | |
| 11 | 6.36% | 26 | 3.07% | 2 | 4.65% | | |
| | 0.00% | 3 | 0.35% | | 0.00% | | |
| | 0.00% | 2 | 0.24% | | 0.00% | | |
| 1 | 0.58% | 30 | 3.55% | 2 | 4.65% | | |
| 6 | 3.47% | 24 | 2.84% | 3 | 6.98% | | |
| 6 | 3.47% | 36 | 4.26% | 2 | 4.65% | | |
| | 0.00% | 5 | 0.59% | | 0.00% | | |
| 2 | 1.16% | 9 | 1.06% | | 0.00% | | |
| 9 | 5.20% | 39 | 4.61% | | 0.00% | | |
| | 0.00% | | 0.00% | | 0.00% | | |
| | 0.00% | 1 | 0.12% | | 0.00% | | |
| | 0.00% | 3 | 0.35% | 1 | 2.33% | | |
| | 0.00% | | 0.00% | | 0.00% | | |
| | 0.00% | 4 | 0.47% | | 0.00% | | |
| 1 | 0.58% | 24 | 2.84% | | 0.00% | | |
| 2 | 1.16% | 8 | 0.95% | | 0.00% | | |
| | 0.00% | 3 | 0.35% | | 0.00% | | |
| 11 | 6.36% | 26 | 3.07% | 1 | 2.33% | | |
| 2 | 1.16% | 5 | 0.59% | | 0.00% | | |
| 2 | 1.16% | 24 | 2.84% | | 0.00% | | |
| | 0.00% | 7 | 0.83% | | 0.00% | | |
| 14 | 8.09% | 56 | 6.62% | 1 | 2.33% | | |
| 3 | 1.73% | 32 | 3.78% | | 0.00% | | |
| 1 | 0.58% | 16 | 1.89% | | 0.00% | | |
| 1 | 0.58% | 33 | 3.90% | 2 | 4.65% | | |
| 2 | 1.16% | 42 | 4.96% | 2 | 4.65% | | |
| 2 | 1.16% | 26 | 3.07% | 1 | 2.33% | | |
| | 0.00% | 13 | 1.54% | | 0.00% | | |
| 2 | 1.16% | 3 | 0.35% | 3 | 6.98% | | |
| 4 | 2.31% | 18 | 2.13% | | 0.00% | | |
| 3 | 1.73% | 38 | 4.49% | 3 | 6.98% | | |
| 9 | 5.20% | 4 | 0.47% | 1 | 2.33% | | |
| | 0.00% | 3 | 0.35% | 1 | 2.33% | | |
| | 0.00% | | 0.00% | | 0.00% | | |
| 173 | 100.00% | 846 | 100.00% | 43 | 100.00% | | |

FIG. 30G

| Liver | | Lung & Bronchus | | Lymph Nodes | | Meninges (Cerebral,Spinal) | |
|---|---|---|---|---|---|---|---|
| 7 | | 81 | | 14 | | 0 | |
| Number of times biomarker flagged as | % in tumor type | Number of times biomarker flagged as | % in tumor type | Number of times biomarker flagged as | % in tumor type | Number of times biomarker flagged as | % in tumor type |
| 2 | 3.33% | 31 | 3.45% | 7 | 5.30% | | |
| | 0.00% | | 0.00% | | 0.00% | | |
| | 0.00% | 1 | 0.11% | 3 | 2.27% | | |
| | 0.00% | | 0.00% | | 0.00% | | |
| | 0.00% | 2 | 0.22% | 1 | 0.76% | | |
| | 0.00% | 2 | 0.22% | 2 | 1.52% | | |
| | 0.00% | | 0.00% | 2 | 1.52% | | |
| | 0.00% | | 0.00% | 4 | 3.03% | | |
| 4 | 6.67% | 18 | 2.00% | 4 | 3.03% | | |
| | 0.00% | 13 | 1.45% | 6 | 4.55% | | |
| | 0.00% | 2 | 0.22% | 2 | 1.52% | | |
| 1 | 1.67% | 12 | 1.34% | 1 | 0.76% | | |
| 2 | 3.33% | 39 | 4.34% | 6 | 4.55% | | |
| 3 | 5.00% | 49 | 5.46% | 2 | 1.52% | | |
| | 0.00% | 19 | 2.12% | 2 | 1.52% | | |
| | 0.00% | 2 | 0.22% | | 0.00% | | |
| 1 | 1.67% | 6 | 0.67% | | 0.00% | | |
| | 0.00% | | 0.00% | | 0.00% | | |
| | 0.00% | 1 | 0.11% | | 0.00% | | |
| | 0.00% | 4 | 0.45% | | 0.00% | | |
| 2 | 3.33% | 46 | 5.12% | 6 | 4.55% | | |
| | 0.00% | | 0.00% | | 0.00% | | |
| 3 | 5.00% | 37 | 4.12% | 3 | 2.27% | | |
| | 0.00% | 12 | 1.34% | 4 | 3.03% | | |
| 1 | 1.67% | 1 | 0.11% | 1 | 0.76% | | |
| | 0.00% | 1 | 0.11% | | 0.00% | | |
| | 0.00% | 2 | 0.22% | 1 | 0.76% | | |
| | 0.00% | 12 | 1.34% | | 0.00% | | |
| | 0.00% | | 0.00% | | 0.00% | | |
| 2 | 3.33% | 50 | 5.57% | 2 | 1.52% | | |
| 1 | 1.67% | | 0.00% | | 0.00% | | |
| | 0.00% | 1 | 0.11% | | 0.00% | | |
| 2 | 3.33% | 52 | 5.79% | | 0.00% | | |
| 2 | 3.33% | 36 | 4.01% | 6 | 4.55% | | |
| 1 | 1.67% | 46 | 5.12% | 4 | 3.03% | | |
| | 0.00% | 4 | 0.45% | | 0.00% | | |
| 1 | 1.67% | 3 | 0.33% | | 0.00% | | |
| 2 | 3.33% | 10 | 1.11% | | 0.00% | | |
| | 0.00% | | 0.00% | | 0.00% | | |
| | 0.00% | 1 | 0.11% | | 0.00% | | |
| | 0.00% | 8 | 0.89% | | 0.00% | | |
| | 0.00% | | 0.00% | 5 | 3.79% | | |
| | 0.00% | 2 | 0.22% | 1 | 0.76% | | |
| | 0.00% | 3 | 0.33% | 6 | 4.55% | | |
| 2 | 3.33% | 24 | 2.67% | | 0.00% | | |
| | 0.00% | 4 | 0.45% | | 0.00% | | |
| 3 | 5.00% | 14 | 1.56% | 1 | 0.76% | | |
| 2 | 3.33% | 6 | 0.67% | 4 | 3.03% | | |
| | 0.00% | 20 | 2.23% | 2 | 1.52% | | |
| 1 | 1.67% | 14 | 1.56% | 2 | 1.52% | | |
| 3 | 5.00% | 43 | 4.79% | 11 | 8.33% | | |
| | 0.00% | 18 | 2.00% | 7 | 5.30% | | |
| 1 | 1.67% | 16 | 1.78% | 3 | 2.27% | | |
| 5 | 8.33% | 39 | 4.34% | 6 | 4.55% | | |
| 2 | 3.33% | 42 | 4.68% | 4 | 3.03% | | |
| 2 | 3.33% | 58 | 6.46% | 7 | 5.30% | | |
| | 0.00% | 1 | 0.11% | 1 | 0.76% | | |
| 3 | 5.00% | 33 | 3.67% | 2 | 1.52% | | |
| 3 | 5.00% | 7 | 0.78% | | 0.00% | | |
| 1 | 1.67% | 13 | 1.45% | 1 | 0.76% | | |
| | 0.00% | 11 | 1.22% | | 0.00% | | |
| 2 | 3.33% | 7 | 0.78% | | 0.00% | | |
| | 0.00% | | 0.00% | | 0.00% | | |
| 60 | 100.00% | 898 | 100.00% | 132 | 100.00% | | |

FIG. 30H

| Nasal Cavity (Including Nasal Cartilage) | | Orbit & Lacrimal Gland, (Excl. Retina, Eye, Nos) | | Oropharynx | | Other Endocrine Glands | |
|---|---|---|---|---|---|---|---|
| 1 | | 0 | | 1 | | 1 | |
| Number of times biomarker flagged as | % in tumor type | Number of times biomarker flagged as | % in tumor type | Number of times biomarker flagged as | % in tumor type | Number of times biomarker flagged as | % in tumor type |
| | 0.00% | | | | 0.00% | 1 | 10.00% |
| | 0.00% | | | | 0.00% | | 0.00% |
| 1 | 5.88% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| 1 | 5.88% | | | | 0.00% | 1 | 10.00% |
| | 0.00% | | | | 0.00% | | 0.00% |
| | 0.00% | | | | 0.00% | | 0.00% |
| | 0.00% | | | | 0.00% | | 0.00% |
| 1 | 5.88% | | | 1 | 11.11% | | 0.00% |
| | 0.00% | | | 1 | 11.11% | | 0.00% |
| 1 | 5.88% | | | | 0.00% | 1 | 10.00% |
| | 0.00% | | | | 0.00% | | 0.00% |
| 1 | 5.88% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| 1 | 5.88% | | | 1 | 11.11% | 1 | 10.00% |
| | 0.00% | | | | 0.00% | | 0.00% |
| | 0.00% | | | | 0.00% | | 0.00% |
| | 0.00% | | | 1 | 11.11% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | 1 | 10.00% |
| | 0.00% | | | | 0.00% | | 0.00% |
| | 0.00% | | | 1 | 11.11% | | 0.00% |
| | 0.00% | | | | 0.00% | | 0.00% |
| | 0.00% | | | | 0.00% | | 0.00% |
| 1 | 5.88% | | | 1 | 11.11% | 1 | 10.00% |
| 1 | 5.88% | | | | 0.00% | | 0.00% |
| 1 | 5.88% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| 1 | 5.88% | | | | 0.00% | | 0.00% |
| | 0.00% | | | | 0.00% | | 0.00% |
| 1 | 5.88% | | | | 0.00% | 1 | 10.00% |
| | 0.00% | | | | 0.00% | | 0.00% |
| 1 | 5.88% | | | | 0.00% | | 0.00% |
| | 0.00% | | | | 0.00% | | 0.00% |
| | 0.00% | | | | 0.00% | | 0.00% |
| | 0.00% | | | 1 | 11.11% | | 0.00% |
| | 0.00% | | | | 0.00% | | 0.00% |
| | 0.00% | | | | 0.00% | | 0.00% |
| 1 | 5.88% | | | | 0.00% | 1 | 10.00% |
| 1 | 5.88% | | | | 0.00% | | 0.00% |
| | 0.00% | | | | 0.00% | | 0.00% |
| 1 | 5.88% | | | | 0.00% | 1 | 10.00% |
| | 0.00% | | | 1 | 11.11% | | 0.00% |
| 1 | 5.88% | | | 1 | 11.11% | | 0.00% |
| | 0.00% | | | | 0.00% | | 0.00% |
| | 0.00% | | | | 0.00% | 1 | 10.00% |
| 1 | 5.88% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| | 0.00% | | | | 0.00% | | 0.00% |
| 17 | 100.00% | | | 9 | 100.00% | 10 | 100.00% |

FIG. 30I

| Other Female Genital | | Ovary | | Pancreas | | Penis & Scrotum | |
|---|---|---|---|---|---|---|---|
| 3 | | 74 | | 60 | | 1 | |
| Number of times biomarker flagged as | % in tumor type | Number of times biomarker flagged as | % in tumor type | Number of times biomarker flagged as | % in tumor type | Number of times biomarker flagged as | % in tumor type |
| 2 | 5.88% | 23 | 2.77% | 18 | 3.76% | 1 | 8.33% |
|  | 0.00% |  | 0.00% | 1 | 0.21% |  | 0.00% |
|  | 0.00% | 1 | 0.12% | 28 | 5.85% |  | 0.00% |
|  | 0.00% |  | 0.00% | 1 | 0.21% |  | 0.00% |
|  | 0.00% | 1 | 0.12% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
| 1 | 2.94% | 14 | 1.68% | 16 | 3.34% |  | 0.00% |
| 2 | 5.88% | 27 | 3.25% | 15 | 3.13% | 1 | 8.33% |
|  | 0.00% | 1 | 0.12% |  | 0.00% |  | 0.00% |
| 1 | 2.94% | 12 | 1.44% | 13 | 2.71% |  | 0.00% |
| 2 | 5.88% | 17 | 2.05% | 10 | 2.09% | 1 | 8.33% |
| 2 | 5.88% | 44 | 5.29% | 4 | 0.84% | 1 | 8.33% |
|  | 0.00% | 5 | 0.60% | 9 | 1.88% |  | 0.00% |
|  | 0.00% | 1 | 0.12% | 4 | 0.84% |  | 0.00% |
|  | 0.00% | 11 | 1.32% | 1 | 0.21% |  | 0.00% |
|  | 0.00% |  | 0.00% |  | 0.00% |  | 0.00% |
|  | 0.00% | 19 | 2.29% |  | 0.00% |  | 0.00% |
|  | 0.00% | 3 | 0.36% | 1 | 0.21% |  | 0.00% |
| 2 | 5.88% | 45 | 5.42% | 29 | 6.05% | 1 | 8.33% |
|  | 0.00% |  | 0.00% |  | 0.00% |  | 0.00% |
| 2 | 5.88% | 46 | 5.54% | 31 | 6.47% | 1 | 8.33% |
|  | 0.00% | 20 | 2.41% | 9 | 1.88% |  | 0.00% |
|  | 0.00% | 12 | 1.44% | 8 | 1.67% |  | 0.00% |
|  | 0.00% | 2 | 0.24% |  | 0.00% |  | 0.00% |
|  | 0.00% | 3 | 0.36% |  | 0.00% |  | 0.00% |
|  | 0.00% | 2 | 0.24% | 4 | 0.84% |  | 0.00% |
|  | 0.00% |  | 0.00% |  | 0.00% |  | 0.00% |
| 2 | 5.88% | 46 | 5.54% | 25 | 5.22% | 1 | 8.33% |
|  | 0.00% | 2 | 0.24% |  | 0.00% |  | 0.00% |
|  | 0.00% | 1 | 0.12% |  | 0.00% |  | 0.00% |
|  | 0.00% | 39 | 4.69% | 4 | 0.84% | 1 | 8.33% |
| 3 | 8.82% | 49 | 5.90% | 19 | 3.97% |  | 0.00% |
| 1 | 2.94% | 24 | 2.89% | 21 | 4.38% |  | 0.00% |
|  | 0.00% | 4 | 0.48% |  | 0.00% |  | 0.00% |
|  | 0.00% |  | 0.00% | 9 | 1.88% |  | 0.00% |
|  | 0.00% | 2 | 0.24% | 17 | 3.55% |  | 0.00% |
|  | 0.00% | 2 | 0.24% |  | 0.00% |  | 0.00% |
|  | 0.00% | 1 | 0.12% | 1 | 0.21% |  | 0.00% |
|  | 0.00% | 3 | 0.36% | 22 | 4.59% |  | 0.00% |
|  | 0.00% | 1 | 0.12% |  | 0.00% |  | 0.00% |
|  | 0.00% | 1 | 0.12% |  | 0.00% |  | 0.00% |
|  | 0.00% |  | 0.00% | 4 | 0.84% |  | 0.00% |
|  | 0.00% | 3 | 0.36% | 4 | 0.84% |  | 0.00% |
|  | 0.00% | 1 | 0.12% |  | 0.00% |  | 0.00% |
| 1 | 2.94% | 14 | 1.68% | 18 | 3.76% |  | 0.00% |
|  | 0.00% | 1 | 0.12% | 5 | 1.04% |  | 0.00% |
|  | 0.00% | 5 | 0.60% | 3 | 0.63% |  | 0.00% |
|  | 0.00% | 3 | 0.36% | 4 | 0.84% |  | 0.00% |
|  | 0.00% | 24 | 2.89% | 3 | 0.63% | 1 | 8.33% |
|  | 0.00% | 10 | 1.20% | 2 | 0.42% |  | 0.00% |
|  | 0.00% | 2 | 0.24% | 1 | 0.21% |  | 0.00% |
| 2 | 5.88% | 56 | 6.74% | 36 | 7.52% |  | 0.00% |
| 2 | 5.88% | 37 | 4.45% | 18 | 3.76% | 1 | 8.33% |
| 3 | 8.82% | 59 | 7.10% | 31 | 6.47% | 1 | 8.33% |
|  | 0.00% | 2 | 0.24% |  | 0.00% |  | 0.00% |
| 2 | 5.88% | 56 | 6.74% | 22 | 4.59% |  | 0.00% |
| 1 | 2.94% | 26 | 3.13% |  | 0.00% |  | 0.00% |
| 1 | 2.94% | 27 | 3.25% | 1 | 0.21% | 1 | 8.33% |
|  | 0.00% | 3 | 0.36% |  | 0.00% |  | 0.00% |
| 2 | 5.88% | 18 | 2.17% | 7 | 1.46% |  | 0.00% |
|  | 0.00% |  | 0.00% |  | 0.00% |  | 0.00% |
| 34 | 100.00% | 831 | 100.00% | 479 | 100.00% | 12 | 100.00% |

FIG. 30J

| Pituitary Gland | | Pleura | | Prostate Gland | | Rectum | |
|---|---|---|---|---|---|---|---|
| 1 | | 1 | | 14 | | 14 | |
| Number of times biomarker flagged as | % in tumor type | Number of times biomarker flagged as | % in tumor type | Number of times biomarker flagged as | % in tumor type | Number of times biomarker flagged as | % in tumor type |
| | 0.00% | | 0.00% | 3 | 2.73% | 5 | 4.27% |
| 1 | 10.00% | | 0.00% | 6 | 5.45% | 1 | 0.85% |
| 1 | 10.00% | | 0.00% | | 0.00% | 1 | 0.85% |
| | 0.00% | | 0.00% | | 0.00% | | 0.00% |
| | 0.00% | 1 | 6.67% | | 0.00% | | 0.00% |
| | 0.00% | 1 | 6.67% | | 0.00% | 1 | 0.85% |
| | 0.00% | | 0.00% | | 0.00% | | 0.00% |
| | 0.00% | | 0.00% | | 0.00% | | 0.00% |
| 1 | 10.00% | | 0.00% | 1 | 0.91% | 3 | 2.56% |
| | 0.00% | | 0.00% | 3 | 2.73% | | 0.00% |
| | 0.00% | 1 | 6.67% | | 0.00% | | 0.00% |
| | 0.00% | | 0.00% | 4 | 3.64% | 3 | 2.56% |
| | 0.00% | 1 | 6.67% | 5 | 4.55% | 5 | 4.27% |
| | 0.00% | | 0.00% | 8 | 7.27% | 5 | 4.27% |
| | 0.00% | | 0.00% | 1 | 0.91% | 3 | 2.56% |
| | 0.00% | | 0.00% | | 0.00% | | 0.00% |
| | 0.00% | | 0.00% | | 0.00% | 1 | 0.85% |
| | 0.00% | | 0.00% | | 0.00% | 1 | 0.85% |
| 1 | 10.00% | | 0.00% | | 0.00% | | 0.00% |
| | 0.00% | 1 | 6.67% | | 0.00% | 2 | 1.71% |
| | 0.00% | | 0.00% | 7 | 6.36% | 5 | 4.27% |
| | 0.00% | | 0.00% | | 0.00% | | 0.00% |
| | 0.00% | | 0.00% | 2 | 1.82% | 5 | 4.27% |
| | 0.00% | | 0.00% | | 0.00% | | 0.00% |
| | 0.00% | | 0.00% | 2 | 1.82% | 2 | 1.71% |
| | 0.00% | | 0.00% | | 0.00% | | 0.00% |
| | 0.00% | | 0.00% | 1 | 0.91% | | 0.00% |
| | 0.00% | | 0.00% | 2 | 1.82% | | 0.00% |
| | 0.00% | | 0.00% | | 0.00% | | 0.00% |
| | 0.00% | | 0.00% | 6 | 5.45% | | 0.00% |
| | 0.00% | | 0.00% | | 0.00% | | 0.00% |
| | 0.00% | | 0.00% | | 0.00% | | 0.00% |
| | 0.00% | | 0.00% | 4 | 3.64% | 4 | 3.42% |
| 1 | 10.00% | 1 | 6.67% | 4 | 3.64% | 7 | 5.98% |
| 1 | 10.00% | | 0.00% | 4 | 3.64% | 5 | 4.27% |
| | 0.00% | | 0.00% | | 0.00% | 1 | 0.85% |
| | 0.00% | | 0.00% | | 0.00% | 1 | 0.85% |
| | 0.00% | 1 | 6.67% | 1 | 0.91% | 4 | 3.42% |
| | 0.00% | | 0.00% | | 0.00% | | 0.00% |
| | 0.00% | | 0.00% | | 0.00% | | 0.00% |
| | 0.00% | 1 | 6.67% | | 0.00% | 1 | 0.85% |
| | 0.00% | | 0.00% | | 0.00% | | 0.00% |
| | 0.00% | 1 | 6.67% | | 0.00% | 1 | 0.85% |
| | 0.00% | 1 | 6.67% | | 0.00% | | 0.00% |
| 1 | 10.00% | 1 | 6.67% | 1 | 0.91% | 3 | 2.56% |
| | 0.00% | | 0.00% | 1 | 0.91% | | 0.00% |
| | 0.00% | 1 | 6.67% | 5 | 4.55% | 6 | 5.13% |
| | 0.00% | | 0.00% | | 0.00% | | 0.00% |
| | 0.00% | | 0.00% | 4 | 3.64% | 1 | 0.85% |
| | 0.00% | 1 | 6.67% | 1 | 0.91% | | 0.00% |
| 1 | 10.00% | 1 | 6.67% | 6 | 5.45% | 6 | 5.13% |
| | 0.00% | | 0.00% | 4 | 3.64% | 3 | 2.56% |
| | 0.00% | | 0.00% | 2 | 1.82% | 1 | 0.85% |
| | 0.00% | | 0.00% | 5 | 4.55% | 6 | 5.13% |
| | 0.00% | | 0.00% | 5 | 4.55% | 8 | 6.84% |
| 1 | 10.00% | | 0.00% | 9 | 8.18% | 2 | 1.71% |
| | 0.00% | 1 | 6.67% | | 0.00% | 1 | 0.85% |
| | 0.00% | | 0.00% | 1 | 0.91% | 1 | 0.85% |
| 1 | 10.00% | | 0.00% | | 0.00% | 8 | 6.84% |
| | 0.00% | | 0.00% | | 0.00% | 4 | 3.42% |
| | 0.00% | | 0.00% | 2 | 1.82% | | 0.00% |
| | 0.00% | | 0.00% | | 0.00% | | 0.00% |
| | 0.00% | | 0.00% | | 0.00% | | 0.00% |
| 10 | 100.00% | 15 | 100.00% | 110 | 100.00% | 117 | 100.00% |

FIG. 30K

| Renal Pelvis, Ureter | | Retroperitoneum & Peritoneum | | Salivary Gland | | Skin | |
|---|---|---|---|---|---|---|---|
| 1 | | 13 | | 11 | | 41 | |
| Number of times biomarker flagged as | % in tumor type | Number of times biomarker flagged as | % in tumor type | Number of times biomarker flagged as | % in tumor type | Number of times biomarker flagged as | % in tumor type |
| 1 | 7.14% | 5 | 4.20% | 3 | 2.03% | 26 | 4.72% |
|  | 0.00% |  | 0.00% | 2 | 1.35% | 2 | 0.36% |
|  | 0.00% | 3 | 2.52% | 5 | 3.38% | 8 | 1.45% |
|  | 0.00% |  | 0.00% |  | 0.00% |  | 0.00% |
|  | 0.00% | 2 | 1.68% |  | 0.00% | 23 | 4.17% |
|  | 0.00% | 1 | 0.84% |  | 0.00% | 14 | 2.54% |
|  | 0.00% |  | 0.00% |  | 0.00% |  | 0.00% |
|  | 0.00% |  | 0.00% |  | 0.00% | 1 | 0.18% |
|  | 0.00% | 4 | 3.36% | 7 | 4.73% | 9 | 1.63% |
|  | 0.00% | 2 | 1.68% | 2 | 1.35% | 4 | 0.73% |
|  | 0.00% | 1 | 0.84% | 1 | 0.68% | 11 | 2.00% |
|  | 0.00% | 3 | 2.52% | 7 | 4.73% | 3 | 0.54% |
|  | 0.00% | 4 | 3.36% | 5 | 3.38% | 11 | 2.00% |
| 1 | 7.14% | 4 | 3.36% | 4 | 2.70% | 9 | 1.63% |
| 1 | 7.14% | 1 | 0.84% |  | 0.00% | 4 | 0.73% |
| 1 | 7.14% | 1 | 0.84% |  | 0.00% | 8 | 1.45% |
|  | 0.00% |  | 0.00% |  | 0.00% | 3 | 0.54% |
|  | 0.00% |  | 0.00% |  | 0.00% |  | 0.00% |
|  | 0.00% |  | 0.00% |  | 0.00% |  | 0.00% |
|  | 0.00% |  | 0.00% | 2 | 1.35% | 17 | 3.09% |
| 1 | 7.14% | 7 | 5.88% | 6 | 4.05% | 15 | 2.72% |
|  | 0.00% |  | 0.00% |  | 0.00% |  | 0.00% |
| 1 | 7.14% | 5 | 4.20% | 9 | 6.08% | 8 | 1.45% |
|  | 0.00% |  | 0.00% | 3 | 2.03% | 3 | 0.54% |
|  | 0.00% | 2 | 1.68% | 2 | 1.35% | 2 | 0.36% |
|  | 0.00% | 1 | 0.84% |  | 0.00% | 1 | 0.18% |
|  | 0.00% |  | 0.00% |  | 0.00% | 3 | 0.54% |
|  | 0.00% | 1 | 0.84% | 3 | 2.03% | 2 | 0.36% |
|  | 0.00% |  | 0.00% |  | 0.00% |  | 0.00% |
| 1 | 7.14% | 5 | 4.20% | 6 | 4.05% | 25 | 4.54% |
|  | 0.00% |  | 0.00% |  | 0.00% | 1 | 0.18% |
|  | 0.00% | 1 | 0.84% |  | 0.00% | 3 | 0.54% |
| 1 | 7.14% | 3 | 2.52% | 4 | 2.70% | 12 | 2.18% |
|  | 0.00% | 6 | 5.04% | 2 | 1.35% | 13 | 2.36% |
|  | 0.00% | 5 | 4.20% | 3 | 2.03% | 33 | 5.99% |
|  | 0.00% | 3 | 2.52% |  | 0.00% | 6 | 1.09% |
|  | 0.00% | 2 | 1.68% | 5 | 3.38% | 7 | 1.27% |
|  | 0.00% | 3 | 2.52% | 6 | 4.05% | 22 | 3.99% |
|  | 0.00% |  | 0.00% |  | 0.00% |  | 0.00% |
|  | 0.00% | 1 | 0.84% |  | 0.00% | 2 | 0.36% |
|  | 0.00% | 2 | 1.68% | 2 | 1.35% | 5 | 0.91% |
|  | 0.00% |  | 0.00% |  | 0.00% |  | 0.00% |
|  | 0.00% | 2 | 1.68% |  | 0.00% | 20 | 3.63% |
|  | 0.00% | 2 | 1.68% |  | 0.00% | 27 | 4.90% |
|  | 0.00% | 2 | 1.68% |  | 0.00% | 12 | 2.18% |
|  | 0.00% |  | 0.00% |  | 0.00% | 6 | 1.09% |
|  | 0.00% | 4 | 3.36% | 6 | 4.05% | 18 | 3.27% |
|  | 0.00% | 1 | 0.84% | 4 | 2.70% | 14 | 2.54% |
|  | 0.00% |  | 0.00% | 2 | 1.35% | 2 | 0.36% |
|  | 0.00% | 2 | 1.68% | 1 | 0.68% | 16 | 2.90% |
| 1 | 7.14% | 5 | 4.20% | 5 | 3.38% | 18 | 3.27% |
| 1 | 7.14% | 2 | 1.68% | 2 | 1.35% | 7 | 1.27% |
|  | 0.00% | 1 | 0.84% |  | 0.00% | 3 | 0.54% |
| 1 | 7.14% | 6 | 5.04% | 10 | 6.76% | 12 | 2.18% |
| 1 | 7.14% | 4 | 3.36% | 6 | 4.05% | 15 | 2.72% |
|  | 0.00% | 3 | 2.52% | 9 | 6.08% | 8 | 1.45% |
|  | 0.00% | 2 | 1.68% |  | 0.00% | 14 | 2.54% |
| 1 | 7.14% | 3 | 2.52% | 9 | 6.08% | 14 | 2.54% |
|  | 0.00% | 2 | 1.68% | 1 | 0.68% | 9 | 1.63% |
|  | 0.00% |  | 0.00% | 2 | 1.35% | 13 | 2.36% |
|  | 0.00% |  | 0.00% |  | 0.00% | 1 | 0.18% |
| 1 | 7.14% |  | 0.00% | 2 | 1.35% | 5 | 0.91% |
|  | 0.00% |  | 0.00% |  | 0.00% | 1 | 0.18% |
| 14 | 100.00% | 119 | 100.00% | 148 | 100.00% | 551 | 100.00% |

FIG. 30L

| Small Intestine | | Stomach | | Testis | | Thymus | |
|---|---|---|---|---|---|---|---|
| 2 | | 13 | | 3 | | 5 | |
| Number of times biomarker flagged as | % in tumor type | Number of times biomarker flagged as | % in tumor type | Number of times biomarker flagged as | % in tumor type | Number of times biomarker flagged as | % in tumor type |
| 2 | 10.53% | 8 | 6.15% | 3 | 7.14% | 4 | 6.35% |
|  | 0.00% | 2 | 1.54% |  | 0.00% | 1 | 1.59% |
|  | 0.00% | 1 | 0.77% | 1 | 2.38% |  | 0.00% |
|  | 0.00% |  | 0.00% |  | 0.00% |  | 0.00% |
| 1 | 5.26% |  | 0.00% | 1 | 2.38% |  | 0.00% |
|  | 0.00% | 2 | 1.54% | 1 | 2.38% |  | 0.00% |
|  | 0.00% |  | 0.00% |  | 0.00% |  | 0.00% |
|  | 0.00% |  | 0.00% |  | 0.00% |  | 0.00% |
|  | 0.00% | 1 | 0.77% | 1 | 2.38% | 1 | 1.59% |
|  | 0.00% | 1 | 0.77% |  | 0.00% |  | 0.00% |
|  | 0.00% |  | 0.00% |  | 0.00% | 2 | 3.17% |
|  | 0.00% | 2 | 1.54% |  | 0.00% |  | 0.00% |
|  | 0.00% | 4 | 3.08% | 2 | 4.76% |  | 0.00% |
|  | 0.00% | 8 | 6.15% | 1 | 2.38% |  | 0.00% |
|  | 0.00% | 2 | 1.54% | 1 | 2.38% | 1 | 1.59% |
|  | 0.00% |  | 0.00% | 1 | 2.38% |  | 0.00% |
|  | 0.00% |  | 0.00% | 2 | 4.76% |  | 0.00% |
|  | 0.00% |  | 0.00% |  | 0.00% |  | 0.00% |
|  | 0.00% | 2 | 1.54% | 1 | 2.38% |  | 0.00% |
|  | 0.00% |  | 0.00% | 1 | 2.38% |  | 0.00% |
|  | 0.00% | 2 | 1.54% | 1 | 2.38% | 1 | 1.59% |
|  | 0.00% |  | 0.00% |  | 0.00% |  | 0.00% |
| 2 | 10.53% | 5 | 3.85% | 2 | 4.76% | 5 | 7.94% |
|  | 0.00% | 2 | 1.54% |  | 0.00% | 1 | 1.59% |
|  | 0.00% | 1 | 0.77% |  | 0.00% | 2 | 3.17% |
|  | 0.00% |  | 0.00% |  | 0.00% |  | 0.00% |
|  | 0.00% | 1 | 0.77% | 1 | 2.38% |  | 0.00% |
| 1 | 5.26% | 1 | 0.77% |  | 0.00% | 3 | 4.76% |
|  | 0.00% |  | 0.00% |  | 0.00% |  | 0.00% |
| 2 | 10.53% | 7 | 5.38% | 1 | 2.38% | 2 | 3.17% |
|  | 0.00% | 1 | 0.77% |  | 0.00% |  | 0.00% |
|  | 0.00% |  | 0.00% |  | 0.00% |  | 0.00% |
|  | 0.00% | 4 | 3.08% |  | 0.00% | 4 | 6.35% |
|  | 0.00% | 6 | 4.62% |  | 0.00% | 3 | 4.76% |
| 1 | 5.26% | 5 | 3.85% | 2 | 4.76% | 3 | 4.76% |
|  | 0.00% |  | 0.00% |  | 0.00% |  | 0.00% |
| 2 | 10.53% |  | 0.00% |  | 0.00% | 1 | 1.59% |
|  | 0.00% | 3 | 2.31% | 2 | 4.76% | 1 | 1.59% |
|  | 0.00% | 1 | 0.77% |  | 0.00% |  | 0.00% |
|  | 0.00% |  | 0.00% |  | 0.00% |  | 0.00% |
|  | 0.00% | 2 | 1.54% | 1 | 2.38% |  | 0.00% |
|  | 0.00% |  | 0.00% |  | 0.00% |  | 0.00% |
|  | 0.00% | 1 | 0.77% |  | 0.00% |  | 0.00% |
| 2 | 10.53% | 3 | 2.31% |  | 0.00% | 4 | 6.35% |
|  | 0.00% | 2 | 1.54% |  | 0.00% |  | 0.00% |
|  | 0.00% | 1 | 0.77% |  | 0.00% |  | 0.00% |
|  | 0.00% | 1 | 0.77% | 1 | 2.38% | 1 | 1.59% |
|  | 0.00% | 3 | 2.31% |  | 0.00% | 1 | 1.59% |
|  | 0.00% | 2 | 1.54% | 1 | 2.38% | 2 | 3.17% |
|  | 0.00% | 2 | 1.54% |  | 0.00% |  | 0.00% |
| 1 | 5.26% | 8 | 6.15% | 2 | 4.76% | 2 | 3.17% |
|  | 0.00% | 5 | 3.85% | 1 | 2.38% |  | 0.00% |
|  | 0.00% | 2 | 1.54% |  | 0.00% |  | 0.00% |
| 2 | 10.53% | 6 | 4.62% | 3 | 7.14% | 4 | 6.35% |
| 1 | 5.26% | 8 | 6.15% | 1 | 2.38% | 1 | 1.59% |
| 2 | 10.53% | 4 | 3.08% | 1 | 2.38% | 5 | 7.94% |
|  | 0.00% |  | 0.00% | 2 | 4.76% | 4 | 6.35% |
|  | 0.00% | 1 | 0.77% | 2 | 4.76% | 3 | 4.76% |
|  | 0.00% | 3 | 2.31% | 1 | 2.38% |  | 0.00% |
|  | 0.00% | 3 | 2.31% | 1 | 2.38% |  | 0.00% |
|  | 0.00% |  | 0.00% |  | 0.00% |  | 0.00% |
|  | 0.00% | 1 | 0.77% |  | 0.00% | 1 | 1.59% |
|  | 0.00% |  | 0.00% |  | 0.00% |  | 0.00% |
| 19 | 100.00% | 130 | 100.00% | 42 | 100.00% | 63 | 100.00% |

FIG. 30M

| Thyroid Gland | | Tongue | | Unknown | | Unspecified Digest. Organs | |
|---|---|---|---|---|---|---|---|
| 8 | | 2 | | 37 | | 0 | |
| Number of times biomarker flagged as | % in tumor type | Number of times biomarker flagged as | % in tumor type | Number of times biomarker flagged as | % in tumor type | Number of times biomarker flagged as | % in tumor type |
| 5 | 4.55% | 1 | 5.56% | 19 | 5.28% | | |
|  | 0.00% |  | 0.00% |  | 0.00% | | |
| 2 | 1.82% |  | 0.00% | 3 | 0.83% | | |
|  | 0.00% |  | 0.00% |  | 0.00% | | |
| 1 | 0.91% |  | 0.00% | 3 | 0.83% | | |
| 4 | 3.64% |  | 0.00% | 5 | 1.39% | | |
|  | 0.00% |  | 0.00% |  | 0.00% | | |
|  | 0.00% |  | 0.00% | 3 | 0.83% | | |
| 2 | 1.82% |  | 0.00% | 9 | 2.50% | | |
|  | 0.00% | 1 | 5.56% | 10 | 2.78% | | |
|  | 0.00% |  | 0.00% | 3 | 0.83% | | |
| 1 | 0.91% | 1 | 5.56% | 7 | 1.94% | | |
| 4 | 3.64% | 1 | 5.56% | 12 | 3.33% | | |
| 4 | 3.64% | 1 | 5.56% | 14 | 3.89% | | |
| 3 | 2.73% |  | 0.00% | 5 | 1.39% | | |
|  | 0.00% |  | 0.00% |  | 0.00% | | |
| 2 | 1.82% |  | 0.00% | 3 | 0.83% | | |
|  | 0.00% |  | 0.00% |  | 0.00% | | |
| 1 | 0.91% |  | 0.00% | 1 | 0.28% | | |
| 1 | 0.91% |  | 0.00% | 6 | 1.67% | | |
| 3 | 2.73% |  | 0.00% | 14 | 3.89% | | |
|  | 0.00% |  | 0.00% |  | 0.00% | | |
| 3 | 2.73% | 2 | 11.11% | 14 | 3.89% | | |
| 1 | 0.91% |  | 0.00% | 7 | 1.94% | | |
|  | 0.00% |  | 0.00% | 1 | 0.28% | | |
|  | 0.00% |  | 0.00% |  | 0.00% | | |
| 1 | 0.91% |  | 0.00% | 4 | 1.11% | | |
|  | 0.00% | 1 | 5.56% | 1 | 0.28% | | |
|  | 0.00% |  | 0.00% |  | 0.00% | | |
| 6 | 5.45% |  | 0.00% | 15 | 4.17% | | |
| 1 | 0.91% |  | 0.00% |  | 0.00% | | |
| 1 | 0.91% |  | 0.00% | 1 | 0.28% | | |
| 5 | 4.55% | 1 | 5.56% | 5 | 1.39% | | |
| 2 | 1.82% | 1 | 5.56% | 11 | 3.06% | | |
| 4 | 3.64% | 1 | 5.56% | 15 | 4.17% | | |
| 2 | 1.82% |  | 0.00% | 2 | 0.56% | | |
| 2 | 1.82% |  | 0.00% | 3 | 0.83% | | |
| 5 | 4.55% |  | 0.00% | 10 | 2.78% | | |
|  | 0.00% |  | 0.00% |  | 0.00% | | |
|  | 0.00% |  | 0.00% | 3 | 0.83% | | |
| 1 | 0.91% |  | 0.00% | 7 | 1.94% | | |
|  | 0.00% |  | 0.00% | 1 | 0.28% | | |
|  | 0.00% |  | 0.00% | 4 | 1.11% | | |
| 5 | 4.55% |  | 0.00% | 6 | 1.67% | | |
| 2 | 1.82% |  | 0.00% | 7 | 1.94% | | |
| 2 | 1.82% |  | 0.00% | 1 | 0.28% | | |
| 3 | 2.73% | 1 | 5.56% | 8 | 2.22% | | |
| 3 | 2.73% |  | 0.00% | 5 | 1.39% | | |
| 2 | 1.82% |  | 0.00% | 8 | 2.22% | | |
| 1 | 0.91% |  | 0.00% | 6 | 1.67% | | |
| 6 | 5.45% | 2 | 11.11% | 14 | 3.89% | | |
| 2 | 1.82% |  | 0.00% | 9 | 2.50% | | |
| 1 | 0.91% |  | 0.00% | 4 | 1.11% | | |
| 3 | 2.73% | 1 | 5.56% | 17 | 4.72% | | |
| 3 | 2.73% | 1 | 5.56% | 16 | 4.44% | | |
| 1 | 0.91% | 1 | 5.56% | 12 | 3.33% | | |
|  | 0.00% |  | 0.00% | 3 | 0.83% | | |
| 4 | 3.64% | 1 | 5.56% | 8 | 2.22% | | |
| 2 | 1.82% |  | 0.00% | 4 | 1.11% | | |
| 3 | 2.73% |  | 0.00% | 6 | 1.67% | | |
|  | 0.00% |  | 0.00% | 5 | 1.39% | | |
|  | 0.00% |  | 0.00% |  | 0.00% | | |
|  | 0.00% |  | 0.00% |  | 0.00% | | |
| 110 | 100.00% | 18 | 100.00% | 360 | 100.00% | | |

FIG. 30N

| Urinary Bladder | | Uterus, Nos | | Vagina & Labia | | Vulva, Nos | |
|---|---|---|---|---|---|---|---|
| 8 | | 8 | | 3 | | 1 | |
| Number of times biomarker flagged as | % in tumor type | Number of times biomarker flagged as | % in tumor type | Number of times biomarker flagged as | % in tumor type | Number of times biomarker flagged as | % in tumor type |
| 4 | 6.67% | 6 | 5.41% | 1 | 2.78% | 1 | 7.14% |
| 1 | 1.67% |  | 0.00% |  | 0.00% |  | 0.00% |
|  | 0.00% | 1 | 0.90% |  | 0.00% |  | 0.00% |
|  | 0.00% |  | 0.00% |  | 0.00% |  | 0.00% |
|  | 0.00% |  | 0.00% | 1 | 2.78% |  | 0.00% |
|  | 0.00% |  | 0.00% | 1 | 2.78% |  | 0.00% |
|  | 0.00% |  | 0.00% |  | 0.00% |  | 0.00% |
|  | 0.00% |  | 0.00% |  | 0.00% |  | 0.00% |
| 5 | 8.33% | 1 | 0.90% |  | 0.00% |  | 0.00% |
| 3 | 5.00% | 4 | 3.60% |  | 0.00% | 1 | 7.14% |
|  | 0.00% |  | 0.00% | 1 | 2.78% |  | 0.00% |
| 1 | 1.67% | 4 | 3.60% | 1 | 2.78% | 1 | 7.14% |
| 2 | 3.33% | 5 | 4.50% | 2 | 5.56% | 1 | 7.14% |
| 1 | 1.67% | 7 | 6.31% | 1 | 2.78% | 1 | 7.14% |
|  | 0.00% | 2 | 1.80% |  | 0.00% |  | 0.00% |
| 1 | 1.67% | 2 | 1.80% | 1 | 2.78% |  | 0.00% |
| 1 | 1.67% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% |  | 0.00% |  | 0.00% |  | 0.00% |
| 1 | 1.67% | 6 | 5.41% | 2 | 5.56% |  | 0.00% |
|  | 0.00% |  | 0.00% |  | 0.00% |  | 0.00% |
| 4 | 6.67% | 6 | 5.41% | 2 | 5.56% |  | 0.00% |
| 1 | 1.67% | 4 | 3.60% |  | 0.00% |  | 0.00% |
|  | 0.00% |  | 0.00% | 1 | 2.78% |  | 0.00% |
|  | 0.00% |  | 0.00% |  | 0.00% |  | 0.00% |
|  | 0.00% |  | 0.00% |  | 0.00% |  | 0.00% |
|  | 0.00% | 1 | 0.90% |  | 0.00% | 1 | 7.14% |
|  | 0.00% |  | 0.00% |  | 0.00% |  | 0.00% |
| 3 | 5.00% | 4 | 3.60% | 1 | 2.78% |  | 0.00% |
|  | 0.00% | 1 | 0.90% |  | 0.00% |  | 0.00% |
|  | 0.00% |  | 0.00% |  | 0.00% |  | 0.00% |
| 1 | 1.67% | 3 | 2.70% | 3 | 8.33% | 1 | 7.14% |
| 1 | 1.67% | 4 | 3.60% | 1 | 2.78% |  | 0.00% |
| 2 | 3.33% | 6 | 5.41% | 2 | 5.56% | 1 | 7.14% |
|  | 0.00% |  | 0.00% |  | 0.00% |  | 0.00% |
|  | 0.00% | 2 | 1.80% |  | 0.00% |  | 0.00% |
|  | 0.00% |  | 0.00% |  | 0.00% |  | 0.00% |
|  | 0.00% |  | 0.00% |  | 0.00% |  | 0.00% |
|  | 0.00% | 5 | 4.50% |  | 0.00% |  | 0.00% |
| 1 | 1.67% | 4 | 3.60% |  | 0.00% |  | 0.00% |
|  | 0.00% |  | 0.00% |  | 0.00% |  | 0.00% |
|  | 0.00% |  | 0.00% | 1 | 2.78% |  | 0.00% |
|  | 0.00% |  | 0.00% | 1 | 2.78% |  | 0.00% |
|  | 0.00% |  | 0.00% |  | 0.00% | 1 | 7.14% |
|  | 0.00% |  | 0.00% |  | 0.00% |  | 0.00% |
| 4 | 6.67% | 1 | 0.90% |  | 0.00% |  | 0.00% |
|  | 0.00% | 1 | 0.90% |  | 0.00% |  | 0.00% |
| 1 | 1.67% |  | 0.00% | 1 | 2.78% | 1 | 7.14% |
|  | 0.00% | 3 | 2.70% | 2 | 5.56% |  | 0.00% |
| 2 | 3.33% | 1 | 0.90% | 3 | 8.33% | 1 | 7.14% |
|  | 0.00% |  | 0.00% |  | 0.00% |  | 0.00% |
|  | 0.00% |  | 0.00% |  | 0.00% | 1 | 7.14% |
| 6 | 10.00% | 5 | 4.50% | 2 | 5.56% |  | 0.00% |
| 4 | 6.67% | 8 | 7.21% | 1 | 2.78% | 1 | 7.14% |
| 2 | 3.33% | 4 | 3.60% | 1 | 2.78% | 1 | 7.14% |
|  | 0.00% |  | 0.00% | 1 | 2.78% |  | 0.00% |
| 5 | 8.33% | 5 | 4.50% | 1 | 2.78% |  | 0.00% |
| 1 | 1.67% |  | 0.00% | 1 | 2.78% |  | 0.00% |
| 1 | 1.67% | 4 | 3.60% |  | 0.00% |  | 0.00% |
| 1 | 1.67% | 1 | 0.90% |  | 0.00% |  | 0.00% |
|  | 0.00% |  | 0.00% |  | 0.00% |  | 0.00% |
|  | 0.00% |  | 0.00% |  | 0.00% |  | 0.00% |
| 60 | 100.00% | 111 | 100.00% | 36 | 100.00% | 14 | 100.00% |

FIG. 30O

| (blank) | | | | |
|---|---|---|---|---|
| 7 | | | | |
| Number of times biomarker flagged as | % in tumor type | Grand Total | % in tumor type | Gene |
| 4 | 4.82% | 370 | 4.18% | ADA |
| | 0.00% | 65 | 0.72% | AR |
| | 0.00% | 102 | 1.13% | ASNS |
| | 0.00% | 1 | 0.01% | ASNS |
| | 0.00% | 76 | 0.84% | BRCA1 |
| 1 | 1.20% | 120 | 1.32% | BRCA2 |
| | 0.00% | 4 | 0.04% | CD52 |
| | 0.00% | 16 | 0.18% | CDW52 |
| | 0.00% | 213 | 2.35% | CES2 |
| 2 | 2.41% | 182 | 2.01% | DCK |
| | 0.00% | 58 | 0.64% | DHFR |
| 3 | 3.61% | 151 | 1.67% | DNMT1 |
| 3 | 3.61% | 267 | 2.95% | DNMT3A |
| 5 | 6.02% | 339 | 3.74% | DNMT3B |
| | 0.00% | 126 | 1.39% | EGFR |
| 1 | 1.20% | 37 | 0.41% | EPHA2 |
| | 0.00% | 66 | 0.73% | ERBB2 |
| | 0.00% | 1 | 0.01% | ERCC3 |
| 2 | 2.41% | 87 | 0.96% | ESR1 |
| 1 | 1.20% | 100 | 1.10% | FLT1 |
| 5 | 6.02% | 366 | 4.04% | GART |
| | 0.00% | 1 | 0.01% | GNRH1 |
| 3 | 3.61% | 346 | 3.82% | HIF1A |
| | 0.00% | 111 | 1.22% | HSP90AA1 |
| 1 | 1.20% | 81 | 0.89% | HSPCA |
| | 0.00% | 6 | 0.07% | IL2RA |
| | 0.00% | 39 | 0.43% | KDR |
| | 0.00% | 88 | 0.97% | KIT |
| | 0.00% | 2 | 0.02% | LCK |
| 4 | 4.82% | 398 | 4.39% | MGMT |
| 1 | 1.20% | 14 | 0.15% | MLH1 |
| 1 | 1.20% | 49 | 0.54% | MSH2 |
| 3 | 3.61% | 278 | 3.07% | NFKB1 |
| 3 | 3.61% | 321 | 3.54% | NFKB2 |
| 4 | 4.82% | 395 | 4.36% | NFKBIA |
| | 0.00% | 41 | 0.45% | PDGFC |
| | 0.00% | 71 | 0.78% | PDGFRA |
| | 0.00% | 229 | 2.53% | PDGFRB |
| | 0.00% | 22 | 0.24% | PGR |
| 1 | 1.20% | 21 | 0.23% | PTEN |
| | 0.00% | 100 | 1.10% | PTGS2 |
| | 0.00% | 9 | 0.10% | RARA |
| | 0.00% | 61 | 0.67% | RRM1 |
| 2 | 2.41% | 159 | 1.75% | RRM2 |
| 1 | 1.20% | 114 | 1.26% | RRM2B |
| 1 | 1.20% | 26 | 0.29% | RXRG |
| 2 | 2.41% | 260 | 2.87% | SPARC |
| 2 | 2.41% | 136 | 1.50% | SRC |
| 1 | 1.20% | 152 | 1.68% | SSTR1 |
| 1 | 1.20% | 101 | 1.11% | SSTR2 |
| 3 | 3.61% | 396 | 4.37% | SSTR3 |
| 2 | 2.41% | 157 | 1.54% | SSTR4 |
| 1 | 1.20% | 96 | 1.06% | SSTR5 |
| 4 | 4.82% | 396 | 4.37% | TOP1 |
| 4 | 4.82% | 384 | 4.24% | TOP2A |
| 4 | 4.82% | 360 | 4.07% | TOP2B |
| 2 | 2.41% | 96 | 1.06% | TYMS |
| 1 | 1.20% | 318 | 3.51% | VDR |
| 1 | 1.20% | 138 | 1.52% | VEGF |
| 2 | 2.41% | 181 | 2.00% | VEGFA |
| 1 | 1.20% | 56 | 0.62% | VHL |
| | 0.00% | 79 | 0.87% | YES1 |
| | 0.00% | 2 | 0.02% | ZAP70 |
| 83 | 100.00% | 9065 | 100.00% | Grand Total |

FIG. 31

| Grand Total | % in tumor type | Gene |
|---|---|---|
| 9065 | 100.00% | Grand Total |
| 398 | 4.39% | MGMT |
| 396 | 4.37% | SSTR3 |
| 396 | 4.37% | TOP1 |
| 395 | 4.36% | NFKBIA |
| 384 | 4.24% | TOP2A |
| 379 | 4.18% | ADA |
| 369 | 4.07% | TOP2B |
| 366 | 4.04% | GART |
| 346 | 3.82% | HIF1A |
| 339 | 3.74% | DNMT3B |
| 321 | 3.54% | NFKB2 |
| 318 | 3.51% | VDR |
| 278 | 3.07% | NFKB1 |
| 267 | 2.95% | DNMT3A |
| 260 | 2.87% | SPARC |
| 229 | 2.53% | PDGFRB |
| 213 | 2.35% | CES2 |
| 182 | 2.01% | DCK |
| 181 | 2.00% | VEGFA |
| 167 | 1.84% | SSTR4 |
| 159 | 1.75% | RRM2 |
| 152 | 1.68% | SSTR1 |
| 151 | 1.67% | DNMT1 |
| 138 | 1.52% | VEGF |
| 136 | 1.50% | SRC |
| 126 | 1.39% | EGFR |
| 120 | 1.32% | BRCA2 |
| 114 | 1.26% | RRM2B |
| 111 | 1.22% | HSP90AA1 |
| 102 | 1.13% | ASNS |
| 101 | 1.11% | SSTR2 |
| 100 | 1.10% | FLT1 |
| 100 | 1.10% | PTGS2 |
| 96 | 1.06% | SSTR5 |
| 96 | 1.06% | TYMS |
| 88 | 0.97% | KIT |
| 87 | 0.96% | ESR1 |
| 81 | 0.89% | HSPCA |
| 79 | 0.87% | YES1 |
| 76 | 0.84% | BRCA1 |
| 71 | 0.78% | PDGFRA |
| 66 | 0.73% | ERBB2 |
| 65 | 0.72% | AR |
| 61 | 0.67% | RRM1 |
| 58 | 0.64% | DHFR |
| 56 | 0.62% | VHL |
| 49 | 0.54% | MSH2 |
| 41 | 0.45% | PDGFC |
| 39 | 0.43% | KDR |
| 37 | 0.41% | EPHA2 |
| 26 | 0.29% | RXRG |
| 22 | 0.24% | PGR |
| 21 | 0.23% | PTEN |
| 16 | 0.18% | CDW52 |
| 14 | 0.15% | MLH1 |
| 9 | 0.10% | RARA |
| 6 | 0.07% | IL2RA |
| 4 | 0.04% | CD52 |
| 2 | 0.02% | LCK |
| 2 | 0.02% | ZAP70 |
| 1 | 0.01% | ASNS |
| 1 | 0.01% | ERCC3 |
| 1 | 0.01% | GNRH1 |

FIG. 39

Microarray Analysis on Formalin-Fixed Tissue for RNA Expression

| Gene | Ratio | Expression | Significant Result | Gene | Ratio | Expression | Significant Result | Gene | Ratio | Expression | Significant Result |
|---|---|---|---|---|---|---|---|---|---|---|---|
| KIT | 0.10 | Indeterminate | | RRM1 | 0.79 | No Change | | DHFR | 1.27 | No Change | |
| TOP2B | 0.22 | Under Expressed* | | PDGFRB | 0.81 | No Change | | ABCG2 | 1.28 | No Change | |
| OGFR | 0.23 | Indeterminate | | NFKB1 | 0.93 | No Change | | TNF | 1.31 | Indeterminate | |
| MLH1 | 0.29 | Indeterminate | | LYN | 0.94 | No Change | | NFKB2 | 1.32 | Indeterminate | |
| CD33 | 0.31 | Indeterminate | | DNMT3A | 0.94 | Indeterminate | | GDA | 1.33 | No Change | |
| SSTR2 | 0.31 | Indeterminate | | CD52 | 0.95 | Indeterminate | | HSP90AA1 | 1.34 | No Change | |
| AR | 0.42 | Indeterminate | | TOP2A | 0.97 | Indeterminate | | RARA | 1.42 | Indeterminate | |
| ERCC3 | 0.43 | Indeterminate | | RXRG | 0.97 | Indeterminate | | CES2 | 1.44 | No Change | |
| PDGFRA | 0.44 | Under Expressed* | | HCK | 0.97 | No Change | | TYMS | 1.50 | Indeterminate | |
| SPARC | 0.45 | Under Expressed* | | PTEN | 1.01 | No Change | | HIF1A | 1.64 | Over Expressed | ✓ |
| PGR | 0.50 | Indeterminate | | BRCA1 | 1.01 | Indeterminate | | SRC | 1.64 | Indeterminate | |
| RAF1 | 0.50 | Under Expressed* | | FLT1 | 1.04 | Indeterminate | | MGMT | 1.73 | Over Expressed | ✓ |
| GART | 0.55 | Under Expressed* | | DNMT3B | 1.05 | Indeterminate | | VDR | 1.83 | Indeterminate | |
| FOLR2 | 0.57 | Under Expressed* | | SSTR3 | 1.06 | Indeterminate | | GSTP1 | 1.84 | Over Expressed | |
| ADA | 0.57 | Under Expressed* | | DNMT1 | 1.11 | No Change | | EGFR | 1.94 | Indeterminate | |
| POLA1 | 0.59 | Indeterminate | | IL2RA | 1.12 | Indeterminate | | TK1 | 1.94 | Over Expressed | |
| ZAP70 | 0.59 | Indeterminate | | SSTR4 | 1.13 | Indeterminate | | BIRC5 | 2.14 | Indeterminate | |
| ESR1 | 0.63 | Indeterminate | | BRCA2 | 1.16 | Indeterminate | | MSH2 | 2.17 | Indeterminate | |
| LCK | 0.63 | Indeterminate | | HDAC1 | 1.17 | No Change | | VEGFA | 2.22 | Over Expressed | |
| TXNRD1 | 0.64 | Indeterminate | | GNRH1 | 1.18 | No Change | | EPHA2 | 2.35 | Indeterminate | |
| SSTR1 | 0.65 | Indeterminate | | ERCC1 | 1.19 | Indeterminate | | VHL | 2.75 | Over Expressed | |
| KDR | 0.66 | Indeterminate | | RRM2B | 1.19 | No Change | | SSTR5 | 3.43 | Indeterminate | |
| PDGFC | 0.68 | No Change | | RXRB | 1.20 | No Change | | ABCC1 | 3.59 | Indeterminate | |
| FYN | 0.71 | No Change | | MS4A1 | 1.20 | Indeterminate | | ECGF1 | 4.08 | Over Expressed | |
| DCK | 0.71 | No Change | | ERBB2 | 1.23 | No Change | | RRM2 | 9.01 | Indeterminate | |
| ASNS | 0.75 | No Change | | TOP1 | 1.25 | Indeterminate | | PTGS2 | 9.21 | Over Expressed | ✓ |
| BCL2 | 0.77 | Indeterminate | | YES1 | 1.25 | No Change | | | | | |

*Degradation of RNA in FFPE samples may lead to a call of under expressed for a particular gene target. However, please note that the RNA extracted from this patient was of acceptable quality for performance of this test.

FIGURE 40A

 

PAGE 1 of 10

| PATIENT | PHYSICIAN | SPECIMEN |
|---|---|---|
| Case Number: MP-TN00-00000 | Test Ordering Physician, MD | Primary Tumor Site: Ovary |
| Patient: Jane Doe | Test Organization | Specimen Site: Connective tissue |
| Date Of Birth: 01/01/1950 | 1234 Main Street | Specimen Collected: 01/16/2000 |
| Sex: Female | Dallas, TX 75133 | Specimen Received: 1/5/2000 |
| SSN: 123-456-7890 | (123)456-7890 | Date Reported: 1/01/2000 |

Interpretation: Received one paraffin block labeled "123456-A1" from Test University Medical Center, Greenville, SC, with the corresponding surgical pathology report disclosing.

Mass right back, excision: Metastatic adenocarcinoma, extending to inked resection margins.

Interpretation is done by Dr. Ashfaq and signed out by Dr. Gupta for Dr. Ashfaq

Clinical History: Per the submitted patient history, the patient is a 50-year-old female with a history of cancer of unknown primary. She underwent a back mass excision in January 2000 showing metastatic adenocarcinoma. No history of prior therapies were provided.

TARGET NOW SUMMARY - AGENTS ASSOCIATED WITH CLINICAL BENEFIT

The role of Target Now is to identify biomarkers and therapies associated with clinical benefit or lack of clinical benefit for cancer patients. The selection of any, all or none of the matched agents resides with the discretion of the treating physician. If a patient's tumor has previously progressed on an agent identified as associated with clinical benefit on this report, the patient should not be re-treated with this agent.

| Biomarker | Assay | Results | Agents Associated With CLINICAL BENEFIT |
|---|---|---|---|
| TOPO1 | IHC | Significant (+2, 85%) | irinotecan |
| PDGFR | IHC | Significant (+2, 80%) | imatinib |
| c - kit | IHC | Significant (+2, 50%) | imatinib |
| SPARC | IHC | Significant (+2, 50%) | nab-paclitaxel |
| ER | IHC | Significant (+1, 20%) | tamoxifen, aromatase inhibitors (anastrozole, letrozole) |
| PTGS2 | Microarray | Increased (9.21) | celecoxib |
| HIF1A | Microarray | Increased (1.64) | sorafenib, sunitinib, bevacizumab |
| GART | Microarray | Decreased (.66) | pemetrexed |

* Caris Dx has defined threshold levels of reactivity for IHC based on published evidence

FIGURE 40B

TARGET NOW.

PAGE 2 of 10

PATIENT INFORMATION
Patient: Jane Doe   Case Number: MP-TN00-00000   Ordering Physician: Test Ordering Physician, MD

TARGET NOW SUMMARY

| Biomarker | Assay | Results | Agents Associated With LACK OF CLINICAL BENEFIT |
|---|---|---|---|
| MGMT | IHC | Significant (+3, 50%) | temozolomide |
| MGMT | Microarray | Increased (1.73) | temozolomide |
| ERCC1 | IHC | Significant (+2, 80%) | cisplatin; carboplatin |
| BCRP | IHC | Significant (+2, 60%) | cisplatin, carboplatin |
| RRM1 | IHC | Significant (+2, 80%) | gemcitabine |
| MRP1 | IHC | Significant (+2, 40%) | etoposide, vincristine |
| PGP | IHC | Significant (+1, 10%) | etoposide, vincristine |
| TS | IHC | Significant (+2, 35%) | fluoropyrimidines |

FIGURE 40C

PATIENT INFORMATION
Patient: Jane Doe   Case Number: MP-TN00-00000   Ordering Physician: Test Ordering Physician, MD

| Biomarker | Information on Therapeutic Impact from Literature | Literature Level of Evidence |
|---|---|---|
| SPARC | High SPARC protein was associated with response to nab-paclitaxel-based combination therapy | III / Good |
| TOPO1 | High expression of TOPO1 has been associated with a higher response rate when treated with irinotecan | II-3 / Fair |
| PGP | High expression of P-glycoprotein has been associated with lack of response to Etoposide and Vincristine | II-3 / Fair |
| BCRP | High expression of BCRP has been associated with shorter progression-free (PFS) and overall survival (OS) when treated with platinum-based combination chemotherapy | II-3 / Good |
| MRP1 | High expression of MRP1 has been associated with lack of response to Etoposide and Vincristine. | II-3 / Fair |
| TS | High TS expression levels are associated with poor response to fluoropyrimidines and shorter OS and DFS. | II-3 / Good |
| ERCC1 | High expression of ERCC1 has been associated with lower response rates and a significantly shorter median progression-free and overall survival when treated with platinum-based chemotherapy. | II-3 / Good |
| RRM1 | High RRM1 expression was associated with lack of response to gemcitabine treatment and poor outcome | II-3 / Good |
| MGMT | High expression of MGMT has been associated with resistance to temozolomide-based therapy | II-3 / Good |
| c - kit | High expression of c-Kit has been associated with significantly better survival, when treated with imatinib | II-2 / Fair |
| PDGFR | High expression of PDGFR a has been associated with response to imatinib treatment | III / Fair |
| ER | High expression of ER has been associated with response to endocrine therapy. | II-3 / Good |
| GART | Biomarker associations with drugs based on microarray results have been identified by mechanistic association | |
| HIF1A | | |
| MGMT | | |
| PTGS2 | | |

FIGURE 40D

PATIENT INFORMATION
Patient: Jane Doe    Case Number: MP-TN00-00000    Ordering Physician: Test Ordering Physician, MD

IHC Biomarker Detail

| Biomarker | Significant Result** | Patient Tumor | | Threshold* Biomarker Intensity/Percentage |
|---|---|---|---|---|
| | | Staining Intensity | Percent Staining | |
| MGMT | ✓ | 3 | 50 | ≥1+ and ≥50% or <1+ and <10% |
| TOPO1 | ✓ | 2 | 65 | ≥10% or <10% |
| ERCC1 | ✓ | 2 | 60 | ≥2+ and ≥50% or ≤1+ and ≤25% |
| RRM1 | ✓ | 2 | 80 | ≥2+ and ≥50% or =0+ and =100% |
| PDGFR | ✓ | 2 | 60 | ≥2+ and ≥30% |
| BCRP | ✓ | 2 | 60 | ≥1+ and ≥10% or <1+ and <10% |
| SPARC *** | ✓ | 2 | 50 | ≥2+ and ≥30% |
| c - kit | ✓ | 2 | 50 | ≥2+ and ≥30% |
| MRP1 | ✓ | 2 | 40 | ≥1+ and ≥10% or <1+ and <10% |
| TS | ✓ | 2 | 35 | ≥2+ and ≥30% or ≤1+ and ≤25% |
| TOP2A | | 2 | 10 | ≥2+ and ≥30% or =0+ and =100% |
| PTEN | | 1 | 70 | ≥2+ and ≥10% or <1+ and ≤10% |
| ER | ✓ | 1 | 20 | ≥2+ and ≥75% |
| Her2/Neu | | 1 | 10 | ≥3+ and ≥30% or ≥2+ and <10% |
| PGP | ✓ | 1 | 10 | ≥1+ and ≥10% or <1+ and <10% |
| PR | | 1 | 5 | ≥1+ and ≥10% or =0% |
| Androgen Receptor | | 0 | 100 | ≥1+ and ≥10% or =0+ and =100% |

*Caris Dx has defined threshold levels of reactivity for IHC to establish cutoff points based on published evidence
** All significant results are reflected in the Target Now Summary.
*** SPARC results reflect analyses performed with both monoclonal and polyclonal antibodies.

FIGURE 40E

PATIENT INFORMATION
Patient: Jane Doe   Case Number: MP-TN00-00000   Ordering Physician: Test Ordering Physician, MD

Microarray Analysis of RNA Expression on Formalin-Fixed Tissue

| Gene | Ratio | Expression | Significant Result | Gene | Ratio | Expression | Significant Result | Gene | Ratio | Expression | Significant Result |
|---|---|---|---|---|---|---|---|---|---|---|---|
| KIT | NI | Not Informative | | RRM1 | 0.79 | No Change | | DHFR | 1.27 | No Change | |
| TOP2B | 0.22 | Under Expressed | | PDGFRB | 0.81 | No Change | | ABCG2 | 1.28 | No Change | |
| OGFR | NI | Not Informative | | NFKB1 | 0.93 | No Change | | TNF | NI | Not Informative | |
| MLH1 | NI | Not Informative | | LYN | 0.94 | No Change | | NFKB2 | NI | Not Informative | |
| CD33 | NI | Not Informative | | DNMT3A | NI | Not Informative | | CDA | 1.33 | No Change | |
| SSTR2 | NI | Not Informative | | CD52 | NI | Not Informative | | HSP90AA1 | 1.34 | No Change | |
| AR | NI | Not Informative | | TOP2A | NI | Not Informative | | RARA | NI | Not Informative | |
| ERCC3 | NI | Not Informative | | RXRG | NI | Not Informative | | CES2 | 1.44 | No Change | |
| PDGFRA | 0.44 | Under Expressed | | HCK | 0.97 | No Change | | TYMS | NI | Not Informative | |
| SPARC | 0.45 | Under Expressed | | PTEN | 1.01 | No Change | | HIF1A | 1.64 | Over Expressed | ✓ |
| PGR | NI | Not Informative | | BRCA1 | NI | Not Informative | | SRC | NI | Not Informative | |
| RAF1 | 0.50 | Under Expressed | | FLT1 | NI | Not Informative | | MGMT | 1.73 | Over Expressed | ✓ |
| GART | 0.55 | Under Expressed | ✓ | DNMT3B | NI | Not Informative | | VDR | NI | Not Informative | |
| FOLR2 | 0.57 | Under Expressed | | SSTR3 | NI | Not Informative | | GSTP1 | 1.84 | Over Expressed | |
| ADA | 0.57 | Under Expressed | | DNMT1 | 1.11 | No Change | | EGFR | NI | Not Informative | |
| POLA1 | NI | Not Informative | | IL2RA | NI | Not Informative | | TK1 | 1.94 | Over Expressed | |
| ZAP70 | NI | Not Informative | | SSTR4 | NI | Not Informative | | BIRC5 | NI | Not Informative | |
| ESR1 | NI | Not Informative | | BRCA2 | NI | Not Informative | | MSH2 | NI | Not Informative | |
| LCK | NI | Not Informative | | HDAC1 | 1.17 | No Change | | VEGFA | 2.22 | Over Expressed | |
| TXNRD1 | NI | Not Informative | | GNRH1 | 1.18 | No Change | | EPHA2 | NI | Not Informative | |
| SSTR1 | NI | Not Informative | | ERCC1 | NI | Not Informative | | VHL | 2.75 | Over Expressed | |
| KDR | NI | Not Informative | | RRM2B | 1.19 | No Change | | SSTR5 | NI | Not Informative | |
| PDGFC | 0.68 | No Change | | RXRB | 1.20 | No Change | | ABCC1 | NI | Not Informative | |
| FYN | 0.71 | No Change | | MS4A1 | NI | Not Informative | | ECGF1 | 4.06 | Over Expressed | |
| DCK | 0.71 | No Change | | ERBB2 | 1.23 | No Change | | RRM2 | NI | Not Informative | |
| ASNS | 0.75 | No Change | | TOP1 | NI | Not Informative | | PTGS2 | 9.21 | Over Expressed | ✓ |
| BCL2 | NI | Not Informative | | YES1 | 1.25 | No Change | | | | | |

"No Change" indicates that there is no difference in expression for this gene between the tumor and control tissues at a significance level of p<=0.001.
A significance level of p<=0.001 has been chosen since genes passing this threshold can be validated as differentially expressed by alternative methods approximately 95% of the time.
"Not Informative" indicates that the data obtained for either the patient sample or the control sample were not of high enough quality to confidently make a call on the expression level of that particular RNA transcript. Therefore, the expression ratios were not informative (NI).

Microarray Comment

RNA extracted from this patient was of acceptable quality for performance of this test.

The expression profiles obtained with FFPE samples show more variability and may differ from expression profiles obtained with fresh frozen samples.

Methodology

Total RNA is extracted from tumor tissue and is converted to cDNA. This cDNA sample is then subjected to a whole genome (24K) microarray analysis using Illumina cDNA-mediated annealing, selection, extension and ligation (DASL) process. The expression of a subset of 80 genes are then compared to a tissue specific normal control and the relative expression ratios of these 80 target genes is determined as well as the statistical significance of the differential expression.

FIGURE 40F

PATIENT INFORMATION
Patient: Jane Doe   Case Number: MP-TN00-00000   Ordering Physician: Test Ordering Physician, MD

Appendix

BIOMARKER DESCRIPTION

| Target | Biomarker Description |
|---|---|
| BCRP | Breast cancer resistance protein (BCRP) is a member of the superfamily of ABC transporter proteins, also known as mitoxantrone resistance protein, ABCP, and ABCG2, was identified in a cancer cell line selected for resistance to daunorubicin. Elevated expression of BCRP in vitro causes resistance to anticancer drugs, including topotecan, irinotecan, mitoxantrone, and doxorubicin. |
| c-kit | c-Kit is a cytokine receptor expressed on the surface of hematopoietic stem cells as well as other cell types. This receptor binds to stem cell factor (SCF, a cell growth factor). As c-Kit is a receptor tyrosine kinase, ligand binding causes receptor dimerizes and initiates a phosphorylation cascade resulting in changes in gene expression. These changes affect proliferation, apoptosis, chemotaxis and adhesion. c-Kit is inhibited by the drugs imatinib, sunitinib and sorafenib. |
| ER | The estrogen receptor (ER) is a member of the nuclear hormone family of intracellular receptors, which is activated by the hormone estrogen. Its main function is as a DNA-binding transcription factor to regulate estrogen-mediated gene expression. ER is expressed in breast, ovarian and endometrial tissue. Estrogen and the receptors are essential for sexual development and reproductive function, but also play a role in other tissues such as bone. Estrogen receptors are over-expressed in many breast cancer cases, referred to as "ER positive". Estrogen binding to ER in cancer cells leads to cancer cell proliferation. Breast tumors marked by ER positivity currently form the basis of selecting patients who will receive and benefit from hormone based therapy. |
| ERCC1 | Nucleotide excision repair (NER) is a DNA repair mechanism necessary for the repair of DNA damage from a vast variety of sources including chemicals and ultraviolet (UV) light from the sun. NER is a particularly important mechanism by which cells prevent unwanted and potentially cancer causing mutations. ERCC1 (excision repair cross complementation group 1) is an important enzyme in the NER pathway. Some anticancer drugs kill cancer cells by causing DNA damage and hence need to overcome the effects of the DNA repair pathways to be effective. For example, platinum based drugs induce DNA cross links that interfere with DNA replication and transcription. Tumors with low ERCC1 expression are more likely to benefit from platinum based DNA damaging agents while tumors that overexpress ERCC1 are more likely to be resistant to such drugs. |
| MGMT | O-6-methylguanine-DNA methyltransferase (MGMT) encodes a DNA repair enzyme. Loss of MGMT expression leads to compromised DNA repair in cells and may play a significant role in cancer formation. Low MGMT expression has been correlated with response to temozolomide. |
| MRP1 | MRP1 (multidrug resistance-associated protein 1) is one of several drug resistance proteins identified to date and is an important mediator of the Multi Drug Resistance (MDR) phenotype in cancer cells. MRP1 is found to confer a lack of response to anthracyclines (eg. doxorubicin, daunorubicin), vinca alkaloids (vincristine, vinblastine), epipodophyllotoxins (etoposide and teniposide), and methotrexate, but probably not taxanes (Paclitaxel, Docetaxel), by causing the efflux of glutathione conjugated natural product agents (glutathione is a peptide composed of 3 amino acids). Elevated levels of MRP1 have been observed in relapsed acute myelogenous leukemia, chronic lymphatic leukemia, small cell and non-small cell lung cancer, and neuroblastoma among other malignancies. |
| PDGFR | Platelet derived growth factors (PDGFs) are important factors regulating many important cellular functions related to cancer development. These growth factors bind to protein tyrosine kinase receptors including PDGFR-α to transmit extracellular signals. Ligand bound receptors form dimers and transphosphorylate tyrosine residues on the receptor leading to activation and changes in gene expression. Imatinib is a drug that targets the tyrosine kinase domain of several tyrosine kinase receptors, including PDGFRs. Imatinib competitively inhibits PDGFR-α activation. Sorafenib and Sunitinib are two additional tyrosine kinase inhibitors which can also block PDGFR-α. |
| PGP | P-glycoprotein (MDR1, ABCB1) is an ATP-dependent transmembrane drug efflux pump with broad substrate specificity, which pumps antitumor drugs out of cells. Its expression is often induced by chemotherapy drugs and is thought to be a major mechanism of chemotherapy resistance. Over-expression of Pgp can be a negative predictive factor for various drugs such as anthracyclines (doxorubicin, epirubicin), paclitaxel, vinblastine etc. Pgp remains the most important and dominant representative of Multi-Drug Resistance phenotype and is correlated with disease state and resistant phenotype. |
| RRM1 | Ribonucleotide reductase subunit M1 (RRM1) is a component of the ribonucleotide reductase holoenzyme consisting of M1 and M2 subunits. The ribonucleotide reductase is a rate-limiting enzyme involved in the production of nucleotides required for DNA synthesis. Gemcitabine is a deoxycytidine analogue which inhibits ribonucleotide reductase activity. Based on the literature, RRM1 levels are a predictor of patient response when treated with gemcitabine. |
| SPARC | SPARC (secreted protein acidic and rich in cysteine) is a calcium binding matricellular glycoprotein secreted by many types of cells. It has a central role in wound repair, cell migration, and cell-matrix interactions. Its over-expression is thought to have a role in tumor invasion and angiogenesis. A few studies indicate that SPARC over-expression improves the response to the anti-cancer drug, nab-paclitaxel. The improved response is thought to be related to SPARC's role in accumulating albumin and albumin targeted agents within tumor tissue. |

FIGURE 40G

TARGET◉NOW.

PAGE 7 of 10

PATIENT INFORMATION
Patient: Jane Doe    Case Number: MP-TN00-00000    Ordering Physician: Test Ordering Physician, MD

Appendix

BIOMARKER DESCRIPTION

| Target | Biomarker Description |
|---|---|
| TOPO1 | Topoisomerase I is an enzyme that alters the supercoiling of double-stranded DNA. Topo1 acts by transiently cutting one strand of the DNA to relax the coil and extend the DNA molecule. The regulation of DNA supercoiling is essential to DNA transcription and replication, when the DNA helix must unwind to permit the proper function of the enzymatic machinery involved in these processes. Higher expression of Topo1 has been associated with response to first line chemotherapy containing irinotecan, a Topo1 inhibitor. |
| TS | Thymidylate synthetase (TS) is an enzyme that generates thymidine monophosphate (dTMP), which get phosphorylated to thymidine triphosphate (dTTP) for use in DNA synthesis and repair. The reactions catalyzed by TS also yield dihydrofolate as a secondary product. As an anti-cancer chemotherapy target, thymidylate synthetase can be inhibited by fluoropyrimidine or certain folate analogues. High TS has been associated with lack of response to fluoropyrimidine whereas low or no TS expression has been associated with improved clinical response to fluoropyrimidine. |

PAGE 9 of 10

PATIENT INFORMATION
Patient: Jane Doe   Case Number: MP-TN00-00000   Ordering Physician: Test Ordering Physician, MD

LITERATURE LEVEL of EVIDENCE

| Target | Reference | Level of Evidence |
|---|---|---|
| SPARC | Yardley, D.A., et al. Phase II study of neoadjuvant gemcitabine, epirubicin, and albumin-bound nab-paclitaxel (GEA) in locally advanced breast cancer with SPARC tumor assessments. J Clin Oncol (May 20 suppl; abst) A03), 2008: 26 | III / Good |
| TOPO1 | Braun, M.S., et al. Predictive biomarkers of chemotherapy efficacy in colorectal cancer: results from the UK MRC FOCUS trial. J Clin Oncol, 2008. 26(16): p. 2690-8. | II-1 / Good |
| TOPO1 | Nanwa, J., et al. Genetic diagnosis for chemosensitivity with drug-resistance genes in epithelial ovarian cancer. Int J Gynecol Cancer, 2007. 17(1): p. 76-82. | II-3 / Good |
| TS | Paradiso, A., G. Simone, et al. (2000). "Thymidylate synthase and p53 primary tumour expression as predictive factors for advanced colorectal cancer patients." Br J Cancer 82(3): 560-7. | II-3 / Good |
| TS | Hu, Y.C., R.A. Komorowski, et al. (2003) "Thymidylate synthase expression predicts the response to 5-fluorouracil-based adjuvant therapy in pancreatic cancer." Clin Cancer Res 9(11): 4165-71. | II-3 / Good |
| TS | Johnston, P.G., R. Mick, et al. (1997) "Thymidylate synthase expression and response to neoadjuvant chemotherapy in patients with advanced head and neck cancer." J Natl Cancer Inst 89(4): 308-13. | II-3 / Good |

FIGURE 40J

TARGET NOW

PAGE 10 of 10

PATIENT INFORMATION
Patient: Jane Doe   Case Number: MP-TN00-00000   Ordering Physician: Test Ordering Physician, MD

LITERATURE LEVEL OF EVIDENCE ASSESSMENT FRAMEWORK*

Study Design

| Hierarchy of Design | Criteria |
|---|---|
| I | Evidence obtained from at least one properly designed randomized controlled trial. |
| II-1 | Evidence obtained from well-designed controlled trials without randomization. |
| II-2 | Evidence obtained from well-designed cohort or case-control analytic studies, preferably from more than one center or research group. |
| II-3 | Evidence obtained from multiple time series with or without the intervention. Dramatic results in uncontrolled trials might also be regarded as this type of evidence. |
| III | Opinions of respected authorities, based on clinical experience, descriptive studies, or reports of expert committees. |

Study Validity

| Grade | Criteria |
|---|---|
| Good | The study is judged to be valid and relevant as regards results, statistical analysis, and conclusions and shows no significant flaws. |
| Fair | The study is judged to be valid and relevant as regards results, statistical analysis, and conclusions, but contains at least one significant but not fatal flaw. |
| Poor | The study is judged to have a fatal flaw such that the conclusions are not valid for the purposes of this test. |

*Adapted from Harris, R., D. Atkins, et al. (2001) "Current Methods of the U.S. Preventive Services Task Force." Am J Prev Med 20(3S).

Disclaimer

This test was developed by Caris MPI and their performance characteristic was determined by Caris MPI. It has not been cleared or approved by the U.S. Food and Drug Administration (FDA). These tests are permitted for clinical purposes and should not be regarded as purely investigational or for research only. Caris MPI is certified under the Clinical Laboratory Improvement Amendments of 1988 (CLIA) as qualified to perform high-complexity clinical testing.

By requesting and/or utilizing this test and the report, you agree that the associated analyses, interpretation, and intellectual property generated by the utilization or included in the report is copyright protected, proprietary, and owned by Caris MPI. Caris MPI grants to the physician a limited right to use the information to care for the associated patient, but for no other purpose, including but not limited to validating or creating a similar test, program, or report, which is strictly prohibited unless by the express written permission of Caris MPI and with appropriate patient consents. By requesting and/or utilizing this report, you agree that in the event of a breach of these provisions, Caris MPI shall be entitled to receive as liquidated damages an immediate payment of $100,000 for each violation and 1% of the total amount for each day that such a breach continues while acknowledging and agreeing that actual damages for such a breach would be difficult to calculate, and that such an amount constitutes a reasonable estimate necessary to compensate Caris MPI for the damage suffered by it as a result of the breach of these provisions that are intended to limit the use of the test for the care of the associated patient.

Decisions on care and treatment should be based on the independent medical judgment of the treating physician taking into consideration all available information concerning the patient's condition, including other laboratory tests, in accordance with the standard of care in a given community. Decisions regarding care and treatment should not be based on a single test such as this test. The finding of a biomarker expression does not necessarily indicate pharmacologic effectiveness or lack thereof. If a patient's tumor has previously progressed on an agent identified as associated with clinical benefit on this report, the patient should not be re-treated with this agent.

MOLECULAR PROFILING OF TUMORS

RELATED APPLICATIONS

This application is a continuation of U.S. patent application Ser. No. 12/658,770, filed Feb. 12, 2010, now U.S. Pat. No. 8,768,629, which issued Jul. 1, 2014 and which claims the benefit of U.S. Provisional Applications 61/151,758, filed on Feb. 11, 2009, 61/170,565, filed on Apr. 17, 2009, 61/217,289, filed on May 28, 2009, 61/229,686, filed on Jul. 29, 2009, 61/279,970, filed on Oct. 27, 2009, 61/261,709, filed on Nov. 16, 2009, and 61/294,440, filed on Jan. 12, 2010; and this application is a continuation-in-part of U.S. patent application Ser. No. 13/188,350, filed Jul. 21, 2011, which is a continuation of U.S. patent application Ser. No. 12/579,241, filed Oct. 14, 2009, which claims the benefit of U.S. Provisional Applications 61/105,335, filed Oct. 14, 2008, and 61/106,921, filed Oct. 20, 2008; and this application is also a continuation-in-part of U.S. patent application Ser. No. 11/750,721, filed on May 18, 2007, now U.S. Pat. No. 8,700,335, issued Apr. 15, 2014, which claims the benefit of U.S. Provisional Application No. 60/747,645, filed May 18, 2006; all of which applications are incorporated herein by reference in their entirety.

BACKGROUND

Disease states in patients are typically treated with treatment regimens or therapies that are selected based on clinical based criteria; that is, a treatment therapy or regimen is selected for a patient based on the determination that the patient has been diagnosed with a particular disease (which diagnosis has been made from classical diagnostic assays). Although the molecular mechanisms behind various disease states have been the subject of studies for years, the specific application of a diseased individual's molecular profile in determining treatment regimens and therapies for that individual has been disease specific and not widely pursued.

Some treatment regimens have been determined using molecular profiling in combination with clinical characterization of a patient such as observations made by a physician (such as a code from the International Classification of Diseases, for example, and the dates such codes were determined), laboratory test results, x-rays, biopsy results, statements made by the patient, and any other medical information typically relied upon by a physician to make a diagnosis in a specific disease. However, using a combination of selection material based on molecular profiling and clinical characterizations (such as the diagnosis of a particular type of cancer) to determine a treatment regimen or therapy presents a risk that an effective treatment regimen may be overlooked for a particular individual since some treatment regimens may work well for different disease states even though they are associated with treating a particular type of disease state.

Patients with refractory and metastatic cancer are of particular concern for treating physicians. The majority of patients with metastatic cancer eventually run out of treatment options for their tumors. These patients have very limited options after their tumor has progressed on standard front line and second line (and sometimes third line and beyond) therapies. Although these patients may participate in Phase I and Phase II clinical trials for new anticancer agents, they must usually meet very strict eligibility criteria to do so. Studies have shown that when patients participate in these types of trials, the new anticancer agent may give response rates of anywhere from 5% to 10% on average in Phase I settings to 12% in Phase II settings. These patients also have the option of electing to receive the best supportive care to treat their symptoms.

There has recently been an explosion of interest in developing new anticancer agents that are more targeted against a cell surface receptor or an upregulated or amplified gene product. This approach has met with some success (e.g. trastuzumab against HER2/neu in breast cancer cells, rituximab against CD20 in lymphoma cells, bevacizamab against VEGF, and cetuximab against EGFR). However, patients' tumors still eventually progress on these therapies. If a larger number of targets or molecular findings such as molecular mechanisms, genes, gene expressed proteins, and/or combinations of such were measured in a patient's tumor, one may find additional targets or molecular findings that can be exploited by using specific therapeutic agents. Identifying multiple agents that can treat multiple targets or underlying mechanisms would provide cancer patients with a viable therapeutic alternative to those treatment regimens which currently exist.

Molecular profiling analysis identifies one or more individual profiles that often drive more informed and effective personalized treatment options, which can result in improved patient care and enhanced treatment outcomes. The present invention provides methods and systems for identifying treatments for these individuals by molecular profiling a sample from the individual.

SUMMARY OF THE INVENTION

The present invention provides methods and system for molecular profiling, using the results from molecular profiling to identify treatments for individuals. In some embodiments, the treatments were not identified initially as a treatment for the disease.

In an aspect, the invention provides a method of identifying a candidate treatment for a subject in need thereof, comprising: performing an immunohistochemistry (IHC) analysis on a sample from the subject to determine an IHC expression profile on at least five proteins; performing a microarray analysis on the sample to determine a microarray expression profile on at least ten genes; performing a fluorescent in-situ hybridization (FISH) analysis on the sample to determine a FISH mutation profile on at least one gene; performing DNA sequencing on the sample to determine a sequencing mutation profile on at least one gene; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have no mutations, or one or more mutations in one or more genes included in the FISH mutation profile; and/or iv. have no mutations, or one or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer.

In some embodiments, the IHC expression profiling comprises assaying one or more of SPARC, PGP, Her2/neu, ER, PR, c-kit, AR, CD52, PDGFR, TOP2A, TS, ERCC1, RRM1, BCRP, TOPO1, PTEN, MGMT, and MRP1.

In some embodiments, the microarray expression profiling comprise assaying one or more of ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70.

In some embodiments, the FISH mutation profiling comprises assaying EGFR and/or HER2.

In some embodiments, the sequencing mutation profiling comprises assaying one or more of KRAS, BRAF, c-KIT and EGFR.

In another aspect, the invention provides a method of identifying a candidate treatment for a subject in need thereof, comprising: performing an immunohistochemistry (IHC) analysis on a sample from the subject to determine an IHC expression profile on at least five of: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least five of: ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on EGFR and/or HER2; performing DNA sequencing on the sample to determine a sequencing mutation profile on at least one of KRAS, BRAF, c-KIT and EGFR; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have no mutations, or one or more mutations in one or more genes included in the FISH mutation profile; and/or iv. have no mutations, or one or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer. In some embodiments, the IHC expression profiling is performed on at least 50%, 60%, 70%, 80% or 90% of the biomarkers listed. In some embodiments, the microarray expression profiling is performed on at least 50%, 60%, 70%, 80% or 90% of the biomarkers listed.

In a third aspect, the invention provides a method of identifying a candidate treatment for a cancer in a subject in need thereof, comprising: performing an immunohistochemistry (IHC) analysis on a sample from the subject to determine an IHC expression profile on at least the group of proteins consisting of: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least the group of genes consisting of ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on at least the group of genes consisting of EGFR and HER2; performing DNA sequencing on the sample to determine a sequencing mutation profile on at least the group of genes consisting of KRAS, BRAF, c-KIT and EGFR; and comparing the IHC expression profile, microarray expression profile, FISH mutation profile and sequencing mutation profile against a rules database. The rules database comprises a mapping of treatments whose biological activity is known against cancer cells that: i. overexpress or underexpress one or more proteins included in the IHC expression profile; ii. overexpress or underexpress one or more genes included in the microarray expression profile; iii. have zero or more mutations in one or more genes included in the FISH mutation profile; and/or iv. have zero or more mutations in one or more genes included in the sequencing mutation profile. The candidate treatment is identified if: i. the comparison step indicates that the treatment should have biological activity against the cancer; and ii. the comparison step does not contraindicate the treatment for treating the cancer.

In some embodiments of the methods of the invention, the sample comprises formalin-fixed paraffin-embedded (FFPE) tissue, fresh frozen (FF) tissue, or tissue comprised in a solution that preserves nucleic acid or protein molecules. In some embodiments, any one of the microarray analysis, the FISH mutational analysis or the sequencing mutation analysis is not performed. For example, a method may not be performed unless the sample passes a quality control test. In some embodiments, the quality control test comprises an A260/A280 ratio or a Ct value of RT-PCR of RPL13a mRNA. For example, the quality control test can require an A260/A280 ratio <1.5 or the RPL13a Ct value is >30.

In some embodiments, the microarray expression profiling is performed using a low density microarray, an expression microarray, a comparative genomic hybridization (CGH) microarray, a single nucleotide polymorphism (SNP) microarray, a proteomic array or an antibody array.

The methods of the invention can require assaying of certain markers, including additional markers. In some embodiments, the IHC expression profiling is performed on at least SPARC, TOP2A and/or PTEN. The microarray expression profiling can be performed on at least CD52. The IHC expression profiling further consists of assaying one or more of DCK, EGFR, BRCA1, CK 14, CK 17, CK 5/6, E-Cadherin, p95, PARP-1, SPARC and TLE3. In some embodiments, the IHC expression profiling further consists of assaying Cox-2 and/or Ki-67. In some embodiments, the microarray expression profiling further consists of assaying HSPCA. In some embodiments, the FISH mutation profiling further consists of assaying c-Myc and/or TOP2A. The sequencing mutation profiling can comprise assaying PI3K.

A number of genes and gene products can be assayed according to the methods of the invention. For example, the genes used for the IHC expression profiling, the microarray expression profiling, the FISH mutation profiling, and the sequencing mutation profiling independently comprise one or more of ABCC1, ABCG2, ACE2, ADA, ADH1C, ADH4, AGT, Androgen receptor, AR, AREG, ASNS, BCL2, BCRP, BDCA1, BIRC5, B-RAF, BRCA1, BRCA2, CA2, caveolin, CD20, CD25, CD33, CD52, CDA, CDK2, CDW52, CES2, CK 14, CK 17, CK 5/6, c-KIT, c-Myc, COX-2, Cyclin D1, DCK, DHFR, DNMT1, DNMT3A, DNMT3B, E-Cadherin, ECGF1, EGFR, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, Her2/Neu, HGF, HIF1A, HIG1, HSP90, HSP90AA1, HSPCA, IL13RA1, IL2RA, KDR, KIT, K-RAS, LCK, LTB, Lymphotoxin Beta Receptor, LYN, MGMT, MLH1, MRP1, MS4A1, MSH2, Myc, NFKB1, NFKB2, NFKBIA, ODC1, OGFR, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SPARC MC, SPARC PC, SRC, SSTR1, SSTR2, SSTR3, SSTR4, SSTR5, Survivin, TK1, TLE3, TNF, TOP1, TOP2A, TOP2B, TOPO1, TOPO2B, Topoisomerase II, TS, TXN, TXNRD1, TYMS, VDR, VEGF, VEGFA, VEGFC, VHL, YES1 and ZAP70.

In some embodiments, the microarray expression analysis comprises identifying whether a gene is upregulated or downregulated relative to a reference with statistical significance. The statistical significance can be determined at a p-value of less than or equal to 0.05, 0.01, 0.005, 0.001, 0.0005, or 0.0001. The p-value can also be corrected for multiple comparisons. Correction for multiple comparisons can include Bonneferoni's correction or a modification thereof.

In some embodiments, the IHC analysis comprises determining whether 30% or more of said sample is +2 or greater in staining intensity.

The rules contained within the rules database used by the methods of the invention can be based on the efficacy of various treatments particular for a target gene or gene product. The rules database can comprise the rules listed herein in Table 1 and/or Table 2.

In some embodiments of the methods of the invention, a prioritized list of candidate treatments are identified. Prioritizing can include ordering the treatments from higher priority to lower priority according to treatments based on microarray analysis and either IHC or FISH analysis; treatments based on IHC analysis but not microarray analysis; and treatments based on microarray analysis but not IHC analysis.

In some embodiments of the methods of the invention, the candidate treatment comprises administration of one or more candidate therapeutic agents. The one or more candidate therapeutic agents can be 5-fluorouracil, abarelix, Alemtuzumab, aminoglutethimide, Anastrazole, aromatase inhibitors (anastrazole, letrozole), asparaginase, aspirin, ATRA, azacitidine, bevacizumab, bexarotene, Bicalutamide, bortezomib, calcitriol, capecitabine, Carboplatin, celecoxib, Cetuximab, Chemoendocrine therapy, cholecalciferol, Cisplatin, carboplatin, Cyclophosphamide, Cyclophosphamide/ Vincristine, cytarabine, dasatinib, decitabine, Doxorubicin, Epirubicin, epirubicin, Erlotinib, Etoposide, exemestane, fluoropyrimidines, Flutamide, fulvestrant, Gefitinib, Gefitinib and Trastuzumab, Gemcitabine, gonadorelin, Goserelin, hydroxyurea, Imatinib, Irinotecan, Ixabepilone, Lapatinib, Letrozole, Leuprolide, liposomal doxorubicin, medroxyprogesterone, megestrol, methotrexate, mitomycin, nab-paclitaxel, octreotide, Oxaliplatin, Paclitaxel, Panitumumab, pegaspargase, pemetrexed, pentostatin, sorafenib, sunitinib, Tamoxifen, Tamoxifen-based treatment, Temozolomide, topotecan, toremifene, Trastuzumab, VBMCP/Cyclophosphamide, Vincristine, or any combination thereof. The one or more candidate therapeutic agents can also be 5FU, bevacizumab, capecitabine, cetuximab, cetuximab+gemcitabine, cetuximab+irinotecan, cyclophosphohamide, diethylstibesterol, doxorubicin, erlotinib, etoposide, exemestane, fluoropyrimidines, gemcitabine, gemcitabine+etoposide, gemcitabine+pemetrexed, irinotecan, irinotecan+sorafenib, lapatinib, lapatinib+tamoxifen, letrozole, letrozole+capecitabine, mitomycin, nab-paclitaxel, nab-paclitaxel+gemcitabine, nab-paclitaxel+trastuzumab, oxaliplatin, oxaliplatin+ 5FU+trastuzumab, panitumumab, pemetrexed, sorafenib, sunitinib, sunitinib, sunitinib+mitomycin, tamoxifen, temozolomide, temozolomide+bevacizumab, temozolomide+sorafenib, trastuzumab, vincristine, or any combination thereof.

In embodiments of the methods of the invention, the sample comprises cancer cells. The cancer can be a metastatic cancer. The cancer can be refractory to a prior treatment. The prior treatment can be the standard of care for the cancer. Sometimes, the subject has been previously treated with one or more therapeutic agents to treat a cancer. Sometimes, the subject has not previously been treated with one or more candidate therapeutic agents identified.

In some embodiments, the cancer comprises a prostate, lung, melanoma, small cell (esopha/retroperit), cholangiocarcinoma, mesothelioma, head and neck (SCC), pancreas, pancreas neuroendocrine, small cell, gastric, peritoneal pseudomyxoma, anal Canal (SCC), vagina (SCC), cervical, renal, eccrine seat adenocarinoma, salivary gland adenocarinoma, uterine soft tissue sarcoma (uterine), GIST (Gastric), or thyroid-anaplastic cancer. In some embodiments, the cancer comprises a cancer of the accessory, sinuses, middle and inner ear, adrenal glands, appendix, hematopoietic system, bones and joints, spinal cord, breast, cerebellum, cervix uteri, connective and soft tissue, corpus uteri, esophagus, eye, nose, eyeball, fallopian tube, extrahepatic bile ducts, mouth, intrahepatic bile ducts, kidney, appendix-colon, larynx, lip, liver, lung and bronchus, lymph nodes, cerebral, spinal, nasal cartilage, retina, eye, oropharynx, endocrine glands, female genital, ovary, pancreas, penis and scrotum, pituitary gland, pleura, prostate gland, rectum renal pelvis, ureter, peritonem, salivary gland, skin, small intestine, stomach, testis, thymus, thyroid gland, tongue, unknown, urinary bladder, uterus, vagina, labia, and vulva. In some embodiments, the sample comprises cells selected from the group consisting of adipose, adrenal cortex, adrenal gland, adrenal gland-medulla, appendix, bladder, blood, blood vessel, bone, bone cartilage, brain, breast, cartilage, cervix, colon, colon sigmoid, dendritic cells, skeletal muscle, enodmetrium, esophagus, fallopian tube, fibroblast, gallbladder, kidney, larynx, liver, lung, lymph node, melanocytes, mesothelial lining, myoepithelial cells, osteoblasts, ovary, pancreas, parotid, prostate, salivary gland, sinus tissue, skeletal muscle, skin, small intestine, smooth muscle, stomach, synovium, joint lining tissue, tendon, testis, thymus, thyroid, uterus, and uterus corpus. In some embodiments, the cancer comprises a breast, colorectal, ovarian, lung, non-small cell lung cancer, cholangiocarcinoma, mesothelioma, sweat gland, or GIST cancer.

Progression free survival (PFS) or disease free survival (DFS) for the subject can be extended using the methods of the invention. For example, the PFS or DFS can be extended by at least about 10%, about 15%, about 20%, about 30%, about 40%, about 50%, about 60%, about 70%, about 80%, about 90%, or at least about 100% compared to prior treatment. In addition, the patient's lifespan can be extended using the methods of the invention to select a candidate treatment. For example, the patient's lifespan can be extended by at least 1 week, 2 weeks, 3 weeks, 4 weeks, 1 month, 5 weeks, 6 weeks, 7 weeks, 8 weeks, 2 months, 9 weeks, 10 weeks, 11 weeks, 12 weeks, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 2 years, 2½ years, 3 years, 4 years, or by at least 5 years.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIGS. 3A through 3D illustrate an exemplary patient profile report in accordance with step 80 of FIG. 2.

FIGS. 15-25 are computer screen print outs associated with various parts of the information-based personalized medicine drug discovery system and method shown in FIGS. 5-14.

FIGS. 26A-26H represent a table that shows the frequency of a significant change in expression of gene expressed proteins by tumor type.

FIGS. 27A-27H represent a table that shows the frequency of a significant change in expression of certain genes by tumor type.

FIGS. 28A-28O represent a table that shows the frequency of a significant change in expression for certain gene expressed proteins by tumor type.

FIG. 29 is a table which shows biomarkers (gene expressed proteins) tagged as targets in order of frequency based on FIG. 28.

FIGS. 30A-30O represent a table that shows the frequency of a significant change in expression for certain genes by tumor type.

FIG. 31 is a table which shows genes tagged as targets in order of frequency based on FIG. 30.

FIG. 39 shows an example output of microarray profiling results and calls made using a cutoff value.

FIGS. 40A-40J illustrate an exemplary patient report based on molecular profiling.

DETAILED DESCRIPTION OF THE INVENTION

Figure 1:
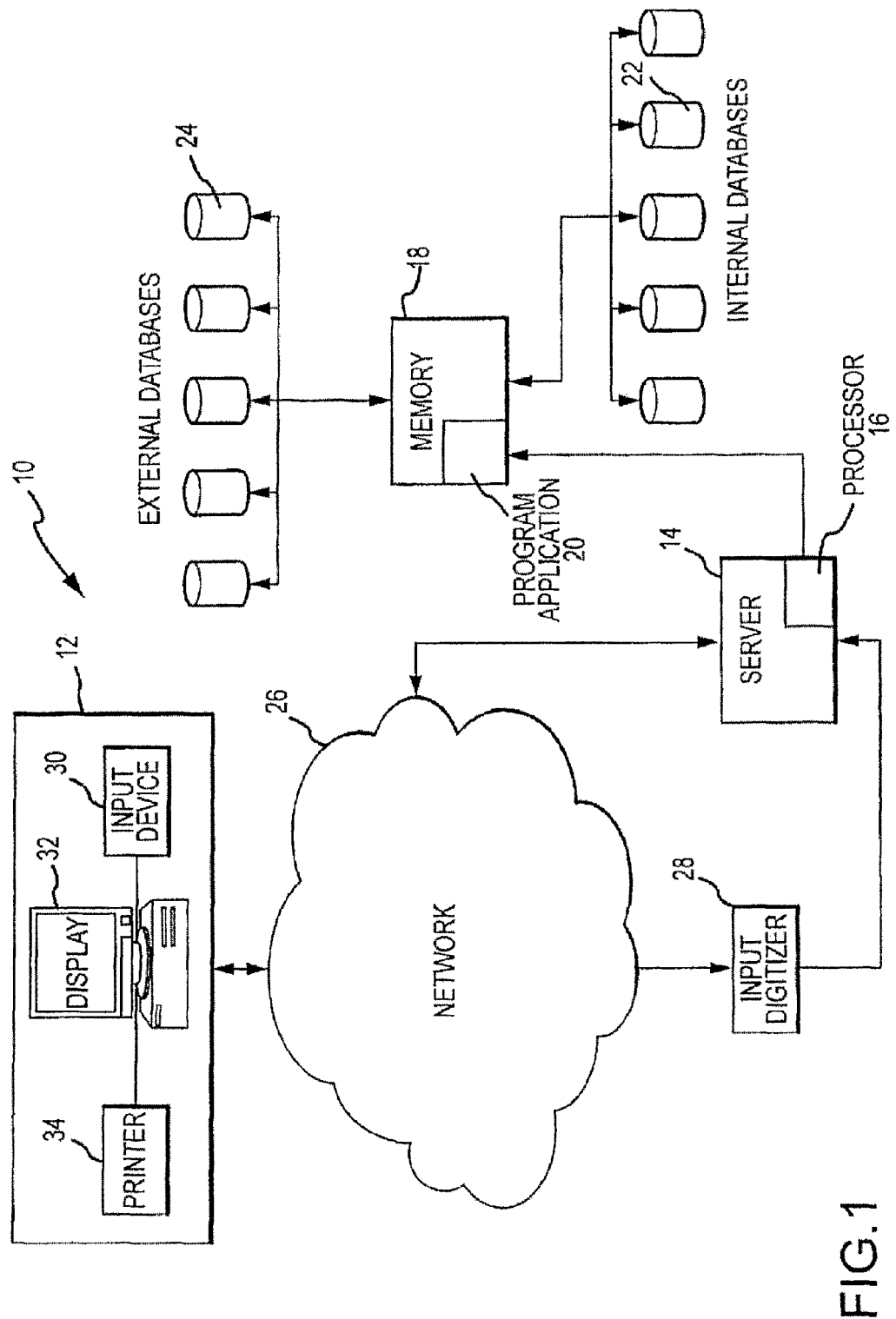
FIG. 1 illustrates a block diagram of an exemplary embodiment of a system for determining individualized medical intervention for a particular disease state that utilizes molecular profiling of a patient's biological specimen that is non disease specific.

The present invention provides methods and systems for identifying targets for treatments by using molecular profiling. The molecular profiling approach provides a method for selecting a candidate treatment for an individual that could favorably change the clinical course for an individual with a condition or disease, such as cancer. The molecular profiling approach can provide clinical benefit for individuals, such as providing a longer progression free survival (PFS), longer disease free survival (DFS), longer overall survival (OS) or extended lifespan when treated using molecular profiling approaches than using conventional approaches to selecting a treatment regimen. Molecular profiling can suggest candidate treatments when a disease is refractory to current therapies, e.g., after a cancer has developed resistance to a standard-of-care treatment.

Molecular profiling can be performed by any known means for detecting a molecule in a biological sample. Profiling can be performed on any applicable biological sample. The sample typically comes from an individual with a suspected or known disease or disorder, such as, but not limited to, a biopsy sample from a cancer patient. Molecular profiling of the sample can also be performed by any number of techniques that assess the amount or state of a biological factor, such as a DNA sequence, an mRNA sequence or a protein. Such techniques include without limitation immunohistochemistry (IHC), in situ hybridization (ISH), fluorescent in situ hybridization (FISH), various types of microarray (mRNA expression arrays, protein arrays, etc), various types of sequencing (Sanger, pyrosequencing, etc), comparative genomic hybridization (CGH), NextGen sequencing, Northern blot, Southern blot, immunoassay, and any other appropriate technique under development to assay the presence or quantity of a biological molecule of interest. Any one or more of these methods can be used concurrently or subsequent to each other.

Molecular profiling is used to select a candidate treatment for a disorder in a subject. For example, the candidate treatment can be a treatment known to have an effect on cells that differentially express genes as identified by molecular profiling techniques. Differential expression can include either overexpression and underexpression of a biological product, e.g., a gene, mRNA or protein, compared to a control. The control can include similar cells to the sample but without the disease. The control can be derived from the same patient, e.g., a normal adjacent portion of the same organ as the diseased cells, or the control can be derived from healthy tissues from other patients. The control can be a control found in the same sample, e.g. a housekeeping gene or a product thereof (e.g., mRNA or protein). For example, a control nucleic acid can be one which is known not to differ depending on the cancerous or non-cancerous state of the cell. The expression level of a control nucleic acid can be used to normalize signal levels in the test and reference populations. Exemplary control genes include, but are not limited to, e.g., β-actin, glyceraldehyde 3-phosphate dehydrogenase and ribosomal protein P1. Multiple controls or types of controls can be used. The source of differential expression can vary. For example, a gene copy number may be increased in a cell, thereby resulting in increased expression of the gene. Alternately, transcription of the gene may be modified, e.g., by chromatin remodeling, differential methylation, differential expression or activity of transcription factors, etc. Translation may also be modified, e.g., by differential expression of factors that degrade mRNA, translate mRNA, or silence translation, e.g., microRNAs or siRNAs. In some embodiments, differential expression comprises differential activity. For example, a protein may carry a mutation that increases the activity of the protein, such as constitutive activation, thereby contributing to a diseased state. Molecular profiling that reveals changes in activity can be used to guide treatment selection.

When multiple drug targets are revealed as differentially expressed by molecular profiling, decision rules can be put in place to prioritize the selection of certain treatments. Any such rule can be used that helps prioritize treatment can be used to prioritize treatments, e.g., direct results of molecular profiling, anticipated efficacy, prior history with the same or other treatments, expected side effects, availability, cost, drug-drug interactions, and other factors considered by a treating physician. The physician can ultimately decide on the course of treatment. Accordingly, molecular profiling can select candidate treatments based on individual characteristics of diseased cells, e.g., tumor cells, and other personalized factors in a subject in need of treatment, as opposed to relying on a traditional one-size fits all approach taken to target therapy against a certain indication. In some cases, the recommended treatments are those not typically used to treat the disease or disorder inflicting the subject. In some cases, the recommended treatments are used after standard-of-care therapies are no longer providing adequate efficacy.

Nucleic acids include deoxyribonucleotides or ribonucleotides and polymers thereof in either single- or double-stranded form, and complements thereof. Nucleic acids can contain known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Nucleic acid sequence can encompass conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid can be used interchangeably with gene, cDNA, mRNA, oligonucleotide, and polynucleotide.

A particular nucleic acid sequence may implicitly encompass the particular sequence and "splice variants" and nucleic acid sequences encoding truncated forms. Similarly, a particular protein encoded by a nucleic acid can encompass any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "genetic variant" and "nucleotide variant" are used herein interchangeably to refer to changes or alterations to the reference human gene or cDNA sequence at a particular locus, including, but not limited to, nucleotide base deletions, insertions, inversions, and substitutions in the coding and non-coding regions. Deletions may be of a single nucleotide base, a portion or a region of the nucleotide sequence of the gene, or of the entire gene sequence. Insertions may be of one or more nucleotide bases. The genetic variant or nucleotide variant may occur in transcriptional regulatory regions, untranslated regions of mRNA, exons, introns, exon/intron junctions, etc. The genetic variant or nucleotide variant can potentially result in stop codons, frame shifts, deletions of amino acids, altered gene transcript splice forms or altered amino acid sequence.

An allele or gene allele comprises generally a naturally occurring gene having a reference sequence or a gene containing a specific nucleotide variant.

A haplotype refers to a combination of genetic (nucleotide) variants in a region of an mRNA or a genomic DNA on a chromosome found in an individual. Thus, a haplotype includes a number of genetically linked polymorphic variants which are typically inherited together as a unit.

As used herein, the term "amino acid variant" is used to refer to an amino acid change to a reference human protein sequence resulting from genetic variants or nucleotide variants to the reference human gene encoding the reference protein. The term "amino acid variant" is intended to encompass not only single amino acid substitutions, but also amino acid deletions, insertions, and other significant changes of amino acid sequence in the reference protein.

The term "genotype" as used herein means the nucleotide characters at a particular nucleotide variant marker (or locus) in either one allele or both alleles of a gene (or a particular chromosome region). With respect to a particular nucleotide position of a gene of interest, the nucleotide(s) at that locus or equivalent thereof in one or both alleles form the genotype of the gene at that locus. A genotype can be homozygous or heterozygous. Accordingly, "genotyping" means determining the genotype, that is, the nucleotide(s) at a particular gene locus. Genotyping can also be done by determining the amino acid variant at a particular position of a protein which can be used to deduce the corresponding nucleotide variant(s).

The term "locus" refers to a specific position or site in a gene sequence or protein. Thus, there may be one or more contiguous nucleotides in a particular gene locus, or one or more amino acids at a particular locus in a polypeptide. Moreover, a locus may refer to a particular position in a gene where one or more nucleotides have been deleted, inserted, or inverted.

As used herein, the terms "polypeptide," "protein," and "peptide" are used interchangeably to refer to an amino acid chain in which the amino acid residues are linked by covalent peptide bonds. The amino acid chain can be of any length of at least two amino acids, including full-length proteins. Unless otherwise specified, polypeptide, protein, and peptide also encompass various modified forms thereof, including but not limited to glycosylated forms, phosphorylated forms, etc. A polypeptide, protein or peptide can also be referred to as a gene product.

Lists of gene and gene products that can be assayed by molecular profiling techniques are presented herein. Lists of genes may be presented in the context of molecular profiling techniques that detect a gene product (e.g., an mRNA or protein). One of skill will understand that this implies detection of the gene product of the listed genes. Similarly, lists of gene products may be presented in the context of molecular profiling techniques that detect a gene sequence or copy number. One of skill will understand that this implies detection of the gene corresponding to the gene products, including as an example DNA encoding the gene products. As will be appreciated by those skilled in the art, a "biomarker" or "marker" comprises a gene and/or gene product depending on the context.

The terms "label" and "detectable label" can refer to any composition detectable by spectroscopic, photochemical, biochemical, immunochemical, electrical, optical, chemical or similar methods. Such labels include biotin for staining with labeled streptavidin conjugate, magnetic beads (e.g., DYNABEADS™) fluorescent dyes (e.g., fluorescein, Texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic (e.g., polystyrene, polypropylene, latex, etc) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label. Labels can include, e.g., ligands that bind to labeled antibodies, fluorophores, chemiluminescent agents, enzymes, and antibodies which can serve as specific binding pair members for a labeled ligand. An introduction to labels, labeling procedures and detection of labels is found in Polak and Van Noorden Introduction to Immunocytochemistry, 2nd ed., Springer Verlag, NY (1997); and in Haugland Handbook of Fluorescent Probes and Research Chemicals, a combined handbook and catalogue Published by Molecular Probes, Inc. (1996).

Detectable labels include, but are not limited to, nucleotides (labeled or unlabelled), compomers, sugars, peptides, proteins, antibodies, chemical compounds, conducting polymers, binding moieties such as biotin, mass tags, calorimetric agents, light emitting agents, chemiluminescent agents, light scattering agents, fluorescent tags, radioactive tags, charge tags (electrical or magnetic charge), volatile tags and hydrophobic tags, biomolecules (e.g., members of a binding pair antibody/antigen, antibody/antibody, antibody/antibody fragment, antibody/antibody receptor, antibody/protein A or protein G, hapten/anti-hapten, biotin/avidin, biotin/streptavidin, folic acid/folate binding protein, vitamin B12/intrinsic factor, chemical reactive group/complementary chemical reactive group (e.g., sulfhydryl/maleimide, sulfhydryl/haloacetyl derivative, amine/isotriocyanate, amine/succinimidyl ester, and amine/sulfonyl halides) and the like.

The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')$_2$, Fab, Fv and rIgG). See also, Pierce Catalog and Handbook, 1994-1995 (Pierce Chemical Co., Rockford, Ill.). See also, e.g., Kuby, J., Immunology, 3.sup.rd Ed., W. H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies are well known to those skilled in the art. See, e.g., Winter and Harris, Immunol. Today 14:243-246 (1993); Ward et al., Nature 341:544-546 (1989); Harlow and Lane, Antibodies, 511-52, Cold Spring Harbor Laboratory publications, New York, 1988; Hilyard et al., Protein Engineering: A practical approach (IRL Press 1992); Borrebaeck, Antibody Engineering, 2d ed. (Oxford University Press 1995); each of which is incorporated herein by reference.

Unless otherwise specified, antibodies can include both polyclonal and monoclonal antibodies. Antibodies also include genetically engineered forms such as chimeric antibodies (e.g., humanized murine antibodies) and heteroconjugate antibodies (e.g., bispecific antibodies). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Holliger et al. (1993) Proc Natl Acad Sci USA. 90:6444, Gruber et al. (1994) J Immunol:5368, Zhu et al. (1997) Protein Sci 6:781, Hu et al. (1997) Cancer Res. 56:3055, Adams et al. (1993) Cancer Res. 53:4026, and McCartney, et al. (1995) Protein Eng. 8:301.

Typically, an antibody has a heavy and light chain. Each heavy and light chain contains a constant region and a variable region, (the regions are also known as "domains"). Light and heavy chain variable regions contain four framework regions interrupted by three hyper-variable regions, also called complementarity-determining regions (CDRs). The extent of the framework regions and CDRs have been defined. The sequences of the framework regions of different light or heavy chains are relatively conserved within a species. The framework region of an antibody, that is the combined framework regions of the constituent light and heavy chains, serves to position and align the CDRs in three dimensional spaces. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. References to $V_H$ refer to the variable region of an immunoglobulin heavy chain of an antibody, including the heavy chain of an Fv, scFv, or Fab. References to $V_L$ refer to the variable region of an immunoglobulin light chain, including the light chain of an Fv, scFv, dsFv or Fab.

The phrase "single chain Fv" or "scFv" refers to an antibody in which the variable domains of the heavy chain and of the light chain of a traditional two chain antibody have been joined to form one chain. Typically, a linker peptide is inserted between the two chains to allow for proper folding and creation of an active binding site. A "chimeric antibody" is an immunoglobulin molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-327 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The terms "epitope" and "antigenic determinant" refer to a site on an antigen to which an antibody binds. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols in Methods in Molecular Biology, Vol. 66, Glenn E. Morris, Ed (1996).

The terms "primer", "probe," and "oligonucleotide" are used herein interchangeably to refer to a relatively short nucleic acid fragment or sequence. They can comprise DNA, RNA, or a hybrid thereof, or chemically modified analog or derivatives thereof. Typically, they are single-stranded. However, they can also be double-stranded having two complementing strands which can be separated by denaturation. Normally, primers, probes and oligonucleotides have a length of from about 8 nucleotides to about 200 nucleotides, preferably from about 12 nucleotides to about 100 nucleotides, and more preferably about 18 to about 50 nucleotides. They can be labeled with detectable markers or modified using conventional manners for various molecular biological applications.

The term "isolated" when used in reference to nucleic acids (e.g., genomic DNAs, cDNAs, mRNAs, or fragments thereof) is intended to mean that a nucleic acid molecule is present in a form that is substantially separated from other naturally occurring nucleic acids that are normally associated with the molecule. Because a naturally existing chromosome (or a viral equivalent thereof) includes a long nucleic acid sequence, an isolated nucleic acid can be a nucleic acid molecule having only a portion of the nucleic acid sequence in the chromosome but not one or more other portions present on the same chromosome. More specifically, an isolated nucleic acid can include naturally occurring nucleic acid sequences that flank the nucleic acid in the naturally existing chromosome (or a viral equivalent thereof). An isolated nucleic acid can be substantially separated from other naturally occurring nucleic acids that are on a different chromosome of the same organism. An isolated nucleic acid can also be a composition in which the specified nucleic acid molecule is significantly enriched so as to constitute at least 10%, 20%, 30%, 40%, 50%, 60%, 70%, 80%, 90%, 95%, or at least 99% of the total nucleic acids in the composition.

An isolated nucleic acid can be a hybrid nucleic acid having the specified nucleic acid molecule covalently linked to one or more nucleic acid molecules that are not the nucleic acids naturally flanking the specified nucleic acid. For example, an isolated nucleic acid can be in a vector. In addition, the specified nucleic acid may have a nucleotide sequence that is identical to a naturally occurring nucleic acid or a modified form or mutein thereof having one or more mutations such as nucleotide substitution, deletion/insertion, inversion, and the like.

An isolated nucleic acid can be prepared from a recombinant host cell (in which the nucleic acids have been recombinantly amplified and/or expressed), or can be a chemically synthesized nucleic acid having a naturally occurring nucleotide sequence or an artificially modified form thereof.

The term "isolated polypeptide" as used herein is defined as a polypeptide molecule that is present in a form other than that found in nature. Thus, an isolated polypeptide can be a non-naturally occurring polypeptide. For example, an isolated polypeptide can be a "hybrid polypeptide." An isolated polypeptide can also be a polypeptide derived from a naturally occurring polypeptide by additions or deletions or substitutions of amino acids. An isolated polypeptide can also be a "purified polypeptide" which is used herein to mean a composition or preparation in which the specified polypeptide molecule is significantly enriched so as to constitute at least 10% of the total protein content in the composition. A "purified polypeptide" can be obtained from natural or recombinant host cells by standard purification techniques, or by chemically synthesis, as will be apparent to skilled artisans.

The terms "hybrid protein," "hybrid polypeptide," "hybrid peptide," "fusion protein," "fusion polypeptide," and "fusion peptide" are used herein interchangeably to mean a non-naturally occurring polypeptide or isolated polypeptide having a specified polypeptide molecule covalently linked to one or more other polypeptide molecules that do not link to the specified polypeptide in nature. Thus, a "hybrid protein" may be two naturally occurring proteins or fragments thereof linked together by a covalent linkage. A "hybrid protein" may also be a protein formed by covalently linking two artificial polypeptides together. Typically but not necessarily, the two or more polypeptide molecules are linked or "fused" together by a peptide bond forming a single non-branched polypeptide chain.

The term "high stringency hybridization conditions," when used in connection with nucleic acid hybridization, includes hybridization conducted overnight at 42° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 0.1×SSC at about 65° C. The term "moderate stringent hybridization conditions," when used in connection with nucleic acid hybridization, includes hybridization conducted overnight at 37° C. in a solution containing 50% formamide, 5×SSC (750 mM NaCl, 75 mM sodium citrate), 50 mM sodium phosphate, pH 7.6, 5×Denhardt's solution, 10% dextran sulfate, and 20 microgram/ml denatured and sheared salmon sperm DNA, with hybridization filters washed in 1×SSC at about 50° C. It is noted that many other hybridization methods, solutions and temperatures can be used to achieve comparable stringent hybridization conditions as will be apparent to skilled artisans.

For the purpose of comparing two different nucleic acid or polypeptide sequences, one sequence (test sequence) may be described to be a specific percentage identical to another sequence (comparison sequence). The percentage identity can be determined by the algorithm of Karlin and Altschul, Proc. Natl. Acad. Sci. USA, 90:5873-5877 (1993), which is incorporated into various BLAST programs. The percentage identity can be determined by the "BLAST 2 Sequences" tool, which is available at the National Center for Biotechnology Information (NCBI) website. See Tatusova and Madden, FEMS Microbiol. Lett., 174(2):247-250 (1999). For pairwise DNA-DNA comparison, the BLASTN program is used with default parameters (e.g., Match: 1; Mismatch: −2; Open gap: 5 penalties; extension gap: 2 penalties; gap x_dropoff: 50; expect: 10; and word size: 11, with filter). For pairwise protein-protein sequence comparison, the BLASTP program can be employed using default parameters (e.g., Matrix: BLOSUM62; gap open: 11; gap extension: 1; x_dropoff: 15; expect: 10.0; and wordsize: 3, with filter). Percent identity of two sequences is calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence. When BLAST is used to compare two sequences, it aligns the sequences and yields the percent identity over defined, aligned regions. If the two sequences are aligned across their entire length, the percent identity yielded by the BLAST is the percent identity of the two sequences. If BLAST does not align the two sequences over their entire length, then the number of identical amino acids or nucleotides in the unaligned regions of the test sequence and comparison sequence is considered to be zero and the percent identity is calculated by adding the number of identical amino acids or nucleotides in the aligned regions and dividing that number by the length of the comparison sequence. Various versions of the BLAST programs can be used to compare sequences, e.g, BLAST 2.1.2 or BLAST+ 2.2.22.

A subject can be any animal which may benefit from the methods of the invention, including, e.g., humans and non-human mammals, such as primates, rodents, horses, dogs and cats. Subjects include without limitation a eukaryotic organisms, most preferably a mammal such as a primate, e.g., chimpanzee or human, cow; dog; cat; a rodent, e.g., guinea pig, rat, mouse; rabbit; or a bird; reptile; or fish. Subjects specifically intended for treatment using the methods described herein include humans. A subject may be referred to as an individual or a patient.

Treatment of a disease or individual according to the invention is an approach for obtaining beneficial or desired medical results, including clinical results, but not necessarily a cure. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. Treatment also includes prolonging survival as compared to expected survival if not receiving treatment or if receiving a different treatment. A treatment can include administration of a therapeutic agent, which can be an agent that exerts a cytotoxic, cytostatic, or immunomodulatory effect on diseased cells, e.g., cancer cells, or other cells that may promote a diseased state, e.g., activated immune cells. Therapeutic agents selected by the methods of the invention are not limited. Any therapeutic agent can be selected where a link can be made between molecular profiling and potential efficacy of the agent. Therapeutic agents include without limitation small molecules, protein therapies, antibody therapies, viral therapies, gene therapies, and the like. Cancer treatments or therapies include apoptosis-mediated and non-apoptosis mediated cancer therapies including, without limitation, chemotherapy, hormonal therapy, radiotherapy, immunotherapy, and combinations thereof. Chemotherapeutic agents comprise therapeutic agents and combination of therapeutic agents that treat, e.g., kill, cancer cells. Examples of different types of chemotherapeutic drugs include without limitation alkylating agents (e.g., nitrogen mustard derivatives, ethylenimines, alkylsulfonates, hydrazines and triazines, nitrosureas, and metal salts), plant alkaloids (e.g., vinca alkaloids, taxanes, podophyllotoxins, and camptothecan analogs), antitumor antibiotics (e.g., anthracyclines, chromomycins, and the like), antimetabolites (e.g., folic acid antagonists, pyrimidine antagonists, purine antagonists, and adenosine deaminase inhibitors), topoisomerase I inhibitors, topoisomerase II inhibitors, and miscellaneous antineoplastics (e.g., ribonucleotide reductase inhibitors, adrenocortical steroid inhibitors, enzymes, antimicrotubule agents, and retinoids).

A sample as used herein includes any relevant sample that can be used for molecular profiling, e.g., sections of tissues such as biopsy or tissue removed during surgical or other procedures, autopsy samples, and frozen sections taken for histological purposes. Such samples include blood and blood fractions or products (e.g., serum, buffy coat, plasma, platelets, red blood cells, and the like), sputum, cheek cells tissue, cultured cells (e.g., primary cultures, explants, and transformed cells), stool, urine, other biological or bodily fluids (e.g., prostatic fluid, gastric fluid, intestinal fluid, renal fluid, lung fluid, cerebrospinal fluid, and the like), etc. A sample may be processed according to techniques understood by those in the art. A sample can be without limitation fresh, frozen or fixed. In some embodiments, a sample comprises formalin-fixed paraffin-embedded (FFPE) tissue or fresh frozen (FF) tissue. A sample can comprise cultured cells, including primary or immortalized cell lines derived from a subject sample. A sample can also refer to an extract from a sample from a subject. For example, a sample can comprise DNA, RNA or protein extracted from a tissue or a bodily fluid. Many techniques and commercial kits are available for such purposes. The fresh sample from the individual can be treated with an agent to preserve RNA prior to further processing, e.g., cell lysis and extraction. Samples can include frozen samples collected for other purposes. Samples can be associated with relevant information such as age, gender, and clinical symptoms present in the subject; source of the sample; and methods of collection and storage of the sample. A sample is typically obtained from a subject.

A biopsy comprises the process of removing a tissue sample for diagnostic or prognostic evaluation, and to the tissue specimen itself. Any biopsy technique known in the art can be applied to the molecular profiling methods of the present invention. The biopsy technique applied can depend on the tissue type to be evaluated (e.g., colon, prostate, kidney, bladder, lymph node, liver, bone marrow, blood cell, lung, breast, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. Molecular profiling can use a "core-needle biopsy" of the tumor mass, or a "fine-needle aspiration biopsy" which generally obtains a suspension of cells from within the tumor mass. Biopsy techniques are discussed, for example, in Harrison's Principles of Internal Medicine, Kasper, et al., eds., 16th ed., 2005, Chapter 70, and throughout Part V.

Standard molecular biology techniques known in the art and not specifically described are generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) can be carried out generally as in PCR Protocols: A Guide to Methods and Applications, Academic Press, San Diego, Calif. (1990).

Gene Expression Profiling

In some aspects of the inventions, the biomarkers are assessed by gene expression profiling. Methods of gene expression profiling include methods based on hybridization analysis of polynucleotides, and methods based on sequencing of polynucleotides. Commonly used methods known in the art for the quantification of mRNA expression in a sample include northern blotting and in situ hybridization (Parker & Barnes (1999) Methods in Molecular Biology 106:247-283); RNAse protection assays (Hod (1992) Biotechniques 13:852-854); and reverse transcription polymerase chain reaction (RT-PCR) (Weis et al. (1992) Trends in Genetics 8:263-264). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Reverse Transcriptase PCR (RT-PCR)

RT-PCR can be used to determine RNA levels, e.g., mRNA or miRNA levels, of the biomarkers of the invention. RT-PCR can be used to compare such RNA levels of the biomarkers of the invention in different sample populations, in normal and tumor tissues, with or without drug treatment, to characterize patterns of gene expression, to discriminate between closely related RNAs, and to analyze RNA structure.

The first step is the isolation of RNA, e.g., mRNA, from a sample. The starting material can be total RNA isolated from human tumors or tumor cell lines, and corresponding normal tissues or cell lines, respectively. Thus RNA can be isolated from a sample, e.g., tumor cells or tumor cell lines, and compared with pooled DNA from healthy donors. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al. (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions (QIAGEN Inc., Valencia, Calif.). For example, total RNA from cells in culture can be isolated using Qiagen RNeasy mini-columns. Numerous RNA isolation kits are commercially available and can be used in the methods of the invention.

In the alternative, the first step is the isolation of miRNA from a target sample. The starting material is typically total RNA isolated from human tumors or tumor cell lines, and corresponding normal tissues or cell lines, respectively. Thus RNA can be isolated from a variety of primary tumors or tumor cell lines, with pooled DNA from healthy donors. If the source of miRNA is a primary tumor, miRNA can be extracted, for example, from frozen or archived paraffin-embedded and fixed (e.g. formalin-fixed) tissue samples.

General methods for miRNA extraction are well known in the art and are disclosed in standard textbooks of molecular biology, including Ausubel et al. (1997) Current Protocols of Molecular Biology, John Wiley and Sons. Methods for RNA extraction from paraffin embedded tissues are disclosed, for example, in Rupp & Locker (1987) Lab Invest. 56:A67, and De Andres et al., BioTechniques 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Numerous RNA isolation kits are commercially available and can be used in the methods of the invention.

Whether the RNA comprises mRNA, miRNA or other types of RNA, gene expression profiling by RT-PCR can include reverse transcription of the RNA template into cDNA, followed by amplification in a PCR reaction. Commonly used reverse transcriptases include, but are not limited to, avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. TaqMan PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan™ RT-PCR can be performed using commercially available equipment, such as, for example, ABI PRISM 7700™ Sequence Detection System™ (Perkin-Elmer-Applied Biosystems, Foster City, Calif., USA), or Lightcycler (Roche Molecular Biochemicals, Mannheim, Germany). In one specific embodiment, the 5' nuclease procedure is run on a real-time quantitative PCR device such as the ABI PRISM 7700™ Sequence Detection System™. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

TaqMan data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

Real time quantitative PCR (also quantitative real time polymerase chain reaction, QRT-PCR or Q-PCR) is a more recent variation of the RT-PCR technique. Q-PCR can measure PCR product accumulation through a dual-labeled fluorigenic probe (i.e., TaqMan™ probe). Real time PCR is compatible both with quantitative competitive PCR, where internal competitor for each target sequence is used for normalization, and with quantitative comparative PCR using a normalization gene contained within the sample, or a housekeeping gene for RT-PCR. See, e.g. Held et al. (1996) Genome Research 6:986-994.

Immunohistochemistry (IHC)

IHC is a process of localizing antigens (e.g., proteins) in cells of a tissue binding antibodies specifically to antigens in the tissues. The antigen-binding antibody can be conjugated or fused to a tag that allows its detection, e.g., via visualization. In some embodiments, the tag is an enzyme that can catalyze a color-producing reaction, such as alkaline phosphatase or horseradish peroxidase. The enzyme can be fused to the antibody or non-covalently bound, e.g., using a biotin-avadin system. Alternatively, the antibody can be tagged with a fluorophore, such as fluorescein, rhodamine, DyLight Fluor or Alexa Fluor. The antigen-binding antibody can be directly tagged or it can itself be recognized by a detection antibody that carries the tag. Using IHC, one or more proteins may be detected. The expression of a gene product can be related to its staining intensity compared to control levels. In some embodiments, the gene product is considered differentially expressed if its staining varies at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold in the sample versus the control.

Microarray

The biomarkers of the invention can also be identified, confirmed, and/or measured using the microarray technique. Thus, the expression profile biomarkers can be measured in either fresh or paraffin-embedded tumor tissue, using microarray technology. In this method, polynucleotide sequences of interest are plated, or arrayed, on a microchip substrate. The arrayed sequences are then hybridized with specific DNA probes from cells or tissues of interest. The source of mRNA can be total RNA isolated from a sample, e.g., human tumors or tumor cell lines and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

The expression profile of biomarkers can be measured in either fresh or paraffin-embedded tumor tissue, or body fluids using microarray technology. In this method, polynucleotide sequences of interest are plated, or arrayed, on a microchip substrate. The arrayed sequences are then hybridized with specific DNA probes from cells or tissues of interest. As with the RT-PCR method, the source of miRNA typically is total RNA isolated from human tumors or tumor cell lines, including body fluids, such as serum, urine, tears, and exosomes and corresponding normal tissues or cell lines. Thus RNA can be isolated from a variety of sources. If the source of miRNA is a primary tumor, miRNA can be extracted, for example, from frozen tissue samples, which are routinely prepared and preserved in everyday clinical practice.

In a specific embodiment of the microarray technique, PCR amplified inserts of cDNA clones are applied to a substrate in a dense array. In one aspect, at least 100, 200, 300, 400, 500, 600, 700, 800, 900, 1,000, 1,500, 2,000, 3000, 4000, 5000, 6000, 7000, 8000, 9000, 10,000, 15,000, 20,000, 25,000, 30,000, 35,000, 40,000, 45,000 or at least 50,000 nucleotide sequences are applied to the substrate. Each sequence can correspond to a different gene, or multiple sequences can be arrayed per gene. The microarrayed genes, immobilized on the microchip, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al. (1996) Proc. Natl. Acad. Sci. USA 93(2): 106-149). Microarray analysis can be performed by commercially available equipment following manufacturer's protocols, including without limitation the Affymetrix GeneChip technology (Affymetrix, Santa Clara, Calif.), Agilent (Agilent Technologies, Inc., Santa Clara, Calif.), or Illumina (Illumina, Inc., San Diego, Calif.) microarray technology.

The development of microarray methods for large-scale analysis of gene expression makes it possible to search systematically for molecular markers of cancer classification and outcome prediction in a variety of tumor types.

In some embodiments, the Agilent Whole Human Genome Microarray Kit (Agilent Technologies, Inc., Santa Clara, Calif.). The system can analyze more than 41,000 unique human genes and transcripts represented, all with public domain annotations. The system is used according to the manufacturer's instructions.

In some embodiments, the Illumina Whole Genome DASL assay (Illumina Inc., San Diego, Calif.) is used. The system offers a method to simultaneously profile over 24,000 transcripts from minimal RNA input, from both fresh frozen (FF) and formalin-fixed paraffin embedded (FFPE) tissue sources, in a high throughput fashion.

Microarray expression analysis comprises identifying whether a gene or gene product is up-regulated or down-regulated relative to a reference. The identification can be performed using a statistical test to determine statistical significance of any differential expression observed. In some embodiments, statistical significance is determined using a parametric statistical test. The parametric statistical test can comprise, for example, a fractional factorial design, analysis of variance (ANOVA), a t-test, least squares, a Pearson correlation, simple linear regression, nonlinear regression, multiple linear regression, or multiple nonlinear regression. Alternatively, the parametric statistical test can comprise a one-way analysis of variance, two-way analysis of variance, or repeated measures analysis of variance. In other embodiments, statistical significance is determined using a nonparametric statistical test. Examples include, but are not limited to, a Wilcoxon signed-rank test, a Mann-Whitney test, a Kruskal-Wallis test, a Friedman test, a Spearman ranked order correlation coefficient, a Kendall Tau analysis, and a nonparametric regression test. In some embodiments, statistical significance is determined at a p-value of less than about 0.05, 0.01, 0.005, 0.001, 0.0005, or 0.0001. Although the microarray systems used in the methods of the invention may assay thousands of transcripts, data analysis need only be performed on the transcripts of interest, thereby reducing the problem of multiple comparisons inherent in performing multiple statistical tests. The p-values can also be corrected for multiple comparisons, e.g., using a Bonferroni correction, a modification thereof, or other technique known to those in the art, e.g., the Hochberg correction, Holm-Bonferroni correction, Šidák correction, or Dunnett's correction. The degree of differential expression can also be taken into account. For example, a gene can be considered as differentially expressed when the fold-change in expression compared to control level is at least 1.2, 1.3, 1.4, 1.5, 1.6, 1.7, 1.8, 1.9, 2.0, 2.2, 2.5, 2.7, 3.0, 4, 5, 6, 7, 8, 9 or 10-fold different in the sample versus the control. The differential expression takes into account both overexpression and underexpression. A gene or gene product can be considered up or down-regulated if the differential expression meets a statistical threshold, a fold-change threshold, or both. For example, the criteria for identifying differential expression can comprise both a p-value of 0.001 and fold change of at least 1.5-fold (up or down). One of skill will understand that such statistical and threshold measures can be adapted to determine differential expression by any molecular profiling technique disclosed herein.

Various methods of the invention make use of many types of microarrays that detect the presence and potentially the amount of biological entities in a sample. Arrays typically contain addressable moieties that can detect the presence of the entity in the sample, e.g., via a binding event. Microarrays include without limitation DNA microarrays, such as cDNA microarrays, oligonucleotide microarrays and SNP microarrays, microRNA arrays, protein microarrays, antibody microarrays, tissue microarrays, cellular microarrays (also called transfection microarrays), chemical compound microarrays, and carbohydrate arrays (glycoarrays). DNA arrays typically comprise addressable nucleotide sequences that can bind to sequences present in a sample. MicroRNA arrays, e.g., the MMChips array from the University of Louisville or commercial systems from Agilent, can be used to detect microRNAs. Protein microarrays can be used to identify protein-protein interactions, including without limitation identifying substrates of protein kinases, transcription factor protein-activation, or to identify the targets of biologically active small molecules. Protein arrays may comprise an array of different protein molecules, commonly antibodies, or nucleotide sequences that bind to proteins of interest. Antibody microarrays comprise antibodies spotted onto the protein chip that are used as capture molecules to detect proteins or other biological materials from a sample, e.g., from cell or tissue lysate solutions. For example, antibody arrays can be used to detect biomarkers from bodily fluids, e.g., serum or urine, for diagnostic applications. Tissue microarrays comprise separate tissue cores assembled in array fashion to allow multiplex histological analysis. Cellular microarrays, also called transfection microarrays, comprise various capture agents, such as antibodies, proteins, or lipids, which can interact with cells to facilitate their capture on addressable locations. Chemical compound microarrays comprise arrays of chemical compounds and can be used to detect protein or other biological materials that bind the compounds. Carbohydrate arrays (glycoarrays) comprise arrays of carbohydrates and can detect, e.g., protein that bind sugar moieties. One of skill will appreciate that similar technologies or improvements can be used according to the methods of the invention.

Gene Expression Analysis by Massively Parallel Signature Sequencing (MPSS)

This method, described by Brenner et al. (2000) Nature Biotechnology 18:630-634, is a sequencing approach that combines non-gel-based signature sequencing with in vitro cloning of millions of templates on separate microbeads. First, a microbead library of DNA templates is constructed by in vitro cloning. This is followed by the assembly of a planar array of the template-containing microbeads in a flow cell at a high density. The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a cDNA library.

MPSS data has many uses. The expression levels of nearly all transcripts can be quantitatively determined; the abundance of signatures is representative of the expression level of the gene in the analyzed tissue. Quantitative methods for the analysis of tag frequencies and detection of differences among libraries have been published and incorporated into public databases for SAGE™ data and are applicable to MPSS data. The availability of complete genome sequences permits the direct comparison of signatures to genomic sequences and further extends the utility of MPSS data. Because the targets for MPSS analysis are not pre-selected (like on a microarray), MPSS data can characterize the full complexity of transcriptomes. This is analogous to sequencing millions of ESTs at once, and genomic sequence data can be used so that the source of the MPSS signature can be readily identified by computational means.

Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (e.g., about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. See, e.g. Velculescu et al. (1995) Science 270:484-487; and Velculescu et al. (1997) Cell 88:243-51.

DNA Copy Number Profiling

Any method capable of determining a DNA copy number profile of a particular sample can be used for molecular profiling according to the invention as along as the resolution is sufficient to identify the biomarkers of the invention. The skilled artisan is aware of and capable of using a number of different platforms for assessing whole genome copy number changes at a resolution sufficient to identify the copy number of the one or more biomarkers of the invention. Some of the platforms and techniques are described in the embodiments below.

In some embodiments, the copy number profile analysis involves amplification of whole genome DNA by a whole genome amplification method. The whole genome amplification method can use a strand displacing polymerase and random primers.

In some aspects of these embodiments, the copy number profile analysis involves hybridization of whole genome amplified DNA with a high density array. In a more specific aspect, the high density array has 5,000 or more different probes. In another specific aspect, the high density array has 5,000, 10,000, 20,000, 50,000, 100,000, 200,000, 300,000, 400,000, 500,000, 600,000, 700,000, 800,000, 900,000, or 1,000,000 or more different probes. In another specific aspect, each of the different probes on the array is an oligonucleotide having from about 15 to 200 bases in length. In another specific aspect, each of the different probes on the array is an oligonucleotide having from about 15 to 200, 15 to 150, 15 to 100, 15 to 75, 15 to 60, or 20 to 55 bases in length.

In some embodiments, a microarray is employed to aid in determining the copy number profile for a sample, e.g., cells from a tumor. Microarrays typically comprise a plurality of oligomers (e.g., DNA or RNA polynucleotides or oligonucleotides, or other polymers), synthesized or deposited on a substrate (e.g., glass support) in an array pattern. The support-bound oligomers are "probes", which function to hybridize or bind with a sample material (e.g., nucleic acids prepared or obtained from the tumor samples), in hybridization experiments. The reverse situation can also be applied: the sample can be bound to the microarray substrate and the oligomer probes are in solution for the hybridization. In use, the array surface is contacted with one or more targets under conditions that promote specific, high-affinity binding of the target to one or more of the probes. In some configurations, the sample nucleic acid is labeled with a detectable label, such as a fluorescent tag, so that the hybridized sample and probes are detectable with scanning equipment. DNA array technology offers the potential of using a multitude (e.g., hundreds of thousands) of different oligonucleotides to analyze DNA copy number profiles. In some embodiments, the substrates used for arrays are surface-derivatized glass or silica, or polymer membrane surfaces (see e.g., in Z. Guo, et al., Nucleic Acids Res, 22, 5456-65 (1994); U. Maskos, E. M. Southern, Nucleic Acids Res, 20, 1679-84 (1992), and E. M. Southern, et al., Nucleic Acids Res, 22, 1368-73 (1994), each incorporated by reference herein). Modification of surfaces of array substrates can be accomplished by many techniques. For example, siliceous or metal oxide surfaces can be derivatized with bifunctional silanes, i.e., silanes having a first functional group enabling covalent binding to the surface (e.g., Si-halogen or Si-alkoxy group, as in —$SiCl_3$ or —$Si(OCH_3)_3$, respectively) and a second functional group that can impart the desired chemical and/or physical modifications to the surface to covalently or non-covalently attach ligands and/or the polymers or monomers for the biological probe array. Silylated derivatizations and other surface derivatizations that are known in the art (see for example U.S. Pat. No. 5,624,711 to Sundberg, U.S. Pat. No. 5,266,222 to Willis, and U.S. Pat. No. 5,137,765 to Farnsworth, each incorporated by reference herein). Other processes for preparing arrays are described in U.S. Pat. No. 6,649,348, to Bass et. al., assigned to Agilent Corp., which disclose DNA arrays created by in situ synthesis methods.

Polymer array synthesis is also described extensively in the literature including in the following: WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, 5,412,087, 6,147,205, 6,262,216, 6,310,189, 5,889,165, and 5,959,098 in PCT Applications Nos. PCT/US99/00730 (International Publication No. WO 99/36760) and PCT/US01/04285 (International Publication No. WO 01/58593), which are all incorporated herein by reference in their entirety for all purposes.

Nucleic acid arrays that are useful in the present invention include, but are not limited to, those that are commercially available from Affymetrix (Santa Clara, Calif.) under the brand name GeneChip™ Example arrays are shown on the website at affymetrix.com. Another microarray supplier is Illumina, Inc., of San Diego, Calif. with example arrays shown on their website at illumina.com.

In some embodiments, the inventive methods provide for sample preparation. Depending on the microarray and experiment to be performed, sample nucleic acid can be prepared in a number of ways by methods known to the skilled artisan. In some aspects of the invention, prior to or concurrent with genotyping (analysis of copy number profiles), the sample may be amplified any number of mechanisms. The most common amplification procedure used involves PCR. See, for example, PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. In some embodiments, the sample may be amplified on the array (e.g., U.S. Pat. No. 6,300,070 which is incorporated herein by reference)

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861, 245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., Genome Research 11, 1418 (2001), in U.S. Pat. Nos. 6,361,947, 6,391,592 and U.S. Ser. No. 09/916,135, 09/920,491 (U.S. Patent Application Publication 20030096235), Ser. No. 09/910,292 (U.S. Patent Application Publication 20030082543), and Ser. No. 10/013,598.

Methods for conducting polynucleotide hybridization assays are well developed in the art. Hybridization assay procedures and conditions used in the methods of the invention will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045, 996 and 6,386,749, 6,391,623 each of which are incorporated herein by reference.

The methods of the invention may also involve signal detection of hybridization between ligands in after (and/or during) hybridization. See U.S. Pat. Nos. 5,143,854, 5,578, 832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Ser. Nos. 10/389,194, 60/493,495 and in PCT Application PCT/US99/06097 (published as WO99/47964), each of which also is hereby incorporated by reference in its entirety for all purposes.

Sequence Analysis

Molecular profiling according to the present invention comprises methods for genotyping one or more biomarkers by determining whether an individual has one or more nucleotide variants (or amino acid variants) in one or more of the genes or gene products. Genotyping one or more genes according to the methods of the invention in some embodiments, can provide more evidence for selecting a treatment.

The biomarkers of the invention can be analyzed by any method useful for determining alterations in nucleic acids or the proteins they encode. According to one embodiment, the ordinary skilled artisan can analyze the one or more genes for mutations including deletion mutants, insertion mutants, frameshift mutants, nonsense mutants, missense mutant, and splice mutants.

Nucleic acid used for analysis of the one or more genes can be isolated from cells in the sample according to standard methodologies (Sambrook et al., 1989). The nucleic acid, for example, may be genomic DNA or fractionated or whole cell RNA, or miRNA acquired from exosomes or cell surfaces. Where RNA is used, it may be desired to convert the RNA to a complementary DNA. In one embodiment, the RNA is whole cell RNA; in another, it is poly-A RNA; in another, it is exosomal RNA. Normally, the nucleic acid is amplified. Depending on the format of the assay for analyzing the one or more genes, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Various types of defects are known to occur in the biomarkers of the invention. Alterations include without limitation deletions, insertions, point mutations, and duplications. Point mutations can be silent or can result in stop codons, frameshift mutations or amino acid substitutions. Mutations in and outside the coding region of the one or more genes may occur and can be analyzed according to the methods of the invention. The target site of a nucleic acid of interest can include the region wherein the sequence varies. Examples include, but are not limited to, polymorphisms which exist in different forms such as single nucleotide variations, nucleotide repeats, multibase deletion (more than one nucleotide deleted from the consensus sequence), multibase insertion (more than one nucleotide inserted from the consensus sequence), microsatellite repeats (small numbers of nucleotide repeats with a typical 5-1000 repeat units), di-nucleotide repeats, tri-nucleotide repeats, sequence rearrangements (including translocation and duplication), chimeric sequence (two sequences from different gene origins are fused together), and the like. Among sequence polymorphisms, the most frequent polymorphisms in the human genome are single-base variations, also called single-nucleotide polymorphisms (SNPs). SNPs are abundant, stable and widely distributed across the genome.

Molecular profiling includes methods for haplotyping one or more genes. The haplotype is a set of genetic determinants located on a single chromosome and it typically contains a particular combination of alleles (all the alternative sequences of a gene) in a region of a chromosome. In other words, the haplotype is phased sequence information on individual chromosomes. Very often, phased SNPs on a chromosome define a haplotype. A combination of haplotypes on chromosomes can determine a genetic profile of a cell. It is the haplotype that determines a linkage between a specific genetic marker and a disease mutation. Haplotyping can be done by any methods known in the art. Common methods of scoring SNPs include hybridization microarray or direct gel sequencing, reviewed in Landgren et al., Genome Research, 8:769-776, 1998. For example, only one copy of one or more genes can be isolated from an individual and the nucleotide at each of the variant positions is determined. Alternatively, an allele specific PCR or a similar method can be used to amplify only one copy of the one or more genes in an individual, and the SNPs at the variant positions of the present invention are determined. The Clark method known in the art can also be employed for haplotyping. A high throughput molecular haplotyping method is also disclosed in Tost et al., Nucleic Acids Res., 30(19):e96 (2002), which is incorporated herein by reference.

Thus, additional variant(s) that are in linkage disequilibrium with the variants and/or haplotypes of the present invention can be identified by a haplotyping method known in the art, as will be apparent to a skilled artisan in the field of genetics and haplotyping. The additional variants that are in linkage disequilibrium with a variant or haplotype of the present invention can also be useful in the various applications as described below.

For purposes of genotyping and haplotyping, both genomic DNA and mRNA/cDNA can be used, and both are herein referred to generically as "gene."

Numerous techniques for detecting nucleotide variants are known in the art and can all be used for the method of this invention. The techniques can be protein-based or nucleic acid-based. In either case, the techniques used must be sufficiently sensitive so as to accurately detect the small nucleotide or amino acid variations. Very often, a probe is utilized which is labeled with a detectable marker. Unless otherwise specified in a particular technique described below, any suitable marker known in the art can be used, including but not limited to, radioactive isotopes, fluorescent compounds, biotin which is detectable using strepavidin, enzymes (e.g., alkaline phosphatase), substrates of an enzyme, ligands and antibodies, etc. See Jablonski et al., Nucleic Acids Res., 14:6115-6128 (1986); Nguyen et al., Biotechniques, 13:116-123 (1992); Rigby et al., J. Mol. Biol., 113:237-251 (1977).

In a nucleic acid-based detection method, target DNA sample, i.e., a sample containing genomic DNA, cDNA, mRNA and/or miRNA, corresponding to the one or more genes must be obtained from the individual to be tested. Any tissue or cell sample containing the genomic DNA, miRNA, mRNA, and/or cDNA (or a portion thereof) corresponding to the one or more genes can be used. For this purpose, a tissue sample containing cell nucleus and thus genomic DNA can be obtained from the individual. Blood samples can also be useful except that only white blood cells and other lymphocytes have cell nucleus, while red blood cells are without a nucleus and contain only mRNA or miRNA. Nevertheless, miRNA and mRNA are also useful as either can be analyzed for the presence of nucleotide variants in its sequence or serve as template for cDNA synthesis. The tissue or cell samples can be analyzed directly without much processing. Alternatively, nucleic acids including the target sequence can be extracted, purified, and/or amplified before they are subject to the various detecting procedures discussed below. Other than tissue or cell samples, cDNAs or genomic DNAs from a cDNA or genomic DNA library constructed using a tissue or cell sample obtained from the individual to be tested are also useful.

Sequence Analysis

To determine the presence or absence of a particular nucleotide variant, sequencing of the target genomic DNA or cDNA, particularly the region encompassing the nucleotide variant locus to be detected. Various sequencing techniques are generally known and widely used in the art including the Sanger method and Gilbert chemical method. The pyrosequencing method monitors DNA synthesis in real time using a luminometric detection system. Pyrosequencing has been shown to be effective in analyzing genetic polymorphisms such as single-nucleotide polymorphisms and can also be used in the present invention. See Nordstrom et al., Biotechnol. Appl. Biochem., 31(2):107-112 (2000); Ahmadian et al., Anal. Biochem., 280:103-110 (2000).

Nucleic acid variants can be detected by a suitable detection process. Non limiting examples of methods of detection, quantification, sequencing and the like are; mass detection of mass modified amplicons (e.g., matrix-assisted laser desorption ionization (MALDI) mass spectrometry and electrospray (ES) mass spectrometry), a primer extension method (e.g., iPLEX™; Sequenom, Inc.), microsequencing methods (e.g., a modification of primer extension methodology), ligase sequence determination methods (e.g., U.S. Pat. Nos. 5,679,524 and 5,952,174, and WO 01/27326), mismatch sequence determination methods (e.g., U.S. Pat. Nos. 5,851, 770; 5,958,692; 6,110,684; and 6,183,958), direct DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension (e.g., microarray sequence determination methods), Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Invader assay, hybridization methods (e.g., hybridization using at least one probe, hybridization using at least one fluorescently labeled probe, and the like), conventional dot blot analyses, single strand conformational polymorphism analysis (SSCP, e.g., U.S. Pat. Nos. 5,891,625 and 6,013,499; Orita et al., Proc. Natl. Acad. Sci. U.S.A. 86: 27776-2770 (1989)), denaturing gradient gel electrophoresis (DGGE), heteroduplex analysis, mismatch cleavage detection, and techniques described in Sheffield et al., Proc. Natl. Acad. Sci. USA 49: 699-706 (1991), White et al., Genomics 12: 301-306 (1992), Grompe et al., Proc. Natl. Acad. Sci. USA 86: 5855-5892 (1989), and Grompe, Nature Genetics 5: 111-117 (1993), cloning and sequencing, electrophoresis, the use of hybridization probes and quantitative real time polymerase chain reaction (QRT-PCR), digital PCR, nanopore sequencing, chips and combinations thereof. The detection and quantification of alleles or paralogs can be carried out using the "closed-tube" methods described in U.S. patent application Ser. No. 11/950,395, filed on Dec. 4, 2007. In some embodiments the amount of a nucleic acid species is determined by mass spectrometry, primer extension, sequencing (e.g., any suitable method, for example nanopore or pyrosequencing), Quantitative PCR (Q-PCR or QRT-PCR), digital PCR, combinations thereof, and the like.

The term "sequence analysis" as used herein refers to determining a nucleotide sequence, e.g., that of an amplification product. The entire sequence or a partial sequence of a polynucleotide, e.g., DNA or mRNA, can be determined, and the determined nucleotide sequence can be referred to as a "read" or "sequence read." For example, linear amplification products may be analyzed directly without further amplification in some embodiments (e.g., by using single-molecule sequencing methodology). In certain embodiments, linear amplification products may be subject to further amplification and then analyzed (e.g., using sequencing by ligation or pyrosequencing methodology). Reads may be subject to different types of sequence analysis. Any suitable sequencing method can be utilized to detect, and determine the amount of, nucleotide sequence species, amplified nucleic acid species, or detectable products generated from the foregoing. Examples of certain sequencing methods are described hereafter.

A sequence analysis apparatus or sequence analysis component(s) includes an apparatus, and one or more components used in conjunction with such apparatus, that can be used by a person of ordinary skill to determine a nucleotide sequence resulting from processes described herein (e.g., linear and/or exponential amplification products). Examples of sequencing platforms include, without limitation, the 454 platform (Roche) (Margulies, M. et al. 2005 Nature 437, 376-380), Illumina Genomic Analyzer (or Solexa platform) or SOLID System (Applied Biosystems) or the Helicos True Single Molecule DNA sequencing technology (Harris T D et al. 2008 Science, 320, 106-109), the single molecule, real-time (SMRT™) technology of Pacific Biosciences, and nanopore sequencing (Soni G V and Meller A. 2007 Clin Chem 53: 1996-2001). Such platforms allow sequencing of many nucleic acid molecules isolated from a specimen at high orders of multiplexing in a parallel manner (Dear Brief Funct Genomic Proteomic 2003; 1: 397-416). Each of these platforms allows sequencing of clonally expanded or non-amplified single molecules of nucleic acid fragments. Certain platforms involve, for example, sequencing by ligation of dye-modified probes (including cyclic ligation and cleavage), pyrosequencing, and single-molecule sequencing. Nucleotide sequence species, amplification nucleic acid species and detectable products generated there from can be analyzed by such sequence analysis platforms.

Sequencing by ligation is a nucleic acid sequencing method that relies on the sensitivity of DNA ligase to base-pairing mismatch. DNA ligase joins together ends of DNA that are correctly base paired. Combining the ability of DNA ligase to join together only correctly base paired DNA ends, with mixed pools of fluorescently labeled oligonucleotides or primers, enables sequence determination by fluorescence detection. Longer sequence reads may be obtained by including primers containing cleavable linkages that can be cleaved after label identification. Cleavage at the linker removes the label and regenerates the 5' phosphate on the end of the ligated primer, preparing the primer for another round of ligation. In some embodiments primers may be labeled with more than one fluorescent label, e.g., at least 1, 2, 3, 4, or 5 fluorescent labels.

Sequencing by ligation generally involves the following steps. Clonal bead populations can be prepared in emulsion microreactors containing target nucleic acid template sequences, amplification reaction components, beads and primers. After amplification, templates are denatured and bead enrichment is performed to separate beads with extended templates from undesired beads (e.g., beads with no extended templates). The template on the selected beads undergoes a 3' modification to allow covalent bonding to the slide, and modified beads can be deposited onto a glass slide. Deposition chambers offer the ability to segment a slide into one, four or eight chambers during the bead loading process. For sequence analysis, primers hybridize to the adapter sequence. A set of four color dye-labeled probes competes for ligation to the sequencing primer. Specificity of probe ligation is achieved by interrogating every 4th and 5th base during the ligation series. Five to seven rounds of ligation, detection and cleavage record the color at every 5th position with the number of rounds determined by the type of library used. Following each round of ligation, a new complimentary primer offset by one base in the 5' direction is laid down for another series of ligations. Primer reset and ligation rounds (5-7 ligation cycles per round) are repeated sequentially five times to generate 25-35 base pairs of sequence for a single tag. With mate-paired sequencing, this process is repeated for a second tag.

Pyrosequencing is a nucleic acid sequencing method based on sequencing by synthesis, which relies on detection of a pyrophosphate released on nucleotide incorporation. Generally, sequencing by synthesis involves synthesizing, one nucleotide at a time, a DNA strand complimentary to the strand whose sequence is being sought. Target nucleic acids may be immobilized to a solid support, hybridized with a sequencing primer, incubated with DNA polymerase, ATP sulfurylase, luciferase, apyrase, adenosine 5' phosphsulfate and luciferin. Nucleotide solutions are sequentially added and removed. Correct incorporation of a nucleotide releases a pyrophosphate, which interacts with ATP sulfurylase and produces ATP in the presence of adenosine 5' phosphsulfate, fueling the luciferin reaction, which produces a chemiluminescent signal allowing sequence determination. The amount of light generated is proportional to the number of bases added. Accordingly, the sequence downstream of the sequencing primer can be determined An exemplary system for pyrosequencing involves the following steps: ligating an adaptor nucleic acid to a nucleic acid under investigation and hybridizing the resulting nucleic acid to a bead; amplifying a nucleotide sequence in an emulsion; sorting beads using a picoliter multiwell solid support; and sequencing amplified nucleotide sequences by pyrosequencing methodology (e.g., Nakano et al., "Single-molecule PCR using water-in-oil emulsion;" Journal of Biotechnology 102: 117-124 (2003)).

Certain single-molecule sequencing embodiments are based on the principal of sequencing by synthesis, and utilize single-pair Fluorescence Resonance Energy Transfer (single pair FRET) as a mechanism by which photons are emitted as a result of successful nucleotide incorporation. The emitted photons often are detected using intensified or high sensitivity cooled charge-couple-devices in conjunction with total internal reflection microscopy (TIRM). Photons are only emitted when the introduced reaction solution contains the correct nucleotide for incorporation into the growing nucleic acid chain that is synthesized as a result of the sequencing process. In FRET based single-molecule sequencing, energy is transferred between two fluorescent dyes, sometimes polymethine cyanine dyes Cy3 and Cy5, through long-range dipole interactions. The donor is excited at its specific excitation wavelength and the excited state energy is transferred, non-radiatively to the acceptor dye, which in turn becomes excited. The acceptor dye eventually returns to the ground state by radiative emission of a photon. The two dyes used in the energy transfer process represent the "single pair" in single pair FRET. Cy3 often is used as the donor fluorophore and often is incorporated as the first labeled nucleotide. Cy5 often is used as the acceptor fluorophore and is used as the nucleotide label for successive nucleotide additions after incorporation of a first Cy3 labeled nucleotide. The fluorophores generally are within 10 nanometers of each for energy transfer to occur successfully.

An example of a system that can be used based on single-molecule sequencing generally involves hybridizing a primer to a target nucleic acid sequence to generate a complex; associating the complex with a solid phase; iteratively extending the primer by a nucleotide tagged with a fluorescent molecule; and capturing an image of fluorescence resonance energy transfer signals after each iteration (e.g., U.S. Pat. No. 7,169,314; Braslaysky et al., PNAS 100(7): 3960-3964 (2003)). Such a system can be used to directly sequence amplification products (linearly or exponentially amplified products) generated by processes described herein. In some embodiments the amplification products can be hybridized to a primer that contains sequences complementary to immobilized capture sequences present on a solid support, a bead or glass slide for example. Hybridization of the primer-amplification product complexes with the immobilized capture sequences, immobilizes amplification products to solid supports for single pair FRET based sequencing by synthesis. The primer often is fluorescent, so that an initial reference image of the surface of the slide with immobilized nucleic acids can be generated. The initial reference image is useful for determining locations at which true nucleotide incorporation is occurring. Fluorescence signals detected in array locations not initially identified in the "primer only" reference image are discarded as non-specific fluorescence. Following immobilization of the primer-amplification product complexes, the bound nucleic acids often are sequenced in parallel by the iterative steps of, a) polymerase extension in the presence of one fluorescently labeled nucleotide, b) detection of fluorescence using appropriate microscopy, TIRM for example, c) removal of fluorescent nucleotide, and d) return to step a with a different fluorescently labeled nucleotide.

In some embodiments, nucleotide sequencing may be by solid phase single nucleotide sequencing methods and processes. Solid phase single nucleotide sequencing methods involve contacting target nucleic acid and solid support under conditions in which a single molecule of sample nucleic acid hybridizes to a single molecule of a solid support. Such conditions can include providing the solid support molecules and a single molecule of target nucleic acid in a "microreactor." Such conditions also can include providing a mixture in which the target nucleic acid molecule can hybridize to solid phase nucleic acid on the solid support. Single nucleotide sequencing methods useful in the embodiments described herein are described in U.S. Provisional Patent Application Ser. No. 61/021,871 filed Jan. 17, 2008.

In certain embodiments, nanopore sequencing detection methods include (a) contacting a target nucleic acid for sequencing ("base nucleic acid," e.g., linked probe molecule) with sequence-specific detectors, under conditions in which the detectors specifically hybridize to substantially complementary subsequences of the base nucleic acid; (b) detecting signals from the detectors and (c) determining the sequence of the base nucleic acid according to the signals detected. In certain embodiments, the detectors hybridized to the base nucleic acid are disassociated from the base nucleic acid (e.g., sequentially dissociated) when the detectors interfere with a nanopore structure as the base nucleic acid passes through a pore, and the detectors disassociated from the base sequence are detected. In some embodiments, a detector disassociated from a base nucleic acid emits a detectable signal, and the detector hybridized to the base nucleic acid emits a different detectable signal or no detectable signal. In certain embodiments, nucleotides in a nucleic acid (e.g., linked probe molecule) are substituted with specific nucleotide sequences corresponding to specific nucleotides ("nucleotide representatives"), thereby giving rise to an expanded nucleic acid (e.g., U.S. Pat. No. 6,723,513), and the detectors hybridize to the nucleotide representatives in the expanded nucleic acid, which serves as a base nucleic acid. In such embodiments, nucleotide representatives may be arranged in a binary or higher order arrangement (e.g., Soni and Meller, Clinical Chemistry 53(11): 1996-2001 (2007)). In some embodiments, a nucleic acid is not expanded, does not give rise to an expanded nucleic acid, and directly serves a base nucleic acid (e.g., a linked probe molecule serves as a non-expanded base nucleic acid), and detectors are directly contacted with the base nucleic acid. For example, a first detector may hybridize to a first subsequence and a second detector may hybridize to a second subsequence, where the first detector and second detector each have detectable labels that can be distinguished from one another, and where the signals from the first detector and second detector can be distinguished from one another when the detectors are disassociated from the base nucleic acid. In certain embodiments, detectors include a region that hybridizes to the base nucleic acid (e.g., two regions), which can be about 3 to about 100 nucleotides in length (e.g., about 4, 5, 6, 7, 8, 9, 10, 11, 12, 13, 14, 15, 16, 17, 18, 19, 20, 25, 30, 35, 40, 50, 55, 60, 65, 70, 75, 80, 85, 90, or 95 nucleotides in length). A detector also may include one or more regions of nucleotides that do not hybridize to the base nucleic acid. In some embodiments, a detector is a molecular beacon. A detector often comprises one or more detectable labels independently selected from those described herein. Each detectable label can be detected by any convenient detection process capable of detecting a signal generated by each label (e.g., magnetic, electric, chemical, optical and the like). For example, a CD camera can be used to detect signals from one or more distinguishable quantum dots linked to a detector.

In certain sequence analysis embodiments, reads may be used to construct a larger nucleotide sequence, which can be facilitated by identifying overlapping sequences in different reads and by using identification sequences in the reads. Such sequence analysis methods and software for constructing larger sequences from reads are known to the person of ordinary skill (e.g., Venter et al., Science 291: 1304-1351 (2001)). Specific reads, partial nucleotide sequence constructs, and full nucleotide sequence constructs may be compared between nucleotide sequences within a sample nucleic acid (i.e., internal comparison) or may be compared with a reference sequence (i.e., reference comparison) in certain sequence analysis embodiments. Internal comparisons can be performed in situations where a sample nucleic acid is prepared from multiple samples or from a single sample source that contains sequence variations. Reference comparisons sometimes are performed when a reference nucleotide sequence is known and an objective is to determine whether a sample nucleic acid contains a nucleotide sequence that is substantially similar or the same, or different, than a reference nucleotide sequence. Sequence analysis can be facilitated by the use of sequence analysis apparatus and components described above.

Primer extension polymorphism detection methods, also referred to herein as "microsequencing" methods, typically are carried out by hybridizing a complementary oligonucleotide to a nucleic acid carrying the polymorphic site. In these methods, the oligonucleotide typically hybridizes adjacent to the polymorphic site. The term "adjacent" as used in reference to "microsequencing" methods, refers to the 3' end of the extension oligonucleotide being sometimes 1 nucleotide from the 5' end of the polymorphic site, often 2 or 3, and at times 4, 5, 6, 7, 8, 9, or 10 nucleotides from the 5' end of the polymorphic site, in the nucleic acid when the extension oligonucleotide is hybridized to the nucleic acid. The extension oligonucleotide then is extended by one or more nucleotides, often 1, 2, or 3 nucleotides, and the number and/or type of nucleotides that are added to the extension oligonucleotide determine which polymorphic variant or variants are present. Oligonucleotide extension methods are disclosed, for example, in U.S. Pat. Nos. 4,656,127; 4,851,331; 5,679,524; 5,834,189; 5,876,934; 5,908,755; 5,912,118; 5,976,802; 5,981,186; 6,004,744; 6,013,431; 6,017,702; 6,046,005; 6,087,095; 6,210,891; and WO 01/20039. The extension products can be detected in any manner, such as by fluorescence methods (see, e.g., Chen & Kwok, Nucleic Acids Research 25: 347-353 (1997) and Chen et al., Proc. Natl. Acad. Sci. USA 94/20: 10756-10761 (1997)) or by mass spectrometric methods (e.g., MALDI-TOF mass spectrometry) and other methods described herein. Oligonucleotide extension methods using mass spectrometry are described, for example, in U.S. Pat. Nos. 5,547,835; 5,605,798; 5,691,141; 5,849,542; 5,869,242; 5,928,906; 6,043,031; 6,194,144; and 6,258,538. Microsequencing detection methods often incorporate an amplification process that proceeds the extension step. The amplification process typically amplifies a region from a nucleic acid sample that comprises the polymorphic site. Amplification can be carried out utilizing methods described above, or for example using a pair of oligonucleotide primers in a polymerase chain reaction (PCR), in which one oligonucleotide primer typically is complementary to a region 3' of the polymorphism and the other typically is complementary to a region 5' of the polymorphism. A PCR primer pair may be used in methods disclosed in U.S. Pat. Nos. 4,683,195; 4,683,202; 4,965,188; 5,656,493; 5,998,143; 6,140,054; WO 01/27327; and WO 01/27329 for example. PCR primer pairs may also be used in any commercially available machines that perform PCR, such as any of the GeneAmp™ Systems available from Applied Biosystems.

Other appropriate sequencing methods include multiplex polony sequencing (as described in Shendure et al., Accurate Multiplex Polony Sequencing of an Evolved Bacterial Genome, Sciencexpress, Aug. 4, 2005, pg 1 available at www.sciencexpress.org/4 Aug. 2005/Page1/10.1126/science. 1117389, incorporated herein by reference), which employs immobilized microbeads, and sequencing in microfabricated picoliter reactors (as described in Margulies et al., Genome Sequencing in Microfabricated High-Density Picoliter Reactors, Nature, August 2005, available at www.nature.com/nature (published online 31 Jul. 2005, doi: 10.1038/nature03959, incorporated herein by reference).

Whole genome sequencing may also be utilized for discriminating alleles of RNA transcripts, in some embodiments. Examples of whole genome sequencing methods include, but are not limited to, nanopore-based sequencing methods, sequencing by synthesis and sequencing by ligation, as described above.

In Situ Hybridization

In situ hybridization assays are well known and are generally described in Angerer et al., Methods Enzymol. 152:649-660 (1987). In an in situ hybridization assay, cells, e.g., from a biopsy, are fixed to a solid support, typically a glass slide. If DNA is to be probed, the cells are denatured with heat or alkali. The cells are then contacted with a hybridization solution at a moderate temperature to permit annealing of specific probes that are labeled. The probes are preferably labeled with radioisotopes or fluorescent reporters. FISH (fluorescence in situ hybridization) uses fluorescent probes that bind to only those parts of a sequence with which they show a high degree of sequence similarity.

FISH is a cytogenetic technique used to detect and localize specific polynucleotide sequences in cells. For example, FISH can be used to detect DNA sequences on chromosomes. FISH can also be used to detect and localize specific RNAs, e.g., mRNAs, within tissue samples. In FISH uses fluorescent probes that bind to specific nucleotide sequences to which they show a high degree of sequence similarity. Fluorescence microscopy can be used to find out whether and where the fluorescent probes are bound. In addition to detecting specific nucleotide sequences, e.g., translocations, fusion, breaks, duplications and other chromosomal abnormalities, FISH can help define the spatial-temporal patterns of specific gene copy number and/or gene expression within cells and tissues.

Comparative Genomic Hybridization (CGH) employs the kinetics of in situ hybridization to compare the copy numbers of different DNA or RNA sequences from a sample, or the copy numbers of different DNA or RNA sequences in one sample to the copy numbers of the substantially identical sequences in another sample. In many useful applications of CGH, the DNA or RNA is isolated from a subject cell or cell population. The comparisons can be qualitative or quantitative. Procedures are described that permit determination of the absolute copy numbers of DNA sequences throughout the genome of a cell or cell population if the absolute copy number is known or determined for one or several sequences. The different sequences are discriminated from each other by the different locations of their binding sites when hybridized to a reference genome, usually metaphase chromosomes but in certain cases interphase nuclei. The copy number information originates from comparisons of the intensities of the hybridization signals among the different locations on the reference genome. The methods, techniques and applications of CGH are known, such as described in U.S. Pat. No. 6,335,167, and in U.S. App. Ser. No. 60/804,818, the relevant parts of which are herein incorporated by reference.

Other Sequence Analysis Methods

Nucleic acid variants can also be detected using standard electrophoretic techniques. Although the detection step can sometimes be preceded by an amplification step, amplification is not required in the embodiments described herein. Examples of methods for detection and quantification of a nucleic acid using electrophoretic techniques can be found in the art. A non-limiting example comprises running a sample (e.g., mixed nucleic acid sample isolated from maternal serum, or amplification nucleic acid species, for example) in an agarose or polyacrylamide gel. The gel may be labeled (e.g., stained) with ethidium bromide (see, Sambrook and Russell, Molecular Cloning: A Laboratory Manual 3d ed., 2001). The presence of a band of the same size as the standard control is an indication of the presence of a target nucleic acid sequence, the amount of which may then be compared to the control based on the intensity of the band, thus detecting and quantifying the target sequence of interest. In some embodiments, restriction enzymes capable of distinguishing between maternal and paternal alleles may be used to detect and quantify target nucleic acid species. In certain embodiments, oligonucleotide probes specific to a sequence of interest are used to detect the presence of the target sequence of interest. The oligonucleotides can also be used to indicate the amount of the target nucleic acid molecules in comparison to the standard control, based on the intensity of signal imparted by the probe.

Sequence-specific probe hybridization can be used to detect a particular nucleic acid in a mixture or mixed population comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch. A number of hybridization formats are known in the art, which include but are not limited to, solution phase, solid phase, or mixed phase hybridization assays. The following articles provide an overview of the various hybridization assay formats: Singer et al., Biotechniques 4:230, 1986; Haase et al., Methods in Virology, pp. 189-226, 1984; Wilkinson, In situ Hybridization, Wilkinson ed., IRL Press, Oxford University Press, Oxford; and Hames and Higgins eds., Nucleic Acid Hybridization: A Practical Approach, IRL Press, 1987.

Hybridization complexes can be detected by techniques known in the art. Nucleic acid probes capable of specifically hybridizing to a target nucleic acid (e.g., mRNA or DNA) can be labeled by any suitable method, and the labeled probe used to detect the presence of hybridized nucleic acids. One commonly used method of detection is autoradiography, using probes labeled with $^3H$, $^{125}I$, $^{35}S$, $^{14}C$, $^{32}P$, $^{33}P$, or the like. The choice of radioactive isotope depends on research preferences due to ease of synthesis, stability, and half-lives of the selected isotopes. Other labels include compounds (e.g., biotin and digoxigenin), which bind to antiligands or antibodies labeled with fluorophores, chemiluminescent agents, and enzymes. In some embodiments, probes can be conjugated directly with labels such as fluorophores, chemiluminescent agents or enzymes. The choice of label depends on sensitivity required, ease of conjugation with the probe, stability requirements, and available instrumentation.

Alternatively, the restriction fragment length polymorphism (RFLP) and AFLP method may be used for molecular profiling. If a nucleotide variant in the target DNA corresponding to the one or more genes results in the elimination or creation of a restriction enzyme recognition site, then digestion of the target DNA with that particular restriction enzyme will generate an altered restriction fragment length pattern. Thus, a detected RFLP or AFLP will indicate the presence of a particular nucleotide variant.

Another useful approach is the single-stranded conformation polymorphism assay (SSCA), which is based on the altered mobility of a single-stranded target DNA spanning the nucleotide variant of interest. A single nucleotide change in the target sequence can result in different intramolecular base pairing pattern, and thus different secondary structure of the single-stranded DNA, which can be detected in a non-denaturing gel. See Orita et al., Proc. Natl. Acad. Sci. USA, 86:2776-2770 (1989). Denaturing gel-based techniques such as clamped denaturing gel electrophoresis (CDGE) and denaturing gradient gel electrophoresis (DGGE) detect differences in migration rates of mutant sequences as compared to wild-type sequences in denaturing gel. See Miller et al., Biotechniques, 5:1016-24 (1999); Sheffield et al., Am. J. Hum, Genet., 49:699-706 (1991); Wartell et al., Nucleic Acids Res., 18:2699-2705 (1990); and Sheffield et al., Proc. Natl. Acad. Sci. USA, 86:232-236 (1989). In addition, the double-strand conformation analysis (DSCA) can also be useful in the present invention. See Arguello et al., Nat. Genet., 18:192-194 (1998).

The presence or absence of a nucleotide variant at a particular locus in the one or more genes of an individual can also be detected using the amplification refractory mutation system (ARMS) technique. See e.g., European Patent No. 0,332,435; Newton et al., Nucleic Acids Res., 17:2503-2515 (1989); Fox et al., Br. J. Cancer, 77:1267-1274 (1998); Robertson et al., Eur. Respir. J., 12:477-482 (1998). In the ARMS method, a primer is synthesized matching the nucleotide sequence immediately 5' upstream from the locus being tested except that the 3'-end nucleotide which corresponds to the nucleotide at the locus is a predetermined nucleotide. For example, the 3'-end nucleotide can be the same as that in the mutated locus. The primer can be of any suitable length so long as it hybridizes to the target DNA under stringent conditions only when its 3'-end nucleotide matches the nucleotide at the locus being tested. Preferably the primer has at least 12 nucleotides, more preferably from about 18 to 50 nucleotides. If the individual tested has a mutation at the locus and the nucleotide therein matches the 3'-end nucleotide of the primer, then the primer can be further extended upon hybridizing to the target DNA template, and the primer can initiate a PCR amplification reaction in conjunction with another suitable PCR primer. In contrast, if the nucleotide at the locus is of wild type, then primer extension cannot be achieved. Various forms of ARMS techniques developed in the past few years can be used. See e.g., Gibson et al., Clin. Chem. 43:1336-1341 (1997).

Similar to the ARMS technique is the mini sequencing or single nucleotide primer extension method, which is based on the incorporation of a single nucleotide. An oligonucleotide primer matching the nucleotide sequence immediately 5' to the locus being tested is hybridized to the target DNA, mRNA or miRNA in the presence of labeled dideoxyribonucleotides. A labeled nucleotide is incorporated or linked to the primer only when the dideoxyribonucleotides matches the nucleotide at the variant locus being detected. Thus, the identity of the nucleotide at the variant locus can be revealed based on the detection label attached to the incorporated dideoxyribonucleotides. See Syvanen et al., Genomics, 8:684-692 (1990); Shumaker et al., Hum. Mutat., 7:346-354 (1996); Chen et al., Genome Res., 10:549-547 (2000).

Another set of techniques useful in the present invention is the so-called "oligonucleotide ligation assay" (OLA) in which differentiation between a wild-type locus and a mutation is based on the ability of two oligonucleotides to anneal adjacent to each other on the target DNA molecule allowing the two oligonucleotides joined together by a DNA ligase. See Landergren et al., Science, 241:1077-1080 (1988); Chen et al, Genome Res., 8:549-556 (1998); Iannone et al., Cytometry, 39:131-140 (2000). Thus, for example, to detect a single-nucleotide mutation at a particular locus in the one or more genes, two oligonucleotides can be synthesized, one having the sequence just 5' upstream from the locus with its 3' end nucleotide being identical to the nucleotide in the variant locus of the particular gene, the other having a nucleotide sequence matching the sequence immediately 3' downstream from the locus in the gene. The oligonucleotides can be labeled for the purpose of detection. Upon hybridizing to the target gene under a stringent condition, the two oligonucleotides are subject to ligation in the presence of a suitable ligase. The ligation of the two oligonucleotides would indicate that the target DNA has a nucleotide variant at the locus being detected.

Detection of small genetic variations can also be accomplished by a variety of hybridization-based approaches. Allele-specific oligonucleotides are most useful. See Conner et al., Proc. Natl. Acad. Sci. USA, 80:278-282 (1983); Saiki et al, Proc. Natl. Acad. Sci. USA, 86:6230-6234 (1989). Oligonucleotide probes (allele-specific) hybridizing specifically to a gene allele having a particular gene variant at a particular locus but not to other alleles can be designed by methods known in the art. The probes can have a length of, e.g., from 10 to about 50 nucleotide bases. The target DNA and the oligonucleotide probe can be contacted with each other under conditions sufficiently stringent such that the nucleotide variant can be distinguished from the wild-type gene based on the presence or absence of hybridization. The probe can be labeled to provide detection signals. Alternatively, the allele-specific oligonucleotide probe can be used as a PCR amplification primer in an "allele-specific PCR" and the presence or absence of a PCR product of the expected length would indicate the presence or absence of a particular nucleotide variant.

Other useful hybridization-based techniques allow two single-stranded nucleic acids annealed together even in the presence of mismatch due to nucleotide substitution, insertion or deletion. The mismatch can then be detected using various techniques. For example, the annealed duplexes can be subject to electrophoresis. The mismatched duplexes can be detected based on their electrophoretic mobility that is different from the perfectly matched duplexes. See Cariello, Human Genetics, 42:726 (1988). Alternatively, in an RNase protection assay, a RNA probe can be prepared spanning the nucleotide variant site to be detected and having a detection marker. See Giunta et al., Diagn. Mol. Path., 5:265-270 (1996); Finkelstein et al., Genomics, 7:167-172 (1990); Kinszler et al., Science 251:1366-1370 (1991). The RNA probe can be hybridized to the target DNA or mRNA forming a heteroduplex that is then subject to the ribonuclease RNase A digestion. RNase A digests the RNA probe in the heteroduplex only at the site of mismatch. The digestion can be determined on a denaturing electrophoresis gel based on size variations. In addition, mismatches can also be detected by chemical cleavage methods known in the art. See e.g., Roberts et al., Nucleic Acids Res., 25:3377-3378 (1997).

In the mutS assay, a probe can be prepared matching the gene sequence surrounding the locus at which the presence or absence of a mutation is to be detected, except that a predetermined nucleotide is used at the variant locus. Upon annealing the probe to the target DNA to form a duplex, the E. coli mutS protein is contacted with the duplex. Since the mutS protein binds only to heteroduplex sequences containing a nucleotide mismatch, the binding of the mutS protein will be indicative of the presence of a mutation. See Modrich et al., Ann. Rev. Genet., 25:229-253 (1991).

A great variety of improvements and variations have been developed in the art on the basis of the above-described basic techniques which can be useful in detecting mutations or nucleotide variants in the present invention. For example, the "sunrise probes" or "molecular beacons" use the fluorescence resonance energy transfer (FRET) property and give rise to high sensitivity. See Wolf et al., Proc. Nat. Acad. Sci. USA, 85:8790-8794 (1988). Typically, a probe spanning the nucleotide locus to be detected are designed into a hairpin-shaped structure and labeled with a quenching fluorophore at one end and a reporter fluorophore at the other end. In its natural state, the fluorescence from the reporter fluorophore is quenched by the quenching fluorophore due to the proximity of one fluorophore to the other. Upon hybridization of the probe to the target DNA, the 5' end is separated apart from the 3'-end and thus fluorescence signal is regenerated. See Nazarenko et al., Nucleic Acids Res., 25:2516-2521 (1997); Rychlik et al., Nucleic Acids Res., 17:8543-8551 (1989); Sharkey et al., Bio/Technology 12:506-509 (1994); Tyagi et al., Nat. Biotechnol., 14:303-308 (1996); Tyagi et al., Nat. Biotechnol., 16:49-53 (1998). The homo-tag assisted non-dimer system (HANDS) can be used in combination with the molecular beacon methods to suppress primer-dimer accumulation. See Brownie et al., Nucleic Acids Res., 25:3235-3241 (1997).

Dye-labeled oligonucleotide ligation assay is a FRET-based method, which combines the OLA assay and PCR. See Chen et al., Genome Res. 8:549-556 (1998). TaqMan is another FRET-based method for detecting nucleotide variants. A TaqMan probe can be oligonucleotides designed to have the nucleotide sequence of the gene spanning the variant locus of interest and to differentially hybridize with different alleles. The two ends of the probe are labeled with a quenching fluorophore and a reporter fluorophore, respectively. The TaqMan probe is incorporated into a PCR reaction for the amplification of a target gene region containing the locus of interest using Taq polymerase. As Taq polymerase exhibits 5'-3' exonuclease activity but has no 3'-5' exonuclease activity, if the TaqMan probe is annealed to the target DNA template, the 5'-end of the TaqMan probe will be degraded by Taq polymerase during the PCR reaction thus separating the reporting fluorophore from the quenching fluorophore and releasing fluorescence signals. See Holland et al., Proc. Natl. Acad. Sci. USA, 88:7276-7280 (1991); Kalinina et al., Nucleic Acids Res., 25:1999-2004 (1997); Whitcombe et al., Clin. Chem., 44:918-923 (1998).

In addition, the detection in the present invention can also employ a chemiluminescence-based technique. For example, an oligonucleotide probe can be designed to hybridize to either the wild-type or a variant gene locus but not both. The probe is labeled with a highly chemiluminescent acridinium ester. Hydrolysis of the acridinium ester destroys chemiluminescence. The hybridization of the probe to the target DNA prevents the hydrolysis of the acridinium ester. Therefore, the presence or absence of a particular mutation in the target DNA is determined by measuring chemiluminescence changes. See Nelson et al., Nucleic Acids Res., 24:4998-5003 (1996).

The detection of genetic variation in the gene in accordance with the present invention can also be based on the "base excision sequence scanning" (BESS) technique. The BESS method is a PCR-based mutation scanning method. BESS T-Scan and BESS G-Tracker are generated which are analogous to T and G ladders of dideoxy sequencing. Mutations are detected by comparing the sequence of normal and mutant DNA. See, e.g., Hawkins et al., Electrophoresis, 20:1171-1176 (1999).

Mass spectrometry can be used for molecular profiling according to the invention. See Graber et al., Curr. Opin. Biotechnol., 9:14-18 (1998). For example, in the primer oligo base extension (PROBE™) method, a target nucleic acid is immobilized to a solid-phase support. A primer is annealed to the target immediately 5' upstream from the locus to be analyzed. Primer extension is carried out in the presence of a selected mixture of deoxyribonucleotides and dideoxyribonucleotides. The resulting mixture of newly extended primers is then analyzed by MALDI-TOF. See e.g., Monforte et al., Nat. Med., 3:360-362 (1997).

In addition, the microchip or microarray technologies are also applicable to the detection method of the present invention. Essentially, in microchips, a large number of different oligonucleotide probes are immobilized in an array on a substrate or carrier, e.g., a silicon chip or glass slide. Target nucleic acid sequences to be analyzed can be contacted with the immobilized oligonucleotide probes on the microchip. See Lipshutz et al., Biotechniques, 19:442-447 (1995); Chee et al., Science, 274:610-614 (1996); Kozal et al., Nat. Med. 2:753-759 (1996); Hacia et al., Nat. Genet., 14:441-447 (1996); Saiki et al., Proc. Natl. Acad. Sci. USA, 86:6230-6234 (1989); Gingeras et al., Genome Res., 8:435-448 (1998). Alternatively, the multiple target nucleic acid sequences to be studied are fixed onto a substrate and an array of probes is contacted with the immobilized target sequences. See Drmanac et al., Nat. Biotechnol., 16:54-58 (1998). Numerous microchip technologies have been developed incorporating one or more of the above described techniques for detecting mutations. The microchip technologies combined with computerized analysis tools allow fast screening in a large scale. The adaptation of the microchip technologies to the present invention will be apparent to a person of skill in the art apprised of the present disclosure. See, e.g., U.S. Pat. No. 5,925,525 to Fodor et al; Wilgenbus et al., J. Mol. Med., 77:761-786 (1999); Graber et al., Curr. Opin. Biotechnol., 9:14-18 (1998); Hacia et al., Nat. Genet., 14:441-447 (1996); Shoemaker et al., Nat. Genet., 14:450-456 (1996); DeRisi et al., Nat. Genet., 14:457-460 (1996); Chee et al., Nat. Genet., 14:610-614 (1996); Lockhart et al., Nat. Genet., 14:675-680 (1996); Drobyshev et al., Gene, 188:45-52 (1997).

As is apparent from the above survey of the suitable detection techniques, it may or may not be necessary to amplify the target DNA, i.e., the gene, cDNA, mRNA, miRNA, or a portion thereof to increase the number of target DNA molecule, depending on the detection techniques used. For example, most PCR-based techniques combine the amplification of a portion of the target and the detection of the mutations. PCR amplification is well known in the art and is disclosed in U.S. Pat. Nos. 4,683,195 and 4,800,159, both which are incorporated herein by reference. For non-PCR-based detection techniques, if necessary, the amplification can be achieved by, e.g., in vivo plasmid multiplication, or by purifying the target DNA from a large amount of tissue or cell samples. See generally, Sambrook et al., Molecular Cloning: A Laboratory Manual, $2^{nd}$ ed., Cold Spring Harbor Laboratory, Cold Spring Harbor, N.Y., 1989. However, even with scarce samples, many sensitive techniques have been developed in which small genetic variations such as single-nucleotide substitutions can be detected without having to amplify the target DNA in the sample. For example, techniques have been developed that amplify the signal as opposed to the target DNA by, e.g., employing branched DNA or dendrimers that can hybridize to the target DNA. The branched or dendrimer DNAs provide multiple hybridization sites for hybridization probes to attach thereto thus amplifying the detection signals. See Detmer et al., J. Clin. Microbiol., 34:901-907 (1996); Collins et al., Nucleic Acids Res., 25:2979-2984 (1997); Horn et al., Nucleic Acids Res., 25:4835-4841 (1997); Horn et al., Nucleic Acids Res., 25:4842-4849 (1997); Nilsen et al., J. Theor. Biol., 187:273-284 (1997).

The Invader™ assay is nother technique for detecting single nucleotide variations that can be used for molecular profiling according to the invention. The Invader™ assay uses a novel linear signal amplification technology that improves upon the long turnaround times required of the typical PCR DNA sequenced-based analysis. See Cooksey et al., Antimicrobial Agents and Chemotherapy 44:1296-1301 (2000). This assay is based on cleavage of a unique secondary structure formed between two overlapping oligonucleotides that hybridize to the target sequence of interest to form a "flap." Each "flap" then generates thousands of signals per hour. Thus, the results of this technique can be easily read, and the methods do not require exponential amplification of the DNA target. The Invader™ system utilizes two short DNA probes, which are hybridized to a DNA target. The structure formed by the hybridization event is recognized by a special cleavase enzyme that cuts one of the probes to release a short DNA "flap." Each released "flap" then binds to a fluorescently-labeled probe to form another cleavage structure. When the cleavase enzyme cuts the labeled probe, the probe emits a detectable fluorescence signal. See e.g. Lyamichev et al., Nat. Biotechnol., 17:292-296 (1999).

The rolling circle method is another method that avoids exponential amplification. Lizardi et al., Nature Genetics, 19:225-232 (1998) (which is incorporated herein by reference). For example, Sniper™, a commercial embodiment of this method, is a sensitive, high-throughput SNP scoring system designed for the accurate fluorescent detection of specific variants. For each nucleotide variant, two linear, allele-specific probes are designed. The two allele-specific probes are identical with the exception of the 3'-base, which is varied to complement the variant site. In the first stage of the assay, target DNA is denatured and then hybridized with a pair of single, allele-specific, open-circle oligonucleotide probes. When the 3'-base exactly complements the target DNA, ligation of the probe will preferentially occur. Subsequent detection of the circularized oligonucleotide probes is by rolling circle amplification, whereupon the amplified probe products are detected by fluorescence. See Clark and Pickering, Life Science News 6, 2000, Amersham Pharmacia Biotech (2000).

A number of other techniques that avoid amplification all together include, e.g., surface-enhanced resonance Raman scattering (SERRS), fluorescence correlation spectroscopy, and single-molecule electrophoresis. In SERRS, a chromophore-nucleic acid conjugate is absorbed onto colloidal silver and is irradiated with laser light at a resonant frequency of the chromophore. See Graham et al., Anal. Chem., 69:4703-4707 (1997). The fluorescence correlation spectroscopy is based on the spatio-temporal correlations among fluctuating light signals and trapping single molecules in an electric field. See Eigen et al., Proc. Natl. Acad. Sci. USA, 91:5740-5747 (1994). In single-molecule electrophoresis, the electrophoretic velocity of a fluorescently tagged nucleic acid is determined by measuring the time required for the molecule to travel a predetermined distance between two laser beams. See Castro et al., Anal. Chem., 67:3181-3186 (1995).

In addition, the allele-specific oligonucleotides (ASO) can also be used in in situ hybridization using tissues or cells as samples. The oligonucleotide probes which can hybridize differentially with the wild-type gene sequence or the gene sequence harboring a mutation may be labeled with radioactive isotopes, fluorescence, or other detectable markers. In situ hybridization techniques are well known in the art and their adaptation to the present invention for detecting the presence or absence of a nucleotide variant in the one or more gene of a particular individual should be apparent to a skilled artisan apprised of this disclosure.

Protein-based detection techniques are also useful for molecular profiling, especially when the nucleotide variant causes amino acid substitutions or deletions or insertions or frameshift that affect the protein primary, secondary or tertiary structure. To detect the amino acid variations, protein sequencing techniques may be used. For example, a protein or fragment thereof corresponding to a gene can be synthesized by recombinant expression using a DNA fragment isolated from an individual to be tested. Preferably, a cDNA fragment of no more than 100 to 150 base pairs encompassing the polymorphic locus to be determined is used. The amino acid sequence of the peptide can then be determined by conventional protein sequencing methods. Alternatively, the HPLC-microscopy tandem mass spectrometry technique can be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., Anal. Chem., 72:757-763 (2000).

Other protein-based detection molecular profiling techniques include immunoaffinity assays based on antibodies selectively immunoreactive with mutant gene encoded protein according to the present invention. Methods for producing such antibodies are known in the art. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well-known antibody-based techniques can also be used including, e.g., enzyme-linked immunosorbent assay (ELISA), radioimmunoassay (RIA), immunoradiometric assays (IRMA) and immunoenzymatic assays (IEMA), including sandwich assays using monoclonal or polyclonal antibodies. See, e.g., U.S. Pat. Nos. 4,376,110 and 4,486,530, both of which are incorporated herein by reference.

Accordingly, the presence or absence of one or more genes nucleotide variant or amino acid variant in an individual can be determined using any of the detection methods described above.

Typically, once the presence or absence of one or more gene nucleotide variants or amino acid variants is determined, physicians or genetic counselors or patients or other researchers may be informed of the result. Specifically the result can be cast in a transmittable form that can be communicated or transmitted to other researchers or physicians or genetic counselors or patients. Such a form can vary and can be tangible or intangible. The result with regard to the presence or absence of a nucleotide variant of the present invention in the individual tested can be embodied in descriptive statements, diagrams, photographs, charts, images or any other visual forms. For example, images of gel electrophoresis of PCR products can be used in explaining the results. Diagrams showing where a variant occurs in an individual's gene are also useful in indicating the testing results. The statements and visual forms can be recorded on a tangible media such as papers, computer readable media such as floppy disks, compact disks, etc., or on an intangible media, e.g., an electronic media in the form of email or website on internet or intranet. In addition, the result with regard to the presence or absence of a nucleotide variant or amino acid variant in the individual tested can also be recorded in a sound form and transmitted through any suitable media, e.g., analog or digital cable lines, fiber optic cables, etc., via telephone, facsimile, wireless mobile phone, internet phone and the like.

Thus, the information and data on a test result can be produced anywhere in the world and transmitted to a different location. For example, when a genotyping assay is conducted offshore, the information and data on a test result may be generated and cast in a transmittable form as described above. The test result in a transmittable form thus can be imported into the U.S. Accordingly, the present invention also encompasses a method for producing a transmittable form of information on the genotype of the two or more suspected cancer samples from an individual. The method comprises the steps of (1) determining the genotype of the DNA from the samples according to methods of the present invention; and (2) embodying the result of the determining step in a transmittable form. The transmittable form is the product of the production method.

Data and Analysis

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2.sup.nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing genetic information over networks such as the Internet as shown in U.S. Ser. Nos. 10/197,621, 10/063,559 (U.S. Publication Number 20020183936), Ser. Nos. 10/065,856, 10/065,868, 10/328,818, 10/328,872, 10/423,403, and 60/482,389. For example, one or more molecular profiling techniques can be performed in one location, e.g., a city, state, country or continent, and the results can be transmitted to a different city, state, country or continent. Treatment selection can then be made in whole or in part in the second location. The methods of the invention comprise transmittal of information between different locations.

Molecular Profiling for Treatment Selection

The methods of the invention provide a candidate treatment selection for a subject in need thereof. Molecular profiling can be used to identify one or more candidate therapeutic agents for an individual suffering from a condition in which one or more of the biomarkers disclosed herein are targets for treatment. For example, the method can identify one or more chemotherapy treatments for a cancer. In an aspect, the invention provides a method comprising: performing an immunohistochemistry (IHC) analysis on a sample from the subject to determine an IHC expression profile on at least five proteins; performing a microarray analysis on the sample to determine a microarray expression profile on at least ten genes; performing a fluorescent in-situ hybridization (FISH) analysis on the sample to determine a FISH mutation profile on at least one gene; performing DNA sequencing on the sample to determine a sequencing mutation profile on at least one gene; and comparing the IHC expression profile, microarray expression profile, FISH mutation profile and sequencing mutation profile against a rules database, wherein the rules database comprises a mapping of treatments whose biological activity is known against diseased cells that: i) overexpress or underexpress one or more proteins included in the IHC expression profile; ii) overexpress or underexpress one or more genes included in the microarray expression profile; iii) have zero or more mutations in one or more genes included in the FISH mutation profile; and/or iv) have zero or more mutations in one or more genes included in the sequencing mutation profile; and identifying the treatment if the comparison against the rules database indicates that the treatment should have biological activity against the diseased cells; and the comparison against the rules database does not contraindicate the treatment for treating the diseased cells. The disease can be a cancer. The molecular profiling steps can be performed in any order. In some embodiments, not all of the molecular profiling steps are performed. As a non-limiting example, microarray analysis is not performed if the sample quality does not meet a threshold value, as described herein. In another example, sequencing is performed only if FISH analysis meets a threshold value. Any relevant biomarker can be assessed using one or more of the molecular profiling techniques described herein or known in the art. The marker need only have some direct or indirect association with a treatment to be useful.

Molecular profiling comprises the profiling of at least one gene (or gene product) for each assay technique that is performed. Different numbers of genes can be assayed with different techniques. Any marker disclosed herein that is associated directly or indirectly with a target therapeutic can be assessed based on either the gene, e.g., DNA sequence, and/or gene product, e.g., mRNA or protein. Such nucleic acid and/or polypeptide can be profiled as applicable as to presence or absence, level or amount, mutation, sequence, haplotype, rearrangement, copy number, etc. In some embodiments, a single gene and/or one or more corresponding gene products is assayed by more than one molecular profiling technique. A gene or gene product (also referred to herein as "marker" or "biomarker"), e.g., an mRNA or protein, is assessed using applicable techniques (e.g., to assess DNA, RNA, protein), including without limitation FISH, microarray, IHC, sequencing or immunoassay. Therefore, any of the markers disclosed herein can be assayed by a single molecular profiling technique or by multiple methods disclosed herein (e.g., a single marker is profiled by one or more of IHC, FISH, sequencing, microarray, etc.). In some embodiments, at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95 or at least about 100 genes or gene products are profiled by at least one technique, a plurality of techniques, or each of FISH, microarray, IHC, and sequencing. In some embodiments, at least about 100, 200, 300, 400, 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, or at least about 50,000 genes or gene products are profiled by each technique. The number of markers assayed can depend on the technique used. For example, microarray and massively parallel sequencing lend themselves to high throughput analysis.

In some embodiments, a sample from a subject in need thereof is profiled using methods which include but are not limited to IHC expression profiling, microarray expression profiling, FISH mutation profiling, and/or sequencing mutation profiling (such as by PCR, RT-PCR, pyrosequencing) for one or more of the following: ABCC1, ABCG2, ACE2, ADA, ADH1C, ADH4, AGT, Androgen receptor, AR, AREG, ASNS, BCL2, BCRP, BDCA1, BIRC5, B-RAF, BRCA1, BRCA2, CA2, caveolin, CD20, CD25, CD33, CD52, CDA, CDK2, CDW52, CES2, CK 14, CK 17, CK 5/6, c-KIT, c-Myc, COX-2, Cyclin D1, DCK, DHFR, DNMT1, DNMT3A, DNMT3B, E-Cadherin, ECGF1, EGFR, EPHA2, Epiregulin, ER, ERBR2, ERCC1, ERCC3, EREG, ESR1, FLT1, folate receptor, FOLR1, FOLR2, FSHB, FSHPRH1, FSHR, FYN, GART, GNRH1, GNRHR1, GSTP1, HCK, HDAC1, Her2/Neu, HGF, HIF1A, HIG1, HSP90, HSP90AA1, HSPCA, IL13RA1, IL2RA, KDR, KIT, K-RAS, LCK, LTB, Lymphotoxin Beta Receptor, LYN, MGMT, MLH1, MRP1, MS4A1, MSH2, Myc, NFKB1, NFKB2, NFKBIA, ODC1, OGFR, p53, p95, PARP-1, PDGFC, PDGFR, PDGFRA, PDGFRB, PGP, PGR, PI3K, POLA, POLA1, PPARG, PPARGC1, PR, PTEN, PTGS2, RAF1, RARA, RRM1, RRM2, RRM2B, RXRB, RXRG, SPARC, SPARC MC, SPARC PC, SRC, SSTR1, SSTR2, SSTR3, SSTR4, SSTR5, Survivin, TK1, TLE3, TNF, TOP1, TOP2A, TOP2B, TOPO1, TOPO2B, Topoisomerase II, TS, TXN, TXNRD1, TYMS, VDR, VEGF, VEGFA, VEGFC, VHL, YES1, ZAP70.

In some embodiments, additional molecular profiling methods are performed. These can include without limitation PCR, RT-PCR, Q-PCR, SAGE, MPSS, immunoassays and other techniques to assess biological systems described herein or known to those of skill in the art. The choice of genes and gene products to be assayed can be updated over time as new treatments and new drug targets are identified. Once the expression or mutation of a biomarker is correlated with a treatment option, it can be assessed by molecular profiling. One of skill will appreciate that such molecular profiling is not limited to those techniques disclosed herein but comprises any methodology conventional for assessing nucleic acid or protein levels, sequence information, or both. The methods of the invention can also take advantage of any improvements to current methods or new molecular profiling techniques developed in the future. In some embodiments, a gene or gene product is assessed by a single molecular profiling technique. In other embodiments, a gene and/or gene product is assessed by multiple molecular profiling techniques. In a non-limiting example, a gene sequence can be assayed by one or more of FISH and pyrosequencing analysis, the mRNA gene product can be assayed by one or more of RT-PCR and microarray, and the protein gene product can be assayed by one or more of IHC and immunoassay. One of skill will appreciate that any combination of biomarkers and molecular profiling techniques that will benefit disease treatment are contemplated by the invention.

Genes and gene products that are known to play a role in cancer and can be assayed by any of the molecular profiling techniques of the invention include without limitation 2AR, A DISINTEGRIN, ACTIVATOR OF THYROID AND RETINOIC ACID RECEPTOR (ACTR), ADAM 11, ADIPOGENESIS INHIBITORY FACTOR (ADIF), ALPHA 6 INTEGRIN SUBUNIT, ALPHA V INTEGRIN SUBUNIT, ALPHA-CATENIN, AMPLIFIED IN BREAST CANCER 1 (AIB1), AMPLIFIED IN BREAST CANCER 3 (AIB3), AMPLIFIED IN BREAST CANCER 4 (AIB4), AMYLOID PRECURSOR PROTEIN SECRETASE (APPS), AP-2 GAMMA, APPS, ATP-BINDING CASSETTE TRANSPORTER (ABCT), PLACENTA-SPECIFIC (ABCP), ATP-BINDING CASSETTE SUBFAMILY C MEMBER (ABCC1), BAG-1, BASIGIN (BSG), BCEI, B-CELL DIFFERENTIATION FACTOR (BCDF), B-CELL LEUKEMIA 2 (BCL-2), B-CELL STIMULATORY FACTOR-2 (BSF-2), BCL-1, BCL-2-ASSOCIATED X PROTEIN (BAX), BCRP, BETA 1 INTEGRIN SUBUNIT, BETA 3 INTEGRIN SUBUNIT, BETA 5 INTEGRIN SUBUNIT, BETA-2 INTERFERON, BETA-CATENIN, BETA-CATENIN, BONE SIALOPROTEIN (BSP), BREAST CANCER ESTROGEN-INDUCIBLE SEQUENCE (BCEI), BREAST CANCER RESISTANCE PROTEIN (BCRP), BREAST CANCER TYPE 1 (BRCA1), BREAST CANCER TYPE 2 (BRCA2), BREAST CARCINOMA AMPLIFIED SEQUENCE 2 (BCAS2), CADHERIN, EPITHELIAL CADHERIN-11, CADHERIN-ASSOCIATED PROTEIN, CALCITONIN RECEPTOR (CTR), CALCIUM PLACENTAL PROTEIN (CAPL), CALCYCLIN, CALLA, CAMS, CAPL, CARCINOEMBRYONIC ANTIGEN (CEA), CATENIN, ALPHA 1, CATHEPSIN B, CATHEPSIN D, CATHEPSIN K, CATHEPSIN L2, CATHEPSIN O, CATHEPSIN O1, CATHEPSIN V, CD10, CD146, CD147, CD24, CD29, CD44, CD51, CD54, CD61, CD66e, CD82, CD87, CD9, CEA, CELLULAR RETINOL-BINDING PROTEIN 1 (CRBP1), c-ERBB-2, CK7, CK8, CK18, CK19, CK20, CLAUDIN-7, c-MET, COLLAGENASE, FIBROBLAST, COLLAGENASE, INTERSTITIAL, COLLAGENASE-3, COMMON ACUTE LYMPHOCYTIC LEUKEMIA ANTIGEN (CALLA), CONNEXIN 26 (Cx26), CONNEXIN 43 (Cx43), CORTACTIN, COX-2, CTLA-8, CTR, CTSD, CYCLIN D1, CYCLOOXYGENASE-2, CYTOKERATIN 18, CYTOKERATIN 19, CYTOKERATIN 8, CYTOTOXIC T-LYMPHOCYTE-ASSOCIATED SERINE ESTERASE 8 (CTLA-8), DIFFERENTIATION-INHIBITING ACTIVITY (DIA), DNA AMPLIFIED IN MAMMARY CARCINOMA 1 (DAM1), DNA TOPOISOMERASE II ALPHA, DR-NM23, E-CADHERIN, EMMPRIN, EMS1, ENDOTHELIAL CELL GROWTH FACTOR (ECGR), PLATELET-DERIVED (PD-ECGF), ENKEPHALINASE, EPIDERMAL GROWTH FACTOR RECEPTOR (EGFR), EPISIALIN, EPITHELIAL MEMBRANE ANTIGEN (EMA), ER-ALPHA, ERBB2, ERBB4, ER-BETA, ERF-1, ERYTHROID-POTENTIATING ACTIVITY (EPA), ESR1, ESTROGEN RECEPTOR-ALPHA, ESTROGEN RECEPTOR-BETA, ETS-1, EXTRACELLULAR MATRIX METALLOPROTEINASE INDUCER (EMMPRIN), FIBRONECTIN RECEPTOR, BETA POLYPEPTIDE (FNRB), FIBRONECTIN RECEPTOR BETA SUBUNIT (FNRB), FLK-1, GA15.3, GA733.2, GALECTIN-3, GAMMA-CATENIN, GAP JUNCTION PROTEIN (26 kDa), GAP JUNCTION PROTEIN (43 kDa), GAP JUNCTION PROTEIN ALPHA-1 (GJA1), GAP JUNCTION PROTEIN BETA-2 (GJB2), GCP1, GELATINASE A, GELATINASE B, GELATINASE (72 kDa), GELATINASE (92 kDa), GLIOSTATIN, GLUCOCORTICOID RECEPTOR INTERACTING PROTEIN 1 (GRIP1), GLUTATHIONE S-TRANSFERASE p, GM-CSF, GRANULOCYTE CHEMOTACTIC PROTEIN 1 (GCP1), GRANULOCYTE-MACROPHAGE-COLONY STIMULATING FACTOR, GROWTH FACTOR RECEPTOR BOUND-7 (GRB-7), GSTp, HAP, HEAT-SHOCK COGNATE PROTEIN 70 (HSC70), HEAT-STABLE ANTIGEN, HEPATOCYTE GROWTH FACTOR (HGF), HEPATOCYTE GROWTH FACTOR RECEPTOR (HGFR), HEPATOCYTE-STIMULATING FACTOR III (HSF III), HER-2, HER2/NEU, HERMES ANTIGEN, HET, HHM, HUMORAL HYPERCALCEMIA OF MALIGNANCY (HHM), ICERE-1, INT-1, INTERCELLULAR ADHESION MOLECULE-1 (ICAM-1), INTERFERON-GAMMA-INDUCING FACTOR (IGIF), INTERLEUKIN-1 ALPHA (IL-1A), INTERLEUKIN-1 BETA (IL-1B), INTERLEUKIN-11 (IL-11), INTERLEUKIN-17 (IL-17), INTERLEUKIN-18 (IL-18), INTERLEUKIN-6 (IL-6), INTERLEUKIN-8 (IL-8), INVERSELY CORRELATED WITH ESTROGEN RECEPTOR EXPRESSION-1 (ICERE-1), KAI1, KDR, KERATIN 8, KERATIN 18, KERATIN 19, KISS-1, LEUKEMIA INHIBITORY FACTOR (LIF), LIF, LOST IN INFLAMMATORY BREAST CANCER (LIBC), LOT ("LOST ON TRANSFORMATION"), LYMPHOCYTE HOMING RECEPTOR, MACROPHAGE-COLONY STIMULATING FACTOR, MAGE-3, MAMMAGLOBIN, MASPIN, MC56, M-CSF, MDC, MDNCF, MDR, MELANOMA CELL ADHESION MOLECULE (MCAM), MEMBRANE METALLOENDOPEPTIDASE (MME), MEMBRANE-ASSOCIATED NEUTRAL ENDOPEPTIDASE (NEP), CYSTEINE-RICH PROTEIN (MDC), METASTASIN (MTS-1), MLN64, MMP1, MMP2, MMP3, MMP7, MMP9, MMP11, MMP13, MMP14, MMP15, MMP16, MMP17, MOESIN, MONOCYTE ARGININE-SERPIN, MONOCYTE-DERIVED NEUTROPHIL CHEMOTACTIC FACTOR, MONOCYTE-DERIVED PLASMINOGEN ACTIVATOR INHIBITOR, MTS-1, MUC-1, MUC18, MUCIN LIKE CANCER ASSOCIATED ANTIGEN (MCA), MUCIN, MUC-1, MULTIDRUG RESISTANCE PROTEIN 1 (MDR, MDR1), MULTIDRUG RESISTANCE RELATED PROTEIN-1 (MRP, MRP-1), N-CADHERIN, NEP, NEU, NEUTRAL ENDOPEPTIDASE, NEUTROPHIL-ACTIVATING PEPTIDE 1 (NAP1), NM23-H1, NM23-H2, NME1, NME2, NUCLEAR RECEPTOR COACTIVATOR-1 (NCoA-1), NUCLEAR RECEPTOR COACTIVATOR-2 (NCoA-2), NUCLEAR RECEPTOR COACTIVATOR-3 (NCoA-3), NUCLEOSIDE DIPHOSPHATE KINASE A (NDPKA), NUCLEOSIDE DIPHOSPHATE KINASE B (NDPKB), ONCOSTATIN M (OSM), ORNITHINE DECARBOXYLASE (ODC), OSTEOCLAST DIFFERENTIATION FACTOR (ODF), OSTEOCLAST DIFFERENTIATION FACTOR RECEPTOR (ODFR), OSTEONECTIN (OSN, ON), OSTEOPONTIN (OPN), OXYTOCIN RECEPTOR (OXTR), p27/kip1, p300/CBP COINTEGRATOR ASSOCIATE PROTEIN (p/CIP), p53, p9Ka, PAI-1, PAI-2, PARATHYROID ADENOMATOSIS 1 (PRAD1), PARATHYROID HORMONE-LIKE HORMONE (PTHLH), PARATHYROID HORMONE-RELATED PEPTIDE (PTHrP), P-CADHERIN, PD-ECGF, PDGF, PEANUT-REACTIVE URINARY MUCIN (PUM), P-GLYCOPROTEIN (P-GP), PGP-1, PHGS-2, PHS-2, PIP, PLAKOGLOBIN, PLASMINOGEN ACTIVATOR INHIBITOR (TYPE 1), PLASMINOGEN ACTIVATOR INHIBITOR (TYPE 2), PLASMINOGEN ACTIVATOR (TISSUE-TYPE), PLASMINOGEN ACTIVATOR (UROKINASE-TYPE), PLATE- LET GLYCOPROTEIN IIIa (GP3A), PLAU, PLEOMORPHIC ADENOMA GENE-LIKE 1 (PLAGL1), POLYMORPHIC EPITHELIAL MUCIN (PEM), PRAD1, PROGESTERONE RECEPTOR (PgR), PROGESTERONE RESISTANCE, PROSTAGLANDIN ENDOPEROXIDE SYNTHASE-2, PROSTAGLANDIN G/H SYNTHASE-2, PROSTAGLANDIN H SYNTHASE-2, pS2, PS6K, PSORIASIN, PTHLH, PTHrP, RAD51, RAD52, RAD54, RAP46, RECEPTOR-ASSOCIATED COACTIVATOR 3 (RAC3), REPRESSOR OF ESTROGEN RECEPTOR ACTIVITY (REA), S100A4, S100A6, S100A7, S6K, SART-1, SCAFFOLD ATTACHMENT FACTOR B (SAF-B), SCATTER FACTOR(SF), SECRETED PHOSPHOPROTEIN-1 (SPP-1), SECRETED PROTEIN, ACIDIC AND RICH IN CYSTEINE (SPARC), STANNICALCIN, STEROID RECEPTOR COACTIVATOR-1 (SRC-1), STEROID RECEPTOR COACTIVATOR-2 (SRC-2), STEROID RECEPTOR COACTIVATOR-3 (SRC-3), STEROID RECEPTOR RNA ACTIVATOR(SRA), STROMELYSIN-1, STROMELYSIN-3, TENASCIN-C (TN-C), TESTES-SPECIFIC PROTEASE 50, THROMBOSPONDIN I, THROMBOSPONDIN II, THYMIDINE PHOSPHORYLASE (TP), THYROID HORMONE RECEPTOR ACTIVATOR MOLECULE 1 (TRAM-1), TIGHT JUNCTION PROTEIN 1 (TJP1), TIMP1, TIMP2, TIMP3, TIMP4, TISSUE-TYPE PLASMINOGEN ACTIVATOR, TN-C, TP53, tPA, TRANSCRIPTIONAL INTERMEDIARY FACTOR 2 (TIF2), TREFOIL FACTOR 1 (TFF1), TSG101, TSP-1, TSP1, TSP-2, TSP2, TSP50, TUMOR CELL COLLAGENASE STIMULATING FACTOR (TCSF), TUMOR-ASSOCIATED EPITHELIAL MUCIN, uPA, uPAR, UROKINASE, UROKINASE-TYPE PLASMINOGEN ACTIVATOR, UROKINASE-TYPE PLASMINOGEN ACTIVATOR RECEPTOR (uPAR), UVOMORULIN, VASCULAR ENDOTHELIAL GROWTH FACTOR, VASCULAR ENDOTHELIAL GROWTH FACTOR RECEPTOR-2 (VEGFR2), VASCULAR ENDOTHELIAL GROWTH FACTOR-A, VASCULAR PERMEABILITY FACTOR, VEGFR2, VERY LATE T-CELL ANTIGEN BETA (VLA-BETA), VIMENTIN, VITRONECTIN RECEPTOR ALPHA POLYPEPTIDE (VNRA), VITRONECTIN RECEPTOR, VON WILLEBRAND FACTOR, VPF, VWF, WNT-1, ZAC, ZO-1, and ZONULA OCCLUDENS-1.

The gene products used for IHC expression profiling include without limitation one or more of SPARC, PGP, Her2/neu, ER, PR, c-kit, AR, CD52, PDGFR, TOP2A, TS, ERCC1, RRM1, BCRP, TOPO1, PTEN, MGMT, and MRP1. IHC profiling of EGFR can also be performed. IHC is also used to detect or test for various gene products, including without limitation one or more of the following: EGFR, SPARC, C-kit, ER, PR, Androgen receptor, PGP, RRM1, TOPO1, BRCP1, MRP1, MGMT, PDGFR, DCK, ERCC1, Thymidylate synthase, Her2/neu, or TOPO2A. In some embodiments, IHC is used to detect on or more of the following proteins, including without limitation: ADA, AR, ASNA, BCL2, BRCA2, CD33, CDW52, CES2, DNMT1, EGFR, ERBB2, ERCC3, ESR1, FOLR2, GART, GSTP1, HDAC1, HIF1A, HSPCA, IL2RA, KIT, MLH1, MS4A1, MASH2, NFKB2, NFKBIA, OGFR, PDGFC, PDGFRA, PDGFRB, PGR, POLA, PTEN, PTGS2, RAF1, RARA, RXRB, SPARC, SSTR1, TK1, TNF, TOP1, TOP2A, TOP2B, TXNRD1, TYMS, VDR, VEGF, VHL, or ZAP70.

Microarray expression profiling can be used to simultaneously measure the expression of one or more genes or gene products, including without limitation ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70. In some embodiments, the genes used for the microarray expression profiling comprise one or more of: EGFR, SPARC, C-kit, ER, PR, Androgen receptor, PGP, RRM1, TOPO1, BRCP1, MRP1, MGMT, PDGFR, DCK, ERCC1, Thymidylate synthase, Her2/neu, TOPO2A, ADA, AR, ASNA, BCL2, BRCA2, CD33, CDW52, CES2, DNMT1, EGFR, ERBB2, ERCC3, ESR1, FOLR2, GART, GSTP1, HDAC1, HIF1A, HSPCA, IL2RA, KIT, MLH1, MS4A1, MASH2, NFKB2, NFKBIA, OGFR, PDGFC, PDGFRA, PDGFRB, PGR, POLA, PTEN, PTGS2, RAF1, RARA, RXRB, SPARC, SSTR1, TK1, TNF, TOP1, TOP2A, TOP2B, TXNRD1, TYMS, VDR, VEGF, VHL, or ZAP70. The microarray expression profiling can be performed using a low density microarray, an expression microarray, a comparative genomic hybridization (CGH) microarray, a single nucleotide polymorphism (SNP) microarray, a proteomic array an antibody array, or other array as disclosed herein or known to those of skill in the art. In some embodiments, high throughput expression arrays are used. Such systems include without limitation commercially available systems from Agilent or Illumina, as described in more detail herein.

FISH mutation profiling can be used to profile one or more of EGFR and HER2. In some embodiments, FISH is used to detect or test for one or more of the following genes, including, but not limited to: EGFR, SPARC, C-kit, ER, PR, Androgen receptor, PGP, RRM1, TOPO1, BRCP1, MRP1, MGMT, PDGFR, DCK, ERCC1, Thymidylate synthase, HER2, or TOPO2A. In some embodiments, FISH is used to detect or test various biomarkers, including without limitation one or more of the following: ADA, AR, ASNA, BCL2, BRCA2, CD33, CDW52, CES2, DNMT1, EGFR, ERBB2, ERCC3, ESR1, FOLR2, GART, GSTP1, HDAC1, HIF1A, HSPCA, IL2RA, KIT, MLH1, MS4A1, MASH2, NFKB2, NFKBIA, OGFR, PDGFC, PDGFRA, PDGFRB, PGR, POLA, PTEN, PTGS2, RAF1, RARA, RXRB, SPARC, SSTR1, TK1, TNF, TOP1, TOP2A, TOP2B, TXNRD1, TYMS, VDR, VEGF, VHL, or ZAP70.

In some embodiments, the genes used for the sequencing mutation profiling comprise one or more of KRAS, BRAF, c-KIT and EGFR. Sequencing analysis can also comprise assessing mutations in one or more ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70.

In a related aspect, the invention provides a method of identifying a candidate treatment for a subject in need thereof by using molecular profiling of sets of known biomarkers. For example, the method can identify a chemotherpeutic agent for an individual with a cancer. The method comprises: obtaining a sample from the subject; performing an immunohistochemistry (IHC) analysis on the sample to determine an IHC expression profile on at least five of: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least five of ABCC1, ABCG2, ADA, AR, ASNS, BCL2, BIRC5, BRCA1, BRCA2, CD33, CD52, CDA, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on at least one of EGFR and HER2; performing DNA sequencing on the sample to determine a sequencing mutation profile on at least one of KRAS, BRAF, c-KIT and EGFR; and comparing the IHC expression profile, microarray expression profile, FISH mutation profile and sequencing mutation profile against a rules database, wherein the rules database comprises a mapping of treatments whose biological activity is known against diseased cells that: i) overexpress or underexpress one or more proteins included in the IHC expression profile; ii) overexpress or underexpress one or more genes included in the microarray expression profile; iii) have zero or more mutations in one or more genes included in the FISH mutation profile; and/or iv) have zero or more mutations in one or more genes included in the sequencing mutation profile; and identifying the treatment if the comparison against the rules database indicates that the treatment should have biological activity against the disease; and the comparison against the rules database does not contraindicate the treatment for treating the disease. The disease can be a cancer. The molecular profiling steps can be performed in any order. In some embodiments, not all of the molecular profiling steps are performed. As a non-limiting example, microarray analysis is not performed if the sample quality does not meet a threshold value, as described herein. In some embodiments, the IHC expression profiling is performed on at least 20%, 30%, 40%, 50%, 60%, 70%, 80%, 90%, or 95% of the gene products above. In some embodiments, the microarray expression profiling is performed on at least 20%, 30%, 40%, 50%, 60%, 70%, 80%, 90%, or 95% of the genes listed above.

In a related aspect, the invention provides a method of identifying a candidate treatment for a subject in need thereof by using molecular profiling of defined sets of known biomarkers. For example, the method can identify a chemotherapeutic agent for an individual with a cancer. The method comprises: obtaining a sample from the subject, wherein the sample comprises formalin-fixed paraffin-embedded (FFPE) tissue or fresh frozen tissue, and wherein the sample comprises cancer cells; performing an immunohistochemistry (IHC) analysis on the sample to determine an IHC expression profile on at least: SPARC, PGP, Her2/neu, ER, PR, c-kit, AR, CD52, PDGFR, TOP2A, TS, ERCC1, RRM1, BCRP, TOPO1, PTEN, MGMT, and MRP1; performing a microarray analysis on the sample to determine a microarray expression profile on at least: ABCC1, ABCG2, ADA, AR, ASNS, BCL2, BIRC5, BRCA1, BRCA2, CD33, CD52, CES2, DCK, DHFR, DNMT1, DNMT3A, DNMT3B, ECGF1, EGFR, EPHA2, ERBB2, ERCC1, ERCC3, ESR1, FLT1, FOLR2, FYN, GART, GNRH1, GSTP1, HCK, HDAC1, HIF1A, HSP90AA1, IL2RA, HSP90AA1, KDR, KIT, LCK, LYN, MGMT, MLH1, MS4A1, MSH2, NFKB1, NFKB2, OGFR, PDGFC, PDGFRA, PDGFRB, PGR, POLA1, PTEN, PTGS2, RAF1, RARA, RRM1, RRM2, RRM2B, RXRB, RXRG, SPARC, SRC, SSTR1, SSTR2, SSTR3, SSTR4, SSTR5, TK1, TNF, TOP1, TOP2A, TOP2B, TXNRD1, TYMS, VDR, VEGFA, VHL, YES1, and ZAP70; performing a fluorescent in-situ hybridization (FISH) analysis on the sample to determine a FISH mutation profile on at least EGFR and HER2; performing DNA sequencing on the sample to determine a sequencing mutation profile on at least KRAS, BRAF, c-KIT and EGFR. The IHC expression profile, microarray expression profile, FISH mutation profile and sequencing mutation profile are compared against a rules database, wherein the rules database comprises a mapping of treatments whose biological activity is known against diseased cells that: i) overexpress or underexpress one or more proteins included in the IHC expression profile; ii) overexpress or underexpress one or more genes included in the microarray expression profile; iii) have zero or more mutations in one or more genes included in the FISH mutation profile; or iv) have zero or more mutations in one or more genes included in the sequencing mutation profile; and identifying the treatment if the comparison against the rules database indicates that the treatment should have biological activity against the disease; and the comparison against the rules database does not contraindicate the treatment for treating the disease. The disease can be a cancer. The molecular profiling steps can be performed in any order. In some embodiments, not all of the molecular profiling steps are performed. As a non-limiting example, microarray analysis is not performed if the sample quality does not meet a threshold value, as described herein. In some embodiments, the biological material is mRNA and the quality control test comprises a A260/A280 ratio and/or a Ct value of RT-PCR using a housekeeping gene, e.g., RPL13a. In embodiments, the mRNA does not pass the quality control test if the A260/A280 ratio <1.5 or the RPL13a Ct value is >30. In that case, microarray analysis may not be performed. Alternately, microarray results may be attenuated, e.g., given a lower priority as compared to the results of other molecular profiling techniques.

In some embodiments, molecular profiling is always performed on certain genes or gene products, whereas the profiling of other genes or gene products is optional. For example, IHC expression profiling may be performed on at least SPARC, TOP2A and/or PTEN. Similarly, microarray expression profiling may be performed on at least CD52. In other embodiments, genes in addition to those listed above are used to identify a treatment. For example, the group of genes used for the IHC expression profiling can further comprise DCK, EGFR, BRCA1, CK 14, CK 17, CK 5/6, E-Cadherin, p95, PARP-1, SPARC and TLE3. In some embodiments, the group of genes used for the IHC expression profiling further comprises Cox-2 and/or Ki-67. In some embodiments, HSPCA is assayed by microarray analysis. In some embodiments, FISH mutation is performed on c-Myc and TOP2A. In some embodiments, sequencing is performed on PI3K.

The methods of the invention can be used in any setting wherein differential expression or mutation analysis have been linked to efficacy of various treatments. In some embodiments, the methods are used to identify candidate treatments for a subject having a cancer. Under these conditions, the sample used for molecular profiling preferably comprises cancer cells. The percentage of cancer in a sample can be determined by methods known to those of skill in the art, e.g., using pathology techniques. Cancer cells can also be enriched from a sample, e.g., using microdissection techniques or the like. A sample may be required to have a certain threshold of cancer cells before it is used for molecular profiling. The threshold can be at least about 5, 10, 20, 30, 40, 50, 60, 70, 80, 90 or 95% cancer cells. The threshold can depend on the analysis method. For example, a technique that reveals expression in individual cells may require a lower threshold that a technique that used a sample extracted from a mixture of different cells. In some embodiments, the diseased sample is compared to a normal sample taken from the same patient, e.g., adjacent but non-cancer tissue.

Treatment Selection

The systems and methods invention can be used to select any treatment whose projected efficacy can be linked to molecular profiling results. The invention comprises use of molecular profiling results to suggest associations with treatment responses. In an embodiment, the appropriate biomarkers for molecular profiling are selected on the basis of the subjects's tumor type. These suggested biomarkers can be used to modify a default list of biomarkers. In other embodiments, the molecular profiling is independent of the source material. In some embodiments, rules are used to provide the suggested chemotherapy treatments based on the molecular profiling test results. In an embodiment, the rules are generated from abstracts of the peer reviewed clinical oncology literature. Expert opinion rules can be used but are optional. In an embodiment, clinical citations are assessed for their relevance to the methods of the invention using a hierarchy derived from the evidence grading system used by the United States Preventive Services Taskforce. The "best evidence" can be used as the basis for a rule. The simplest rules are constructed in the format of "if biomarker positive then treatment option one, else treatment option two." Treatment options comprise no treatment with a specific drug, treatment with a specific drug or treatment with a combination of drugs. In some embodiments, more complex rules are constructed that involve the interaction of two or more biomarkers. In such cases, the more complex interactions are typically supported by clinical studies that analyze the interaction between the biomarkers included in the rule. Finally, a report can be generated that describes the association of the chemotherapy response and the biomarker and a summary statement of the best evidence supporting the treatments selected. Ultimately, the treating physician will decide on the best course of treatment.

As a non-limiting example, molecular profiling might reveal that the EGFR gene is amplified or overexpressed, thus indicating selection of a treatment that can block EGFR activity, such as the monoclonal antibody inhibitors cetuximab and panitumumab, or small molecule kinase inhibitors effective in patients with activating mutations in EGFR such as gefitinib, erlotinib, and lapatinib. Other anti-EGFR monoclonal antibodies in clinical development include zalutumumab, nimotuzumab, and matuzumab. The candidate treatment selected can depend on the setting revealed by molecular profiling. E.g., kinase inhibitors are often prescribed with EGFR is found to have activating mutations. Continuing with the exemplary embodiment, molecular profiling may also reveal that some or all of these treatments are likely to be less effective. For example, patients taking gefitinib or erlotinib eventually develop drug resistance mutations in EGFR. Accordingly, the presence of a drug resistance mutation would contraindicate selection of the small molecule kinase inhibitors. One of skill will appreciate that this example can be expanded to guide the selection of other candidate treatments that act against genes or gene products whose differential expression is revealed by molecular profiling. Similarly, candidate agents known to be effective against diseased cells carrying certain nucleic acid variants can be selected if molecular profiling reveals such variants.

Cancer therapies that can be identified as candidate treatments by the methods of the invention include without limitation: 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate Dexamethasone Sodium Phosphate, Dexasone, Dexrazoxane, DHAD, DIC, Diodex Docetaxel, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™ Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oraped®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRONT™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®, and combinations of any thereof.

In some embodiments, a database is created that maps treatments and molecular profiling results. The treatment information can include the projected efficacy of a therapeutic agent against cells having certain attributes that can be measured by molecular profiling. The molecular profiling can include differential expression or mutations in certain genes, proteins, or other biological molecules of interest. Through the mapping, the results of the molecular profiling can be compared against the database to select treatments. The database can include both positive and negative mappings between treatments and molecular profiling results. In some embodiments, the mapping is created by reviewing the literature for links between biological agents and therapeutic agents. For example, a journal article, patent publication or patent application publication, scientific presentation, etc can be reviewed for potential mappings. The mapping can include results of in vivo, e.g., animal studies or clinical trials, or in vitro experiments, e.g., cell culture. Any mappings that are found can be entered into the database, e.g., cytotoxic effects of a therapeutic agent against cells expressing a gene or protein. In this manner, the database can be continuously updated. It will be appreciated that the methods of the invention are updated as well.

The rules for the mappings can contain a variety of supplemental information. In some embodiments, the database contains prioritization criteria. For example, a treatment with more projected efficacy in a given setting can be preferred over a treatment projected to have lesser efficacy. A mapping derived from a certain setting, e.g., a clinical trial, may be prioritized over a mapping derived from another setting, e.g., cell culture experiments. A treatment with strong literature support may be prioritized over a treatment supported by more preliminary results. A treatment generally applied to the type of disease in question, e.g., cancer of a certain tissue origin, may be prioritized over a treatment that is not indicated for that particular disease. Mappings can include both positive and negative correlations between a treatment and a molecular profiling result. In a non-limiting example, one mapping might suggest use of a kinase inhibior like erlotinib against a tumor having an activating mutation in EGFR, whereas another mapping might suggest against that treatment if the EGFR also has a drug resistance mutation. Similarly, a treatment might be indicated as effective in cells that overexpress a certain gene or protein but indicated as not effective if the gene or protein is underexpressed.

The selection of a candidate treatment for an individual can be based on molecular profiling results from any one or more of the methods described. Alternatively, selection of a candidate treatment for an individual can be based on molecular profiling results from more than one of the methods described. For example, selection of treatment for an individual can be based on molecular profiling results from FISH alone, IHC alone, or microarray analysis alone. In other embodiments, selection of treatment for an individual can be based on molecular profiling results from IHC, FISH, and microarray analysis; IHC and FISH; IHC and microarray analysis, or FISH and microarray analysis. Selection of treatment for an individual can also be based on molecular profiling results from sequencing or other methods of mutation detection. Molecular profiling results may include mutation analysis along with one or more methods, such as IHC, immunoassay, and/or microarray analysis. Different combinations and sequential results can be used. For example, treatment can be prioritized according the results obtained by molecular profiling. In an embodiment, the prioritization is based on the following algorithm: 1) IHC/FISH and microarray indicates same target as a first priority; 2) IHC positive result alone next priority; or 3) microarray positive result alone as last priority. Sequencing can also be used to guide selection. In some embodiments, sequencing reveals a drug resistance mutation so that the effected drug is not selected even if techniques including IHC, microarray and/or FISH indicate differntial expression of the target molecule. Any such contraindication, e.g., differential expression or mutation of another gene or gene product may override selection of a treatment.

An exemplary listing of microarray expression results versus predicted treatments is presented in Table 1. Molecular profiling is performed to determine whether a gene or gene product is differentially expressed in a sample as compared to a control. The control can be any appropriate control for the setting, including without limitation the expression level of a control gene such as a housekeeping gene, the expression of the same gene in healthy tissue from the same or other individuals, a statistical measure, a level of detection, etc. One of skill will appreciate that the results of any applicable molecular profiling techinque, e.g., microarray analysis PCR, Q-PCR, RT-PCR, immunoassay, SAGE, IHC, FISH or sequencing, can be used to determine expression status. The expression status of the gene or gene product is used to select agents that are predicted to be efficacious or not. For example, Table 1 shows that overexpression of the ADA gene or protein points to pentostatin as a possible treatment. On the other hand, underexpression of the ADA gene or protein implicates resistance to cytarabine, suggesting that cytarabine is not an optimal treatment.

TABLE 1

Molecular Profiling Results and Predicted Treatments

| Gene Name | Expression Status | Possible Agent(s) | Possible Resistance |
|---|---|---|---|
| ADA | Overexpressed | pentostatin | |
| ADA | Underexpressed | | cytarabine |
| AR | Overexpressed | abarelix, bicalutamide, flutamide, gonadorelin, goserelin, leuprolide | |
| ASNS | Underexpressed | asparaginase, pegaspargase | |
| BCRP (ABCG2) | Overexpressed | | cisplatin, carboplatin, irinotecan, topotecan |
| BRCA1 | Underexpressed | mitomycin | |
| BRCA2 | Underexpressed | mitomycin | |
| CD52 | Overexpressed | alemtuzumab | |
| CDA | Overexpressed | | cytarabine |
| CES2 | Overexpressed | irinotecan | |
| c-kit | Overexpressed | sorafenib, sunitinib, imatinib | |
| COX-2 | Overexpressed | celecoxib | |
| DCK | Overexpressed | gemcitabine | cytarabine |
| DHFR | Underexpressed | methotrexate, pemetrexed | |
| DHFR | Overexpressed | | methotrexate |
| DNMT1 | Overexpressed | azacitidine, decitabine | |
| DNMT3A | Overexpressed | azacitidine, decitabine | |
| DNMT3B | Overexpressed | azacitidine, decitabine | |
| EGFR | Overexpressed | erlotinib, gefitinib, cetuximab, panitumumab | |
| EPHA2 | Overexpressed | dasatinib | |
| ER | Overexpressed | anastrazole, exemestane, fulvestrant, letrozole, megestrol, tamoxifen, medroxyprogesterone, toremifene, aminoglutethimide | |
| ERCC1 | Overexpressed | | carboplatin, cisplatin |
| GART | Underexpressed | pemetrexed | |
| HER-2 (ERBB2) | Overexpressed | trastuzumab, lapatinib | |
| HIF-1α | Overexpressed | sorafenib, sunitinib, bevacizumab | |
| IκB-α | Overexpressed | bortezomib | |
| MGMT | Underexpressed | temozolomide | |
| MGMT | Overexpressed | | temozolomide |
| MRP1 (ABCC1) | Overexpressed | | etoposide, paclitaxel, docetaxel, vinblastine, vinorelbine, topotecan, teniposide |
| P-gp (ABCB1) | Overexpressed | | doxorubicin, etoposide, epirubicin, paclitaxel, docetaxel, vinblastine, vinorelbine, topotecan, teniposide, liposomal doxorubicin |
| PDGFR-α | Overexpressed | sorafenib, sunitinib, imatinib | |
| PDGFR-β | Overexpressed | sorafenib, sunitinib, imatinib | |
| PR | Overexpressed | exemestane, fulvestrant, gonadorelin, goserelin, medroxyprogesterone, megestrol, tamoxifen, toremifene | |
| RARA | Overexpressed | ATRA | |
| RRM1 | Underexpressed | gemcitabine, hydroxyurea | |
| RRM2 | Underexpressed | gemcitabine, hydroxyurea | |
| RRM2B | Underexpressed | gemcitabine, hydroxyurea | |
| RXR-α | Overexpressed | bexarotene | |
| RXR-β | Overexpressed | bexarotene | |
| SPARC | Overexpressed | nab-paclitaxel | |
| SRC | Overexpressed | dasatinib | |
| SSTR2 | Overexpressed | octreotide | |
| SSTR5 | Overexpressed | octreotide | |
| TOPO I | Overexpressed | irinotecan, topotecan | |
| TOPO IIα | Overexpressed | doxorubicin, epirubicin, liposomal-doxorubicin | |

TABLE 1-continued

Molecular Profiling Results and Predicted Treatments

| Gene Name | Expression Status | Possible Agent(s) | Possible Resistance |
|---|---|---|---|
| TOPO IIβ | Overexpressed | doxorubicin, epirubicin, liposomal-doxorubicin | |
| TS | Underexpressed | capecitabine, 5-fluorouracil, pemetrexed | |
| TS | Overexpressed | | capecitabine, 5-fluorouracil |
| VDR | Overexpressed | calcitriol, cholecalciferol | |
| VEGFR1 (Flt1) | Overexpressed | sorafenib, sunitinib, bevacizumab | |
| VEGFR2 | Overexpressed | sorafenib, sunitinib, bevacizumab | |
| VHL | Underexpressed | sorafenib, sunitinib | |

Table 2 presents a more comprehensive rules summary for treatment selection. For each biomarker in the table, an assay type and assay results are shown. A summary of the efficacy of various therapeutic agents given the assay results can be derived from the medical literature or other medical knowledge base. The results can be used to guide the selection of certain therapeutic agents as recommended or not. In some embodiments, the table is continuously updated as new literature reports and treatments become available. In this manner, the molecular profiling of the invention will evolve and improve over time. The rules in Table 2 can be stored in a database. When molecular profiling results are obtained, e.g., differential expression or mutation of a gene or gene product, the results can be compared against the database to guide treatment selection. The set of rules in the database can be updated as new treatments and new treatment data become available. In some embodiments, the rules database is updated continuously. In some embodiments, the rules database is updated on a periodic basis. The rules database can be updated at least every 1 day, 2 days, 3 days, 4 days, 5 days, 6 days, 1 week, 10 days, 2 weeks, 3 weeks, 4 weeks, 1 month, 6 weeks, 2 months, 3 months, 4 months, 5 months, 6 months, 7 months, 8 months, 9 months, 10 months, 11 months, 12 months, 1 year, 18 months, 2 years, or at least every 3 years. Any relevant correlative or comparative approach can be used to compare the molecular profiling results to the rules database. In one embodiment, a gene or gene product is identified as differentially expressed by molecular profiling. The rules database is queried to select entries for that gene or gene product. Treatment selection information selected from the rules database is extracted and used to select a treatment. The information, e.g., to recommend or not recommend a particular treatment, can be dependent on whether the gene or gene product is over or underexpressed. In some cases, multiple rules and treatments may be pulled from the database depending on the results of the molecular profiling. In some embodiments, the treatment options are prioritized in a list to present to an end user. In some embodiments, the treatment options are presented without prioritization information. In either case, an individual, e.g., the treating physician or similar caregiver, may choose from the available options.

TABLE 2

Rules Summary for Treatment Selection

| Biomarker | Assay | Result | Summary | Recommended Agents | Resistant Agents |
|---|---|---|---|---|---|
| Androgen Receptor | IHC | Above Threshold | High expression of AR protein can be associated with response to androgen ablation therapy (bicalutamide, flutamide, leuprolide, and goserelin) and longer RFS. | Bicalutamide, Flutamide, Leuprolide, Goserelin | |
| Androgen Receptor | IHC | Negative | Low expression of AR protein can be associated with lack of response to androgen ablation therapy (Bicalutamide, Flutamide, Leuprolide and Goserelin) and longer RFS. | | Bicalutamide, Flutamide, Leuprolide, Goserelin |
| BCRP | IHC | Above Threshold | High expression of BCRP has been associated with shorter progression-free (PFS) and overall survival (OS), when treated with platinum-based combination chemotherapy | | Cisplatin, Carboplatin |
| BCRP | IHC | Negative | Low expression of BCRP has been associated with longer progression-free (PFS) and overall survival (OS), when treated with platinum-based combination chemotherapy | Cisplatin, Carboplatin | |
| BRAF | Mutational Analysis | Mutated | BRAF mutations are associated with resistance to EGFR-targeted antibody therapies and associated decreased survival. | | Cetuximab, Panitumumab |
| BRAF | Mutational Analysis | Wild type genotype | Wild-type BRAF is associated with potential response to EGFR-targeted antibody therapies and associated increased survival. | Cetuximab, Panitumumab | |
| CD52 | IHC | Above Threshold | High expression of CD52 has been associated with benefit from alemtuzumab treatment. | Alemtuzumab | |
| CD52 | IHC | Negative | | | Alemtuzumab |
| c-kit | IHC | Above Threshold | High expression of c-Kit has been associated with significantly better survival, when treated with imatinib | Imatinib | |
| c-kit | IHC | Negative | | | Imatinib |
| EGFR | FISH | Positive | High EGFR gene copy number is associated with increased response and longer survival with EGFR targeted tyrosine kinase inhibitors | Erlotinib, Gefitinib | |
| EGFR | FISH | Negative | Lack of EGFR gene copy number increase is associated with reduced response and shorter survival with EGFR targeted tyrosine kinase inhibitors. | | Erlotinib, Gefitinib |
| EGFR | FISH | Positive | High EGFR gene copy number is associated with increased response and longer survival with EGFR targeted therapies | Cetuximab, Panitumumab, Erlotinib, Gefitinib | |
| EGFR | FISH | Negative | Lack of EGFR gene copy number increase is associated with reduced response and shorter survival with EGFR targeted therapies | | Cetuximab, Panitumumab, Erlotinib, Gefitinib |
| ER | IHC | Above Threshold | High expression of ER has been associated with response to endocrine therapy. | Tamoxifen-based treatment, aromatase inhibitors (anastrazole, letrozole) | |
| ER | IHC | Negative | Low expression of ER has been associated with response to ixabepilone. | Ixabepilone | Tamoxifen-based treatment, aromatase inhibitors (anastrazole, letrozole) |
| ERCC1 | IHC | Above Threshold | High expression of ERCC1 has been associated with lower response rates and a significantly shorter median progression-free and overall survival when treated with platinum-based chemotherapy. | | Carboplatin, Cisplatin, Oxaliplatin |

TABLE 2-continued

Rules Summary for Treatment Selection

| Biomarker | Assay | Result | Summary | Recommended Agents | Resistant Agents |
|---|---|---|---|---|---|
| ERCC1 | IHC | Negative | Low expression of ERCC1 has been associated with higher response rates and a significantly longer median progression-free and overall survival when treated with platinum-based chemotherapy. | Carboplatin, Cisplatin, Oxaliplatin | |
| Her2/Neu | IHC | Above Threshold | High expression and/or high gene copy number of Her-2 has been associated with improved response rate to trastuzumab or enhanced benefit or improved clinical outcome from lapatinib. | Lapatinib, Trastuzumab | |
| Her2/Neu | IHC | Negative | | | Lapatinib, Trastuzumab |
| Her2/Neu | FISH | Amplified | High expression and/or high gene copy number of Her-2 has been associated with improved response rate to trastuzumab or enhanced benefit or improved clinical outcome from lapatinib. | Lapatinib, Trastuzumab | |
| KRAS | Mutational Analysis | Mutated | The presence of a KRAS mutation has been associated with a lack of response, disease progression and decreased survival when patients are treated with EGFR targeted antibodies. | | Cetuximab, Panitumumab, |
| KRAS | Mutational Analysis | Wild type genotype | The absence of a KRAS mutation (wild-type) has been associated with response, slower disease progression and increased survival when patients are treated with EGFR targeted antibodies. | Cetuximab, Panitumumab, | |
| KRAS | Mutational Analysis | Mutated | The presence of a KRAS mutation has been associated with progressive disease, shorter median time to progression and decreased survival when patients are treated with EGFR targeted tyrosine kinase inhibitors. | | Erlotinib, Gefitinib |
| KRAS | Mutational Analysis | Wild type genotype | The absence of a KRAS mutation (wild-type) has been associated with stable disease and longer median time to progression when patients are treated with EGFR targeted tyrosine kinase inhibitors. | Erlotinib, Gefitinib | |
| KRAS | Mutational Analysis | Mutated | The presence of a KRAS mutation (wild-type) has been associated with shorter median survival when patients are treated with VBMCP/Cyclophosphamide | | VBMCP/Cyclophosphamide |
| KRAS | Mutational Analysis | Wild type genotype | The absence of a KRAS mutation (wild-type) has been associated with response. | VBMCP/Cyclophosphamide | |
| KRAS | Mutational Analysis | Mutated | The presence of a KRAS mutation in codon 61 has been implicated as an activating mutation in multiple malignancies including colorectal cancer and as such it could be associated with a lack of clinical benefit from cetuximab or panitumumab therapy. | | Cetuximab, Panitumumab |
| KRAS_OLD | Mutational Analysis | Wild type genotype | The absence of a KRAS mutation in codon 61 (wild-type) has been associated with response, slower disease progression and increased survival when patients are treated with cetuximab or panitumumab therapy. | Cetuximab, panitumumab | |
| KRAS | Mutational Analysis | Mutated | The presence of a KRAS mutation has been associated with a lack of response, faster disease progression and decreased survival when patients are treated with EGFR targeted therapies | | Cetuximab, Erlotinib, Panitumumab, Gefitinib |
| KRAS | Mutational Analysis | Wild type genotype | The absence of a KRAS mutation (wild-type) has been associated with response, slower disease progression and increased survival when patients are treated with EGFR targeted therapies | Cetuximab, Erlotinib, Panitumumab, Gefitinib | |
| MGMT | IHC | Above Threshold | High expression of MGMT has been associated with resistance to temozolomide-based therapy | | Temozolomide |
| MGMT | IHC | Negative | Low expression of MGMT has been associated with response to temozolomide-based therapy | Temozolomide | |
| MRP1 | IHC | Above Threshold | High expression of MRP1 has been associated with significantly shorter relapse-free (RFS) and overall survival (OS) when treated with Cyclophosphamide | | Cyclophosphamide |

TABLE 2-continued

Rules Summary for Treatment Selection

| Biomarker | Assay | Result | Summary | Recommended Agents | Resistant Agents |
|---|---|---|---|---|---|
| MRP1 | IHC | Negative | Low expression of MRP1 has been associated with significantly longer relapse-free (RFS) and overall survival (OS) when treated with Cyclophosphamide | Cyclophosphamide | |
| MRP1 | IHC | Above Threshold | High expression of MRP1 has been associated with significantly poorer response to etoposide | | Etoposide |
| MRP1 | IHC | Negative | Low expression of MRP1 has been associated with significantly better response to etoposide | Etoposide | |
| MRP1 | IHC | Above Threshold | High expression of MRP1 has been associated with a lower complete response rate (CR) to cyclophosphamide/vincristine | | Cyclophosphamide/Vincristine |
| MRP1 | IHC | Negative | Low expression of MRP1 has been associated with a higher complete response rate (CR) to cyclophosphamide/vincristine | Cyclophosphamide/Vincristine | |
| MRP1 | IHC | Above Threshold | High expression of MRP1 has been associated with significantly poorer response and shorter relapse-free (RFS) and overall survival (OS) when treated with cyclophosphamide, etoposide or vincristine | | Cyclophosphamide, Etoposide, Vincristine |
| MRP1 | IHC | Negative | Low expression of MRP1 has been associated with significantly better response, longer relapse-free (RFS) and overall survival (OS) when treated with cyclophosphamide, etoposide or vincristine | Cyclophosphamide, Etoposide, Vincristine | |
| PDGFR | IHC | Above Threshold | High expression of PDGFR a has been associated with response to imatinib treatment | Imatinib | |
| PDGFR | IHC | Negative | | | |
| PGP | IHC | Above Threshold | High p-glycoprotein expression can be associated with lack of response to induction therapy and shorter OS when treated with etoposide | | Etoposide |
| PGP | IHC | Negative | Low p-glycoprotein expression can be associated with response to induction therapy and longer OS when treated with etoposide | Etoposide | |
| PGP | IHC | Above Threshold | High p-glycoprotein expression can be associated with resistance to doxorubicin treatment | | Doxorubicin |
| PGP | IHC | Negative | Low p-glycoprotein expression can be associated with response to doxorubicin treatment | Doxorubicin | |
| PGP | IHC | Above Threshold | High p-glycoprotein expression can be associated with lack of response to paclitaxel | | Paclitaxel |
| PGP | IHC | Negative | Low p-glycoprotein expression can be associated with response to paclitaxel | Paclitaxel | |
| PGP | IHC | Above Threshold | High p-glycoprotein expression can be associated with shorter DFS and OS following vincristine chemotherapy | | Vincristine |
| PGP | IHC | Negative | Low p-glycoprotein expression can be associated with longer DFS and OS following vincristine chemotherapy | Vincristine | |
| PGP | IHC | Above Threshold | High p-glycoprotein expression can be associated with lack of response to etoposide, doxorubicin, paclitaxel or vincristine and shorter DFS and OS following radiochemotherapy | | Vincristine, Etoposide, Doxorubicin, Paclitaxel |
| PGP | IHC | Negative | Low p-glycoprotein expression can be associated with response to etoposide, doxorubicin, paclitaxel or vincristine and longer DFS and OS following radiochemotherapy | Vincristine, Etoposide, Doxorubicin, Paclitaxel | |
| PR | IHC | Above Threshold | High PR expression can be associated with benefit from tamoxifen, anastrazole and letrozole but a lack of benefit from chemoendocrine therapy | Tamoxifen, Anastrazole, Letrozole | Chemoendocrine therapy |

TABLE 2-continued

Rules Summary for Treatment Selection

| Biomarker | Assay | Result | Summary | Recommended Agents | Resistant Agents |
|---|---|---|---|---|---|
| PR | IHC | Negative | | Chemoendocrine therapy | Tamoxifen, Anastrazole, Letrozole |
| PTEN | IHC | Above Threshold | High PTEN expression can be associated with response to trastuzumab and longer TTP in breast cancer patients | Trastuzumab | |
| PTEN | IHC | Negative | Low PTEN expression can be associated with lack of response to trastuzumab and shorter TTP in breast cancer patients | | Trastuzumab |
| PTEN | IHC | Above Threshold | High PTEN expression can be associated with response to gefitinib and longer OS | Gefitinib | |
| PTEN | IHC | Negative | Low PTEN expression can be associated with lack of response to gefitinib and shorter OS | | Gefitinib |
| PTEN | IHC | Above Threshold | PTEN protein expression can be associated with response to EGFR targeted therapies including cetuximab and panitumumab | Cetuximab, Panitumumab | |
| PTEN | IHC | Negative | Loss of PTEN protein expression can be associated with resistance to EGFR targeted therapies including cetuximab and panitumumab | | Cetuximab, Panitumumab |
| PTEN | IHC | Above Threshold | PTEN protein expression can be associated with response to EGFR targeted therapies including erlotinib and gefitinib | Erlotinib, Gefitinib | |
| PTEN | IHC | Negative | Loss of PTEN protein expression can be associated with resistance to EGFR targeted therapies including erlotinib and gefitinib | | Erlotinib, Gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab | Cetuximab, Panitumumab, Erlotinib, Gefitinib and Trastuzumab | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab | | Cetuximab, Panitumumab, Erlotinib, Gefitinib and Trastuzumab |
| RRM1 | IHC | Above Threshold | High RRM1 expression can be associated with lack of response to gemcitabine-based treatment and poor outcome | | Gemcitabine |
| RRM1 | IHC | Negative | Low RRM1 expression can be associated with response to gemcitabine-based treatment and improved outcome | Gemcitabine | |
| SPARC | IHC | Above Threshold | High SPARC protein can be associated with response to nab-paclitaxel-based combination therapy | nab-paclitaxel | |
| SPARC | IHC | Negative | Low SPARC protein can be associated with lack of response to nab-paclitaxel-based combination therapy | | nab-paclitaxel |
| TS | IHC | Above Threshold | High TS expression levels are associated with poor response to fluoropyrimidines and shorter OS and DFS. | | fluoropyrimidines |
| TS | IHC | Negative | Lack of TS expression is associated with response to fluoropyrimidines and longer OS and DFS | fluoropyrimidines, pemetrexed | |
| TOPO1 | IHC | Above Threshold | High expression of TOPO1 has been associated with an overall survival benefit with first line combination chemotherapy that includes irinotecan | Irinotecan | |
| TOPO1 | IHC | Negative | Low expression of TOPO1 has been associated with a lack of response to first line combination chemotherapy that includes irinotecan | | Irinotecan |
| TOP2A | IHC | Above Threshold | High topo IIa expression can be associated with response to anthracyline-based (doxorubicin, liposomal-doxorubicin, epirubicin) therapy. | Doxorubicin, liposomal-Doxorubicin, Epirubicin | |

TABLE 2-continued

Rules Summary for Treatment Selection

| Biomarker | Assay | Result | Summary | Recommended Agents | Resistant Agents |
|---|---|---|---|---|---|
| TOP2A | IHC | Negative | Low topo IIa expression can be associated with lack of response to anthracycline-based (doxorubicin, liposomal-doxorubicin, epirubicin) therapy. | | Doxorubicin, liposomal-Doxorubicin, Epirubicin |
| ADA | Microarray | Overexpressed | | pentostatin | |
| ADA | Microarray | Underexpressed | | cytarabine | |
| AR | Microarray | Overexpressed | | abarelix, bicalutamide, flutamide, gonadorelin, goserelin, leuprolide | |
| ASNS | Microarray | Underexpressed | | asparaginase, pegaspargase | |
| ABCG2 | Microarray | Overexpressed | | | cisplatin, carboplatin, irinotecan, topotecan |
| BRCA1 | Microarray | Underexpressed | | mitomycin | |
| BRCA2 | Microarray | Underexpressed | | mitomycin | |
| CD52 | Microarray | Overexpressed | | alemtuzumab | |
| CDA | Microarray | Overexpressed | | | cytarabine |
| CES2 | Microarray | Overexpressed | | irinotecan | |
| KIT | Microarray | Overexpressed | | sorafenib, sunitinib, imatinib | |
| PTGS2 | Microarray | Overexpressed | | celecoxib | |
| DCK | Microarray | Overexpressed | | gemcitabine | |
| DHFR | Microarray | Underexpressed | | methotrexate, pemetrexed | |
| DHFR | Microarray | Overexpressed | | | methotrexate |
| DNMT1 | Microarray | Overexpressed | | azacitidine, decitabine | |
| DNMT3A | Microarray | Overexpressed | | azacitidine, decitabine | |
| DNMT3B | Microarray | Overexpressed | | azacitidine, decitabine | |
| EGFR | Microarray | Overexpressed | | erlotinib, gefitinib, cetuximab, panitumumab | |
| EPHA2 | Microarray | Overexpressed | | dasatinib | |
| ESR1 | Microarray | Overexpressed | | anastrazole, exemestane, fulvestrant, letrozole, megestrol, tamoxifen, medroxyprogesterone, toremifene, aminoglutethimide | |
| ERCC1 | Microarray | Overexpressed | | | carboplatin, cisplatin |
| GART | Microarray | Underexpressed | | pemetrexed | |

TABLE 2-continued

Rules Summary for Treatment Selection

| Biomarker | Assay | Result | Summary | Recommended Agents | Resistant Agents |
|---|---|---|---|---|---|
| ERBB2 | Microarray | Overexpressed | | trastuzumab, lapatinib | |
| HIF1A | Microarray | Overexpressed | | sorafenib, sunitinib, bevacizumab | |
| IL2RA | Microarray | Overexpressed | | bortezomib | |
| MGMT | Microarray | Underexpressed | | temozolomide | |
| MGMT | Microarray | Overexpressed | | | temozolomide |
| ABCC1 | Microarray | Overexpressed | | | etoposide, paclitaxel, docetaxel, vinblastine, vinorelbine, topotecan, teniposide |
| PGP | Microarray | Overexpressed | | | doxorubicin, etoposide, epirubicin, paclitaxel, docetaxel, vinblastine, vinorelbine, topotecan, teniposide, liposomal doxorubicin |
| PDGFRA | Microarray | Overexpressed | | sorafenib, sunitinib, imatinib | |
| PDGFRB | Microarray | Overexpressed | | sorafenib, sunitinib, imatinib | |
| PGR | Microarray | Overexpressed | | exemestane, fulvestrant, gonadorelin, goserelin, medroxyprogesterone, megestrol, tamoxifen, toremifene | |
| RARA | Microarray | Overexpressed | | ATRA | |
| RRM1 | Microarray | Underexpressed | | gemcitabine, hydroxyurea | |
| RRM2 | Microarray | Underexpressed | | gemcitabine, hydroxyurea | |
| RRM2B | Microarray | Underexpressed | | gemcitabine, hydroxyurea | |
| RXR-α | Microarray | Overexpressed | | bexarotene | |
| RXRB | Microarray | Overexpressed | | bexarotene | |
| SPARC | Microarray | Overexpressed | | nab-paclitaxel | |
| SRC | Microarray | Overexpressed | | dasatinib | |

TABLE 2-continued

Rules Summary for Treatment Selection

| Biomarker | Assay | Result | Summary | Recommended Agents | Resistant Agents |
|---|---|---|---|---|---|
| SSTR2 | Microarray | Overexpressed | | octreotide | |
| SSTR5 | Microarray | Overexpressed | | octreotide | |
| TOP1 | Microarray | Overexpressed | | irinotecan, topotecan | |
| TOP2A | Microarray | Overexpressed | | doxorubicin, epirubicin, liposomal-doxorubicin | |
| TOP2B | Microarray | Overexpressed | | doxorubicin, epirubicin, liposomal-doxorubicin | |
| TYMS | Microarray | Underexpressed | | capecitabine, 5-fluorouracil, pemetrexed | capecitabine, 5-fluorouracil |
| TYMS | Microarray | Overexpressed | | | |
| VDR | Microarray | Overexpressed | | calcitriol, cholecalciferol | |
| FLT1 | Microarray | Overexpressed | | sorafenib, sunitinib, bevacizumab | |
| KDR | Microarray | Overexpressed | | sorafenib, sunitinib, bevacizumab | |
| VHL | Microarray | Underexpressed | | sorafenib, sunitinib | |
| TOP2A | IHC | Negative | Low TOPO IIA expression has been associated with lack of response to anthracycline-based therapy. | | doxorubicin |
| PGP | IHC | Above Threshold | High p-glycoprotein expression has been associated with lack of response to anthracycline-based therapy. | | doxorubicin |
| TOP2A | IHC | Negative | Low TOPO IIA expression has been associated with lack of response to anthracycline-based therapy | | doxorubicin |
| PGP | IHC | Above Threshold | Anthracycline-based therapy is potentially of minimal benefit due to low TOPO IIA. | | doxorubicin |
| TOP2A | IHC | Above Threshold | Anthracycline-based therapy is potentially of minimal benefit due to high P-glycoprotein. | | doxorubicin |
| PGP | IHC | Above Threshold | High p-glycoprotein expression has been associated with lack of response to anthracycline-based therapy. | | |
| TOP2A | IHC | Above Threshold | High TOPO IIA expression has been associated with response to anthracycline-based therapy. | doxorubicin | |
| PGP | IHC | Negative | Low p-glycoprotein expression has been associated with response to anthracycline-based therapy. | doxorubicin | |
| TOP2A | IHC | Negative | Low TOPO IIA expression has been associated with lack of response to anthracycline-based therapy. | | doxorubicin |
| PGP | IHC | Above Threshold | High p-glycoprotein expression has been associated with lack of response to anthracycline-based therapy. | | doxorubicin |
| TOP2B | Microarray | Overexpressed | Anthracycline-based therapy is potentially of minimal benefit due to high p-glycoprotein. | | doxorubicin |
| TOP2A | IHC | Negative | Anthracycline-based therapy is of potential benefit due to low p-glycoprotein by IHC and high TOP2B by MA. | doxorubicin | |

TABLE 2-continued

Rules Summary for Treatment Selection

| Biomarker | Assay | Result | Summary | Recommended Agents | Resistant Agents |
|---|---|---|---|---|---|
| PGP | IHC | Negative | Low p-glycoprotein expression has been associated with response to anthracycline-based therapy. | doxorubicin | |
| TOP2B | Microarray | Overexpressed | Anthracycline-based therapy is potentially of minimal benefit due to high P-glycoprotein by IHC. | doxorubicin | doxorubicin |
| TOP2A | IHC | Above Threshold | | | |
| PGP | IHC | Above Threshold | High p-glycoprotein expression has been associated with lack of response to anthracycline-based therapy. | | doxorubicin |
| TOP2B | Microarray | Overexpressed | Anthracycline-based therapy is potentially of minimal benefit due to high p-glycoprotein by IHC. | | doxorubicin |
| TOP2A | IHC | Above Threshold | High TOPO IIA expression has been associated with response to anthracycline-based therapy. | doxorubicin | |
| PGP | IHC | Negative | Low p-glycoprotein expression has been associated with response to anthracycline-based therapy. | doxorubicin | |
| TOP2B | Microarray | Overexpressed | High topo IIa expression can be associated with response to anthracycline-based (doxorubicin, liposomal-doxorubicin, epirubicin) therapy | doxorubicin, liposomal doxorubicin epirubicin | |
| TOP2A | IHC | Above Threshold | | | |
| TOP2B | Microarray | Overexpressed | Anthracyclines are of potential value due to expression of Topo II alpha and beta | doxorubicin, liposomal doxorubicin epirubicin | |
| ABCB1 | Microarray | Overexpressed | Anthracyclines are of potential value due to expression of Topo II alpha and beta | doxorubicin, liposomal doxorubicin epirubicin | |
| TOP2A | IHC | Above Threshold | High TOPO IIA expression has been associated with response to anthracycline-based therapy. | doxorubicin, liposomal doxorubicin epirubicin | |
| TOP2B | Microarray | Overexpressed | | doxorubicin, liposomal doxorubicin epirubicin | |
| TOP2A | IHC | Above Threshold | High topo IIa expression can be associated with response to anthracycline-based (doxorubicin, liposomal-doxorubicin, epirubicin) therapy | doxorubicin, liposomal doxorubicin epirubicin | |
| ABCB1 | Microarray | Overexpressed | Anthracyclines are of potential value due to expression of Topo II alpha and beta | doxorubicin, liposomal doxorubicin epirubicin | |
| TOP2A | IHC | Negative | Low TOPO IIA expression has been associated with lack of response to anthracycline-based therapy. | | doxorubicin, liposomal doxorubicin epirubicin |

TABLE 2-continued

Rules Summary for Treatment Selection

| Biomarker | Assay | Result | Summary | Recommended Agents | Resistant Agents |
|---|---|---|---|---|---|
| TOP2B | Microarray | Overexpressed | Anthracycline-based therapy is potentially of minimal benefit due to high P-glycoprotein by microarray. | | doxorubicin, liposomal doxorubicin epirubicin |
| ABCB1 | Microarray | Overexpressed | | | doxorubicin, liposomal doxorubicin epirubicin |
| TOP2A | IHC | Negative | Anthracycline-based therapy may be of potential benefit due to high TOPOIIB by microarray. | doxorubicin, liposomal doxorubicin epirubicin | |
| TOP2B | Microarray | Overexpressed | | doxorubicin, liposomal doxorubicin epirubicin | |
| TOP2A | IHC | Negative | Low TOPO IIA expression has been associated with lack of response to anthracycline-based therapy. | | doxorubicin, liposomal doxorubicin epirubicin |
| ABCB1 | Microarray | Overexpressed | | | doxorubicin, liposomal doxorubicin epirubicin |
| PGP | IHC | Above Threshold | High p-glycoprotein expression has been associated with lack of response to paclitaxel. | | paclitaxel |
| ABCC1 | Microarray | Overexpressed | | | paclitaxel |
| PGP | IHC | Negative | Paclitaxel is potentially of minimal benefit due to high ABCC1 by microarray. | | paclitaxel |
| ABCC1 | Microarray | Overexpressed | | | paclitaxel |
| TOPO1 | IHC | Negative | Low TOPO I expression has been associated with lack of response to Irinotecan. | | irinotecan |
| CES2 | Microarray | Overexpressed | Irinotecan may be of potential benefit due to low TOPO I. | irinotecan | |
| TOPO1 | IHC | Above Threshold | High TOPO I expression has been associated with response to Irinotecan. | irinotecan | |
| CES2 | Microarray | Overexpressed | Topotecan is of potentially of minimal benefit due to high P-glycoprotein and high MRP1 by microarray. | | topotecan |
| TOP1 | Microarray | Overexpressed | | | topotecan |
| ABCB1 | Microarray | Overexpressed | Topotecan is potentially of minimal benefit due to high P-glycoprotein by microarray. | | topotecan |
| ABCC1 | Microarray | Overexpressed | | | topotecan |
| TOP1 | Microarray | Overexpressed | | | topotecan |
| ABCB1 | Microarray | Overexpressed | Topotecan is potentially of minimal benefit due to high MRP1 by microarray. | | topotecan |
| TOP1 | Microarray | Overexpressed | | | topotecan |
| ABCC1 | Microarray | Overexpressed | | | topotecan |
| PGP | IHC | Negative | Etoposide and Vincristine are potentially of minimal benefit due to high MRP1 by IHC. | | etoposide, vincristine |
| MRP1 | IHC | Above Threshold | High expression of MRP1 has been associated with lack of response to Etoposide and Vincristine. | | etoposide, vincristine |

TABLE 2-continued

Rules Summary for Treatment Selection

| Biomarker | Assay | Result | Summary | Recommended Agents | Resistant Agents |
|---|---|---|---|---|---|
| PGP | IHC | Negative | Low expression of P-glycoprotein has been associated with response to Etoposide and Vincristine. | etoposide, vincristine | |
| MRP1 | IHC | Negative | Low expression of MRP1 has been associated with response to Etoposide and Vincristine. | etoposide, vincristine | |
| PGP | IHC | Above Threshold | High expression of P-glycoprotein has been associated with lack of response to Etoposide and Vincristine. | | etoposide, vincristine |
| MRP1 | IHC | Negative | Etoposide and Vincristine are potentially of minimal benefit due to high P-glycoprotein by IHC. | | etoposide, vincristine |
| Her2/Neu | IHC | Negative | Low expression of HER-2 has been associated with lack of response to trastuzumab or lapatinib. | | trastuzumab, lapatinib |
| PTEN | IHC | Above Threshold | Trastuzumab or lapatinib may be of minimal benefit due to the lack of Her2 elevation. | | trastuzumab, lapatinib |
| Her2/Neu | IHC | Negative | Low expression of HER-2 has been associated with lack of response to trastuzumab or lapatinib. | | trastuzumab, lapatinib |
| PTEN | IHC | Negative | Trastuzumab or lapatinib may be of minimal benefit due to the lack of Her2 elevation. | | trastuzumab, lapatinib |
| Her2/Neu | IHC | Above Threshold | High expression of HER-2 has been associated with response to trastuzumab or lapatinib. | trastuzumab, lapatinib | |
| PTEN | IHC | Above Threshold | High expression of PTEN has been associated with response to trastuzumab or lapatinib. | trastuzumab, lapatinib | |
| Her2/Neu | IHC | Above Threshold | Trastuzumab may be of minimal benefit due to loss of PTEN, however Lapatinib may be of potential benefit due to elevated HER-2. | | trastuzumab |
| PTEN | IHC | Negative | Low expression of PTEN and high expression of HER-2 has been associated with response to lapatinib but not trastuzumab. | | trastuzumab |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib |
| BRAF | Mutational Analysis | Mutated | BRAF mutations are associated with resistance to EGFR-targeted antibody therapies and associated decreased survival. | | cetuximab, panitumumab, erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib |
| BRAF | Mutational Analysis | Wild type genotype | EGFR-targeted therapy is potentially of minimal benefit due to loss of PTEN expression, mutation of KRAS and FISH negative EGFR. | | cetuximab, panitumumab, erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Mutated | EGFR-targeted therapy is potentially of minimal benefit due to loss of PTEN expression, mutation of KRAS and FISH negative EGFR. | | cetuximab, panitumumab erlotinib, gefitinib |
| KRAS | Mutational Analysis | Wild type genotype | EGFR-targeted therapy is potentially of minimal benefit due to loss of PTEN expression, mutation of BRAF and FISH negative EGFR. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Wild type genotype | EGFR-targeted therapy is potentially of minimal benefit due to loss of PTEN expression and FISH negative EGFR. | | cetuximab, panitumumab erlotinib, gefitinib |
| KRAS | Mutational Analysis | Wild type genotype | EGFR-targeted therapy is potentially of minimal benefit due to loss of PTEN expression and FISH negative EGFR. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Positive | EGFR-targeted therapy is potentially of minimal benefit due to loss of PTEN expression and mutation of BRAF and KRAS. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Wild type genotype | EGFR-targeted therapy is potentially of minimal benefit due to loss of PTEN expression and mutation of KRAS. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Positive | EGFR-targeted therapy is potentially of minimal benefit due to loss of PTEN expression and mutation of KRAS. | | cetuximab, panitumumab erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Wild type genotype | EGFR-targeted therapy is potentially of minimal benefit due to loss of PTEN expression. | | cetuximab, panitumumab erlotinib, gefitinib |
| KRAS | Mutational Analysis | Wild type genotype | EGFR-targeted therapy is potentially of minimal benefit due to loss of PTEN expression. | | cetuximab, panitumumab erlotinib, gefitinib |
| EGFR | FISH | Positive | | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Wild type genotype | EGFR-targeted therapy is potentially of minimal benefit due to loss of PTEN expression and mutation of BRAF. | | cetuximab, panitumumab erlotinib, gefitinib |
| EGFR | FISH | Positive | EGFR-targeted therapy is potentially of minimal benefit due to loss of PTEN expression and mutation of BRAF. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation in codon 61 has been implicated as an activating mutation in multiple malignancies including colorectal cancer and as such it could be associated with a lack of clinical benefit from cetuximab or panitumumab therapy. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Wild type genotype | EGFR-targeted therapy is potentially of minimal benefit due to loss of PTEN expression, mutation of KRAS and FISH negative EGFR. | | cetuximab, panitumumab erlotinib, gefitinib |
| KRAS | Mutational Analysis | Mutated | The presence of a KRAS mutation in codon 61 has been implicated as an activating mutation in multiple malignancies including colorectal cancer and as such it could be associated with a lack of clinical benefit from cetuximab or panitumumab therapy. | | |

TABLE 2-continued

Rules Summary for Treatment Selection

| Biomarker | Assay | Result | Summary | Recommended Agents | Resistant Agents |
|---|---|---|---|---|---|
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Positive | EGFR-targeted therapy is potentially of minimal benefit due to loss of PTEN expression and mutation of BRAF and KRAS. | | cetuximab, panitumumab erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab erlotinib, gefitinib |
| BRAF | Mutational Analysis | Wild type genotype | EGFR-targeted therapy is potentially of minimal benefit due to loss of PTEN expression and mutation of KRAS. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Positive | EGFR-targeted therapy is potentially of minimal benefit due to loss of PTEN expression and mutation of KRAS. | | cetuximab, panitumumab erlotinib, gefitinib |
| PTEN | IHC | Above Threshold | EGFR-targeted therapy is potentially of minimal benefit due to mutation of KRAS and FISH negative EGFR. | | cetuximab, panitumumab erlotinib, gefitinib |
| BRAF | Mutational Analysis | Wild type genotype | EGFR-targeted therapy is potentially of minimal benefit due to mutation of KRAS and FISH negative EGFR. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Above Threshold | EGFR-targeted therapy is potentially of minimal benefit due to mutation of BRAF and FISH negative EGFR. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Wild type genotype | EGFR-targeted therapy is potentially of minimal benefit due to mutation of BRAF and FISH negative EGFR. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Above Threshold | EGFR-targeted therapy is potentially of minimal benefit due to FISH negative EGFR. | | cetuximab, panitumumab erlotinib, gefitinib |
| BRAF | Mutational Analysis | Wild type genotype | EGFR-targeted therapy is potentially of minimal benefit due to FISH negative EGFR. | | cetuximab, panitumumab erlotinib, gefitinib |
| KRAS | Mutational Analysis | Wild type genotype | EGFR-targeted therapy is potentially of minimal benefit due to FISH negative EGFR. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Above Threshold | EGFR-targeted therapy is potentially of minimal benefit due to mutation of KRAS and BRAF. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Positive | EGFR-targeted therapy is potentially of minimal benefit due to mutation of KRAS and BRAF. | | cetuximab, panitumumab erlotinib, gefitinib |
| PTEN | IHC | Above Threshold | EGFR-targeted therapy is potentially of minimal benefit due to mutation of KRAS. | | cetuximab, panitumumab erlotinib, gefitinib |
| BRAF | Mutational Analysis | Wild type genotype | EGFR-targeted therapy is potentially of minimal benefit due to mutation of KRAS. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Positive | EGFR-targeted therapy is potentially of minimal benefit due to mutation of KRAS. | | cetuximab, panitumumab erlotinib, gefitinib |
| PTEN | IHC | Above Threshold | EGFR-targeted therapy is potentially of minimal benefit due to mutation of BRAF. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Wild type genotype | EGFR-targeted therapy is potentially of minimal benefit due to mutation of BRAF. | | cetuximab, panitumumab erlotinib, gefitinib |
| EGFR | FISH | Positive | EGFR-targeted therapy is potentially of minimal benefit due to mutation of BRAF. | | cetuximab, panitumumab erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | cetuximab, panitumumab erlotinib, gefitinib | |
| BRAF | Mutational Analysis | Wild type genotype | Wild-type BRAF is associated with potential response to EGFR-targeted antibody therapies and associated increased survival. | cetuximab, panitumumab erlotinib, gefitinib | |
| KRAS | Mutational Analysis | Wild type genotype | The absence of a KRAS mutation (wild-type) has been associated with response, slower disease progression and increased survival when patients are treated with EGFR targeted therapies. | cetuximab, panitumumab erlotinib, gefitinib | |
| EGFR | FISH | Positive | High EGFR gene copy number is associated with increased response and longer survival with EGFR targeted therapies. | cetuximab, panitumumab erlotinib, gefitinib | |
| PTEN | IHC | Above Threshold | EGFR-targeted therapy is potentially of minimal benefit due to mutation of BRAF and KRAS, and FISH negative EGFR. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Above Threshold | EGFR-targeted therapy is potentially of minimal benefit due to mutation of KRAS and FISH negative EGFR. | | cetuximab, panitumumab erlotinib, gefitinib |
| BRAF | Mutational Analysis | Wild type genotype | EGFR-targeted therapy is potentially of minimal benefit due to mutation of KRAS and FISH negative EGFR. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| PTEN | IHC | Above Threshold | EGFR-targeted therapy is potentially of minimal benefit due to mutation of BRAF and KRAS. | | cetuximab, panitumumab erlotinib, gefitinib |

TABLE 2-continued

Rules Summary for Treatment Selection

| Biomarker | Assay | Result | Summary | Recommended Agents | Resistant Agents |
|---|---|---|---|---|---|
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Positive | EGFR-targeted therapy is potentially of minimal benefit due to mutation of BRAF and KRAS. | | cetuximab, panitumumab erlotinib, gefitinib |
| PTEN | IHC | Above Threshold | EGFR-targeted therapy is potentially of minimal benefit due to mutation of KRAS. | | cetuximab, panitumumab erlotinib, gefitinib |
| BRAF | Mutational Analysis | Wild type genotype | EGFR-targeted therapy is potentially of minimal benefit due to mutation of KRAS. | | cetuximab, panitumumab erlotinib, gefitinib |
| KRAS | Mutational Analysis | Mutated | The presence of a KRAS mutation in codon 61 has been implicated as an activating mutation in multiple malignancies including colo-rectal cancer and as such it could be associated with a lack of clinical benefit from cetuximab or panitumumab therapy. | | cetuximab, panitumumab erlotinib, gefitinib |
| EGFR | FISH | Positive | EGFR-targeted therapy is potentially of minimal benefit due to mutation of KRAS. | | cetuximab, panitumumab erlotinib, gefitinib |
| ER | IHC | Negative | Tamoxifen, anastrazole and letrozole are potentially of benefit due to expression of PR. Low expression of ER has been associated with response to ixabepilone in breast cancer only. | tamoxifen, anastrazole, letrozole, ixabepilone | |
| PR | IHC | Above Threshold | High PR expression can be associated with benefit from tamoxifen, anastrazole and letrozole but a lack of benefit from chemoendocrine therapy. | | tamoxifen, anastrazole, letrozole |
| ER | IHC | Negative | Low expression of ER has been associated with response to ixabepilone. | | |
| PR | IHC | Negative | Low expression of PR has been associated with lack of response to Tamoxifen and Aromatase Inhibitors. | | tamoxifen, anastrazole, letrozole |
| ER | IHC | Above Threshold | High expression of ER has been associated with response to endocrine therapy and lack of response to ixabepilone in all cancers except ovarian. | tamoxifen, anastrazole, letrozole | |
| PR | IHC | Above Threshold | High PR expression can be associated with benefit from tamoxifen, anastrazole and letrozole. | tamoxifen, anastrazole, letrozole | |
| ER | IHC | Above Threshold | High expression of ER has been associated with response to endocrine therapy and lack of response to ixabepilone in all cancers except ovarian. | tamoxifen, anastrazole, letrozole | |
| PR | IHC | Negative | Tamoxifen therapy is of potential benefit due to high ER expression. | tamoxifen, anastrazole, letrozole | |
| Androgen Receptor | IHC | Above Threshold | High expression of AR protein can be associated with response to androgen ablation therapy (Bicalutamide, Flutamide, Leuprolide, and Goserelin) longer RFS. | goserelin, leuprolide | |
| PR | Microarray | Overexpressed | | goserelin, leuprolide | |
| Androgen Receptor | IHC | Negative | Goserelin and leuprolide may be of potential benefit due to high PR by microarray. | goserelin, leuprolide | |
| PR | Microarray | Overexpressed | | | |

TABLE 2-continued

Rules Summary for Treatment Selection

| Biomarker | Assay | Result | Summary | Recommended Agents | Resistant Agents |
|---|---|---|---|---|---|
| ERCC1 | IHC | Negative | Platinum-based therapy is potentially of minimal benefit due to high BCRP | | cisplatin; carboplatin |
| BCRP | IHC | Above Threshold | High expression of BCRP has been associated with shorter progression-free (PFS) and overall survival (OS), when treated with platinum-based combination chemotherapy. | | cisplatin; carboplatin |
| ERCC1 | IHC | Negative | Low expression of ERCC1 has been associated with higher response rates and a significantly longer median progression-free and overall survival when treated with platinum-based chemotherapy. | cisplatin; carboplatin | |
| BCRP | IHC | Negative | Low expression of BCRP has been associated with longer progression-free (PFS) and overall survival (OS), when treated with platinum-based combination chemotherapy. | cisplatin; carboplatin | |
| ERCC1 | IHC | Above Threshold | High expression of ERCC1 has been associated with lower response rates and a significantly shorter median progression-free and overall survival when treated with platinum-based chemotherapy. | | cisplatin; carboplatin |
| BCRP | IHC | Above Threshold | High expression of BCRP has been associated with shorter progression-free (PFS) and overall survival (OS), when treated with platinum-based combination chemotherapy. | | cisplatin; carboplatin |
| ERCC1 | IHC | Above Threshold | High expression of ERCC1 has been associated with lower response rates and a significantly shorter median progression-free and overall survival when treated with platinum-based chemotherapy. | | cisplatin; carboplatin |
| BCRP | IHC | Negative | Platinum-based therapy is potentially of minimal benefit due to high ERCC1. | | cisplatin; carboplatin |
| RRM1 | IHC | Negative | Low RRM1 expression can be associated with response to gemcitabine treatment and improved outcome. | gemcitabine | |
| DCK RRM1 | Microarray IHC | Overexpressed Negative | Low RRM1 expression can be associated with response to gemcitabine treatment and improved outcome. | gemcitabine gemcitabine | |
| DCK RRM2 RRM1 | Microarray Microarray IHC | Overexpressed Underexpressed Negative | Low RRM1 expression can be associated with response to gemcitabine treatment and improved outcome. | gemcitabine gemcitabine gemcitabine | |
| DCK RRM2B RRM1 | Microarray Microarray IHC | Overexpressed Underexpressed Negative | Low RRM1 expression can be associated with response to gemcitabine treatment and improved outcome. | gemcitabine gemcitabine gemcitabine | |
| DCK RRM2 RRM2B RRM1 | Microarray Microarray Microarray IHC | Overexpressed Underexpressed Underexpressed Negative | Low RRM1 expression can be associated with response to gemcitabine treatment and improved outcome. | gemcitabine gemcitabine gemcitabine gemcitabine | |
| RRM2 RRM1 | Microarray IHC | Underexpressed Negative | Low RRM1 expression can be associated with response to gemcitabine treatment and improved outcome. | gemcitabine gemcitabine | |
| RRM2B RRM1 | Microarray IHC | Underexpressed Negative | Low RRM1 expression can be associated with response to gemcitabine treatment and improved outcome. | gemcitabine gemcitabine | |
| RRM2 RRM2B | Microarray Microarray | Underexpressed Underexpressed | Low RRM1 expression can be associated with response to gemcitabine treatment and improved outcome. | gemcitabine gemcitabine | |

TABLE 2-continued

Rules Summary for Treatment Selection

| Biomarker | Assay | Result | Summary | Recommended Agents | Resistant Agents |
|---|---|---|---|---|---|
| RRM1 | IHC | Above Threshold | High RRM1 expression can be associated with lack of response to gemcitabine treatment and poor outcome. | | gemcitabine |
| DCK | Microarray | Overexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| DCK | Microarray | Overexpressed | Gemcitabine is potentially of minimal benefit due to high RRM1 by IHC. | | gemcitabine |
| RRM2 | Microarray | Underexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| DCK | Microarray | Overexpressed | Gemcitabine is potentially of minimal benefit due to high RRM1 by IHC. | | gemcitabine |
| RRM2B | Microarray | Underexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| DCK | Microarray | Overexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| RRM2 | Microarray | Underexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| RRM2B | Microarray | Underexpressed | Gemcitabine is potentially of minimal benefit due to high RRM1 by IHC. | | gemcitabine |
| RRM1 | IHC | Above Threshold | High RRM1 expression can be associated with lack of response to gemcitabine treatment and poor outcome. | | gemcitabine |
| RRM2 | Microarray | Underexpressed | Gemcitabine is potentially of minimal benefit due to high RRM1 by IHC. | | gemcitabine |
| RRM2B | Microarray | Underexpressed | Gemcitabine is potentially of minimal benefit due to high RRM1 by IHC. | | gemcitabine |
| CDA | Microarray | Overexpressed | | | cytarabine |
| DCK | Microarray | Overexpressed | | | cytarabine |
| ADA | Microarray | Underexpressed | Cytarabine is potentially of minimal benefit due to high CDA and high DCK by microarray. | | cytarabine |
| CDA | Microarray | Overexpressed | | | cytarabine |
| DCK | Microarray | Overexpressed | | | cytarabine |
| CDA | Microarray | Overexpressed | | | cytarabine |
| ADA | Microarray | Underexpressed | Cytarabine is potentially of minimal benefit due to high CDA by Microarray. | | cytarabine |
| DCK | Microarray | Overexpressed | | | cytarabine |
| ADA | Microarray | Underexpressed | Cytarabine is potentially of minimal benefit due to high DCK by Microarray. | | cytarabine |
| c-kit | IHC | Negative | Imatinib may be of potential benefit due to high PDGFRA by IHC and high PDGFRB by MA. | imatinib | |
| PDGFR | IHC | Above Threshold | High expression of PDGFR a has been associated with response to imatinib treatment | imatinib | |
| PDGFRB | Microarray | Overexpressed | | imatinib | |
| c-kit | IHC | Negative | Imatinib may be of potential benefit due to high PDGFRB by MA. | imatinib | |
| PDGFR | IHC | Negative | Imatinib may be of potential benefit due to high PDGFRB by MA. | imatinib | |
| PDGFRB | Microarray | Overexpressed | | imatinib | |
| c-kit | IHC | Above Threshold | High expression of c-Kit has been associated with significantly better survival, when treated with imatinib. | imatinib | |
| PDGFR | IHC | Negative | Imatinib may be of potential benefit due to high c-kit by IHC and high PDGFRB by MA. | imatinib | |
| PDGFRB | Microarray | Overexpressed | | imatinib | |

TABLE 2-continued

Rules Summary for Treatment Selection

| Biomarker | Assay | Result | Summary | Recommended Agents | Resistant Agents |
|---|---|---|---|---|---|
| PGP | IHC | Above Threshold | High expression of P-glycoprotein has been associated with lack of response to Etoposide and Vincristine. | | etoposide, vincristine |
| MRP1 | IHC | Above Threshold | High expression of MRP1 has been associated with lack of response to Etoposide and Vincristine. | | etoposide, vincristine |
| RRM2 | Microarray | Underexpressed | Gemcitabine is potentially of minimal benefit due to high RRM1 by IHC. | | gemcitabine |
| RRM2B | Microarray | Underexpressed | Gemcitabine is potentially of minimal benefit due to high RRM1 by IHC. | | gemcitabine |
| c-kit | IHC | Above Threshold | High expression of c-Kit has been associated with significantly better survival, when treated with imatinib. | imatinib | |
| PDGFR | IHC | Above Threshold | High expression of PDGFR a has been associated with response to imatinib treatment | imatinib | |
| PDGFRB | Microarray | Overexpressed | | imatinib | |
| PTEN | IHC | Above Threshold | EGFR-targeted therapy is potentially of minimal benefit due to mutation of BRAF and KRAS, and FISH negative EGFR. | | cetuximab, panitumumab erlotinib, gefitinib |
| BRAF | Mutational Analysis | Mutated | BRAF mutations are associated with resistance to EGFR-targeted antibody therapies and associated decreased survival. | | cetuximab, panitumumab erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| CES2 | Microarray | Overexpressed | Irinotecan may be of minimal benefit due to low TOPO I and high ABCG2. | | irinotecan |
| ABCG2 | Microarray | Overexpressed | | | irinotecan |
| ABCG2 | Microarray | Overexpressed | | | irinotecan |
| CES2 | Microarray | Overexpressed | | irinotecan | |
| ABCG2 | Microarray | Overexpressed | Irinotecan may be of clinical benefit due to high expression of Topo I. | irinotecan | |
| ABCG2 | Microarray | Overexpressed | Irinotecan may be of clinical benefit due to high expression of Topo I. | irinotecan | |
| TOP2A | Microarray | Overexpressed | Anthracycline-based therapy is potentially of minimal benefit due to high P-glycoprotein. | | doxorubicin |
| ER | IHC | Above Threshold | High expression of ER has been associated with response to endocrine therapy and lack of response to ixabepilone. | Tamoxifen-based treatment, aromatase inhibitors (anastrazole, letrozole) | |
| ER | IHC | Negative | Low expression of ER has been associated with response to ixabepilone. | Ixabepilone | Tamoxifen-based treatment, aromatase inhibitors (anastrazole, letrozole) |
| ER | IHC | Negative | Tamoxifen, anastrazole and letrozole are potentially of benefit due to expression of PR. | tamoxifen, anastrozole, letrozole | |
| PR | IHC | Above Threshold | High PR expression can be associated with benefit from tamoxifen, anastrozole and letrozole but a lack of benefit from chemoendocrine therapy. | tamoxifen, anastrozole, letrozole | |

TABLE 2-continued

Rules Summary for Treatment Selection

| Biomarker | Assay | Result | Summary | Recommended Agents | Resistant Agents |
|---|---|---|---|---|---|
| ER | IHC | Above Threshold | High expression of ER has been associated with response to endocrine therapy. | Tamoxifen-based treatment, aromatase inhibitors (anastrozole, letrozole) | |
| PR | IHC | Above Threshold | High PR expression can be associated with benefit from tamoxifen, anastrozole and letrozole but a lack of benefit from chemoendocrine therapy. | tamoxifen, anastrozole, letrozole | |
| ER | IHC | Above Threshold | High expression of ER has been associated with response to endocrine therapy. | Tamoxifen-based treatment, aromatase inhibitors (anastrozole, letrozole) | |
| PR | IHC | Negative | Tamoxifen therapy is of potential benefit due to high ER expression. | Tamoxifen-based treatment, aromatase inhibitors (anastrozole, letrozole) | |
| ER | IHC | Negative | Tamoxifen, anastrozole and letrozole are potentially of benefit due to expression of PR. Low expression of ER has been associated with response to ixabepilone. | tamoxifen, anastrozole, letrozole, ixabepilone | |
| PR | IHC | Above Threshold | High PR expression can be associated with benefit from tamoxifen, anastrozole and letrozole but a lack of benefit from chemoendocrine therapy. | tamoxifen, anastrozole, letrozole | |
| ER | IHC | Above Threshold | High expression of ER has been associated with response to endocrine therapy and lack of response to ixabepilone. | Tamoxifen-based treatment, aromatase inhibitors (anastrozole, letrozole) | ixabepilone |
| PR | IHC | Above Threshold | High PR expression can be associated with benefit from tamoxifen, anastrozole and letrozole. | tamoxifen, anastrozole, letrozole | |
| ER | IHC | Above Threshold | High expression of ER has been associated with response to endocrine therapy and lack of response to ixabepilone. | Tamoxifen-based treatment, aromatase inhibitors (anastrozole, letrozole) | ixabepilone |
| PR | IHC | Negative | Tamoxifen therapy is of potential benefit due to high ER expression. | Tamoxifen-based treatment, aromatase inhibitors (anastrozole, letrozole) | |
| ER | IHC | Negative | Tamoxifen, anastrozole and letrozole are potentially of benefit due to expression of PR. | tamoxifen, anastrozole, letrozole | |
| PR | IHC | Above Threshold | High PR expression can be associated with benefit from tamoxifen, anastrozole and letrozole but a lack of benefit from chemoendocrine therapy. | tamoxifen, anastrozole, letrozole | |
| ER | IHC | Above Threshold | High expression of ER has been associated with response to endocrine therapy. | Tamoxifen-based treatment, aromatase inhibitors (anastrozole, letrozole) | |

TABLE 2-continued

Rules Summary for Treatment Selection

| Biomarker | Assay | Result | Summary | Recommended Agents | Resistant Agents |
|---|---|---|---|---|---|
| PR | IHC | Above Threshold | High PR expression can be associated with benefit from tamoxifen, anastrozole and letrozole but a lack of benefit from chemoendocrine therapy. | tamoxifen, anastrozole, letrozole | |
| ER | IHC | Above Threshold | High expression of ER has been associated with response to endocrine therapy. | Tamoxifen-based treatment, aromatase inhibitors (anastrozole, letrozole) | |
| PR | IHC | Negative | Tamoxifen therapy is of potential benefit due to high ER expression. | Tamoxifen-based treatment, aromatase inhibitors (anastrozole, letrozole) | |
| Her2/Neu | IHC | Above Threshold | | lapatinib | |
| SPARC Poly | IHC | Above Threshold | High SPARC protein can be associated with response to nab-paclitaxel-based combination therapy | nab-paclitaxel | |
| SPARC Poly | IHC | Above Threshold | High SPARC protein can be associated with response to nab-paclitaxel-based combination therapy | nab-paclitaxel | |
| SPARC Mono | IHC | Above Threshold | High SPARC protein can be associated with response to nab-paclitaxel-based combination therapy | nab-paclitaxel | |
| SPARC Mono | IHC | Above Threshold | High SPARC protein can be associated with response to nab-paclitaxel-based combination therapy | nab-paclitaxel | |
| COX-2 | IHC | Above Threshold | High COX-2 protein expression can be associated with better survival when patients were treated with aspirin. | | |
| COX-2 | IHC | Negative | Lack of COX-2 protein expression can be associated with reduced survival when patients were treated with aspirin. | | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| KRAS | Mutational Analysis | Mutated | The presence of a KRAS mutation has been associated with non-response when patients are treated with erlotinib. | | Erlotinib |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| KRAS | Mutational Analysis | Wild type genotype | Erlotinib is potentially of minimal benefit due to loss of PTEN expression and FISH negative EGFR. | | Erlotinib |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Mutated | The presence of a KRAS mutation has been associated with non-response when patients are treated with Erlotinib. | | Erlotinib |
| EGFR | FISH | Positive | EGFR-targeted therapy is potentially of minimal benefit due to loss of PTEN expression and mutation of KRAS. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| KRAS | Mutational Analysis | Wild type genotype | Erlotinib is potentially of minimal benefit due to loss of PTEN expression. | | Erlotinib |
| EGFR | FISH | Positive | EGFR-targeted therapy is potentially of minimal benefit due to loss of PTEN expression. | | Cetuximab, Panitumumab, Erlotinib, Gefitinib |
| PTEN | IHC | Above Threshold | EGFR-targeted therapy is potentially of minimal benefit due to mutation of KRAS and FISH negative EGFR. | | Cetuximab, Panitumumab, Erlotinib, Gefitinib, Trastuzumab |
| KRAS | Mutational Analysis | Mutated | The presence of a KRAS mutation has been associated with non-response when patients are treated with Erlotinib. | | Erlotinib |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Above Threshold | EGFR-targeted therapy is potentially of minimal benefit due to FISH negative EGFR. | | Cetuximab, Panitumumab, Erlotinib, Gefitinib, Trastuzumab |
| KRAS | Mutational Analysis | Wild type genotype | Erlotinib is potentially of minimal benefit due to FISH negative EGFR. | | Erlotinib |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Above Threshold | EGFR-targeted therapy is potentially of minimal benefit due to mutation of KRAS. | | Cetuximab, Panitumumab, Erlotinib, Gefitinib, Trastuzumab |
| KRAS | Mutational Analysis | Mutated | The presence of a KRAS mutation has been associated with non-response when patients are treated with Erlotinib. | | Erlotinib |
| EGFR | FISH | Positive | EGFR-targeted therapy is potentially of minimal benefit due to mutation of KRAS. | | Cetuximab, Panitumumab, Erlotinib, Gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | Cetuximab, Panitumumab, Erlotinib, Gefitinib, Trastuzumab | |
| KRAS | Mutational Analysis | Wild type genotype | The absence of a KRAS mutation (wild-type) has been associated with response when patients are treated with Erlotinib. | Erlotinib | |

TABLE 2-continued

Rules Summary for Treatment Selection

| Biomarker | Assay | Result | Summary | Recommended Agents | Resistant Agents |
|---|---|---|---|---|---|
| EGFR | FISH | Positive | High EGFR gene copy number is associated with increased response and longer survival with EGFR targeted therapies. | Cetuximab, Panitumumab, Erlotinib, Gefitinib | |
| PTEN | IHC | Negative | Loss of PTEN protein expression can be associated with resistance to EGFR targeted therapies including erlotinib and gefitinib | | erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including erlotinib and gefitinib | | erlotinib, gefitinib |
| EGFR | FISH | Positive | EGFR-targeted therapy is potentially of minimal benefit due to loss of PTEN expression. | | cetuximab, panitumumab, erlotinib, gefitinib |
| PTEN | IHC | Above Threshold | EGFR-targeted tyrosine kinase inhibitors are potentially of minimal benefit due to FISH negative EGFR. | | erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | PTEN protein expression is associated with response to EGFR targeted therapies including erlotinib and gefitinib | erlotinib, gefitinib | |
| EGFR | FISH | Positive | High EGFR gene copy number is associated with increased response and longer survival with EGFR targeted therapies. | cetuximab, panitumumab, erlotinib, gefitinib | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| EGFR | FISH | Negative | Lack of EGFR gene copy number increase is associated with reduced response and shorter survival with Erlotinib and Gefitinib. | | erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| EGFR | FISH | Positive | EGFR targeted tyrosine kinase inhibitors are potentially of minimal benefit due to loss of PTEN expression. | | erlotinib, gefitinib |
| PTEN | IHC | Above Threshold | EGFR-targeted therapy is potentially of minimal benefit due to FISH negative EGFR. | | Cetuximab, Panitumumab, Erlotinib, Gefitinib, Trastuzumab |
| EGFR | FISH | Negative | Lack of EGFR gene copy number increase is associated with reduced response and shorter survival with Erlotinib and Gefitinib. | | erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | Cetuximab, Panitumumab, Erlotinib, Gefitinib, Trastuzumab | |
| EGFR | FISH | Positive | High EGFR gene copy number is associated with increased response and longer survival with erlotinib or gefitinib treatment | erlotinib, gefitinib | |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to EGFR targeted antibody therapies including cetuximab and panitumumab | | cetuximab, panitumumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab |
| PTEN | IHC | Negative | Loss of PTEN protein expression can be associated with resistance to EGFR targeted antibody therapies including cetuximab and panitumumab | | cetuximab, panitumumab |
| BRAF | Mutational Analysis | Wild type genotype | EGFR-targeted antibody therapy is potentially of minimal benefit due to loss of PTEN expression and mutation of KRAS. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab |
| PTEN | IHC | Negative | Loss of PTEN protein expression can be associated with resistance to EGFR targeted antibody therapies including cetuximab and panitumumab | | cetuximab, panitumumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted antibody therapy is potentially of minimal benefit due to loss of PTEN expression and mutation of BRAF. | | cetuximab, panitumumab |
| PTEN | IHC | Negative | Loss of PTEN protein expression can be associated with resistance to EGFR targeted antibody therapies including cetuximab and panitumumab | | cetuximab, panitumumab |
| BRAF | Mutational Analysis | Wild type genotype | EGFR-targeted antibody therapy is potentially of minimal benefit due to loss of PTEN expression. | | cetuximab, panitumumab |
| KRAS | Mutational Analysis | Wild type genotype | EGFR-targeted antibody therapy is potentially of minimal benefit due to loss of PTEN expression. | | cetuximab, panitumumab |
| PTEN | IHC | Above Threshold | EGFR-targeted antibody therapy is potentially of minimal benefit due to mutation of BRAF and KRAS. | | cetuximab, panitumumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab |
| PTEN | IHC | Above Threshold | EGFR-targeted antibody therapy is potentially of minimal benefit due to mutation of KRAS. | | cetuximab, panitumumab |
| BRAF | Mutational Analysis | Wild type genotype | EGFR-targeted antibody therapy is potentially of minimal benefit due to mutation of KRAS. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab |
| PTEN | IHC | Above Threshold | EGFR-targeted antibody therapy is potentially of minimal benefit due to mutation of BRAF | | cetuximab, panitumumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted antibody therapy is potentially of minimal benefit due to mutation of BRAF. | | cetuximab, panitumumab |
| PTEN | IHC | Above Threshold | PTEN protein expression can be associated with response to EGFR targeted therapies including cetuximab and panitumumab | cetuximab, panitumumab | |

TABLE 2-continued

Rules Summary for Treatment Selection

| Biomarker | Assay | Result | Summary | Recommended Agents | Resistant Agents |
|---|---|---|---|---|---|
| BRAF | Mutational Analysis | Wild type genotype | Wild-type BRAF is associated with potential response to EGFR-targeted antibody therapies and associated increased survival. | cetuximab, panitumumab | |
| KRAS | Mutational Analysis | Wild type genotype | The absence of a KRAS mutation (wild-type) has been associated with response, slower disease progression and increased survival when patients are treated with EGFR targeted antibodies. | cetuximab, panitumumab | |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Mutated | The presence of EGFR mutations has been associated with response and longer OS and PFS when treated with EGFR-targeted tyrosine kinase inhibitors. | erlotinib, gefitinib | |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Wild type genotype | EGFR-targeted tyrosine kinase inhbitors are potentially of minimal benefit due to loss of PTEN expression and FISH negative EGFR. | | erlotinib, gefitinib |
| EGFR | Mutational Analysis | Mutated | EGFR-targeted tyrosine kinase inhibitors are potentially of minimal benefit due to loss of PTEN expression and FISH negative EGFR. | | erlotinib, gefitinib |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Wild type genotype | EGFR-targeted tyrosine kinase inhibitors are potentially of minimal benefit due to loss of PTEN expression and wild-type and FISH negative EGFR. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Mutated | EGFR-targeted tyrosine kinase inhibitors are potentially of minimal benefit due to loss of PTEN expression and mutation of KRAS. | | erlotinib, gefitinib |
| EGFR | FISH | Positive | EGFR-targeted tyrosine kinase inhibitors are potentially of minimal benefit due to loss of PTEN expression and mutation of KRAS. | | erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to the EGFR targeted tyrosine kinase inhibtor Gefitinib. | | gefitinib |
| KRAS | Mutational Analysis | Mutated | The presence of a KRAS mutation has been associated with a lack of response, faster disease progression and decreased survival when patients are treated with EGFR targeted tyrosine kinase inhbitors. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Positive | EGFR-targeted tyrosine kinase inhibitors are potentially of minimal benefit due to loss of PTEN expression, mutation of KRAS and wild-type EGFR. | | erlotinib, gefitinib |
| PTEN | IHC | Negative | Loss of PTEN protein expression can be associated with resistance to the EGFR targeted therapy Gefitinib. | | gefitinib |
| KRAS | Mutational Analysis | Wild type genotype | EGFR-targeted tyrosine kinase inhibitors are potentially of minimal benefit due to loss of PTEN expression. | | erlotinib, gefitinib |
| EGFR | Mutational Analysis | Mutated | EGFR-targeted tyrosine kinase inhibitors are potentially of minimal benefit due to loss of PTEN expression. | | erlotinib, gefitinib |
| EGFR | FISH | Positive | EGFR-targeted tyrosine kinase inhibitors are potentially of minimal benefit due to loss of PTEN expression. | | erlotinib, gefitinib |
| PTEN | IHC | Negative | Loss of PTEN protein expression can be associated with resistance to the EGFR targeted tyrosine kinase inhibitor Gefitinib. | | gefitinib |
| KRAS | Mutational Analysis | Wild type genotype | EGFR-targeted tyrosine kinase inhibitors are potentially of minimal benefit due to loss of PTEN expression and wild-type EGFR. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Positive | EGFR-targeted tyrosine kinase inhibitors are potentially of minimal benefit due to loss of PTEN expression and wild-type EGFR | | erlotinib, gefitinib |
| PTEN | IHC | Above Threshold | The EGFR-targeted tyrosine kinase inhibitor Gefitinib is potentially of minimal benefit due to mutation of KRAS and FISH negative EGFR. | trastuzumab | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Mutated | EGFR-targeted tyrosine kinase inhibitors are potentially of minimal benefit due to mutation of KRAS and FISH negative EGFR. | | erlotinib, gefitinib |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Above Threshold | The EGFR-targeted tyrosine kinase inhibitor Gefitinib is potentially of minimal benefit due to mutation of KRAS and wild-type and FISH negative EGFR. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Negative | Lack of EGFR gene copy number increase is associated with reduced response and shorter survival with EGFR targeted tyrosine kinase inhibitors. | | erlotinib, gefitinib |
| PTEN | IHC | Above Threshold | The EGFR-targeted tyrosine kinase inhibitor Gefitinib is potentially of minimal benefit due to FISH negative EGFR. | | gefitinib |
| KRAS | Mutational Analysis | Wild type genotype | EGFR-targeted tyrosine kinase inhibitors are potentially of minimal benefit due to FISH negative EGFR. | | erlotinib, gefitinib |

TABLE 2-continued

Rules Summary for Treatment Selection

| Biomarker | Assay | Result | Summary | Recommended Agents | Resistant Agents |
|---|---|---|---|---|---|
| EGFR | Mutational Analysis | Mutated | EGFR-targeted tyrosine kinase inhibitors are potentially of minimal benefit due to FISH negative EGFR. | | erlotinib, gefitinib |
| EGFR | FISH | Negative | Lack of EGFR gene copy number increase is associated with reduced response and shorter survival with EGFR targeted therapies. | | erlotinib, gefitinib |
| PTEN | IHC | Above Threshold | The EGFR-targeted tyrosine kinase inhibitor Gefitinib is potentially of minimal benefit due to wild-type and FISH negative EGFR. | | gefitinib |
| KRAS | Mutational Analysis | Wild type genotype | EGFR-targeted therapy is potentially of minimal benefit due to wild-type and FISH negative EGFR. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Negative | Lack of EGFR gene copy number increase is associated with reduced response and shorter survival with EGFR targeted therapies. | | erlotinib, gefitinib |
| PTEN | IHC | Above Threshold | The EGFR-targeted tyrosine kinase inhibitor Gefitinib is potentially of minimal benefit due to mutation of KRAS. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Mutated | EGFR-targeted tyrosine kinase inhibitors are potentially of minimal benefit due to mutation of KRAS. | | erlotinib, gefitinib |
| EGFR | FISH | Positive | EGFR-targeted tyrosine kinase inhibitors are potentially of minimal benefit due to mutation of KRAS. | | erlotinib, gefitinib |
| PTEN | IHC | Above Threshold | The EGFR-targeted tyrosine kinase inhibitor Gefitinib is potentially of minimal benefit due to mutation of KRAS and wild-type EGFR. | | gefitinib |
| KRAS | Mutational Analysis | Mutated | The presence of a KRAS mutation has been associated with a lack of response, faster disease progression and decreased survival when patients are treated with EGFR targeted tyrosine kinase inhibitors. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Positive | EGFR-targeted tyrosine kinase inhibitors are potentially of minimal benefit due to mutation of KRAS and wild-type EGFR. | | erlotinib, gefitinib |
| PTEN | IHC | Above Threshold | PTEN protein expression can be associated with response to the EGFR targeted tyrosine kinase inhibitor gefitinib. | gefitinib | |
| KRAS | Mutational Analysis | Wild type genotype | The absence of a KRAS mutation (wild-type) has been associated with response, slower disease progression and increased survival when patients are treated with EGFR targeted tyrosine kinase inhibitors. | erlotinib, gefitinib | |
| EGFR | Mutational Analysis | Mutated | The presence of EGFR mutations has been associated with response and longer OS and PFS with EGFR-targeted tyrosine kinase inhibitors. | erlotinib, gefitinib | |
| EGFR | FISH | Positive | High EGFR gene copy number is associated with increased response and longer survival with EGFR targeted tyrosine kinase inhibitors. | erlotinib, gefitinib | |
| PTEN | IHC | Above Threshold | The EGFR-targeted tyrosine kinase inhibitor Gefitinib is potentially of minimal benefit due to wild-type EGFR. | | gefitinib |
| KRAS | Mutational Analysis | Wild type genotype | EGFR-targeted tyrosine kinase inhibitors are potentially of minimal benefit due to wild-type EGFR. | | erlotinib, gefitinib |
| EGFR | Mutational Analysis | Wild type genotype | The absence of EGFR mutations has been associated with lack of response and shorter OS and PFS with EGFR-targeted tyrosine kinase inhibitors. | | erlotinib, gefitinib |
| EGFR | FISH | Positive | EGFR-targeted tyrosine kinase inhibitors are potentially of minimal benefit due to wild-type EGFR. | | erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Wild type genotype | EGFR-targeted therapy is potentially of minimal benefit due to loss of PTEN expression, mutation of KRAS and FISH negative EGFR. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted therapy is potentially of minimal benefit due to loss of PTEN expression, mutation of BRAF and FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Wild type genotype | EGFR-targeted therapy is potentially of minimal benefit due to loss of PTEN expression and FISH negative EGFR. | | cetuximab, panitumumab |
| KRAS | Mutational Analysis | Wild type genotype | EGFR-targeted therapy is potentially of minimal benefit due to loss of PTEN expression and FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Positive | EGFR-targeted therapy is potentially of minimal benefit due to loss of PTEN expression and mutation of BRAF and KRAS. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Wild type genotype | EGFR-targeted therapy is potentially of minimal benefit due to loss of PTEN expression and mutation of KRAS. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Positive | EGFR-targeted therapy is potentially of minimal benefit due to loss of PTEN expression and mutation of KRAS. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib, trastuzumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted therapy is potentially of minimal benefit due to loss of PTEN expression and mutation of BRAF. | | cetuximab, panitumumab, erlotinib, gefitinib |
| EGFR | FISH | Positive | EGFR-targeted therapy is potentially of minimal benefit due to loss of PTEN expression and mutation of BRAF. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib, trastuzumab |
| BRAF | Mutational Analysis | Wild type genotype | EGFR-targeted therapy is potentially of minimal benefit due to loss of PTEN expression. | | cetuximab, panitumumab |
| KRAS | Mutational Analysis | Wild type genotype | EGFR-targeted therapy is potentially of minimal benefit due to loss of PTEN expression. | | cetuximab, panitumumab, erlotinib, gefitinib |
| EGFR | FISH | Positive | EGFR-targeted therapy is potentially of minimal benefit due to loss of PTEN expression. | | cetuximab, panitumumab, erlotinib, gefitinib |

TABLE 2-continued

Rules Summary for Treatment Selection

| Biomarker | Assay | Result | Summary | Recommended Agents | Resistant Agents |
|---|---|---|---|---|---|
| PTEN | IHC | Above Threshold | EGFR-targeted therapy is potentially of minimal benefit due to mutation of BRAF and KRAS, and FISH negative EGFR. PTEN expression has been associated with clinical benefit from trastuzumab. | | cetuximab, panitumumab, erlotinib, gefitinib, trastuzumab |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to mutation of KRAS and FISH negative EGFR. PTEN expression has been associated with clinical benefit from trastuzumab. | trastuzumab | Cetuximab, Panitumumab, Erlotinib, Gefitinib |
| BRAF | Mutational Analysis | Wild type genotype | EGFR-targeted therapy is potentially of minimal benefit due to mutation of KRAS and FISH negative EGFR. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to mutation of BRAF and FISH negative EGFR. PTEN expression has been associated with clinical benefit from trastuzumab. | trastuzumab | Cetuximab, Panitumumab, Erlotinib, Gefitinib |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted therapy is potentially of minimal benefit due to mutation of BRAF and FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to FISH negative EGFR. PTEN expression has been associated with clinical benefit from trastuzumab. | trastuzumab | Cetuximab, Panitumumab, Erlotinib, Gefitinib |
| BRAF | Mutational Analysis | Wild type genotype | EGFR-targeted therapy is potentially of minimal benefit due to FISH negative EGFR. | | cetuximab, panitumumab |
| KRAS | Mutational Analysis | Wild type genotype | EGFR-targeted therapy is potentially of minimal benefit due to FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to mutation of KRAS and BRAF. PTEN expression has been associated with clinical benefit from trastuzumab. | trastuzumab | Cetuximab, Panitumumab, Erlotinib, Gefitinib |

TABLE 2-continued

Rules Summary for Treatment Selection

| Biomarker | Assay | Result | Summary | Recommended Agents | Resistant Agents |
|---|---|---|---|---|---|
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Positive | EGFR-targeted therapy is potentially of minimal benefit due to mutation of KRAS and BRAF. | | cetuximab, panitumumab, erlotinib, gefitinib |
| PTEN | IHC | Above Threshold | EGFR-targeted therapy is potentially of minimal benefit due to mutation of KRAS. PTEN expression has been associated with clinical benefit from trastuzumab. | trastuzumab | Cetuximab, Panitumumab, Erlotinib, Gefitinib |
| BRAF | Mutational Analysis | Wild type genotype | EGFR-targeted therapy is potentially of minimal benefit due to mutation of KRAS. | | cetuximab, panitumumab |
| KRAS | Mutational Analysis | Mutated | The presence of an activating mutation in KRAS has been associated with a lack of response, disease progression and decreased survival when patients are treated with EGFR targeted antibodies | | cetuximab, panitumumab, erlotinib, gefitinib |
| EGFR | FISH | Positive | EGFR-targeted therapy is potentially of minimal benefit due to mutation of KRAS. | | cetuximab, panitumumab, erlotinib, gefitinib |
| PTEN | IHC | Above Threshold | EGFR-targeted therapy is potentially of minimal benefit due to mutation of BRAF. PTEN expression has been associated with clinical benefit from trastuzumab. | trastuzumab | Cetuximab, Panitumumab, Erlotinib, Gefitinib |
| BRAF | Mutational Analysis | Mutated | BRAF mutations are associated with resistance to EGFR-targeted antibody therapies and associated decreased survival. | | cetuximab, panitumumab |
| KRAS | Mutational Analysis | Wild type genotype | EGFR-targeted therapy is potentially of minimal benefit due to mutation of BRAF. | | cetuximab, panitumumab, erlotinib, gefitinib |
| EGFR | FISH | Positive | EGFR-targeted therapy is potentially of minimal benefit due to mutation of BRAF. | | cetuximab, panitumumab, erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | Cetuximab, Panitumumab, Erlotinib, Gefitinib, Trastuzumab | |
| BRAF | Mutational Analysis | Wild type genotype | Wild-type BRAF is associated with potential response to EGFR-targeted antibody therapies and associated increased survival. | cetuximab, panitumumab | |
| KRAS | Mutational Analysis | Wild type genotype | The absence of a KRAS mutation (wild-type) has been associated with response, slower disease progression and increased survival when patients are treated with EGFR targeted therapies. | cetuximab, panitumumab, erlotinib, gefitinib | |
| EGFR | FISH | Positive | High EGFR gene copy number is associated with increased response and longer survival with EGFR targeted therapies. | cetuximab, panitumumab, erlotinib, gefitinib | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |

TABLE 2-continued

Rules Summary for Treatment Selection

| Biomarker | Assay | Result | Summary | Recommended Agents | Resistant Agents |
|---|---|---|---|---|---|
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| EGFR | FISH | Positive | EGFR-targeted therapy is potentially of minimal benefit due to loss of PTEN expression. | | cetuximab, panitumumab, erlotinib, gefitinib |
| PTEN | IHC | Above Threshold | EGFR-targeted therapy is potentially of minimal benefit due to FISH negative EGFR. PTEN expression has been associated with clinical benefit from trastuzumab. | trastuzumab | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | Cetuximab, Panitumumab, Erlotinib, Gefitinib, Trastuzumab | |
| EGFR | FISH | Positive | High EGFR gene copy number is associated with increased response and longer survival with EGFR targeted therapies. | cetuximab, panitumumab, erlotinib, gefitinib | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab | | cetuximab, panitumumab, erlotinib, gefitinib, trastuzumab |
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib, trastuzumab |
| KRAS | Mutational Analysis | Wild type genotype | EGFR-targeted therapy is potentially of minimal benefit due to loss of PTEN expression and FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib, trastuzumab |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Positive | EGFR-targeted therapy is potentially of minimal benefit due to loss of PTEN expression and mutation of KRAS. | | cetuximab, panitumumab, erlotinib, gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | cetuximab, panitumumab, erlotinib, gefitinib, trastuzumab |
| KRAS | Mutational Analysis | Wild type genotype | EGFR-targeted therapy is potentially of minimal benefit due to loss of PTEN expression. | | cetuximab, panitumumab, erlotinib, gefitinib |
| EGFR | FISH | Positive | EGFR-targeted therapy is potentially of minimal benefit due to loss of PTEN expression. | | cetuximab, panitumumab, erlotinib, gefitinib |
| PTEN | IHC | Above Threshold | EGFR-targeted therapy is potentially of minimal benefit due to mutation of BRAF and KRAS, and FISH negative EGFR. PTEN expression has been associated with clinical benefit from trastuzumab. | trastuzumab | cetuximab, panitumumab, erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to FISH negative EGFR. PTEN expression has been associated with clinical benefit from trastuzumab. | trastuzumab | cetuximab, panitumumab, erlotinib, gefitinib |
| KRAS | Mutational Analysis | Wild type genotype | EGFR-targeted therapy is potentially of minimal benefit due to FISH negative EGFR. | | cetuximab, panitumumab, erlotinib, gefitinib |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to mutation of KRAS. PTEN expression has been associated with clinical benefit from trastuzumab. | trastuzumab | cetuximab, panitumumab, erlotinib, gefitinib |
| KRAS | Mutational Analysis | Mutated | The presence of a KRAS mutation has been associated with a lack of response, faster disease progression and decreased survival when patients are treated with EGFR targeted therapies. | | cetuximab, panitumumab, erlotinib, gefitinib |
| EGFR | FISH | Positive | EGFR-targeted therapy is potentially of minimal benefit due to mutation of KRAS. | | cetuximab, panitumumab, erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | cetuximab, panitumumab, erlotinib, gefitinib, trastuzumab | |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Wild type genotype | The absence of a KRAS mutation (wild-type) has been associated with response, slower disease progression and increased survival when patients are treated with EGFR targeted therapies. | cetuximab, panitumumab, erlotinib, gefitinib | |
| EGFR | FISH | Positive | High EGFR gene copy number is associated with increased response and longer survival with EGFR targeted therapies. | cetuximab, panitumumab, erlotinib, gefitinib | |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Mutated | BRAF mutations are associated with resistance to EGFR-targeted antibody therapies and associated decreased survival. | | cetuximab, panitumumab |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Wild type genotype | EGFR-targeted antibody therapies are potentially of minimal benefit due to loss of PTEN expression and FISH negative EGFR. | | cetuximab, panitumumab |
| EGFR | FISH | Negative | Lack of EGFR gene copy number increase is associated with reduced response and shorter survival with EGFR targeted therapies. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Mutated | BRAF mutations are associated with resistance to EGFR-targeted antibody therapies and associated decreased survival. | | cetuximab, panitumumab |
| EGFR | FISH | Positive | EGFR-targeted therapy is potentially of minimal benefit due to loss of PTEN expression and mutation of BRAF. | | Cetuximab, Panitumumab, Erlotinib, Gefitinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. | | Cetuximab, Panitumumab, Erlotinib, Gefitinib, Trastuzumab |
| BRAF | Mutational Analysis | Wild type genotype | EGFR-targeted antibody therapies are potentially of minimal benefit due to loss of PTEN expression. | | cetuximab, panitumumab |
| EGFR | FISH | Positive | EGFR-targeted therapy is potentially of minimal benefit due to loss of PTEN expression. | | Cetuximab, Panitumumab, Erlotinib, Gefitinib |
| PTEN | IHC | Above Threshold | EGFR-targeted therapy is potentially of minimal benefit due to mutation of BRAF and FISH negative EGFR. PTEN expression has been associated with clinical benefit from trastuzumab. | trastuzumab | cetuximab, panitumumab, erlotinib, gefitinib |
| BRAF | Mutational Analysis | Mutated | BRAF mutations are associated with resistance to EGFR-targeted antibody therapies and associated decreased survival. | | cetuximab, panitumumab |

TABLE 2-continued

Rules Summary for Treatment Selection

| Biomarker | Assay | Result | Summary | Recommended Agents | Resistant Agents |
|---|---|---|---|---|---|
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to FISH negative EGFR. PTEN expression has been associated with clinical benefit from trastuzumab. | trastuzumab | cetuximab, panitumumab, erlotinib, Gefitinib |
| BRAF | Mutational Analysis | Wild type genotype | EGFR-targeted antibody therapies are potentially of minimal benefit due to FISH negative EGFR. | | cetuximab, panitumumab |
| EGFR | FISH | Negative | Lack of EGFR gene copy number increase is associated with reduced response and shorter survival with EGFR targeted therapies. | | cetuximab, panitumumab, erlotinib, gefitinib |
| PTEN | IHC | Above Threshold | EGFR-targeted therapy is potentially of minimal benefit due to mutation of BRAF. PTEN expression has been associated with clinical benefit from trastuzumab. | trastuzumab | cetuximab, panitumumab, erlotinib, Gefitinib |
| BRAF | Mutational Analysis | Mutated | BRAF mutations are associated with resistance to EGFR-targeted antibody therapies and decreased survival. | | cetuximab, panitumumab |
| EGFR | FISH | Positive | EGFR-targeted therapy is potentially of minimal benefit due to mutation of BRAF. | | cetuximab, panitumumab, erlotinib, gefitinib |
| PTEN | IHC | Above Threshold | PTEN protein expression can be associated with response to EGFR targeted therapies including cetuximab, panitumumab, erlotinib and gefitinib, as well as the Her2 targeted therapy trastuzumab. | cetuximab, panitumumab, erlotinib, gefitinib, trastuzumab | |
| BRAF | Mutational Analysis | Wild type genotype | Wild-type BRAF is associated with potential response to EGFR-targeted antibody therapies and associated increased survival. | cetuximab, panitumumab | |
| EGFR | FISH | Positive | High EGFR gene copy number is associated with increased response and longer survival with EGFR targeted therapies. | cetuximab, panitumumab, erlotinib, gefitinib | |
| Her2/Neu | IHC | Negative | (do not report) | | trastuzumab, lapatinib |
| PTEN | IHC | Above Threshold | PTEN protein expression can be associated with response to EGFR targeted therapies including cetuximab, panitumumab, erlotinib and gefitinib. Trastuzumab or lapatinib may be of minimal benefit due to lack of elevation of Her2. | erlotinib, gefitinib, cetuximab, panitumumab | trastuzumab, lapatinib |
| Her2/Neu | IHC | Negative | (do not report) | | trastuzumab, lapatinib |
| PTEN | IHC | Negative | Loss of PTEN protein expression can be associated with resistance to EGFR targeted therapies including cetuximab, panitumumab, erlotinib and gefitinib, as well as the Her2 targeted therapy trastuzumab. Lapatinib may be of minimal value due to lack of Her2 elevation. | | erlotinib, gefitinib, cetuximab, panitumumab, trastuzumab, lapatinib |
| Her2/Neu | IHC | Above Threshold | High expression of HER-2 has been associated with response to trastuzumab or lapatinib. | trastuzumab, lapatinib | |
| PTEN | IHC | Above Threshold | High expression of PTEN can be associated with response to EGFR targeted therapies including cetuximab, panitumumab, erlotinib and gefitinib, as well as the Her2 targeted therapy trastuzumab. | erlotinib, gefitinib, cetuximab, panitumumab, trastuzumab | |

TABLE 2-continued

Rules Summary for Treatment Selection

| Biomarker | Assay | Result | Summary | Recommended Agents | Resistant Agents |
|---|---|---|---|---|---|
| Her2/Neu | IHC | Above Threshold | Trastuzumab is potentially of minimal benefit due to loss of PTEN but lapatinib is of potential benefit due to elevated HER-2. | lapatinib | trastuzumab |
| PTEN | IHC | Negative | Low expression of PTEN and high expression of HER-2 has been associated lack of response to trastuzumab. Low PTEN expression is also associated with a lack of clinical benefit from EGFR targeted agents. | | erlotinib, gefitinib, cetuximab, panitumumab, trastuzumab |
| Her2/Neu | IHC | Negative | (do not report) | | trastuzumab, lapatinib |
| PTEN | IHC | Above Threshold | Trastuzumab or lapatinib may be of minimal benefit due to lack of Her2 elevation. | | trastuzumab, lapatinib |
| Her2/Neu | IHC | Negative | (do not report) | | trastuzumab, lapatinib |
| PTEN | IHC | Negative | Low PTEN expression can be associated with lack of response to trastuzumab and shorter TTP in breast cancer patients | | trastuzumab |
| Her2/Neu | IHC | Above Threshold | High expression of HER-2 has been associated with response to trastuzumab or lapatinib. | trastuzumab, lapatinib | |
| PTEN | IHC | Above Threshold | High expression of PTEN can be associated with response to trastuzumab. | trastuzumab | |
| Her2/Neu | IHC | Above Threshold | Trastuzumab may be of minimal benefit due to loss of PTEN, however Lapatinib may be of potential benefit due to elevated HER-2. | lapatinib | trastuzumab |
| PTEN | IHC | Negative | Low expression of PTEN and high expression of HER-2 has been associated with response to lapatinib but not trastuzumab. | | trastuzumab |
| COX-2 | Microarray | Overexpressed | For use only on hematologic malignancies | celecoxib, asprin | |
| RARA | Microarray | Overexpressed | | ATRA | |
| CD52 | Microarray | Overexpressed | For use only on hematologic malignancies | alemturzumab | |
| COX-2 | IHC | Above Threshold | High COX-2 protein expression can be associated with better survival when patients were treated with aspirin. | aspirin | |
| COX-2 | IHC | Negative | Lack of COX-2 protein expression can be associated with reduced survival when patients were treated with aspirin. | | aspirin |
| c-kit | Mutational Analysis | Mutated | c-Kit mutations in exon 11 were associated with a higher rate of objective response, superior event-free and overall survival when treated with imatinib, but lower clinical benefit and objective response when treated with sunitinib. | sunitinib | imatinib |
| c-kit | Mutational Analysis | Mutated | c-Kit mutations in exon 9 were associated with a lower rate of objective response, inferior event-free and overall survival when treated with imatinib, but increased clinical benefit and objective response when treated with sunitinib. | imatinib | sunitinib |
| c-kit | Mutational Analysis | Wild type genotype | Lack of c-Kit mutations can be associated with a lower rate of objective response, inferior event-free and overall survival when treated with imatinib, but increased clinical benefit and objective response when treated with sunitinib. | imatinib | sunitinib |
| c-kit | Mutational Analysis | Mutated | The L576P mutation has been associated with clinical benefit in only two metastatic melanoma patients treated with dasatinib | | dasatinib |
| c-kit | Mutational Analysis | Mutated | c-Kit mutations in exon 11 were associated with a higher rate of objective response, superior event-free and overall survival when treated with imatinib, but lower clinical benefit and objective response when treated with sunitinib. | sunitinib | imatinib |

TABLE 2-continued

Rules Summary for Treatment Selection

| Biomarker | Assay | Result | Summary | Recommended Agents | Resistant Agents |
|---|---|---|---|---|---|
| c-kit | Mutational Analysis | Mutated | c-Kit mutations in exon 9 were associated with a lower rate of objective response, inferior event-free and overall survival when treated with imatinib, but increased clinical benefit and objective response when treated with sunitinib. | imatinib | sunitinib |
| c-kit | Mutational Analysis | Wild type genotype | Lack of c-Kit mutations can be associated with a lower rate of objective response, inferior event-free and overall survival when treated with imatinib, but increased clinical benefit and objective response when treated with sunitinib. | imatinib | sunitinib |
| c-kit | Mutational Analysis | Mutated | The L576P mutation has been associated with clinical benefit in only two metastatic melanoma patients treated with dasatinib | | dasatinib |
| EGFR | Mutational Analysis | Mutated | EGFR-targeted tyrosine kinase inhibitors are potentially of minimal benefit due to loss of PTEN expression, mutated KRAS and FISH negative EGFR. | Erlotinib, Gefitinib | |
| EGFR | Mutational Analysis | Wild type genotype | The absence of EGFR mutations has been associated with lack of response and shorter OS and PFS when treated with EGFR-targeted tyrosine kinase inhibitors. | | Erlotinib, Gefitinib |
| EGFR | Mutational Analysis | Mutated | The presence of EGFR mutations has been associated with response and longer OS and PFS when treated with EGFR-targeted tyrosine kinase inhibitors. | Erlotinib, Gefitinib | |
| EGFR | Mutational Analysis | Wild type genotype | The absence of EGFR mutations has been associated with lack of response and shorter OS and PFS when treated with EGFR-targeted tyrosine kinase inhibitors. | | Erlotinib, Gefitinib |
| Her2/Neu | FISH | Amplified | High expression of HER-2 has been associated with response to trastuzumab or lapatinib. | trastuzumab, lapatinib | |
| Her2/Neu | FISH | Amplified | Trastuzumab may be of minimal benefit due to loss of PTEN, however Lapatinib may be of potential benefit due to elevated HER-2. | lapatinib | trastuzumab |
| Her2/Neu | FISH | Amplified | Trastuzumab may be of minimal benefit due to loss of PTEN, however Lapatinib may be of potential benefit due to elevated HER-2. | lapatinib | |
| Her2/Neu | FISH | Not Amplified | (do not report) | | trastuzumab, lapatinib |
| Her2/Neu | FISH | Amplified | High expression of HER-2 has been associated with response to trastuzumab or lapatinib. | trastuzumab, lapatinib | |
| Her2/Neu | FISH | Amplified | High expression of HER-2 has been associated with response to trastuzumab or lapatinib. | trastuzumab, lapatinib | |
| Her2/Neu | FISH | Amplified | Trastuzumab is potentially of minimal benefit due to loss of PTEN but lapatinib is of potential benefit due to elevated HER-2. | lapatinib | trastuzumab, lapatinib |
| Her2/Neu | FISH | Not Amplified | (do not report) | | trastuzumab, lapatinib |
| Her2/Neu | FISH | Amplified | High expression of HER-2 has been associated with response to trastuzumab or lapatinib. | trastuzumab, lapatinib | |
| Her2/Neu | FISH | Amplified | Trastuzumab may be of minimal benefit due to loss of PTEN, however Lapatinib may be of potential benefit due to elevated HER-2. | lapatinib | trastuzumab |
| Her2/Neu BRAF | FISH Mutational Analysis | Amplified Mutated | BRAF mutations are associated with resistance to EGFR-targeted antibody therapies and associated decreased survival. | lapatinib | cetuximab, panitumumab |

TABLE 2-continued

Rules Summary for Treatment Selection

| Biomarker | Assay | Result | Summary | Recommended Agents | Resistant Agents |
|---|---|---|---|---|---|
| KRAS | Mutational Analysis | Wild type genotype | EGFR-targeted therapy is potentially of minimal benefit due to mutation of BRAF. | | cetuximab, panitumumab, erlotinib, gefitinib |
| PTEN | IHC | Above Threshold | EGFR-targeted therapy is potentially of minimal benefit due to FISH negative EGFR. | | cetuximab, panitumumab erlotinib, gefitinib |
| BRAF | Mutational Analysis | Wild type genotype | EGFR-targeted therapy is potentially of minimal benefit due to FISH negative EGFR. | | cetuximab, panitumumab erlotinib, gefitinib |
| EGFR | FISH | Negative | Lack of EGFR gene copy number increase is associated with reduced response and shorter survival with EGFR targeted therapies. | | cetuximab, panitumumab erlotinib, gefitinib |
| EGFR | Microarray | Overexpressed | EGFR-targeted therapy is potentially of minimal benefit due to loss of PTEN expression. | | cetuximab, panitumumab erlotinib, gefitinib |
| EGFR | Microarray | Overexpressed | EGFR-targeted tyrosine kinase inhibitors are potentially of minimal benefit due to loss of PTEN expression. | | erlotinib, gefitinib |
| KRAS | Mutational Analysis | Wild type genotype | EGFR-targeted therapy is potentially of minimal benefit due to FISH negative EGFR. | | cetuximab, panitumumab, erlotinib, gefitinib |
| KRAS | Mutational Analysis | Wild type genotype | EGFR-targeted tyrosine kinase inhibitors are potentially of minimal benefit due to wild-type EGFR. | | erlotinib, gefitinib |
| PTEN | IHC | Above Threshold | The EGFR-targeted tyrosine kinase inhibitor Gefitinib is potentially of minimal benefit due to FISH negative EGFR. | | gefitinib |
| KRAS | Mutational Analysis | Wild type genotype | EGFR-targeted tyrosine kinase inhibitors are potentially of minimal benefit due to FISH negative EGFR. | | erlotinib, gefitinib |
| Her2/Neu | FISH | Amplified | Trastuzumab may be of minimal benefit due to loss of PTEN, however Lapatinib may be of potential benefit due to elevated HER-2. | lapatinib | trastuzumab |

The methods described herein can be used to prolong survival of a subject by providing personalized treatment options. In some embodiments, the subject has been previously treated with one or more therapeutic agents to treat the disease, e.g., a cancer. The cancer may be refractory to one of these agents, e.g., by acquiring drug resistance mutations. In some embodiments, the cancer is metastatic. In some embodiments, the subject has not previously been treated with one or more therapeutic agents identified by the method. Using molecular profiling, candidate treatments can be selected regardless of the stage, anatomical location, or anatomical origin of the cancer cells.

Progression-free survival (PFS) denotes the chances of staying free of disease progression for an individual or a group of individuals suffering from a disease, e.g., a cancer, after initiating a course of treatment. It can refer to the percentage of individuals in a group whose disease is likely to remain stable (e.g., not show signs of progression) after a specified duration of time. Progression-free survival rates are an indication of the effectiveness of a particular treatment. Similarly, disease-free survival (DFS) denotes the chances of staying free of disease after initiating a particular treatment for an individual or a group of individuals suffering from a cancer. It can refer to the percentage of individuals in a group who are likely to be free of disease after a specified duration of time. Disease-free survival rates are an indication of the effectiveness of a particular treatment. Treatment strategies can be compared on the basis of the PFS or DFS that is achieved in similar groups of patients. Disease-free survival is often used with the term overall survival when cancer survival is described.

The candidate treatment selected by molecular profiling according to the invention can be compared to a non-molecular profiling selected treatment by comparing the progression free survival (PFS) using therapy selected by molecular profiling (period B) with PFS for the most recent therapy on which the patient has just progressed (period A). See FIG. 32. In one setting, a PFS(B)/PFS(A) ratio ≥1.3 was used to indicate that the molecular profiling selected therapy provides benefit for patient (Robert Temple, *Clinical measurement in drug evaluation*. Edited by Wu Ningano and G. T. Thicker John Wiley and Sons Ltd. 1995; Von Hoff D. D. *Clin Can Res*. 4: 1079, 1999: Dhani et al. *Clin Cancer Res*. 15: 118-123, 2009). Other methods of comparing the treatment selected by molecular profiling to a non-molecular profiling selected treatment include determining response rate (RECIST) and percent of patients without progression or death at 4 months. The term "about" as used in the context of a numerical value for PFS means a variation of +/−ten percent (10%) relative to the numerical value. The PFS from a treatment selected by molecular profiling can be extended by at least 10%, 15%, 20%, 30%, 40%, 50%, 60%, 70%, 80%, or at least 90% as compared to a non-molecular profiling selected treatment. In some embodiments, the PFS from a treatment selected by molecular profiling can be extended by at least 100%, 150%, 200%, 300%, 400%, 500%, 600%, 700%, 800%, 900%, or at least about 1000% as compared to a non-molecular profiling selected treatment. In yet other embodiments, the PFS ratio (PFS on molecular profiling selected therapy or new treatment/PFS on prior therapy or treatment) is at least about 1.3. In yet other embodiments, the PFS ratio is at least about 1.1, 1.2, 1.3, 1.4, 1.5, 1.6, 1.7, 1.8, 1.9, or 2.0. In yet other embodiments, the PFS ratio is at least about 3, 4, 5, 6, 7, 8, 9 or 10.

Similarly, the DFS can be compared in patients whose treatment is selected with or without molecular profiling. In embodiments, DFS from a treatment selected by molecular profiling is extended by at least 10%, 15%, 20%, 30%, 40%, 50%, 60%, 70%, 80%, or at least 90% as compared to a non-molecular profiling selected treatment. In some embodiments, the DFS from a treatment selected by molecular profiling can be extended by at least 100%, 150%, 200%, 300%, 400%, 500%, 600%, 700%, 800%, 900%, or at least about 1000% as compared to a non-molecular profiling selected treatment. In yet other embodiments, the DFS ratio (DFS on molecular profiling selected therapy or new treatment/DFS on prior therapy or treatment) is at least about 1.3. In yet other embodiments, the DFS ratio is at least about 1.1, 1.2, 1.3, 1.4, 1.5, 1.6, 1.7, 1.8, 1.9, or 2.0. In yet other embodiments, the DFS ratio is at least about 3, 4, 5, 6, 7, 8, 9 or 10.

In some embodiments, the candidate treatment of the invention will not increase the PFS ratio or the DFS ratio in the patient, nevertheless molecular profiling provides invaluable patient benefit. For example, in some instances no preferable treatment has been identified for the patient. In such cases, molecular profiling provides a method to identify a candidate treatment where none is currently identified. The molecular profiling may extend PFS, DFS or lifespan by at least 1 week, 2 weeks, 3 weeks, 4 weeks, 1 month, 5 weeks, 6 weeks, 7 weeks, 8 weeks, 2 months, 9 weeks, 10 weeks, 11 weeks, 12 weeks, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months or 2 years. The molecular profiling may extend PFS, DFS or lifespan by at least 2½ years, 3 years, 4 years, 5 years, or more. In some embodiments, the methods of the invention improve outcome so that patient is in remission.

The effectiveness of a treatment can be monitored by other measures. A complete response (CR) comprises a complete disappearance of the disease: no disease is evident on examination, scans or other tests. A partial response (PR) refers to some disease remaining in the body, but there has been a decrease in size or number of the lesions by 30% or more. Stable disease (SD) refers to a disease that has remained relatively unchanged in size and number of lesions. Generally, less than a 50% decrease or a slight increase in size would be described as stable disease. Progressive disease (PD) means that the disease has increased in size or number on treatment. In some embodiments, molecular profiling according to the invention results in a complete response or partial response. In some embodiments, the methods of the invention result in stable disease. In some embodiments, the invention is able to achieve stable disease where non-molecular profiling results in progressive disease.

Computer Systems

Conventional data networking, application development and other functional aspects of the systems (and components of the individual operating components of the systems) may not be described in detail herein but are part of the invention. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: patient data such as family history, demography and environmental data, biological sample data, prior treatment and protocol data, patient clinical data, molecular profiling data of biological samples, data on therapeutic drug agents and/or investigative drugs, a gene library, a disease library, a drug library, patient tracking data, file management data, financial management data, billing data and/or like data useful in the operation of the system. As those skilled in the art will appreciate, user computer may include an operating system (e.g., Windows NT, 95/98/2000, OS2, UNIX, Linux, Solaris, MacOS, etc.) as well as various conventional support software and drivers typically associated with computers. The computer may include any suitable personal computer, network computer, workstation, minicomputer, mainframe or the like. User computer can be in a home or medical/business environment with access to a network. In an exemplary embodiment, access is through a network or the Internet through a commercially-available web-browser software package.

As used herein, the term "network" shall include any electronic communications means which incorporates both hardware and software components of such. Communication among the parties may be accomplished through any suitable communication channels, such as, for example, a telephone network, an extranet, an intranet, Internet, point of interaction device, personal digital assistant (e.g., Palm Pilot®, Blackberry®), cellular phone, kiosk, etc.), online communications, satellite communications, off-line communications, wireless communications, transponder communications, local area network (LAN), wide area network (WAN), networked or linked devices, keyboard, mouse and/or any suitable communication or data input modality. Moreover, although the system is frequently described herein as being implemented with TCP/IP communications protocols, the system may also be implemented using IPX, Appletalk, IP-6, NetBIOS, OSI or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish networks, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

As used herein, "transmit" may include sending electronic data from one system component to another over a network connection. Additionally, as used herein, "data" may include encompassing information such as commands, queries, files, data for storage, and the like in digital or any other form.

The system contemplates uses in association with web services, utility computing, pervasive and individualized computing, security and identity solutions, autonomic computing, commodity computing, mobility and wireless solutions, open source, biometrics, grid computing and/or mesh computing.

Any databases discussed herein may include relational, hierarchical, graphical, or object-oriented structure and/or any other database configurations. Common database products that may be used to implement the databases include DB2 by IBM (White Plains, N.Y.), various database products available from Oracle Corporation (Redwood Shores, Calif.), Microsoft Access or Microsoft SQL Server by Microsoft Corporation (Redmond, Wash.), or any other suitable database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In one exemplary embodiment, the ability to store a wide variety of information in different formats is facilitated by storing the information as a BLOB. Thus, any binary information can be stored in a storage space associated with a data set. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data by multiple and unrelated owners of the data sets. For example, a first data set which may be stored may be provided by a first party, a second data set which may be stored may be provided by an unrelated second party, and yet a third data set which may be stored, may be provided by a third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, in one exemplary embodiment, the data set (e.g., BLOB) may be annotated in a standard manner when provided for manipulating the data. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. Subsequent bytes of data may be used to indicate for example, the identity of the issuer or owner of the data, user, transaction/membership account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the transaction, issuer or owner of data, user or the like. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate. The data, including the header or trailer may be received by a stand alone interaction device configured to add, delete, modify, or augment the data in accordance with the header or trailer.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

The computing unit of the web client may be further equipped with an Internet browser connected to the Internet or an intranet using standard dial-up, cable, DSL or any other Internet protocol known in the art. Transactions originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based and Packet Filtering among others. Firewall may be integrated within an web server or any other CMS components or may further reside as a separate entity.

The computers discussed herein may provide a suitable website or other Internet-based graphical user interface which is accessible by users. In one embodiment, the Microsoft Internet Information Server (IIS), Microsoft Transaction Server (MTS), and Microsoft SQL Server, are used in conjunction with the Microsoft operating system, Microsoft NT web server software, a Microsoft SQL Server database system, and a Microsoft Commerce Server. Additionally, components such as Access or Microsoft SQL Server, Oracle, Sybase, Informix MySQL, Interbase, etc., may be used to provide an Active Data Object (ADO) compliant database management system.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, Java applets, JavaScript, active server pages (ASP), common gateway interface scripts (CGI), extensible markup language (XML), dynamic HTML, cascading style sheets (CSS), helper applications, plug-ins, and the like. A server may include a web service that receives a request from a web server, the request including a URL (http://yahoo.com/stockquotes/ge) and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, XSLT, SOAP, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference.

The web-based clinical database for the system and method of the present invention preferably has the ability to upload and store clinical data files in native formats and is searchable on any clinical parameter. The database is also scalable and may utilize an EAV data model (metadata) to enter clinical annotations from any study for easy integration with other studies. In addition, the web-based clinical database is flexible and may be XML and XSLT enabled to be able to add user customized questions dynamically. Further, the database includes exportability to CDISC ODM.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, Macromedia Cold Fusion, Microsoft Active Server Pages, Java, COBOL, assembler, PERL, Visual Basic, SQL Stored Procedures, extensible markup language (XML), with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JavaScript, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "Java Cryptography" by Jonathan Knudson, published by O'Reilly & Associates (1998); (3) "Cryptography & Network Security: Principles & Practice" by William Stallings, published by Prentice Hall; all of which are hereby incorporated by reference.

As used herein, the term "end user", "consumer", "customer", "client", "treating physician", "hospital", or "business" may be used interchangeably with each other, and each shall mean any person, entity, machine, hardware, software or business. Each participant is equipped with a computing device in order to interact with the system and facilitate online data access and data input. The customer has a computing unit in the form of a personal computer, although other types of computing units may be used including laptops, notebooks, hand held computers, set-top boxes, cellular telephones, touch-tone telephones and the like. The owner/operator of the system and method of the present invention has a computing unit implemented in the form of a computer-server, although other implementations are contemplated by the system including a computing center shown as a main frame computer, a mini-computer, a PC server, a network of computers located in the same of different geographic locations, or the like. Moreover, the system contemplates the use, sale or distribution of any goods, services or information over any network having similar functionality described herein.

In one exemplary embodiment, each client customer may be issued an "account" or "account number". As used herein, the account or account number may include any device, code, number, letter, symbol, digital certificate, smart chip, digital signal, analog signal, biometric or other identifier/indicia suitably configured to allow the consumer to access, interact with or communicate with the system (e.g., one or more of an authorization/access code, personal identification number (PIN), Internet code, other identification code, and/or the like). The account number may optionally be located on or associated with a charge card, credit card, debit card, prepaid card, embossed card, smart card, magnetic stripe card, bar code card, transponder, radio frequency card or an associated account. The system may include or interface with any of the foregoing cards or devices, or a fob having a transponder and RFID reader in RF communication with the fob. Although the system may include a fob embodiment, the invention is not to be so limited. Indeed, system may include any device having a transponder which is configured to communicate with RFID reader via RF communication. Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit. The account number may be distributed and stored in any form of plastic, electronic, magnetic, radio frequency, wireless, audio and/or optical device capable of transmitting or downloading data from itself to a second device.

As will be appreciated by one of ordinary skill in the art, the system may be embodied as a customization of an existing system, an add-on product, upgraded software, a stand alone system, a distributed system, a method, a data processing system, a device for data processing, and/or a computer program product. Accordingly, the system may take the form of an entirely software embodiment, an entirely hardware embodiment, or an embodiment combining aspects of both software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

Referring now to FIGS. 2-25 the process flows and screenshots depicted are merely embodiments and are not intended to limit the scope of the invention as described herein. For example, the steps recited in any of the method or process descriptions may be executed in any order and are not limited to the order presented. It will be appreciated that the following description makes appropriate references not only to the steps and user interface elements depicted in FIGS. 2-25, but also to the various system components as described above with reference to FIG. 1.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, webpages, websites, web forms, prompts, etc. Practitioners will appreciate that the illustrated steps described herein may comprise in any number of configurations including the use of windows, webpages, web forms, popup windows, prompts and the like. It should be further appreciated that the multiple steps as illustrated and described may be combined into single webpages and/or windows but have been expanded for the sake of simplicity. In other cases, steps illustrated and described as single process steps may be separated into multiple webpages and/or windows but have been combined for simplicity.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical".

FIG. 1 illustrates a block diagram of an exemplary embodiment of a system 10 for determining individualized medical intervention for a particular disease state that utilizes molecular profiling of a patient's biological specimen. System 10 includes a user interface 12, a host server 14 including a processor 16 for processing data, a memory 18 coupled to the processor, an application program 20 stored in the memory 18 and accessible by the processor 16 for directing processing of the data by the processor 16, a plurality of internal databases 22 and external databases 24, and an interface with a wired or wireless communications network 26 (such as the Internet, for example). System 10 may also include an input digitizer 28 coupled to the processor 16 for inputting digital data from data that is received from user interface 12.

User interface 12 includes an input device 30 and a display 32 for inputting data into system 10 and for displaying information derived from the data processed by processor 16. User interface 12 may also include a printer 34 for printing the information derived from the data processed by the processor 16 such as patient reports that may include test results for targets and proposed drug therapies based on the test results.

Internal databases 22 may include, but are not limited to, patient biological sample/specimen information and tracking, clinical data, patient data, patient tracking, file management, study protocols, patient test results from molecular profiling, and billing information and tracking. External databases 24 nay include, but are not limited to, drug libraries, gene libraries, disease libraries, and public and private databases such as UniGene, OMIM, GO, TIGR, GenBank, KEGG and Biocarta.

Molecular Profiling Methods

Figure 2:
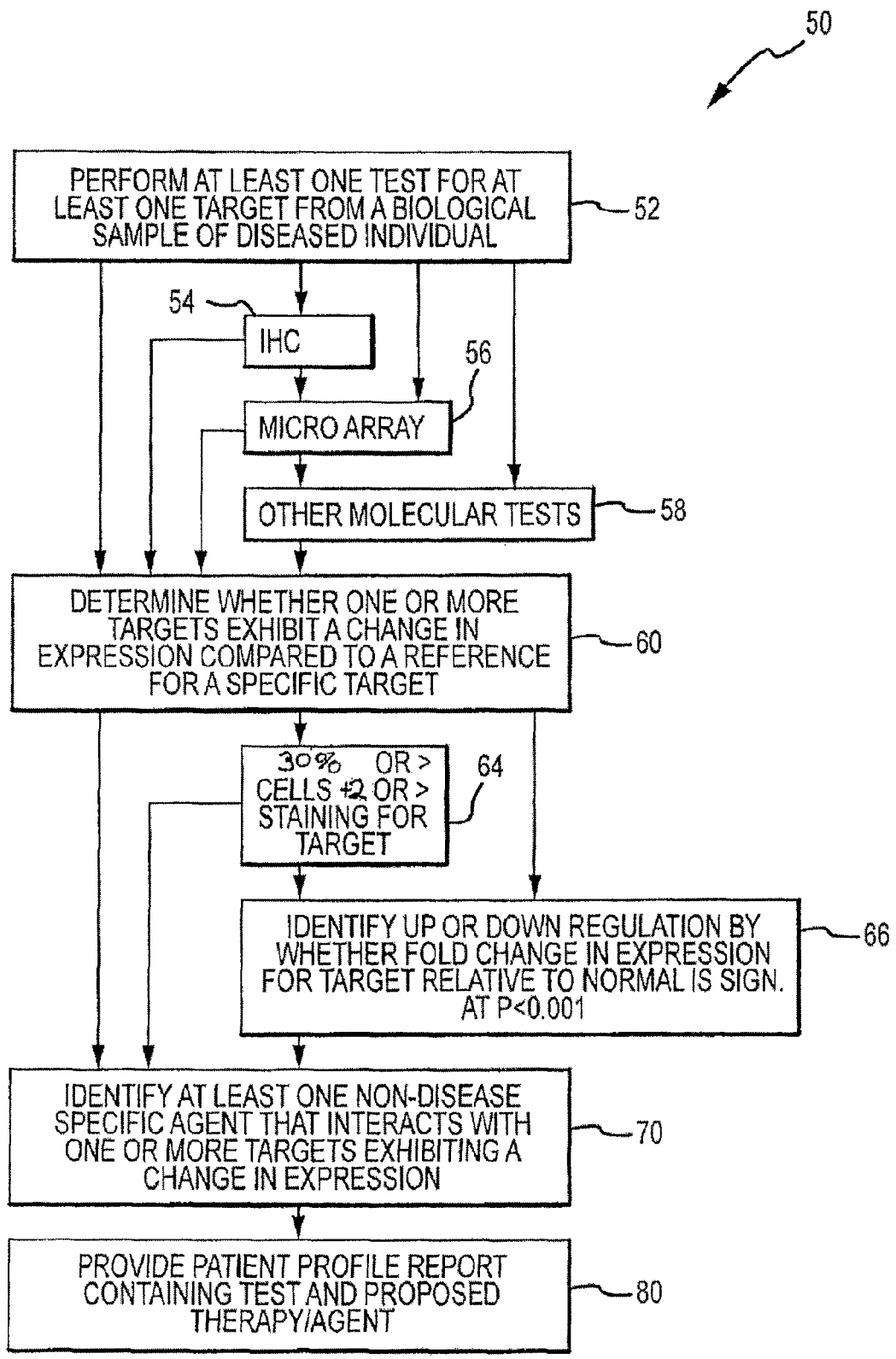
FIG. 2 is a flowchart of an exemplary embodiment of a method for determining individualized medical intervention for a particular disease state that utilizes molecular profiling of a patient's biological specimen that is non disease specific.
Figure 3A:
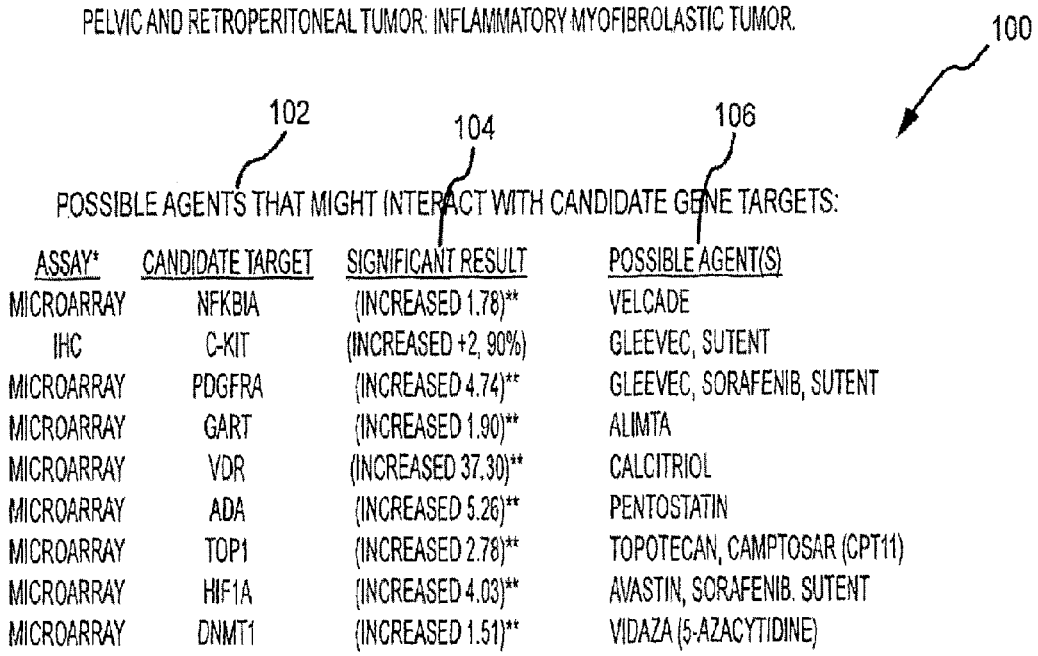

Various methods may be used in accordance with system 10. FIG. 2 shows a flowchart of an exemplary embodiment of a method 50 for determining individualized medical intervention for a particular disease state that utilizes molecular profiling of a patient's biological specimen that is non disease specific. In order to determine a medical intervention for a particular disease state using molecular profiling that is independent of disease lineage diagnosis (i.e. not single disease restricted), at least one test is performed for at least one target from a biological sample of a diseased patient in step 52. A target is defined as any molecular finding that may be obtained from molecular testing. For example, a target may include one or more genes, one or more gene expressed proteins, one or more molecular mechanisms, and/or combinations of such. For example, the expression level of a target can be determined by the analysis of mRNA levels or the target or gene, or protein levels of the gene. Tests for finding such targets may include, but are not limited, fluorescent in-situ hybridization (FISH), an in-situ hybridization (ISH), and other molecular tests known to those skilled in the art. PCR-based methods, such as real-time PCR or quantitative PCR can be used. Furthermore, microarray analysis, such as a comparative genomic hybridization (CGH) micro array, a single nucleotide polymorphism (SNP) microarray, a proteomic array, or antibody array analysis can also be used in the methods disclosed herein. In some embodiments, microarray analysis comprises identifying whether a gene is up-regulated or down-regulated relative to a reference with a significance of $p<0.001$. Tests or analyses of targets can also comprise immunohistochemical (IHC) analysis. In some embodiments, IHC analysis comprises determining whether 30% or more of a sample is stained, if the staining intensity is +2 or greater, or both.

Furthermore, the methods disclosed herein also including profiling more than one target. For example, the expression of a plurality of genes can be identified. Furthermore, identification of a plurality of targets in a sample can be by one method or by various means. For example, the expression of a first gene can be determined by one method and the expression level of a second gene determined by a different method. Alternatively, the same method can be used to detect the expression level of the first and second gene. For example, the first method can be IHC and the second by microarray analysis, such as detecting the gene expression of a gene.

In some embodiments, molecular profiling can also including identifying a genetic variant, such as a mutation, polymorphism (such as a SNP), deletion, or insertion of a target. For example, identifying a SNP in a gene can be determined by microarray analysis, real-time PCR, or sequencing. Other methods disclosed herein can also be used to identify variants of one or more targets.

Accordingly, one or more of the following may be performed: an IHC analysis in step 54, a microanalysis in step 56, and other molecular tests know to those skilled in the art in step 58.

Biological samples are obtained from diseased patients by taking a biopsy of a tumor, conducting minimally invasive surgery if no recent tumor is available, obtaining a sample of the patient's blood, or a sample of any other biological fluid including, but not limited to, cell extracts, nuclear extracts, cell lysates or biological products or substances of biological origin such as excretions, blood, sera, plasma, urine, sputum, tears, feces, saliva, membrane extracts, and the like.

In step 60, a determination is made as to whether one or more of the targets that were tested for in step 52 exhibit a change in expression compared to a normal reference for that particular target. In one exemplary method of the invention, an IHC analysis may be performed in step 54 and a determination as to whether any targets from the IHC analysis exhibit a change in expression is made in step 64 by determining whether 30% or more of the biological sample cells were +2 or greater staining for the particular target. It will be understood by those skilled in the art that there will be instances where +1 or greater staining will indicate a change in expression in that staining results may vary depending on the technician performing the test and type of target being tested. In another exemplary embodiment of the invention, a micro array analysis may be performed in step 56 and a determination as to whether any targets from the micro array analysis exhibit a change in expression is made in step 66 by identifying which targets are up-regulated or down-regulated by determining whether the fold change in expression for a particular target relative to a normal tissue of origin reference is significant at $p<0.001$. A change in expression may also be evidenced by an absence of one or more genes, gene expressed proteins, molecular mechanisms, or other molecular findings.

After determining which targets exhibit a change in expression in step 60, at least one non-disease specific agent is identified that interacts with each target having a changed expression in step 70. An agent may be any drug or compound having a therapeutic effect. A non-disease specific agent is a therapeutic drug or compound not previously associated with treating the patient's diagnosed disease that is capable of interacting with the target from the patient's biological sample that has exhibited a change in expression. Some of the non-disease specific agents that have been found to interact with specific targets found in different cancer patients are shown in Table 3 below.

TABLE 3

| Patients | Target(s) Found | Treatment(s) |
|---|---|---|
| Advanced Pancreatic Cancer | HER 2/neu (IHC/Array) | Herceptin ™ |
| Advanced Pancreatic Cancer | EGFR (IHC), HIF 1α | Erbitux ™, Rapamycin ™ |
| Advanced Ovarian Cancer | ERCC3 (Array) | Irofulvene |
| Advanced Adenoid Cystic Carcinoma | Vitamin D receptors, Androgen receptors | Calcitriol ™, Flutamide ™ |

Finally, in step 80, a patient profile report may be provided which includes the patient's test results for various targets and any proposed therapies based on those results. An exemplary patient profile report 100 is shown in FIGS. 3A-3D. Patient profile report 100 shown in FIG. 3A identifies the targets tested 102, those targets tested that exhibited significant changes in expression 104, and proposed non-disease specific agents for interacting with the targets 106. Patient profile report 100 shown in FIG. 3B identifies the results 108 of immunohistochemical analysis for certain gene expressed proteins 110 and whether a gene expressed protein is a molecular target 112 by determining whether 30% or more of the tumor cells were +2 or greater staining Report 100 also identifies immunohistochemical tests that were not performed 114. Patient profile report 100 shown in FIG. 3C identifies the genes analyzed 116 with a micro array analysis and whether the genes were under expressed or over expressed 118 compared to a reference. Finally, patient profile report 100 shown in FIG. 3D identifies the clinical history 120 of the patient and the specimens that were submitted 122 from the patient. The molecular profiling techniques can be performed anywhere, e.g., a foreign country, and the results sent by network to an appropriate party, e.g., the patient, a physician, lab or other party located remotely.

Figure 4:
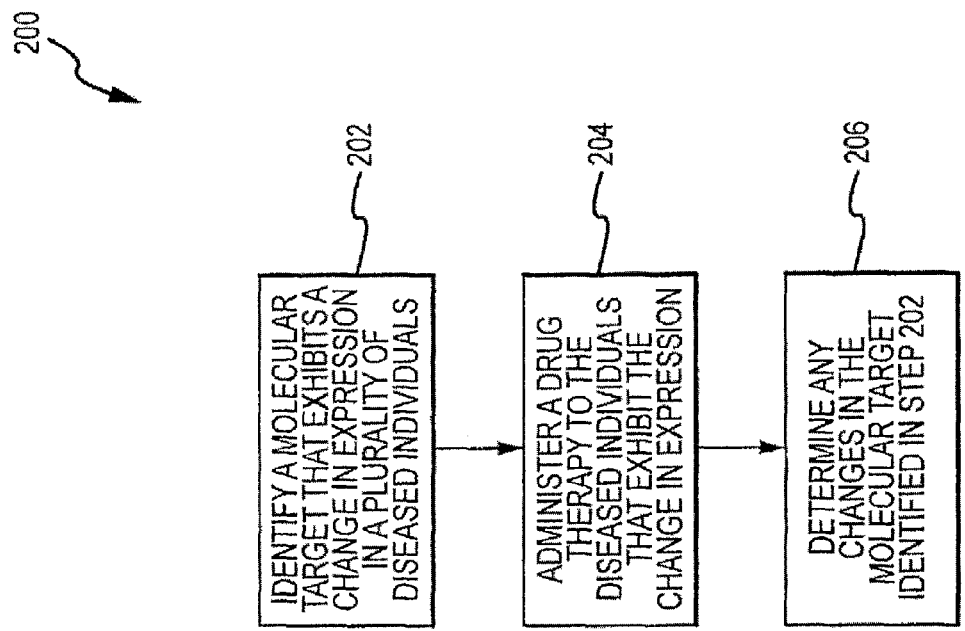
FIG. 4 is a flowchart of an exemplary embodiment of a method for identifying a drug therapy/agent capable of interacting with a target.

FIG. 4 shows a flowchart of an exemplary embodiment of a method 200 for identifying a drug therapy/agent capable of interacting with a target. In step 202, a molecular target is identified which exhibits a change in expression in a number of diseased individuals. Next, in step 204, a drug therapy/agent is administered to the diseased individuals. After drug therapy/agent administration, any changes in the molecular target identified in step 202 are identified in step 206 in order to determine if the drug therapy/agent administered in step 204 interacts with the molecular targets identified in step 202. If it is determined that the drug therapy/agent administered in step 204 interacts with a molecular target identified in step 202, the drug therapy/agent may be approved for treating patients exhibiting a change in expression of the identified molecular target instead of approving the drug therapy/agent for a particular disease.

Figure 5:
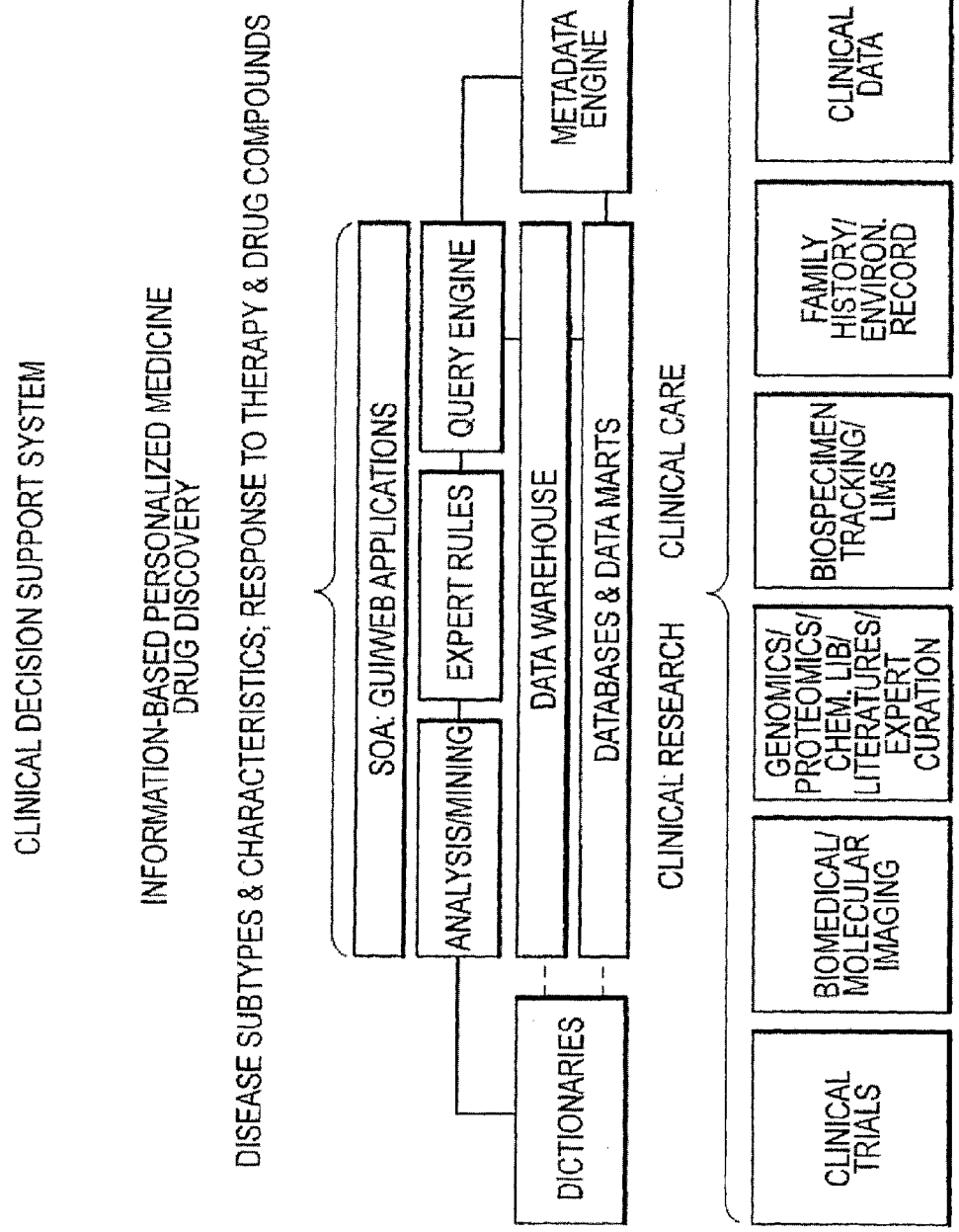
FIGS. 5-14 are flowcharts and diagrams illustrating various parts of an information-based personalized medicine drug discovery system and method in accordance with the present invention.
Figure 6:
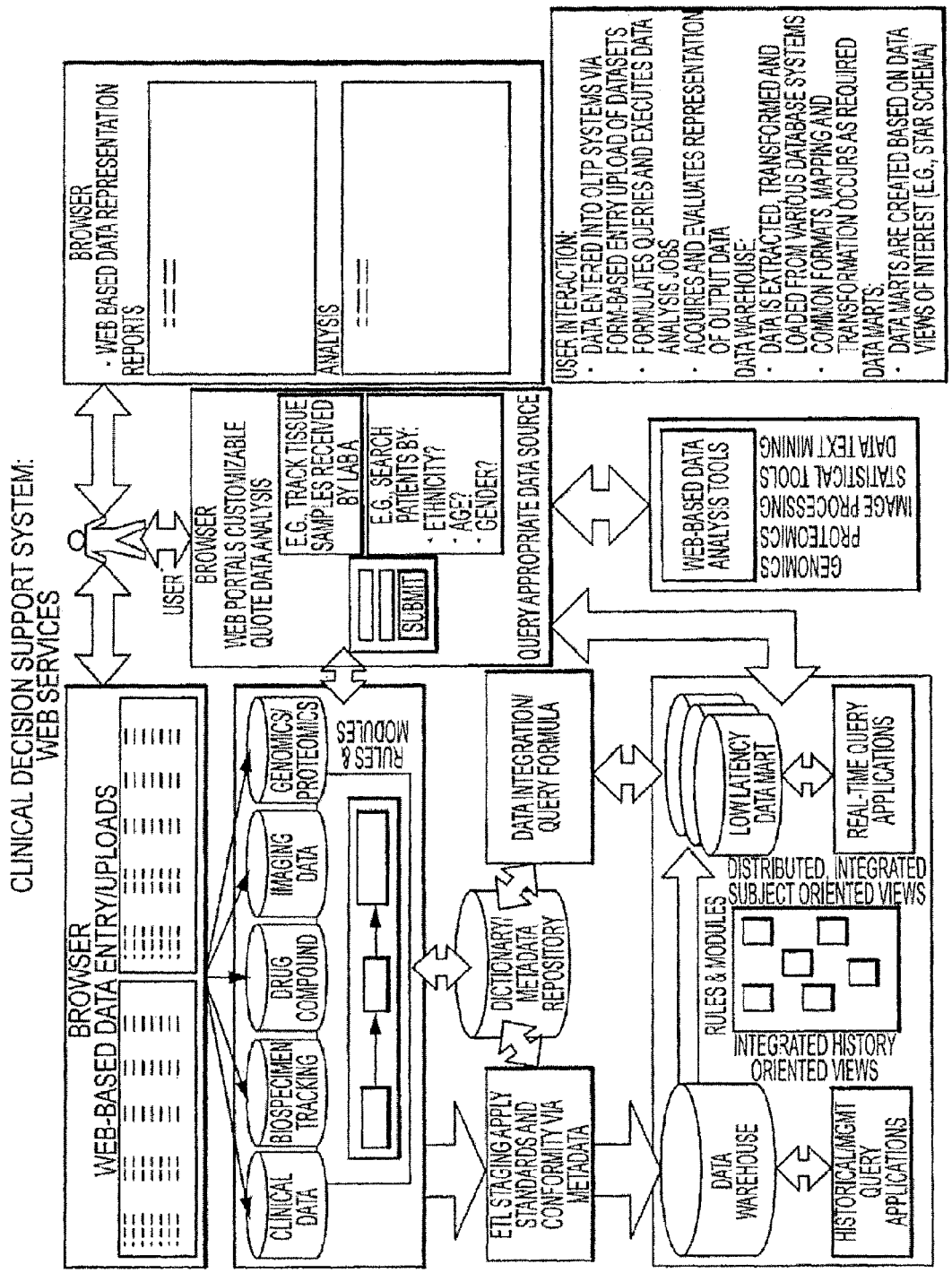

FIGS. 5-14 are flowcharts and diagrams illustrating various parts of an information-based personalized medicine drug discovery system and method in accordance with the present invention. FIG. 5 is a diagram showing an exemplary clinical decision support system of the information-based personalized medicine drug discovery system and method of the present invention. Data obtained through clinical research and clinical care such as clinical trial data, biomedical/molecular imaging data, genomics/proteomics/chemical library/literature/expert curation, biospecimen tracking/LIMS, family history/environmental records, and clinical data are collected and stored as databases and datamarts within a data warehouse. FIG. 6 is a diagram showing the flow of information through the clinical decision support system of the information-based personalized medicine drug discovery system and method of the present invention using web services. A user interacts with the system by entering data into the system via form-based entry/upload of data sets, formulating queries and executing data analysis jobs, and acquiring and evaluating representations of output data. The data warehouse in the web based system is where data is extracted, transformed, and loaded from various database systems. The data warehouse is also where common formats, mapping and transformation occurs. The web based system also includes datamarts which are created based on data views of interest.

Figure 7:
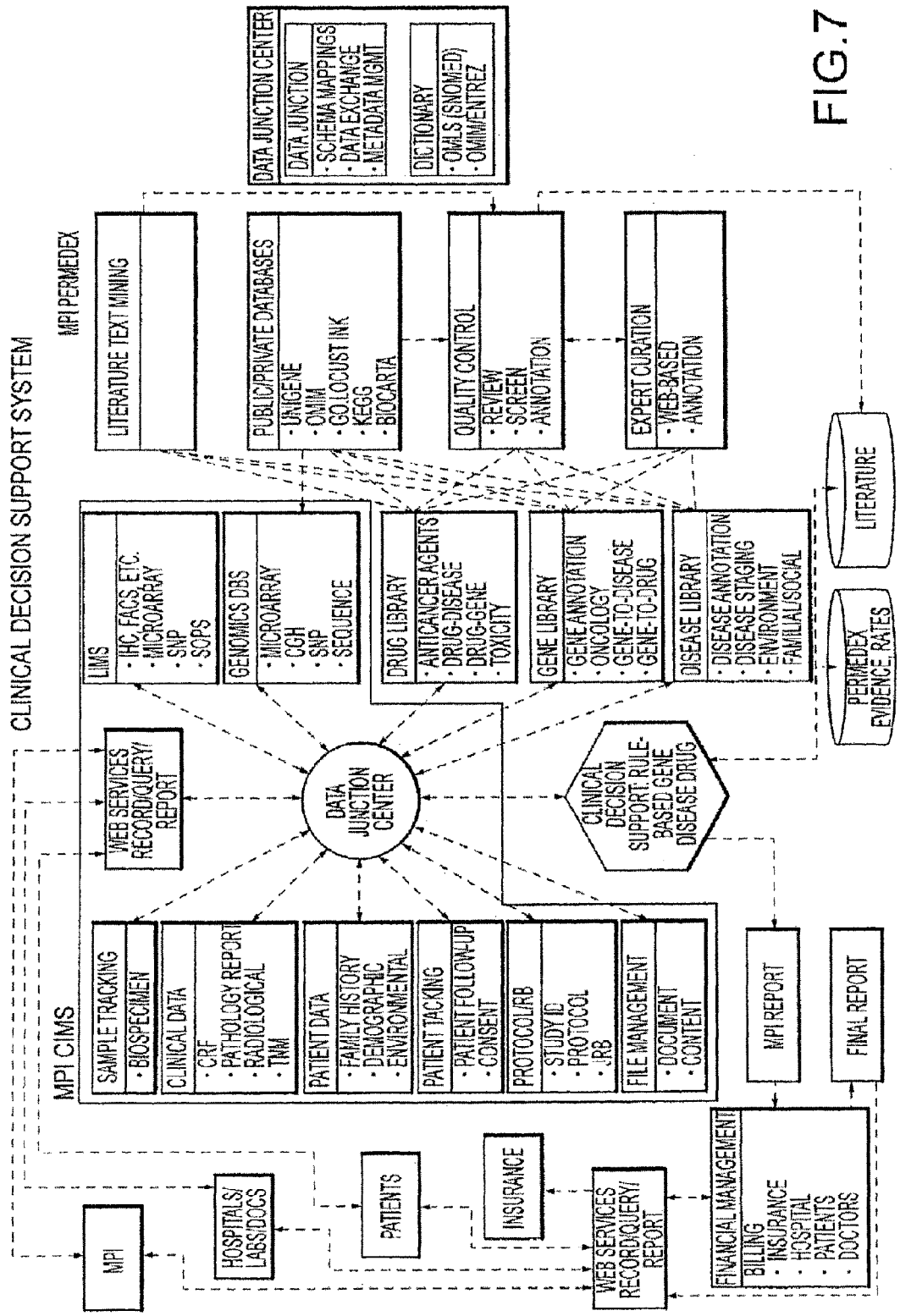

A flow chart of an exemplary clinical decision support system of the information-based personalized medicine drug discovery system and method of the present invention is shown in FIG. 7. The clinical information management system includes the laboratory information management system and the medical information contained in the data warehouses and databases includes medical information libraries, such as drug libraries, gene libraries, and disease libraries, in addition to literature text mining. Both the information management systems relating to particular patients and the medical information databases and data warehouses come together at a data junction center where diagnostic information and therapeutic options can be obtained. A financial management system may also be incorporated in the clinical decision support system of the information-based personalized medicine drug discovery system and method of the present invention.

Figure 8:
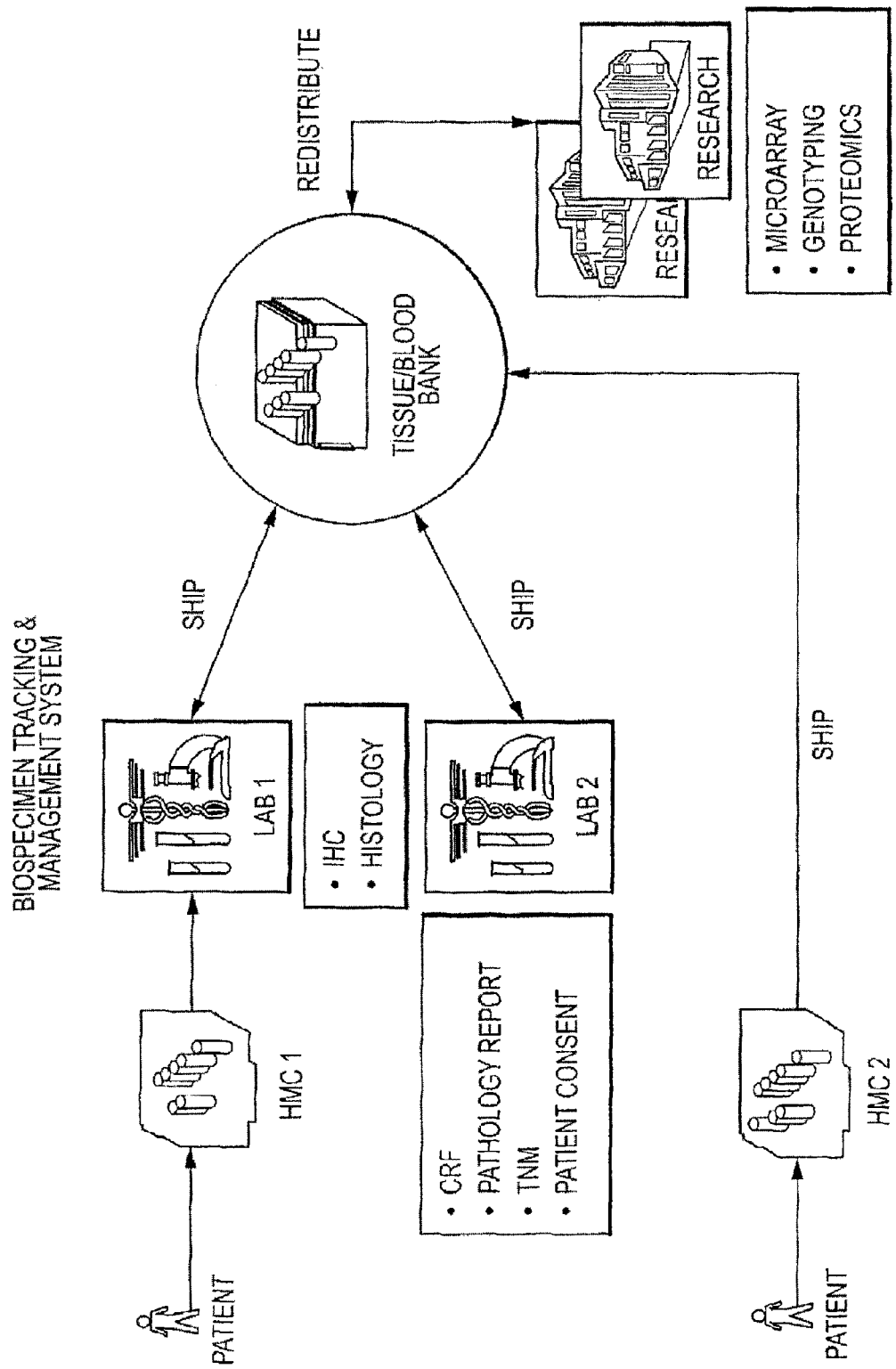
Figure 9:
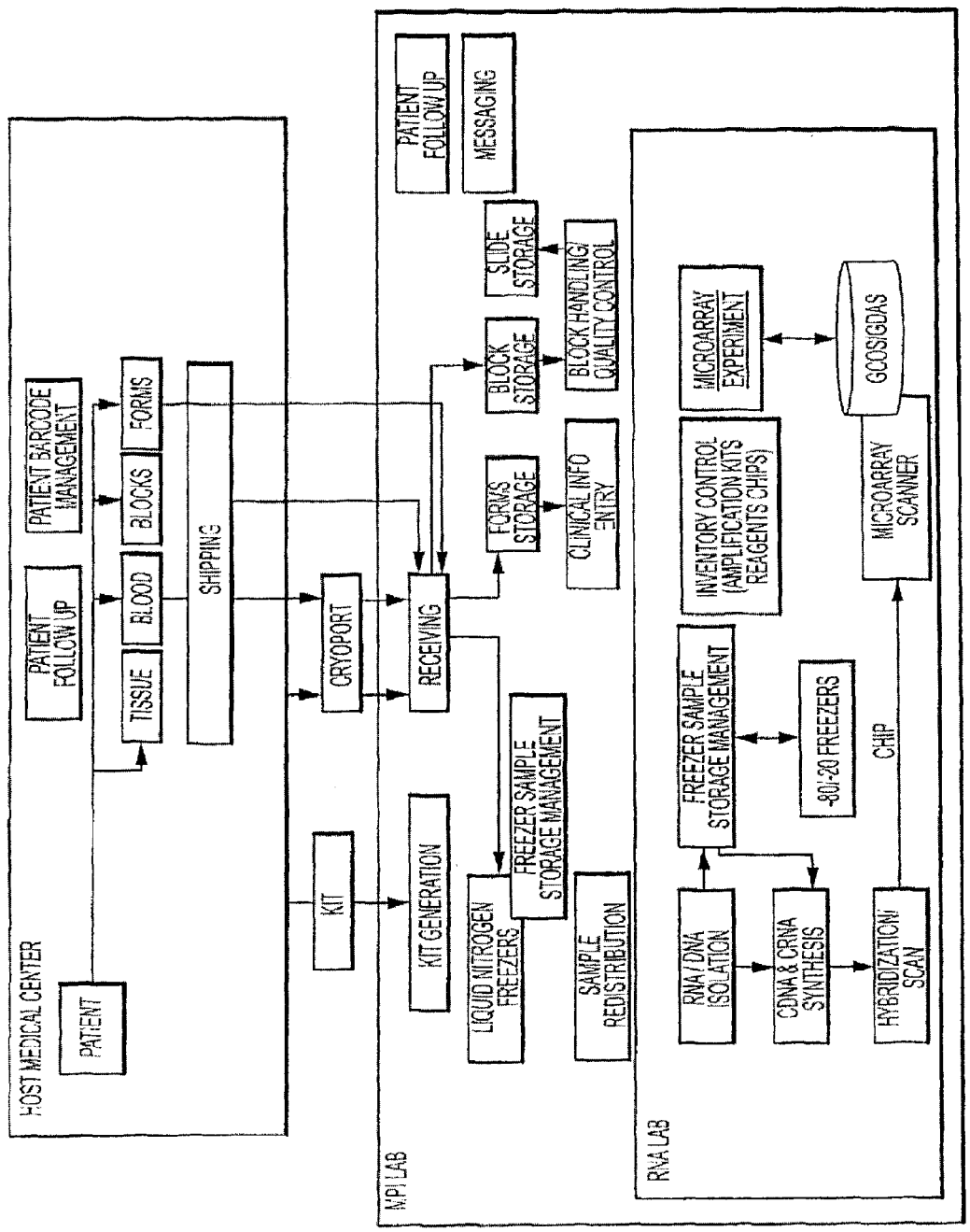

FIG. 8 is a diagram showing an exemplary biospecimen tracking and management system which may be utilized as part of the information-based personalized medicine drug discovery system and method of the present invention. FIG. 8 shows two host medical centers which forward specimens to a tissue/blood bank. The specimens may go through laboratory analysis prior to shipment. Research may also be conducted on the samples via micro array, genotyping, and proteomic analysis. This information can be redistributed to the tissue/blood bank. FIG. 9 depicts a flow chart of an exemplary biospecimen tracking and management system which may be utilized with the information-based personalized medicine drug discovery system and method of the present invention. The host medical center obtains samples from patients and then ships the patient samples to a molecular profiling laboratory which may also perform RNA and DNA isolation and analysis.

Figure 10:
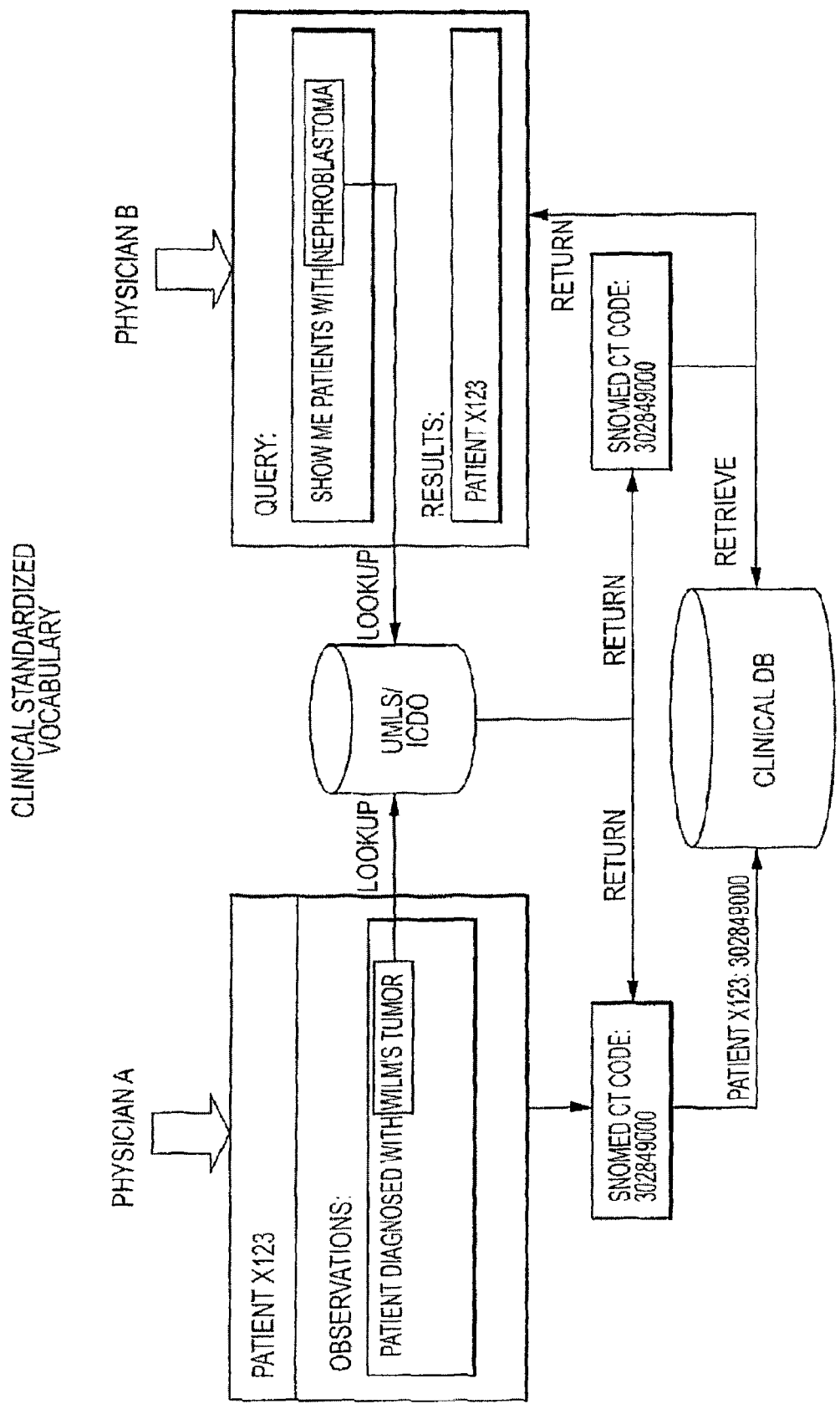

A diagram showing a method for maintaining a clinical standardized vocabulary for use with the information-based personalized medicine drug discovery system and method of the present invention is shown in FIG. 10. FIG. 10 illustrates how physician observations and patient information associated with one physician's patient may be made accessible to another physician to enable the other physician to utilize the data in making diagnostic and therapeutic decisions for their patients.

Figure 11:
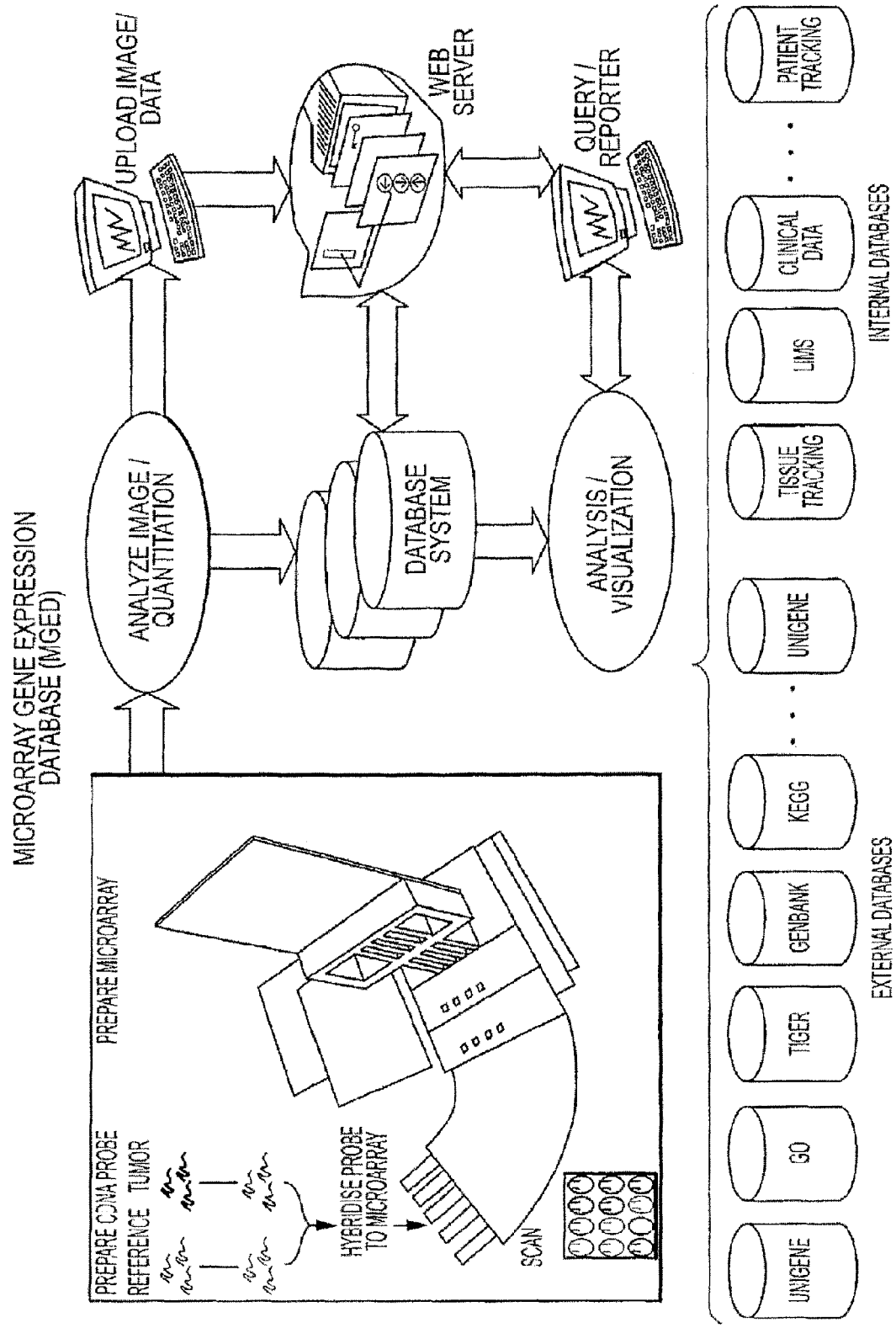
Figure 12:
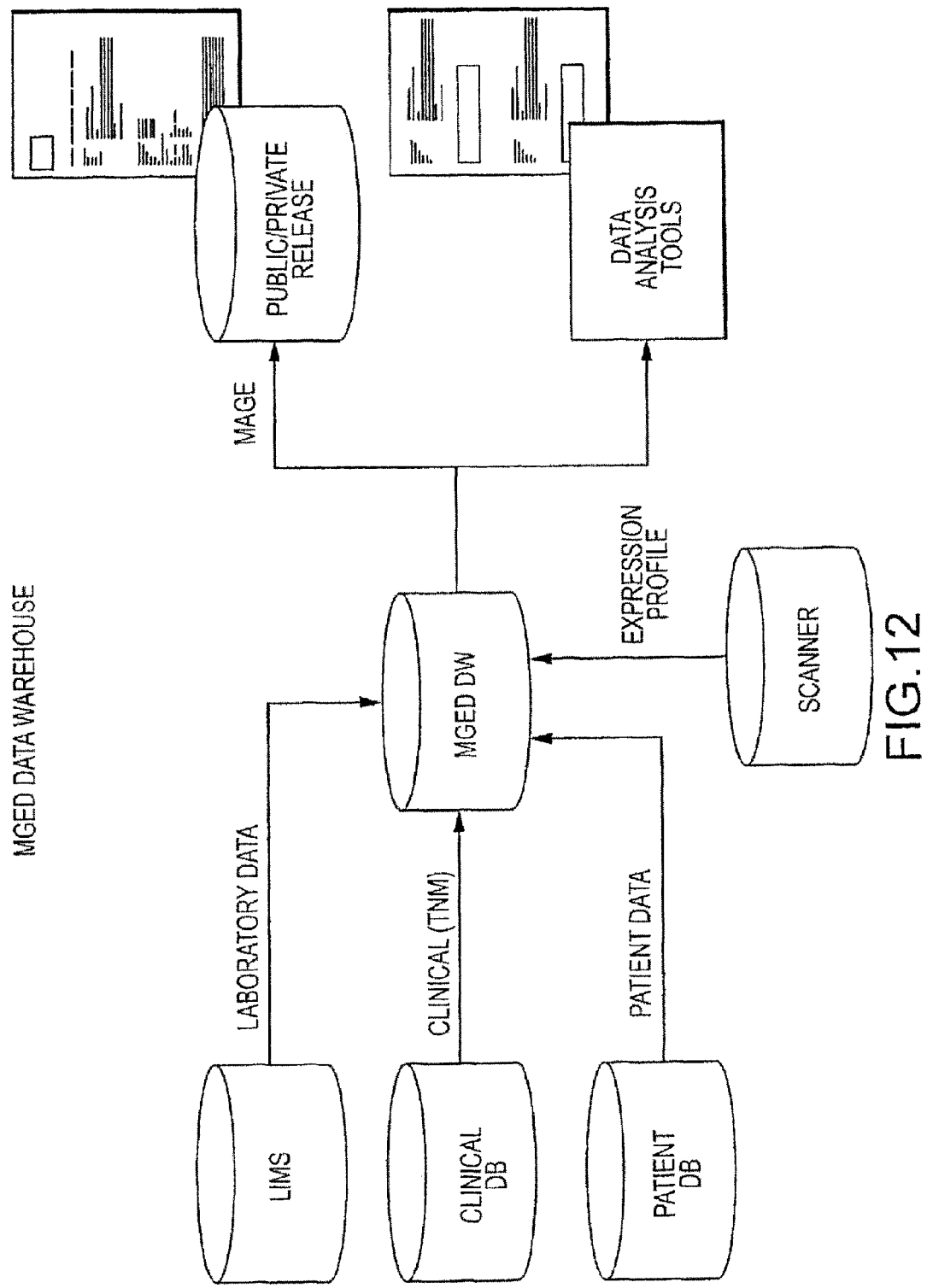

FIG. 11 shows a schematic of an exemplary micro array gene expression database which may be used as part of the information-based personalized medicine drug discovery system and method of the present invention. The micro array gene expression database includes both external databases and internal databases which can be accessed via the web based system. External databases may include, but are not limited to, UniGene, GO, TIGR, GenBank, KEGG. The internal databases may include, but are not limited to, tissue tracking, LIMS, clinical data, and patient tracking. FIG. 12 shows a diagram of an exemplary micro array gene expression database data warehouse which may be used as part of the information-based personalized medicine drug discovery system and method of the present invention. Laboratory data, clinical data, and patient data may all be housed in the micro array gene expression database data warehouse and the data may in turn be accessed by public/private release and utilized by data analysis tools.

Figure 13:
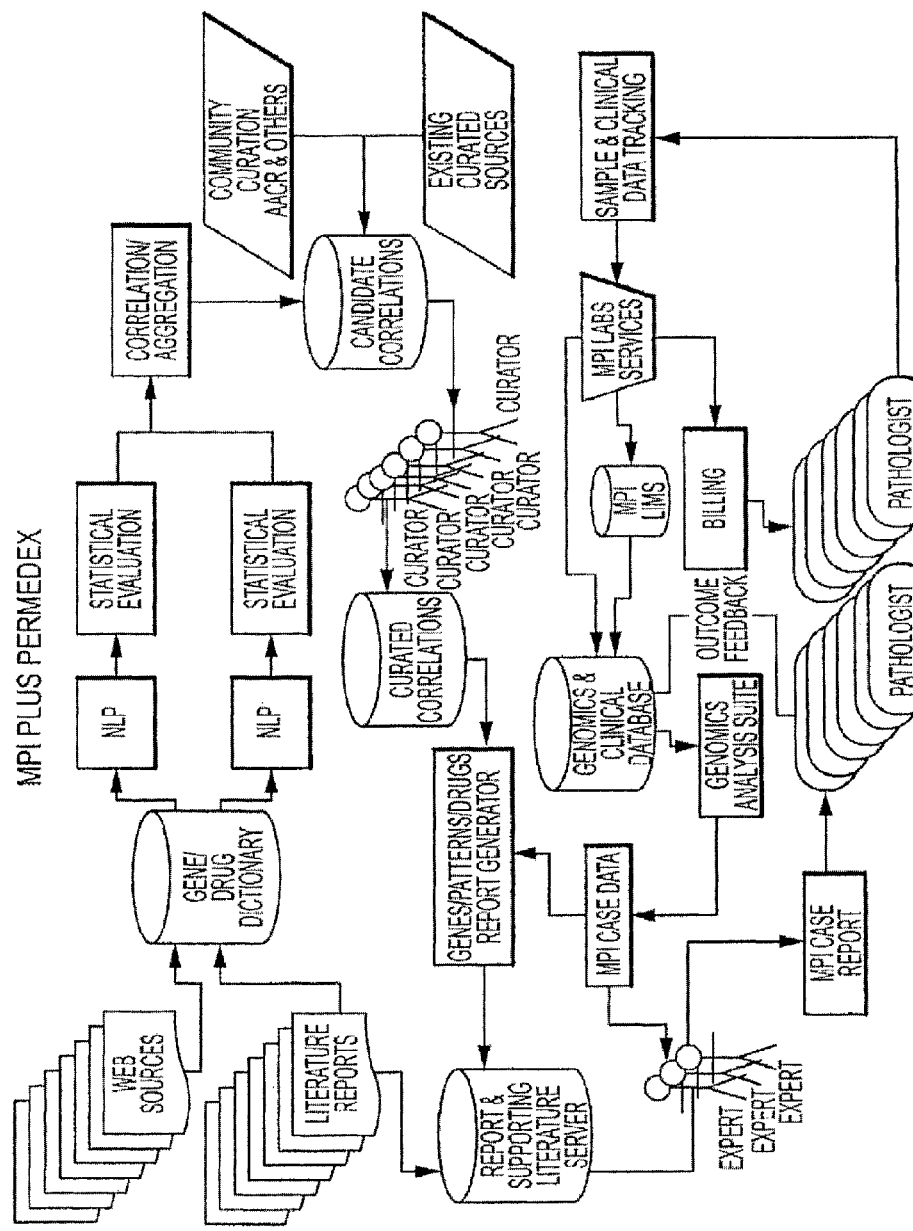
Figure 14:
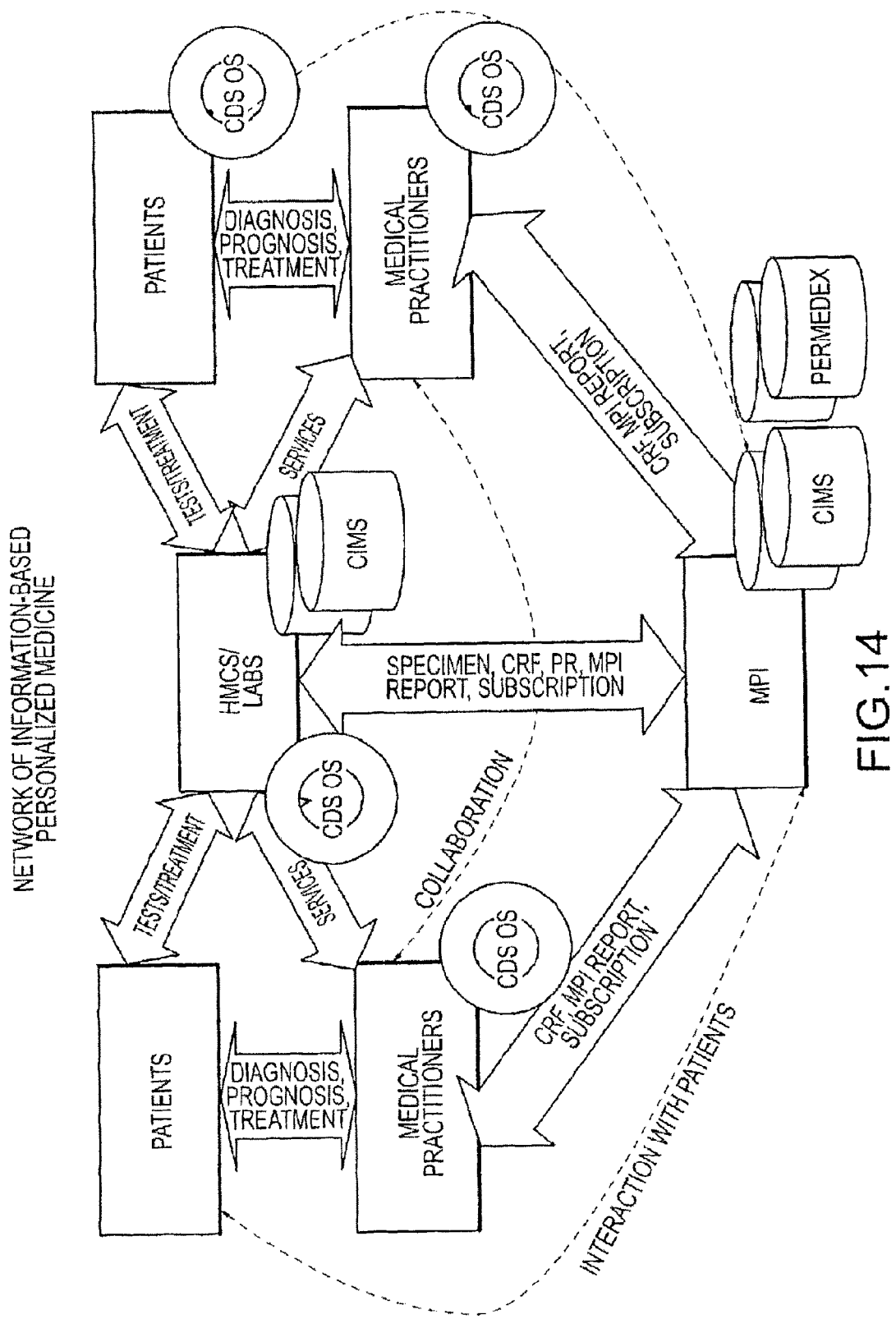

Another schematic showing the flow of information through an information-based personalized medicine drug discovery system and method of the present invention is shown in FIG. 13. Like FIG. 7, the schematic includes clinical information management, medical and literature information management, and financial management of the information-based personalized medicine drug discovery system and method of the present invention. FIG. 14 is a schematic showing an exemplary network of the information-based personalized medicine drug discovery system and method of the present invention. Patients, medical practitioners, host medical centers, and labs all share and exchange a variety of information in order to provide a patient with a proposed therapy or agent based on various identified targets.

Figure 15:
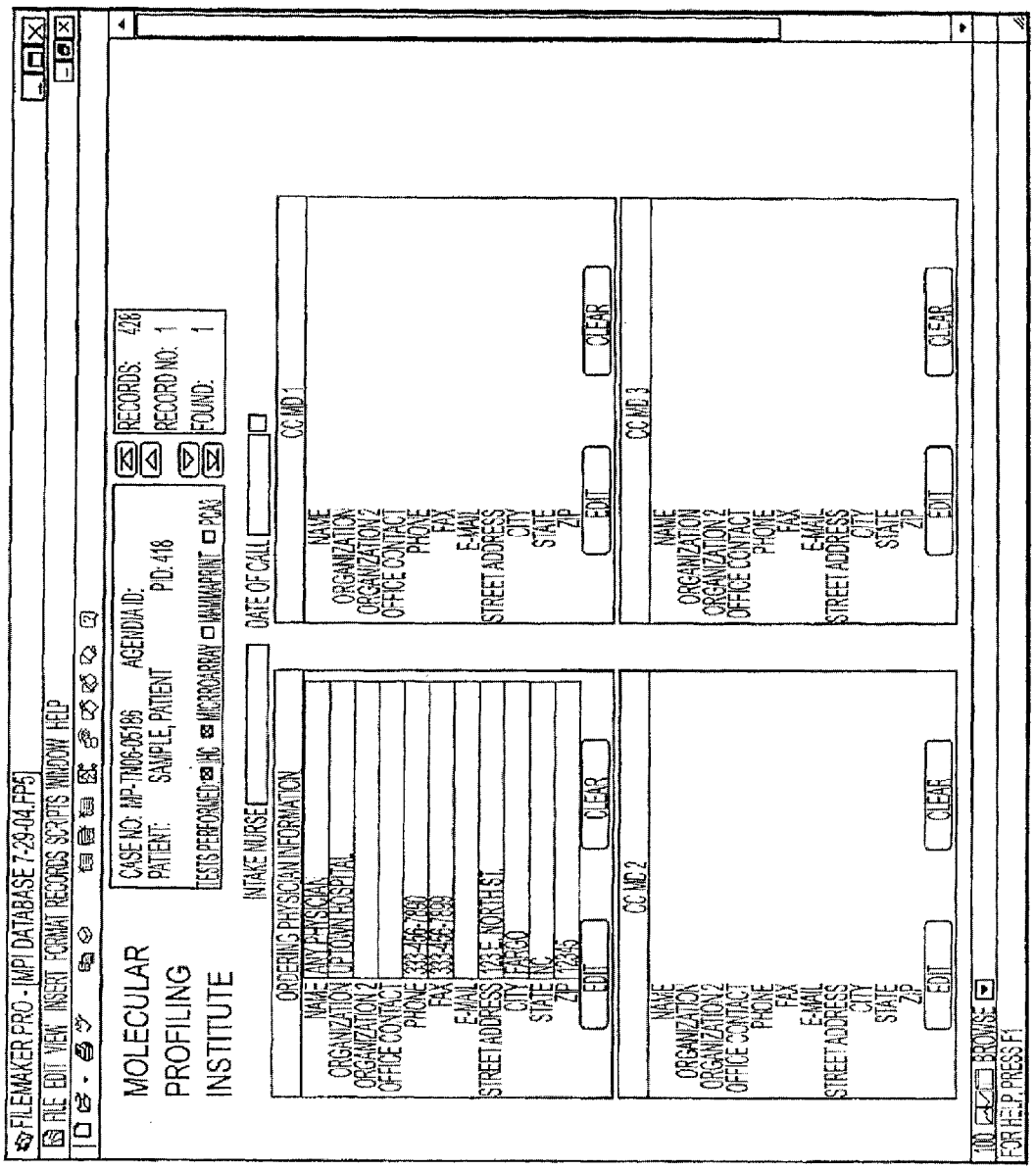
Figure 16:
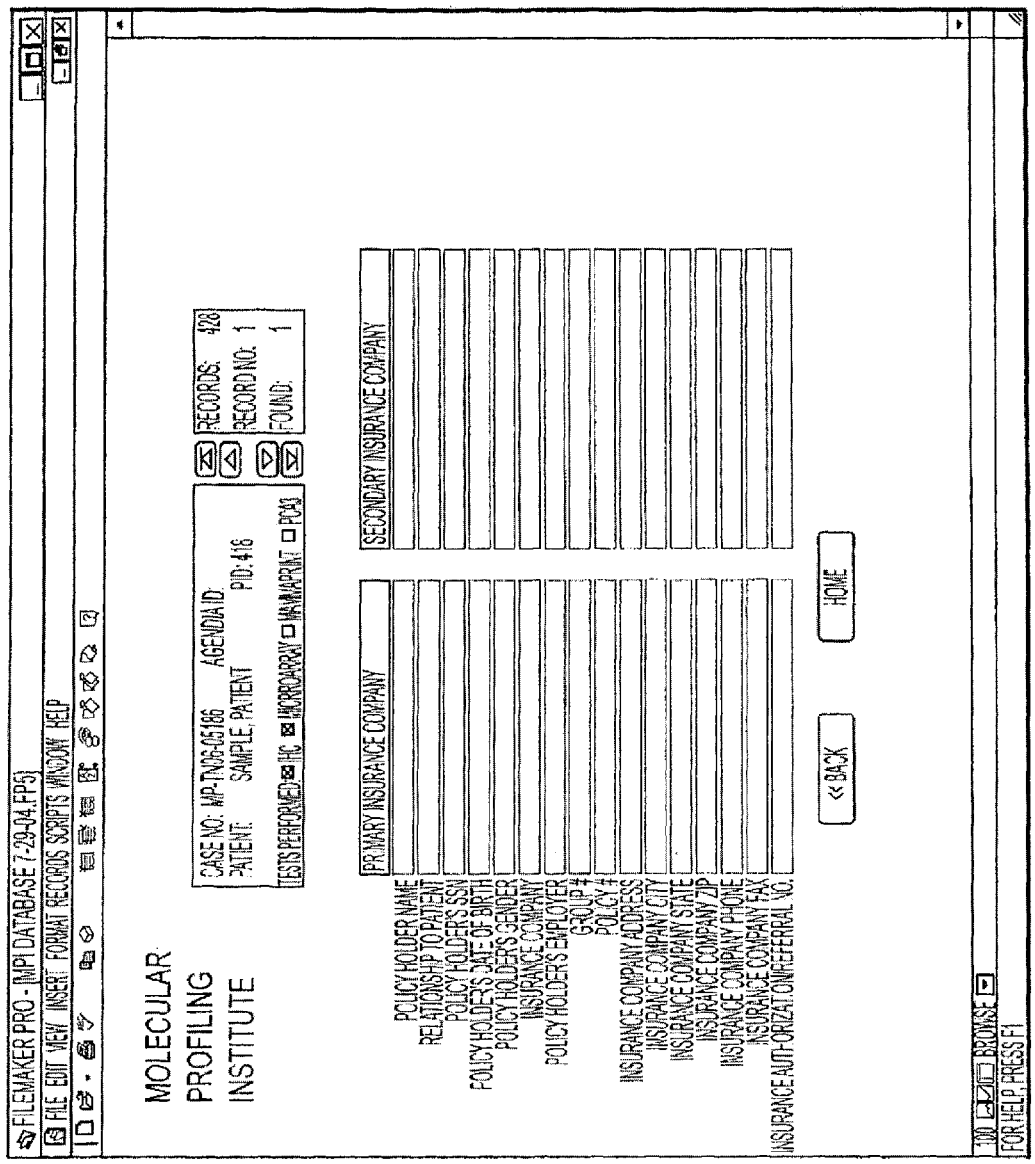
Figure 18:
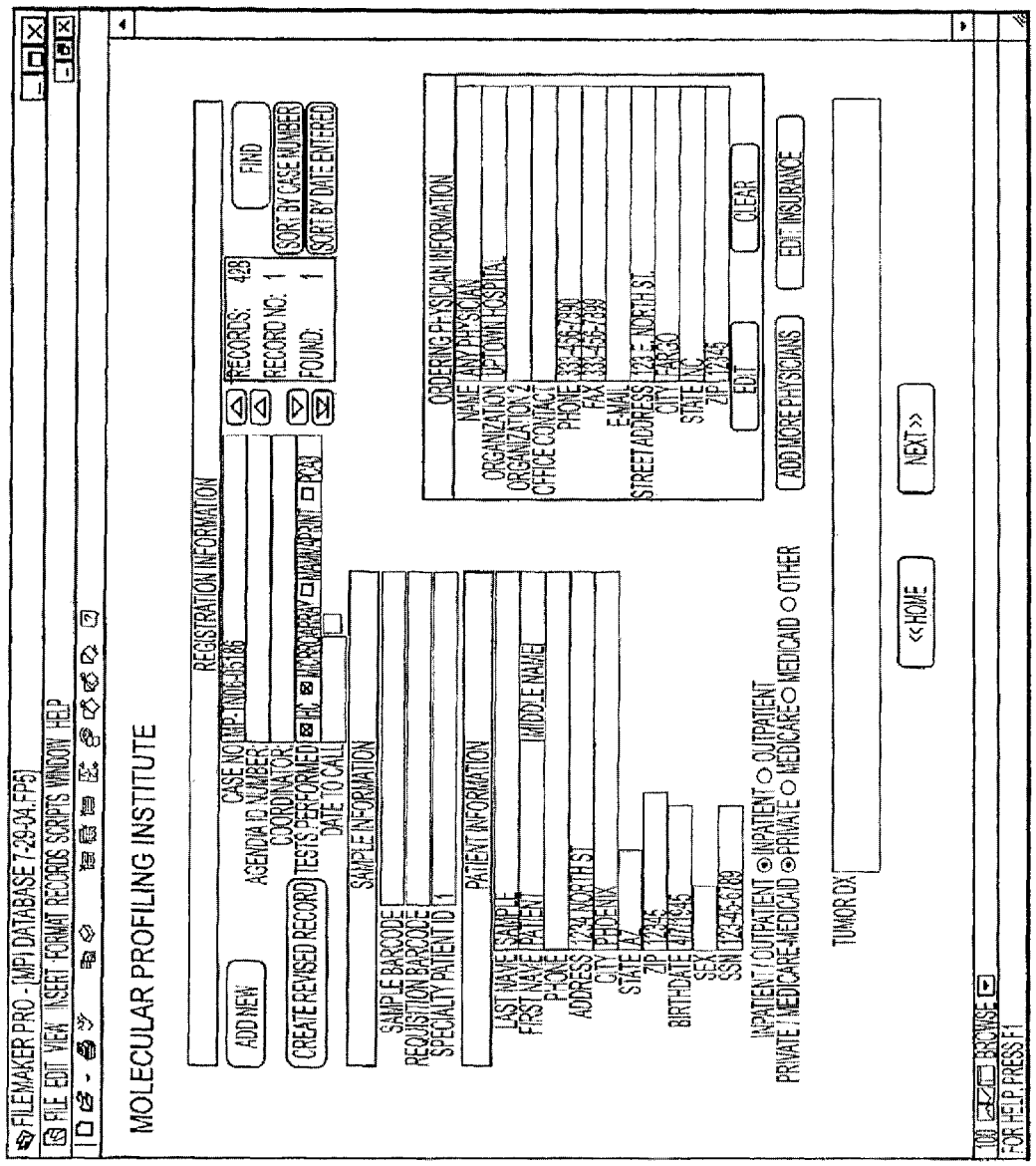
Figure 19:
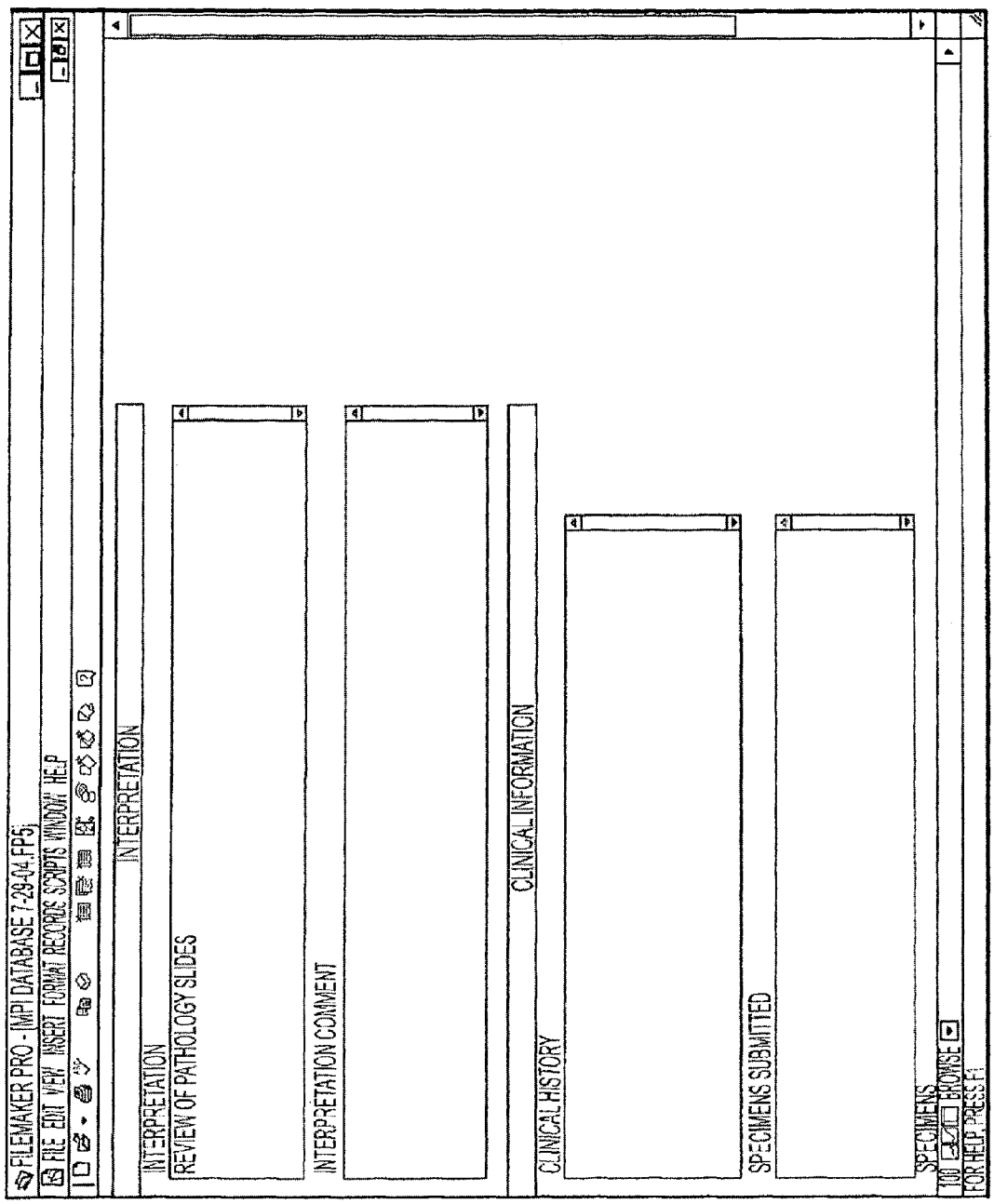

FIGS. 15-25 are computer screen print outs associated with various parts of the information-based personalized medicine drug discovery system and method shown in FIGS. 5-14. FIGS. 15 and 16 show computer screens where physician information and insurance company information is entered on behalf of a client. FIGS. 17-19 show computer screens in which information can be entered for ordering analysis and tests on patient samples.

Figure 20:
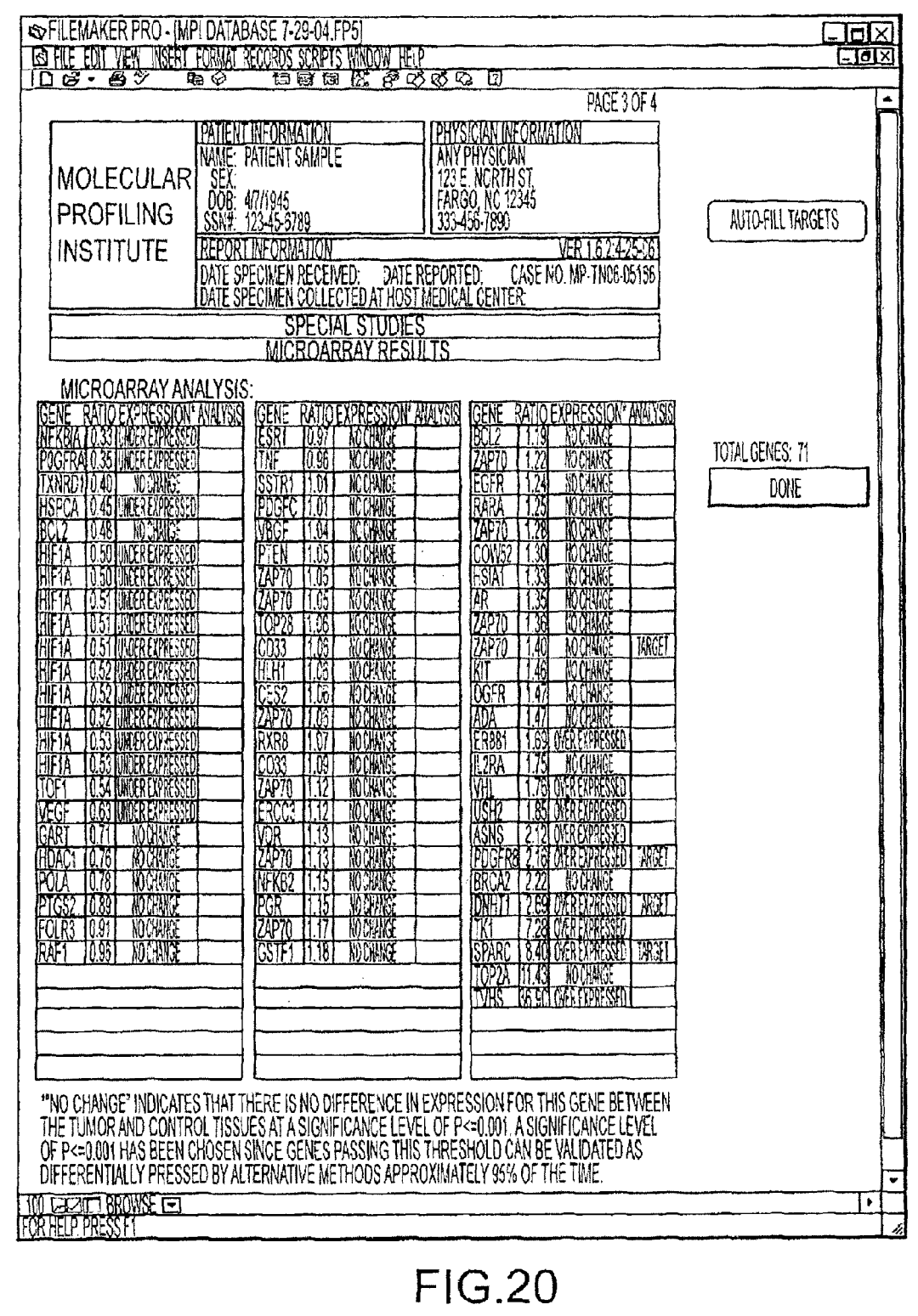

FIG. 20 is a computer screen showing micro array analysis results of specific genes tested with patient samples. This information and computer screen is similar to the information detailed in the patient profile report shown in FIG. 3C. FIG. 22 is a computer screen that shows immunohistochemistry test results for a particular patient for various genes. This information is similar to the information contained in the patient profile report shown in FIG. 3B.

Figure 21:
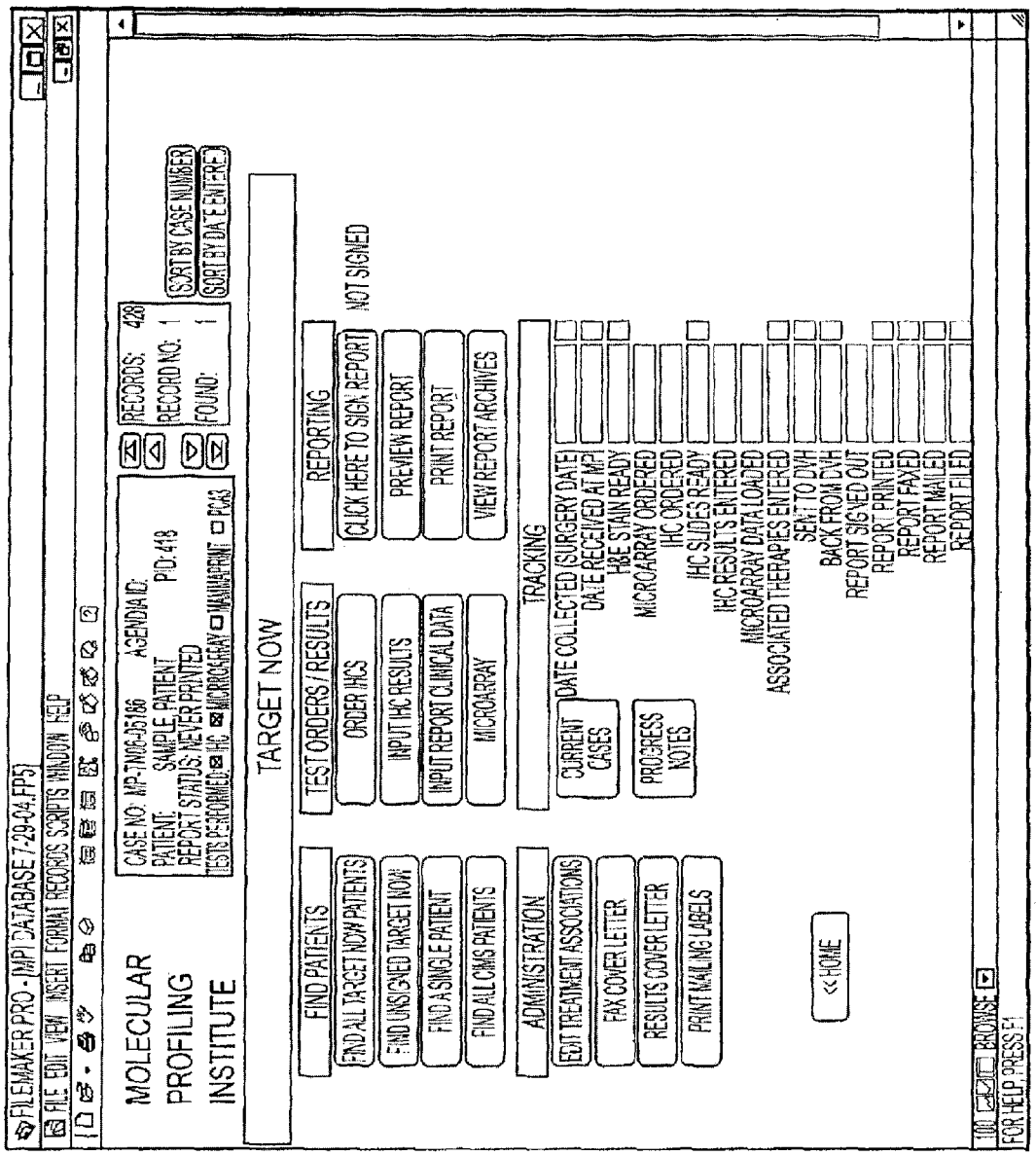

FIG. 21 is a computer screen showing selection options for finding particular patients, ordering tests and/or results, issuing patient reports, and tracking current cases/patients.

Figure 23:
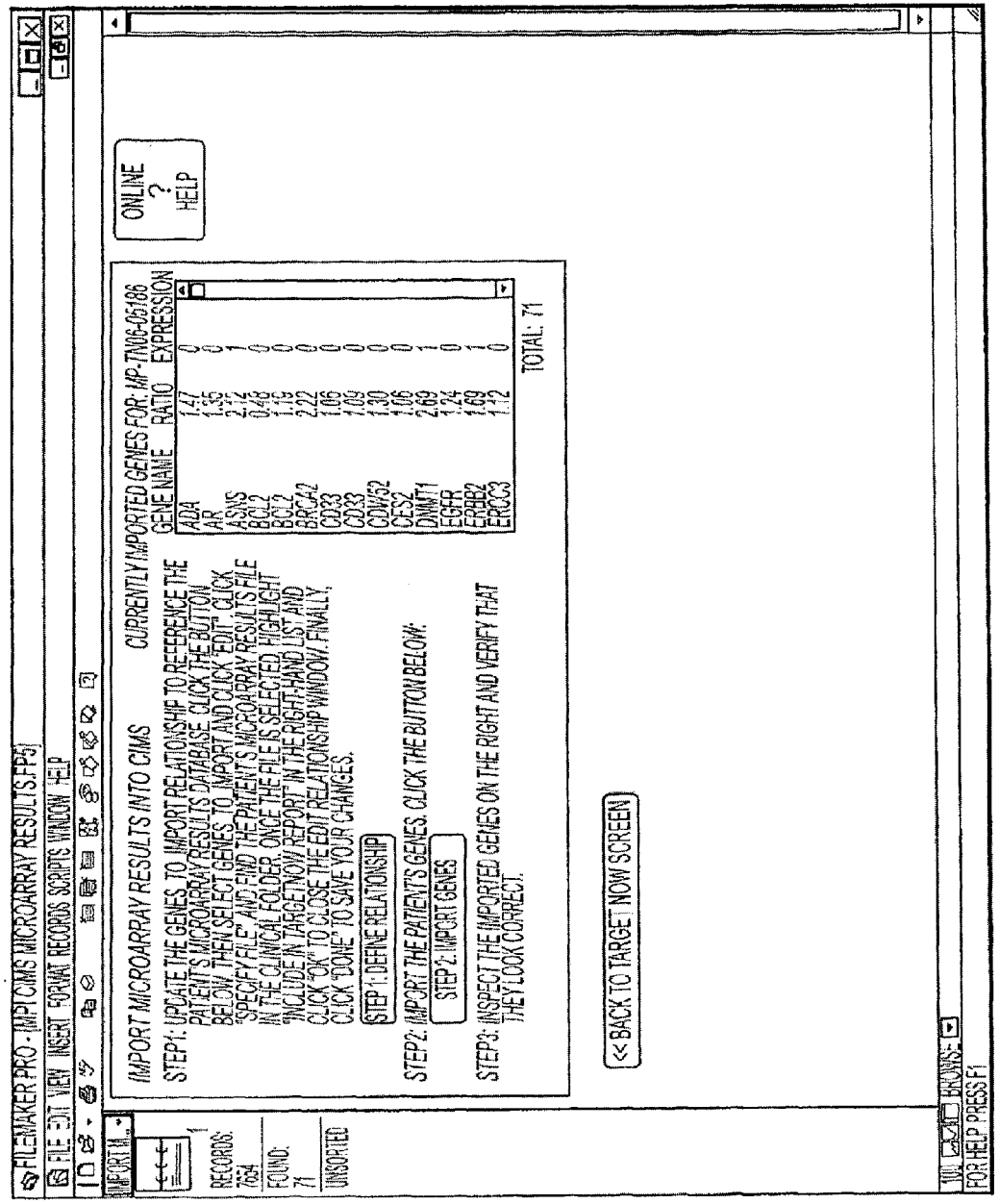
Figure 24:
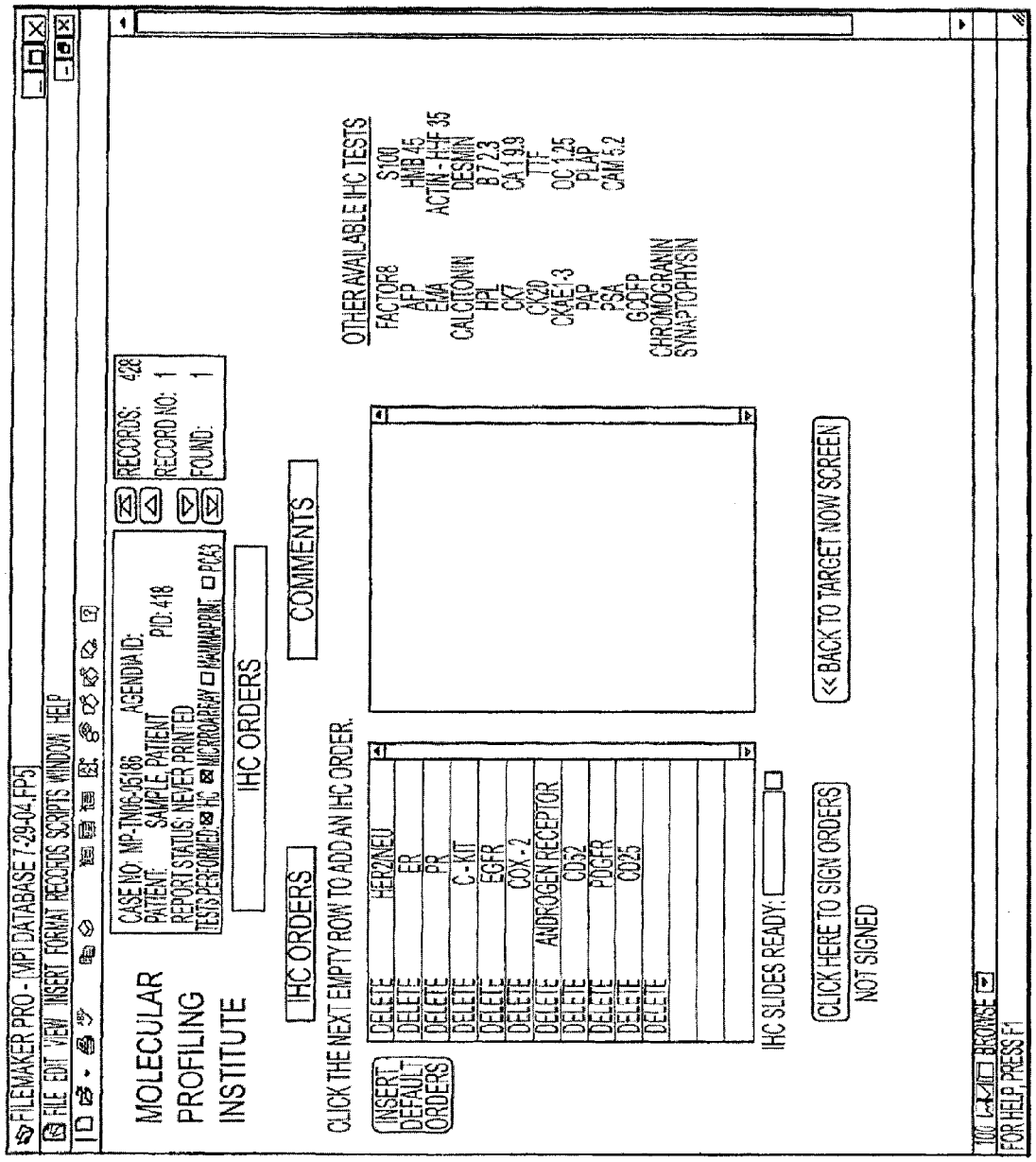
Figure 25:
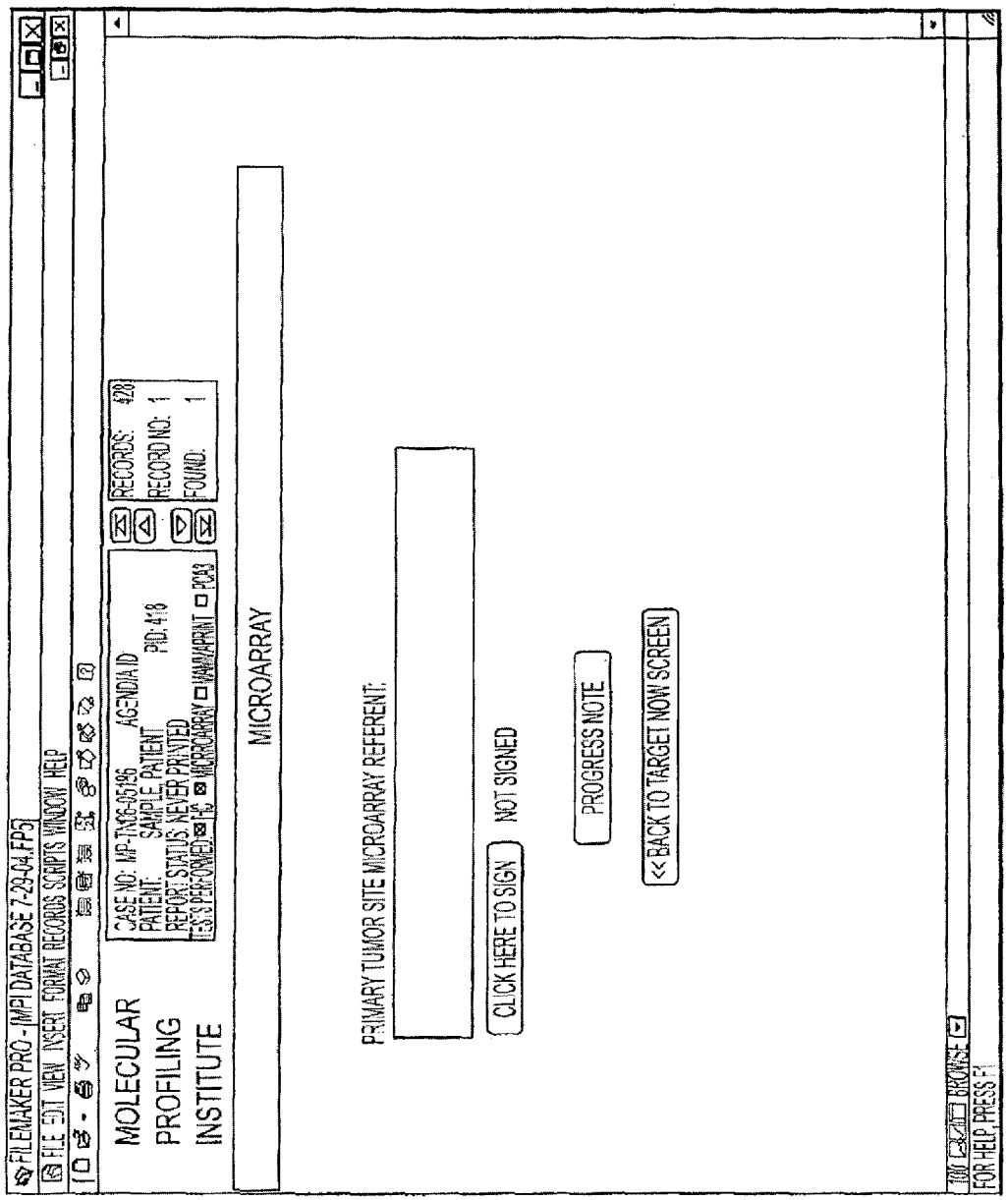

FIG. 23 is a computer screen which outlines some of the steps for creating a patient profile report as shown in FIGS. 3A through 3D. FIG. 24 shows a computer screen for ordering an immunohistochemistry test on a patient sample and FIG. 25 shows a computer screen for entering information regarding a primary tumor site for micro array analysis. It will be understood by those skilled in the art that any number and variety of computer screens may be utilized to enter the information necessary for utilizing the information-based personalized medicine drug discovery system and method of the present invention and to obtain information resulting from utilizing the information-based personalized medicine drug discovery system and method of the present invention.

FIGS. 26-31 represent tables that show the frequency of a significant change in expression of certain genes and/or gene expressed proteins by tumor type, i.e. the number of times that a gene and/or gene expressed protein was flagged as a target by tumor type as being significantly overexpressed or underexpressed (see also Examples 1-3). The tables show the total number of times a gene and/or gene expressed protein was overexpressed or underexpressed in a particular tumor type and whether the change in expression was determined by immunohistochemistry analysis (FIG. 26, FIG. 28) or microarray analysis (FIGS. 27, 30). The tables also identify the total number of times an overexpression of any gene expressed protein occurred in a particular tumor type using immunohistochemistry and the total number of times an overexpression or underexpression of any gene occurred in a particular tumor type using gene microarray analysis.

Thus the present invention provides methods and systems for analyzing diseased tissue using IHC testing and gene microarray testing in accordance with IHC and microarray testing as previously described above. The patients can be in an advanced stage of disease. The biomarker patterns or biomarker signature sets in a number of tumor types, diseased tissue types, or diseased cells including adipose, adrenal cortex, adrenal gland, adrenal gland-medulla, appendix, bladder, blood vessel, bone, bone cartilage, brain, breast, cartilage, cervix, colon, colon sigmoid, dendritic cells, skeletal muscle, enodmetrium, esophagus, fallopian tube, fibroblast, gallbladder, kidney, larynx, liver, lung, lymph node, melanocytes, mesothelial lining, myoepithelial cells, osteoblasts, ovary, pancreas, parotid, prostate, salivary gland, sinus tissue, skeletal muscle, skin, small intestine, smooth muscle, stomach, synovium, joint lining tissue, tendon, testis, thymus, thyroid, uterus, and uterus corpus can be determined.

The methods of the present invention can be used for selecting a treatment of any cancer, including but not limited to breast cancer, pancreatic cancer, cancer of the colon and/or rectum, leukemia, skin cancer, bone cancer, prostate cancer, liver cancer, lung cancer, brain cancer, cancer of the larynx, gallbladder, parathyroid, thyroid, adrenal, neural tissue, head and neck, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell carcinoma, primary brain tumor, acute and chronic lymphocytic and granulocytic tumors, hairy-cell tumor, adenoma, hyperplasia, medullary carcinoma, pheochromocytoma, mucosal neuroma, intestinal ganglioneuroma, hyperplastic corneal nerve tumor, marfanoid habitus tumor, Wilm's tumor, seminoma, ovarian tumor, leiomyoma, cervical dysplasia and in situ carcinoma, neuroblastoma, retinoblastoma, soft tissue sarcoma, malignant carcinoid, topical skin lesion, mycosis fungoides, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

The biomarker patterns or biomarker signature sets in a number of tumor types, diseased tissue types, or diseased cells including accessory, sinuses, middle and inner ear, adrenal glands, appendix, hematopoietic system, bones and joints, spinal cord, breast, cerebellum, cervix uteri, connective and soft tissue, corpus uteri, esophagus, eye, nose, eyeball, fallopian tube, extrahepatic bile ducts, other mouth, intrahepatic bile ducts, kidney, appendix-colon, larynx, lip, liver, lung and bronchus, lymph nodes, cerebral, spinal, nasal cartilage, excl. retina, eye, nos, oropharynx, other endocrine glands, other female genital, ovary, pancreas, penis and scrotum, pituitary gland, pleura, prostate gland, rectum renal pelvis, ureter, peritonem, salivary gland, skin, small intestine, stomach, testis, thymus, thyroid gland, tongue, unknown, urinary bladder, uterus, nos, vagina & labia, and vulva, nos can also be determined.

Thus the biomarker patterns or biomarker signature sets can be used to determine a therapeutic agent or therapeutic protocol that is capable of interacting with the biomarker pattern or signature set. For example, with advanced breast cancer, immunohistochemistry analysis can be used to determine one or more gene expressed proteins that are overexpressed. Accordingly, a biomarker pattern or biomarker signature set can be identified for advanced stage breast cancer and a therapeutic agent or therapeutic protocol can be identified which is capable of interacting with the biomarker pattern or signature set.

These examples of biomarker patterns or biomarker signature sets for advanced stage breast cancer are just one example of the extensive number of biomarker patterns or biomarker signature sets for a number of advanced stage diseases or cancers that can be identified from the tables depicted in FIGS. 26-31. In addition, a number of non disease specific therapies or therapeutic protocols may be identified for treating patients with these biomarker patterns or biomarker signature sets by utilizing method steps of the present invention described above such as depicted in FIGS. 1-2 and FIGS. 5-14.

The biomarker patterns and/or biomarker signature sets disclosed in the table depicted in FIGS. 26 and 28, and the tables depicted in FIGS. 27 and 30 may be used for a number of purposes including, but not limited to, specific cancer/disease detection, specific cancer/disease treatment, and identification of new drug therapies or protocols for specific cancers/diseases. The biomarker patterns and/or biomarker signature sets disclosed in the table depicted in FIGS. 26 and 28, and the tables depicted in FIGS. 27 and 30 can also represent drug resistant expression profiles for the specific tumor type or cancer type. The biomarker patterns and/or biomarker signature sets disclosed in the table depicted in FIGS. 26 and 28, and the tables depicted in FIGS. 27 and 30 represent advanced stage drug resistant profiles.

The biomarker patterns and/or biomarker signature sets can comprise at least one biomarker. In yet other embodiments, the biomarker patterns or signature sets can comprise at least 2, 3, 4, 5, 6, 7, 8, 9, or 10 biomarkers. In some embodiments, the biomarker signature sets or biomarker patterns can comprise at least 15, 20, 30, 40, 50, or 60 biomarkers. In some embodiments, the biomarker signature sets or biomarker patterns can comprise at least 70, 80, 90, 100, 200, 300, 400, 500, 600, 700, 800, 900, 1000, 2000, 3000, 4000, 5000, 6000, 7000, 8000, 9000, 10,000, 15,000, 20,000, 25,000, 30,000, 35,000, 40,000, 45,000 or 50,000 biomarkers. Analysis of the one or more biomarkers can be by one or more methods. For example, analysis of 2 biomarkers can be performed using microarrays. Alternatively, one biomarker may be analyzed by IHC and another by microarray. Any such combinations of methods and biomarkers are contemplated herein.

The one or more biomarkers can be selected from the group consisting of, but not limited to: Her2/Neu, ER, PR, c-kit, EGFR, MLH1, MSH2, CD20, p53, Cyclin D1, bcl2, COX-2, Androgen receptor, CD52, PDGFR, AR, CD25, VEGF, HSP90, PTEN, RRM1, SPARC, Survivin, TOP2A, BCL2, HIF1A, AR, ESR1, PDGFRA, KIT, PDGFRB, CDW52, ZAP70, PGR, SPARC, GART, GSTP1, NFKBIA, MSH2, TXNRD1, HDAC1, PDGFC, PTEN, CD33, TYMS, RXRB, ADA, TNF, ERCC3, RAF1, VEGF, TOP1, TOP2A, BRCA2, TK1, FOLR2, TOP2B, MLH1, IL2RA, DNMT1, HSPCA, ERBR2, ERBB2, SSTR1, VHL, VDR, PTGS2, POLA, CES2, EGFR, OGFR, ASNS, NFKB2, RARA, MS4A1, DCK, DNMT3A, EREG, Epiregulin, FOLR1, GNRH1, GNRHR1, FSHB, FSHR, FSHPRH1, folate receptor, HGF, HIG1, IL13RA1, LTB, ODC1, PPARG, PPARGC1, Lymphotoxin Beta Receptor, Myc, Topoisomerase II, TOPO2B, TXN, VEGFC, ACE2, ADH1C, ADH4, AGT, AREG, CA2, CDK2, caveolin, NFKB1, ASNS, BDCA1, CD52, DHFR, DNMT3B, EPHA2, FLT1, HSP90AA1, KDR, LCK, MGMT, RRM1, RRM2, RRM2B, RXRG, SRC, SSTR2, SSTR3, SSTR4, SSTR5, VEGFA, or YES1.

For example, a biological sample from an individual can be analyzed to determine a biomarker pattern or biomarker signature set that comprises a biomarker such as HSP90, Survivin, RRM1, SSTRS3, DNMT3B, VEGFA, SSTR4, RRM2, SRC, RRM2B, HSP90AA1, STR2, FLT1, SSTR5, YES1, BRCA1, RRM1, DHFR, KDR, EPHA2, RXRG, or LCK. In other embodiments, the biomarker SPARC, HSP90, TOP2A, PTEN, Survivin, or RRM1 forms part of the biomarker pattern or biomarker signature set. In yet other embodiments, the biomarker MGMT, SSTRS3, DNMT3B, VEGFA, SSTR4, RRM2, SRC, RRM2B, HSP90AA1, STR2, FLT1, SSTR5, YES1, BRCA1, RRM1, DHFR, KDR, EPHA2, RXRG, CD52, or LCK is included in a biomarker pattern or biomarker signature set.

The expression level of HSP90, Survivin, RRM1, SSTRS3, DNMT3B, VEGFA, SSTR4, RRM2, SRC, RRM2B, HSP90AA1, STR2, FLT1, SSTR5, YES1, BRCA1, RRM1, DHFR, KDR, EPHA2, RXRG, or LCK can be determined and used to identify a therapeutic for an individual. The expression level of the biomarker can be used to form a biomarker pattern or biomarker signature set. Determining the expression level can be by analyzing the levels of mRNA or protein, such as by microarray analysis or IHC. In some embodiments, the expression level of a biomarker is performed by IHC, such as for SPARC, TOP2A, or PTEN, and used to identify a therapeutic for an individual. The results of the IHC can be used to form a biomarker pattern or biomarker signature set. In yet other embodiments, a biological sample from an individual or subject is analyzed for the expression level of CD52, such as by determining the mRNA expression level by methods including, but not limited to, microarray analysis. The expression level of CD52 can be used to identify a therapeutic for the individual. The expression level of CD52 can be used to form a biomarker pattern or biomarker signature set.

As described herein, the molecular profiling of one or more targets can be used to determine or identify a therapeutic for an individual. For example, the expression level of one or more biomarkers can be used to determine or identify a therapeutic for an individual. The one or more biomarkers, such as those disclosed herein, can be used to form a biomarker pattern or biomarker signature set, which is used to identify a therapeutic for an individual. In some embodiments, the therapeutic identified is one that the individual has not previously been treated with.

For example, a reference biomarker pattern has been established for a particular therapeutic, such that individuals with the reference biomarker pattern will be responsive to that therapeutic. An individual with a biomarker pattern that differs from the reference, for example the expression of a gene in the biomarker pattern is changed or different from that of the reference, would not be administered that therapeutic. In another example, an individual exhibiting a biomarker pattern that is the same or substantially the same as the reference is advised to be treated with that therapeutic. In some embodiments, the individual has not previously been treated with that therapeutic and thus a new therapeutic has been identified for the individual.

EXAMPLES

Example 1

IHC and Microarray Testing of Over 500 Patients

The data reflected in the table depicted in FIGS. 26A-H and FIGS. 27A-27H relates to 544 patients whose diseased tissue underwent IHC testing (FIG. 26) and 540 patients whose diseased tissue underwent gene microarray testing (FIG. 27) in accordance with IHC and microarray testing as previously described above. The patients were all in advanced stages of disease.

The data show biomarker patterns or biomarker signature sets in a number of tumor types, diseased tissue types, or diseased cells including adipose, adrenal cortex, adrenal gland, adrenal gland-medulla, appendix, bladder, blood vessel, bone, bone cartilage, brain, breast, cartilage, cervix, colon, colon sigmoid, dendritic cells, skeletal muscle, enodmetrium, esophagus, fallopian tube, fibroblast, gallbladder, kidney, larynx, liver, lung, lymph node, melanocytes, mesothelial lining, myoepithelial cells, osteoblasts, ovary, pancreas, parotid, prostate, salivary gland, sinus tissue, skeletal muscle, skin, small intestine, smooth muscle, stomach, synovium, joint lining tissue, tendon, testis, thymus, thyroid, uterus, and uterus corpus.

In 99 individuals with advanced breast cancer, immunohistochemistry analysis of 20 gene expressed proteins (FIG. 26B) showed that the gene expressed proteins analyzed were overexpressed a total of 367 times and that 16.35% of that total overexpression was attributable to HSP90 overexpression followed by 12.53% of the overexpression being attributable to TOP2A overexpression and 11.17% of the overexpression being attributable to SPARC. In addition, 9.81% of the overexpression was attributable to androgen receptor overexpression, 9.54% of the overexpression was attributable to PDGFR overexpression, and 9.26% of the overexpression was attributable to c-kit overexpression.

Accordingly, a biomarker pattern or biomarker signature set can be identified for advanced stage breast cancer and a therapeutic agent or therapeutic protocol can be identified which is capable of interacting with the biomarker pattern or signature set.

Another biomarker pattern or biomarker signature set for advanced stage breast cancer is shown from the microarray data in the table represented by FIGS. 27A-H. For example, in 100 individuals with advanced breast cancer (FIG. 27B), gene microarray analysis of 64 genes showed that the genes analyzed exhibited a change in expression a total of 1,158 times and that 6.39% of that total change in expression was attributable to SSTR3 change in expression followed by 5.79% of the change in expression being attributable to VDR change in expression and 5.35% of the change in expression being attributable to BRCA2 change in expression. Accordingly, another biomarker pattern or biomarker signature set can be identified for advanced stage breast cancer and another therapeutic agent or therapeutic protocol can be identified which is capable of interacting with this biomarker pattern or signature set.

Example 2

IHC Testing of Over 1300 Patients

FIGS. 28A through 28O represent a table that shows the frequency of a significant change in expression of certain gene expressed proteins by tumor type, i.e. the number of times that a gene expressed protein was flagged as a target by tumor type as being significantly overexpressed by immunohistochemistry analysis. The table also identifies the total number of times an overexpression of any gene expressed protein occurred in a particular tumor type using immunohistochemistry.

The data reflected in the table depicted in FIGS. 28A through 28O relates to 1392 patients whose diseased tissue underwent IHC testing in accordance with IHC testing as previously described above. The patients were all in advanced stages of disease.

The data show biomarker patterns or biomarker signature sets in a number of tumor types, diseased tissue types, or diseased cells including accessory, sinuses, middle and inner ear, adrenal glands, appendix, hematopoietic system, bones and joints, spinal cord, breast, cerebellum, cervix uteri, connective and soft tissue, corpus uteri, esophagus, eye, nose, eyeball, fallopian tube, extrahepatic bile ducts, other mouth, intrahepatic bile ducts, kidney, appendix-colon, larynx, lip, liver, lung and bronchus, lymph nodes, cerebral, spinal, nasal cartilage, excl. retina, eye, nos, oropharynx, other endocrine glands, other female genital, ovary, pancreas, penis and scrotum, pituitary gland, pleura, prostate gland, rectum renal pelvis, ureter, peritonem, salivary gland, skin, small intestine, stomach, testis, thymus, thyroid gland, tongue, unknown, urinary bladder, uterus, nos, vagina & labia, and vulva, nos.

In 254 individuals with advanced breast cancer, immunohistochemistry analysis of 19 gene expressed proteins (FIG. 28C) showed that the gene expressed proteins analyzed were overexpressed a total of 767 times and that 13.43% of that total overexpression was attributable to SPARC overexpression followed by 12.26% of the overexpression being attributable to c-kit overexpression and 11.47% of the overexpression being attributable to EGFR. In addition, 11.34% of the overexpression was attributable to androgen receptor overexpression, 11.08% of the overexpression was attributable to HSP90 overexpression, and 10.43% of the overexpression was attributable to PDGFR overexpression. Accordingly, a biomarker pattern or biomarker signature set can be identified for advanced stage breast cancer and a therapeutic agent or therapeutic protocol can be identified which is capable of interacting with the biomarker pattern or signature set.

FIG. 29 depicts a table showing biomarkers (gene expressed proteins) tagged as targets in order of frequency in all tissues that were IHC tested Immunohistochemistry of the 19 gene expressed proteins showed that the 19 gene expressed proteins were tagged 3878 times as targets in the various tissues tested and that EGFR was the gene expressed protein that was overexpressed the most frequently followed by SPARC.

Example 3

Microarray Testing of Over 300 Patients

FIGS. 30A through 30O represent a table that shows the frequency of a significant change in expression of certain genes by tumor type, i.e. the number of times that a gene was flagged as a target by tumor type as being significantly overexpressed or underexpressed by microarray analysis. The table also identifies the total number of times an overexpression or underexpression of any gene occurred in a particular tumor type using gene microarray analysis.

The data reflected in the table depicted in FIGS. 30A through 30O relates to 379 patients whose diseased tissue underwent gene microarray testing in accordance microarray testing as previously described above. The patients were all in advanced stages of disease. The data show biomarker patterns or biomarker signature sets in a number of tumor types, diseased tissue types, or diseased cells including accessory, sinuses, middle and inner ear, adrenal glands, anal canal and anus, appendix, blood, bone marrow & hematopoietic sys, bones and joints, brain & cranial nerves and spinal cord (excl. ventricle & cerebellum), breast, cerebellum, cervix uteri, connective & soft tissue, corpus uteri, esophagus, eye, nos, eyeball, fallopian tube, gallbladder 7 extrahepatic bile ducts, gum, floor of mouth & other mouth, intrahepatic bile ducts, kidney, large intestine (excl. appendix-colon), larynx, lip, liver, lung & bronchus, lymph nodes, meninges (cerebral, spinal), nasal cavity (including nasal cartilage), orbit & lacrimal gland (excl. retina, eye, nos), oropharynx, other endocrine glands, other fenale genital, ovary, pancreas, penis & scrotum, pituitary gland, pleura, prostate gland, rectum, renal pelvis & ureter, retroperitoneum & peritoneum, salivary gland, skin, small intestine, stomach, testis, thymus, thyroid gland, tongue, unknown, unspecified digestive organs, urinary bladder, uterus, nos, vagina & labia, and vulva, nos.

For example, in 168 individuals with advanced breast cancer (FIG. 30C), microarray analysis of 63 genes showed that the genes analyzed were either overexpressed or underexpressed a total of 1863 times and that 5.05% of that total change in expression was attributable to SSTR3 change in expression followed by 4.83% of the change in expression being attributable to NKFBIA change in expression and 4.62% of the change in expression being attributable to VDR. In addition, 4.35% of the change in expression was attributable to MGMT change in expression, 4.19% of the change in expression was attributable to ADA change in expression, and 3.97% of the change in expression was attributable to CES2 change in expression.

FIG. 31 depicts a table showing biomarkers as targets in order of frequency in all tissues that were tested.

Example 4

Figure 32:
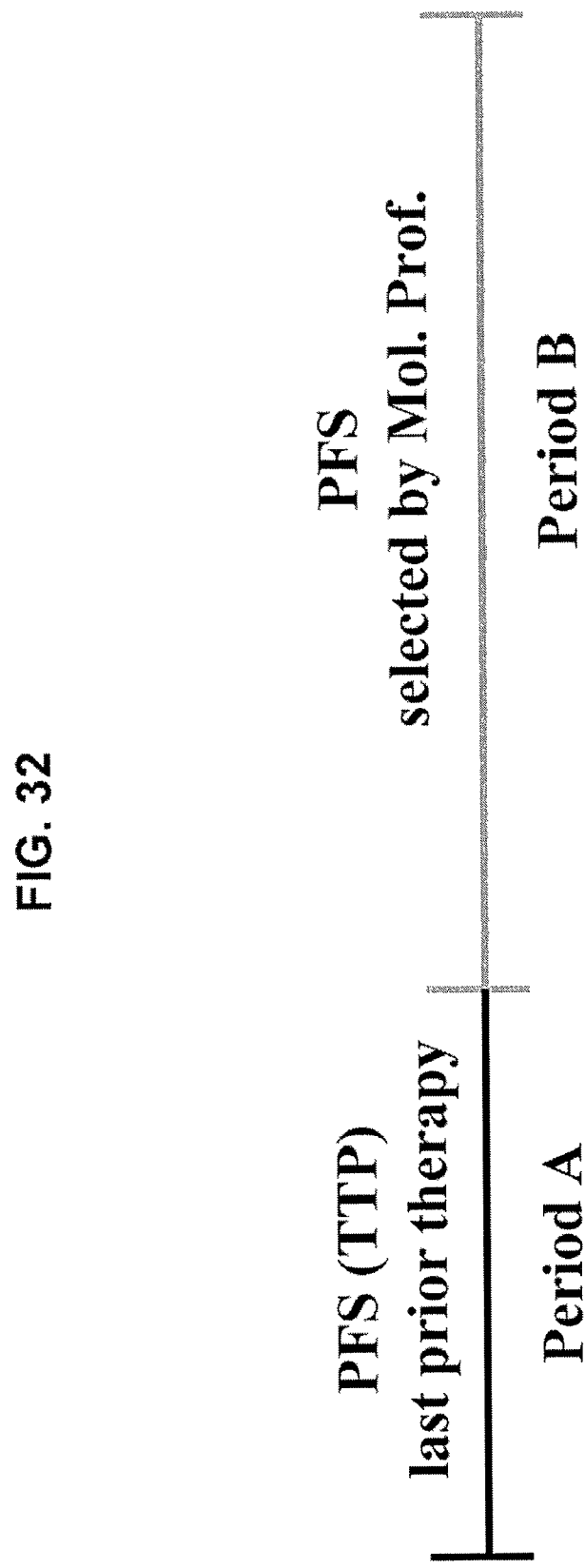
FIG. 32 illustrates progression free survival (PFS) using therapy selected by molecular profiling (period B) with PFS for the most recent therapy on which the patient has just progressed (period A). If PFS(B)/PFS(A) ratio ≥1.3, then molecular profiling selected therapy was defined as having benefit for patient.

A Pilot Study Utilizing Molecular Profiling of Patients' Tumors to Find Targets and Select Treatments for Refractory Cancers The primary objective was to compare progression free survival (PFS) using a treatment regimen selected by molecular profiling with the PFS for the most recent regimen the patient progressed on (e.g. patients are their own control) (FIG. 32). The molecular profiling approach was deemed of clinical benefit for the individual patient who had a PFS ratio (PFS on molecular profiling selected therapy/PFS on prior therapy) of ≥1.3.

The study was also performed to determine the frequency with which molecular profiling by IHC, FISH and microarray yielded a target against which there is a commercially available therapeutic agent and to determine response rate (RECIST) and percent of patients without progression or death at 4 months.

Figure 33:
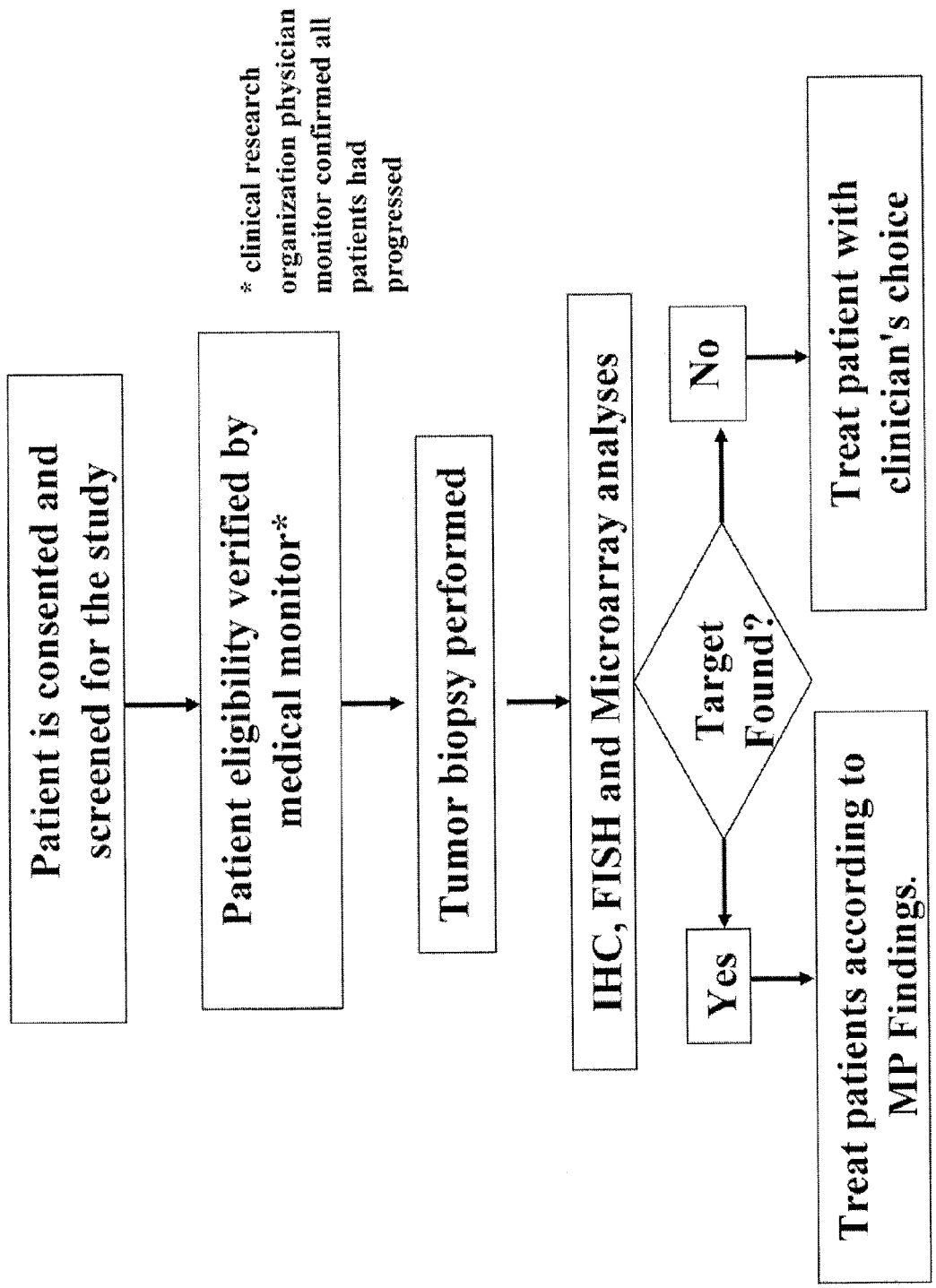
FIG. 33 is a schematic of methods for identifying treatments by molecular profiling if a target is identified.

The study was conducted in 9 centers throughout the United States. An overview of the method is depicted in FIG. 33. As can be seen in FIG. 33, the patient was screened and consented for the study. Patient eligibility was verified by one of two physician monitors. The same physicians confirmed whether the patients had progressed on their prior therapy and how long that PFS (TTP) was. A tumor biopsy was then performed, as discussed below. The tumor was assayed using IHC, FISH (on paraffin-embedded material) and microarray (on fresh frozen tissue) analyses.

The results of the IHC/FISH and microarray were given to two study physicians who in general used the following algorithm in suggesting therapy to the physician caring for the patient: 1) IHC/FISH and microarray indicated same target was first priority; 2) IHC positive result alone next priority; and 3) microarray positive result alone the last priority.

The patient's physician was informed of the suggested treatment and the patient was treated with the suggested agent(s) (package insert recommendations). The patient's disease status was assessed every 8 weeks and adverse effects were assessed by the NCI CTCAE version 3.0.

To be eligible for the study, the patient was required to: 1) provide informed consent and HIPAA authorization; 2) have any histologic type of metastatic cancer; 3) have progressed by RECIST criteria on at least 2 prior regimens for advanced disease; 4) be able to undergo a biopsy or surgical procedure to obtain tumor samples; 5) be ≥18 years, have a life expectancy >3 months, and an Eastern Cooperative Oncology Group (ECOG) Performance Status or 0-1; 6) have measurable or evaluable disease; 7) be refractory to last line of therapy (documented disease progression under last treatment; received ≥6 weeks of last treatment; discontinued last treatment for progression); 8) have adequate organ and bone marrow function; 9) have adequate methods of birth control; and 10) if CNS metastases then adequately controlled. The ECOG performance scale is described in Oken, M. M., Creech, R. H., Tormey, D. C., Horton, J., Davis, T. E., McFadden, E. T., Carbone, P. P.: Toxicity And Response Criteria Of The Eastern Cooperative Oncology Group. Am J Clin Oncol 5:649-655, 1982, which is incorporated by reference in its entirety. Before molecular profiling was performed, the principal investigator at the site caring for the patient must designate what they would treat the patient with if no molecular profiling results were available.

Methods

All biopsies were done at local investigators' sites. For needle biopsies, 2-3 18 gauge needle core biopsies were performed. For DNA microarray (MA) analysis, tissue was immediately frozen and shipped on dry ice via FedEx to a central CLIA certified laboratory, Caris MPI in Phoenix, Ariz. For IHC, paraffin blocks were shipped on cold packs. IHC was considered positive for target if 2+ in ≥30% of cells. The MA was considered positive for a target if the difference in expression for a gene between tumor and control organ tissue was at a significance level of p≤0.001.

I) IHC

For IHC studies, the formalin fixed, paraffin embedded tumor samples had slices from these blocks submitted for IHC testing for the following proteins: EGFR, SPARC, C-kit, ER, PR, Androgen receptor, PGP, RRM1, TOPO1, BRCP1, MRP1, MGMT, PDGFR, DCK, ERCC1, Thymidylate synthase, Her2/neu and TOPO2A. IHCs for all proteins were not carried out on all patients' tumors.

Formalin-fixed paraffin-embedded patient tissue blocks were sectioned (4 μm thick) and mounted onto glass slides. After deparaffination and rehydration through a series of graded alcohols, pretreatment was performed as required to expose the targeted antigen.

Her-2 and EGFR were stained as specified by the vendor (DAKO, Denmark). All other antibodies were purchased from commercial sources and visualized with a DAB biotin-free polymer detection kit. Appropriate positive control tissue was used for each antibody. Negative control slides were stained by replacing the primary antibody with an appropriately matched isotype negative control reagent. All slides were counterstained with hemtoxylin as the final step and cover slipped. Tissue microarray sections were analyzed by FISH for EGFR and HER-2/neu copy number per the manufacturer's instructions. FISH for HER-2/neu (was done with the PathVysion HER2 DNA Probe Kit (Vysis, Inc). FISH for EGFR was done with the LSI EGFR/CEP 7 Probe (Vysis).

All slides were evaluated semi-quantitatively by a first pathologist, who confirmed the original diagnosis as well as read each of the immunohistochemical stains using a light microscope. Some lineage immunohistochemical stains were performed to confirm the original diagnosis, as necessary. Staining intensity and extent of staining were determined; both positive, tumor-specific staining of tumor cells and highly positive (≥2+), pervasive (≥30%) tumor specific staining results were recorded. A standard 10% quality control was performed by a second pathologist.

II) Microarray

Tumor samples obtained for microarray were snap frozen within 30 minutes of resection and transmitted to Caris-MPI on dry ice. The frozen tumor fragments were placed on a 0.5 mL aliquot of frozen 0.5M guanidine isothiocyanate solution in a glass tube, and simultaneously thawed and homogenized with a Covaris focused acoustic wave homogenizer. A 0.5 mL aliquot of TriZol was added, mixed and the solution was heated to 65° C. for 5 minutes then cooled on ice and phase separated by the addition of chloroform followed by centrifugation. An equal volume of 70% ethanol was added to the aqueous phase and the mixture was chromatographed on a Qiagen Rneasy column. RNA was specifically bound and then eluted. The RNA was tested for integrity by assessing the ratio of 28S to 18S ribosomal RNA on an Agilent BioAnalyzer. Two to five micrograms of tumor RNA and two to five micrograms of RNA from a sample of a normal tissue representative of the tumor's tissue of origin were separately converted to cDNA and then labeled during T7 polymerase amplification with contrasting fluor tagged (Cy3, Cy5) CTP. The labeled tumor and its tissue of origin reference were hybridized to an Agilent H1Av2 60 mer olio array chip with 17,085 unique probes.

The arrays contain probes for 50 genes for which there is a possible therapeutic agent that would potentially interact with that gene (with either high expression or low expression). Those 50 genes included: ADA, AR, ASNA, BCL2, BRCA2, CD33, CDW52, CES2, DNMT1, EGFR, ERBB2, ERCC3, ESR1, FOLR2, GART, GSTP1, HDAC1, HIF1A, HSPCA, IL2RA, KIT, MLH1, MS4A1, MASH2, NFKB2, NFKBIA, OGFR, PDGFC, PDGFRA, PDGFRB, PGR, POLA, PTEN, PTGS2, RAF1, RARA, RXRB, SPARC, SSTR1, TK1, TNF, TOP1, TOP2A, TOP2B, TXNRD1, TYMS, VDR, VEGF, VHL, and ZAP70.

The chips were hybridized from 16 to 18 hours at 60° C. and then washed to remove non-stringently hybridized probe and scanned on an Agilent Microarray Scanner. Fluorescent intensity data were extracted, normalized, and analyzed using Agilent Feature Extraction Software. Gene expression was judged to be different from its reference based on an estimate of the significance of the extent of change, which was estimated using an error model that takes into account the levels of signal to noise for each channel, and uses a large number of positive and negative controls replicated on the chip to condition the estimate. Expression changes at the level of p≤0.001 were considered as significantly different.

III) Statistical Considerations

The protocol called for a planned 92 patients to be enrolled of which an estimated 64 patients would be treated with therapy assigned by molecular profiling. The other 28 patients were projected to not have molecular profiling results available because of (a) inability to biopsy the patient; (b) no target identified by the molecular profiling; or (c) deteriorating performance status. Sixty four patients were required to receive molecular profiling treatment in order to reject the null hypothesis (Ho) that: ≤15% of patients would have a PFS ratio of ≥1.3 (e.g. a non-promising outcome).

IV) Treatment Selection

Treatment for the patients based on molecular profiling results was selected using the following algorithm: 1) IHC/FISH and microarray indicates same target; 2) IHC positive result alone; 3) microarray positive result alone. The patient's physician was informed of suggested treatment and the patient was treated based on package insert recommendations. Disease status was assessed every 8 weeks. Adverse effects were assessed by NCI CTCAE version 3.0.

Results

Figure 34:
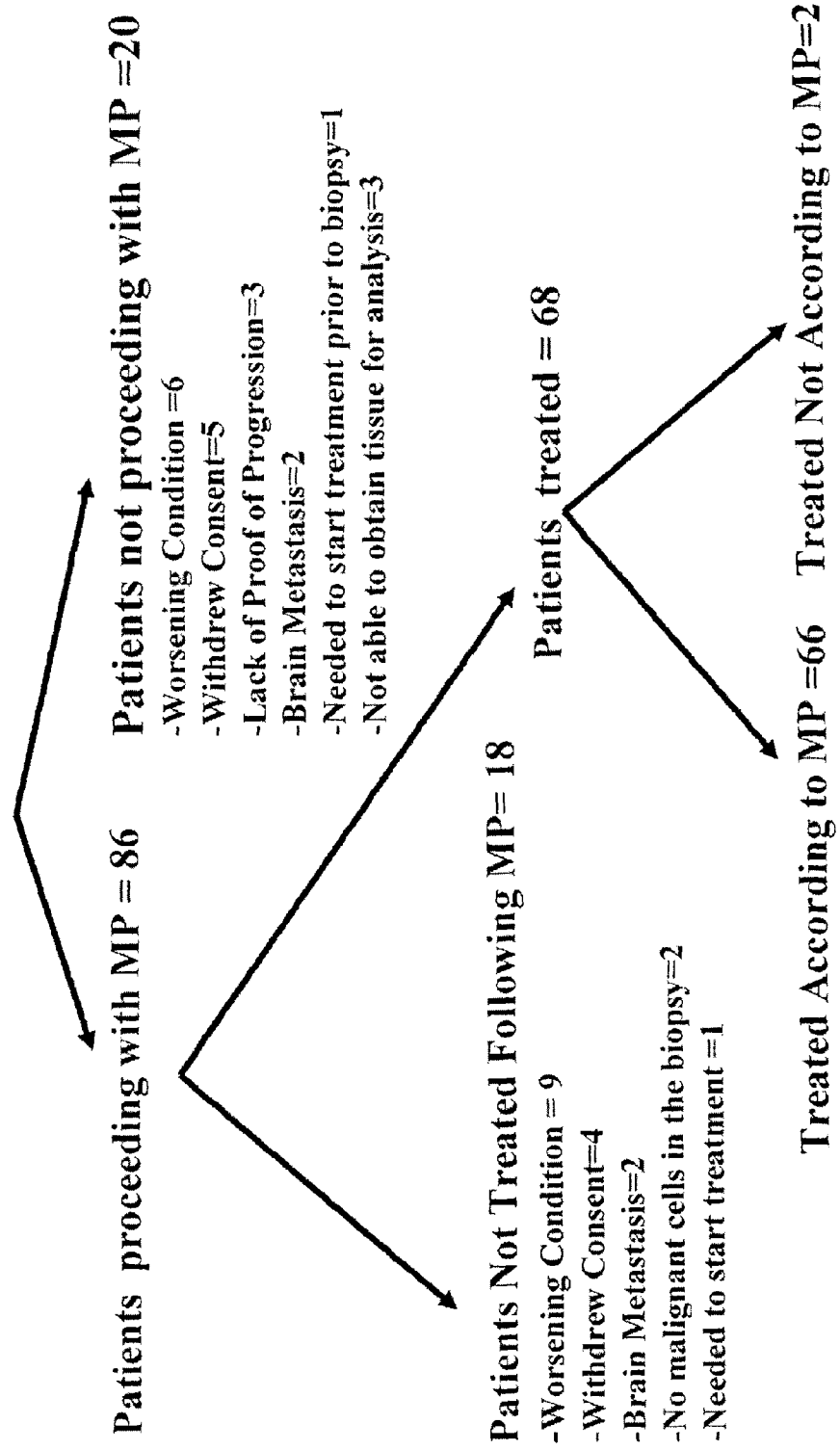
FIG. 34 illustrates the distribution of the patients in the study as performed in Example 1.

The distribution of the patients is diagrammed in FIG. 34 and the characteristics of the patients shown in TABLES 4 and 5. As can be seen in FIG. 34, 106 patients were consented and evaluated. There were 20 patients who did not proceed with molecular profiling for the reasons outlined in FIG. 34 (mainly worsening condition or withdrawing their consent or they did not want any additional therapy). There were 18 patients who were not treated following molecular profiling (mainly due to worsening condition or withdrawing consent because they did not want additional therapy). There were 68 patients treated, with 66 of them treated according to molecular profiling results and 2 not treated according to molecular profiling results. One of the two was treated with another agent because the clinician caring for the patient felt a sense of urgency to treat and the other was treated with another agent because the insurance company would not cover the molecular profiling suggested treatment.

The median time for molecular profiling results being made accessible to a clinician was 16 days from biopsy (range 8 to 30 days) and a median of 8 days (range 0 to 23 days) from receipt of the tissue sample for analysis. Some modest delays were caused by the local teams not sending the patients' blocks immediately (due to their need for a pathology workup of the specimen). Patient tumors were sent from 9 sites throughout the United States including: Greenville, S.C.; Tyler, Tex.; Beverly Hills, Calif.; Huntsville, Ala.; Indianapolis, Ind.; San Antonio, Tex.; Scottsdale, Ariz. and Los Angeles, Calif.

Table 4 details the characteristics of the 66 patients who had molecular profiling performed on their tumors and who had treatment according to the molecular profiling results. As seen in Table 1, of the 66 patients the majority were female, with a median age of 60 (range 27-75). The number of prior treatment regimens was 2-4 in 53% of patients and 5-13 in 38% of patients. There were 6 patients (9%), who had only 1 prior therapy because no approved active $2^{nd}$ line therapy was available. Twenty patients had progressed on prior phase I therapies. The majority of patients had an ECOG performance status of 1.

TABLE 4

Patient Characteristics (n = 66)

| Characteristic | n | % |
| --- | --- | --- |
| Gender | | |
| Female | 43 | 65 |
| Male | 23 | 35 |
| Age | | |
| Median (range) | 60 | (27-75) |
| Number of Prior Treatments | | |
| 2-4* | 35 | 53 |
| 5-13 | 25 | 38 |
| ECOG | | |
| 0 | 18 | 27 |
| 1 | 48 | 73 |

*Note:
6 patients (9%) had 1 prior

As seen in Table 5, tumor types in the 66 patients included breast cancer 18 (27%), colorectal 11 (17%), ovarian 5 (8%), and 32 patients (48%) were in the miscellaneous categories. Many patients had the more rare types of cancers.

TABLE 5

Results - Patient Tumor Types (n = 66)

| Tumor Type | n | % |
| --- | --- | --- |
| Breast | 18 | 27 |
| Colorectal | 11 | 17 |
| Ovarian | 5 | 8 |
| Miscellaneous | 32 | 48 |
| Prostate | 4 | 6 |
| Lung | 3 | 5 |
| Melanoma | 2 | 3 |
| Small cell (esopha/retroperit) | 2 | 3 |
| Cholangiocarcinoma | 2 | 3 |
| Mesothelioma | 2 | 3 |
| H&N (SCC) | 2 | 3 |
| Pancreas | 2 | 3 |
| Pancreas neuroendocrine | 1 | 1.5 |
| Unknown (SCC) | 1 | 1.5 |
| Gastric | 1 | 1.5 |
| Peritoneal pseudomyxoma | 1 | 1.5 |

TABLE 5-continued

Results - Patient Tumor Types (n = 66)

| Tumor Type | n | % |
| --- | --- | --- |
| Anal Canal (SCC) | 1 | 1.5 |
| Vagina (SCC) | 1 | 1.5 |
| Cervis | 1 | 1.5 |
| Renal | 1 | 1.5 |
| Eccrine seat adenocarinoma | 1 | 1.5 |
| Salivary gland adenocarinoma | 1 | 1.5 |
| Soft tissue sarcoma (uterine) | 1 | 1.5 |
| GIST (Gastric) | 1 | 1.5 |
| Thyroid-Anaplastic | 1 | 1.5 |

Primary Endpoint: PFS Ratio≥1.3

Figure 35:
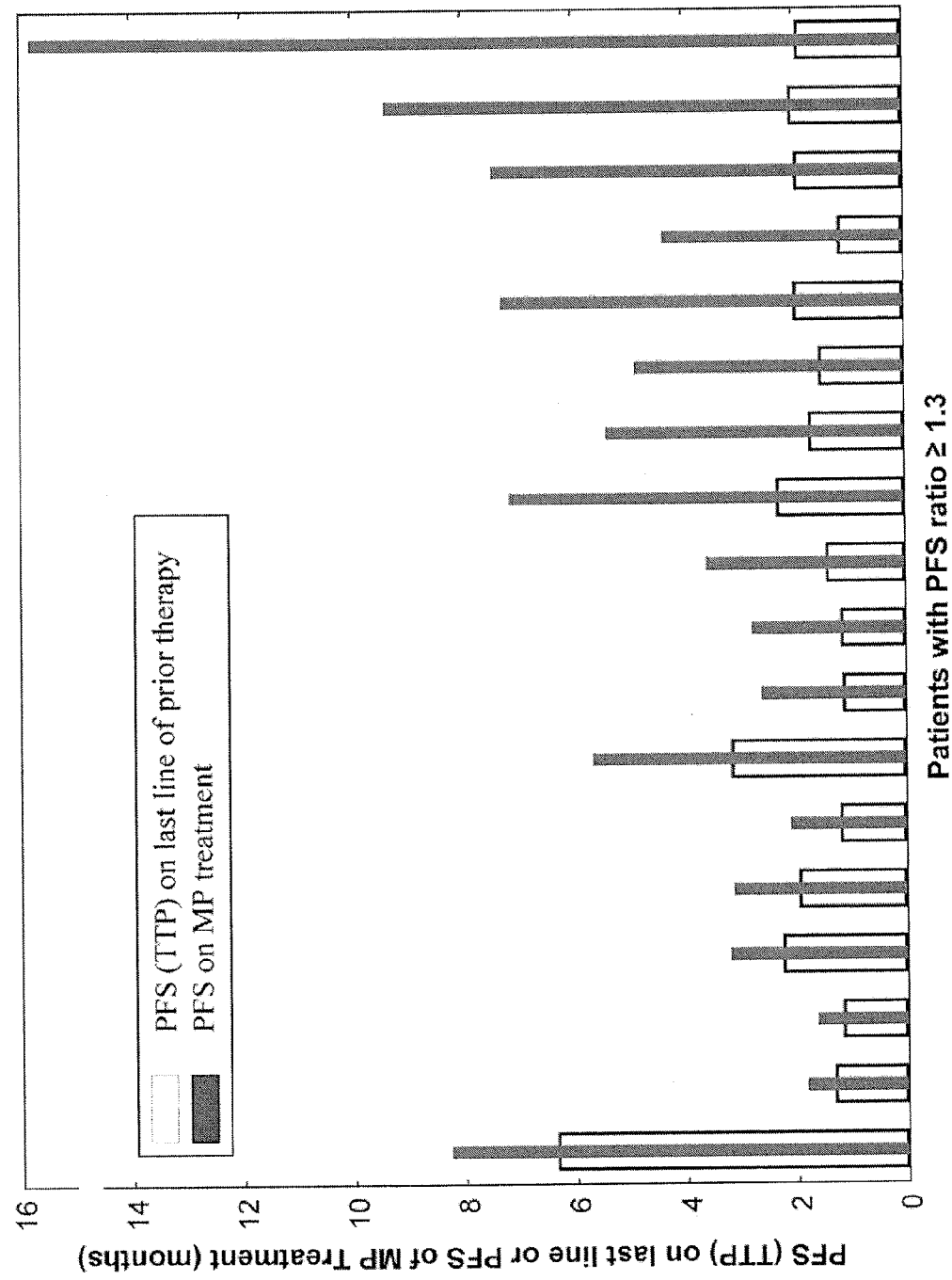
FIG. 35 is graph depicting the results of the study with patients having PFS ratio ≥1.3 was 18/66 (27%).

As far as the primary endpoint for the study is concerned (PFS ratio of ≥1.3), in the 66 patients treated according to molecular profiling results, the number of patients with PFS ratio greater or equal to 1.3 was 18 out of the 66 or 27%, 95% CI 17-38% one-sided, one-sample non parametric test p=0.007. The null hypothesis was that ≤15% of this patient population would have a PFS ratio of ≥1.3. Therefore, the null hypothesis is rejected and our conclusion is that this molecular profiling approach is beneficial. FIG. 35 details the comparison of PFS on molecular profiling therapy (the bar) versus PFS (TTP) on the patient's last prior therapy (the boxes) for the 18 patients. The median PFS ratio is 2.9 (range 1.3-8.15).

If the primary endpoint is examined, as shown in Table 6, a PFS ratio ≥1.3 was achieved in 8/18 (44%) of patients with breast cancer, 4/11 (36%) patients with colorectal cancer, 1/5 (20%) of patients with ovarian cancer and 5/32 (16%) patients in the miscellaneous tumor types (note that miscellaneous tumor types with PFS ratio ≥1.3 included: lung 1/3, cholangiocarcinoma 1/3, mesothelioma 1/2, eccrine sweat gland tumor 1/1, and GIST (gastric) 1/1).

TABLE 6

Primary Endpoint - PFS Ratio ≥1.3 By Tumor Type

| Tumor Type | Total Treated | Number with PFS Ratio ≥1.3 | % |
| --- | --- | --- | --- |
| Breast | 18 | 8 | 44 |
| Colorectal | 11 | 4 | 36 |
| Ovarian | 5 | 1 | 20 |
| Miscellaneous* | 32 | 5 | 16 |
| Total | 66 | 18 | 27 |

*lung 1/3, cholangiocarcinoma 1/2, mesothelioma 1/2, eccrine sweat 1/1, GIST (gastric) 1/1

The treatment that the 18 patients with the PFS ≥1.3 received based on profiling is detailed in Table 7. As can be seen in that table for breast cancer patients, the treatment ranged from diethylstibesterol to nab paclitaxel+gemcitabine to doxorubicin. Treatments for patients with other tumor types are also detailed in Table 7. Overall, 14 were treated with combinations and 4 were treated with single agents.

TABLE 7

Treatment that 18 Patients with PFS Ratio ≥1.3 Received (based on molecular profiling)

| Tumor Type | Therapy Patient Received |
| --- | --- |
| Breast | diethylstibesterol |
| Breast | nab-paclitaxel + trastuzumab |
| Breast | nab-paclitaxel + gemcitabine |
| Breast | letrozole + capecitabine |
| Breast | oxaliplatin + 5FU + trastuzumab |

TABLE 7-continued

Treatment that 18 Patients with PFS Ratio ≥1.3 Received (based on molecular profiling)

| Tumor Type | Therapy Patient Received |
|---|---|
| Breast | gemcitabine + pemetrexed |
| Breast | doxorubicin |
| Breast | exemestane |
| Coloretal | irinotecan + sorafenib |
| Coloretal | temozolomide + bevacizumab |
| Coloretal | sunitinib + mitomycin |
| Coloretal | temozolomide + sorafenib |
| Ovarian | lapatinib + tamoxifen |
| NSCLC | cetuximab + irinotecan |
| Cholangiocarcinoma | cetuximab + irinotecan |
| Mesothelioma | gemcitabine + etoposide |
| Eccrine sweat gland | sunitinib |
| GIST (Gastric) | cetuximab + gemcitabine |

Secondary Endpoints

The results for the secondary endpoint for this study are as follows. The frequency with which molecular profiling of a patients' tumor yielded a target in the 86 patients where molecular profiling was attempted was 84/86 (98%). Broken down by methodology, 83/86 (97%) yielded a target by IHC/FISH and 81/86 (94%) yielding a target by microarray. RNA was tested for integrity by assessing the ratio of 28S to 18S ribosomal RNA on an Agilent Bioanalyzer. 83/86 (97%) specimens had ratios of 1 or greater and gave high intra-chip reproducibility ratios. This demonstrates that very good collection and shipment of patients' specimens throughout the United States and excellent technical results can be obtained.

By RECIST criteria in 66 patients, there was 1 complete response and 5 partial responses for an overall response rate of 10% (one CR in a patient with breast cancer and PRs in breast, ovarian, colorectal and NSCL cancer patients). Patients without progression at 4 months included 14 out of 66 or 21%.

Figure 36:
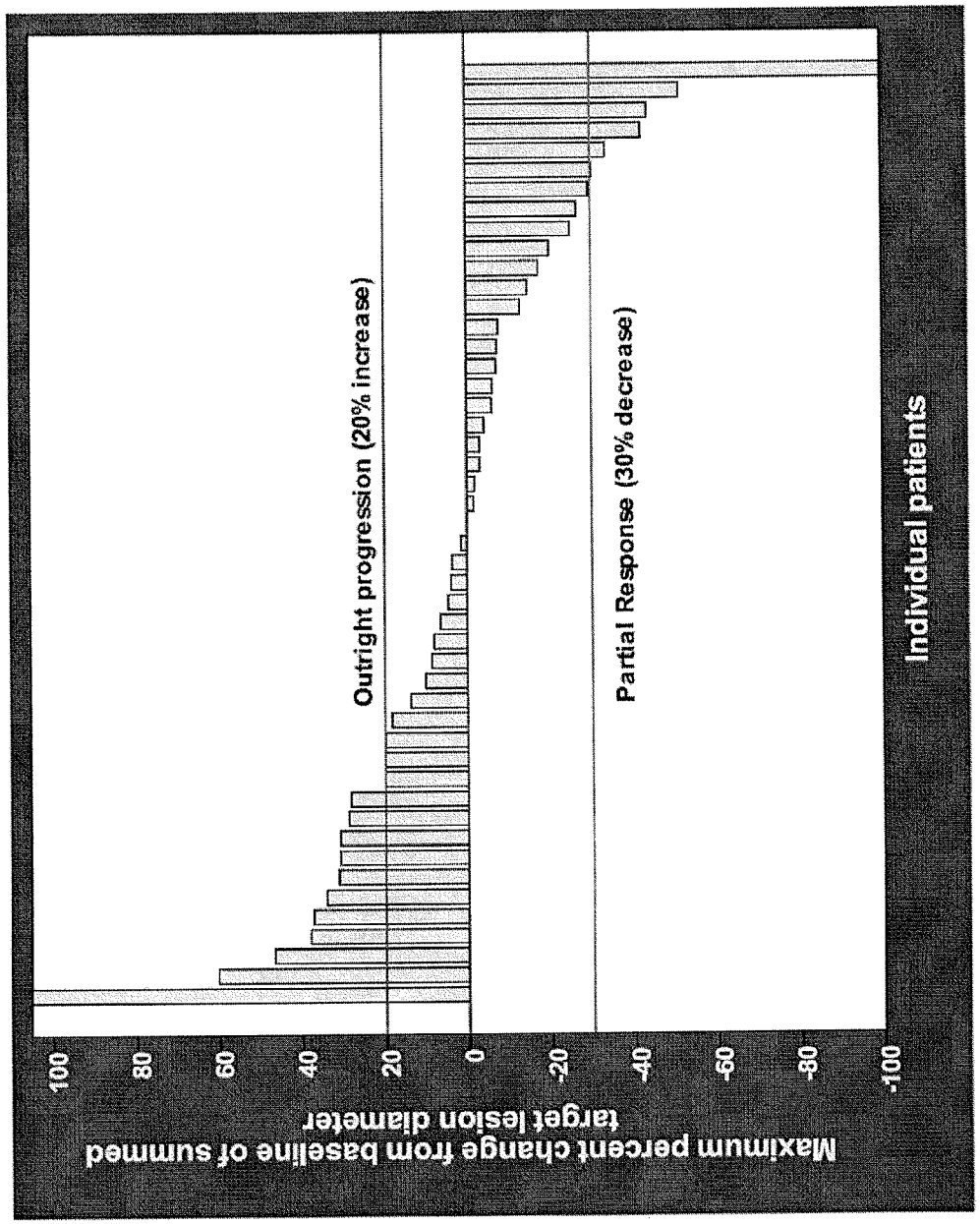
FIG. 36 is a waterfall plot of all the patients for maximum % change of summed siameters of target lesions with respect to baseline diameter.

In an exploratory analysis, a waterfall plot for all patients for maximum % change of the summed diameters of target lesions with respect to baseline diameters was generated. The patients who had progression and the patients who had some shrinkage of their tumor sometime during their course along with those partial responses by RECIST criteria is demonstrated in FIG. 36. There is some shrinkage of patient's tumors in over 47% of the patients (where 2 or more evaluations were completed).

Other Analyses—Safety

As far as safety analyses there were no treatment related deaths. There were nine treatment related serious adverse events including anemia (2 patients), neutropenia (2 patients), dehydration (1 patient), pancreatitis (1 patient), nausea (1 patient), vomiting (1 patient), and febrile neutropenia (1 patient). Only one patient (1.5%) was discontinued due to a treatment related adverse event of grade 2 fatigue.

Figure 37:
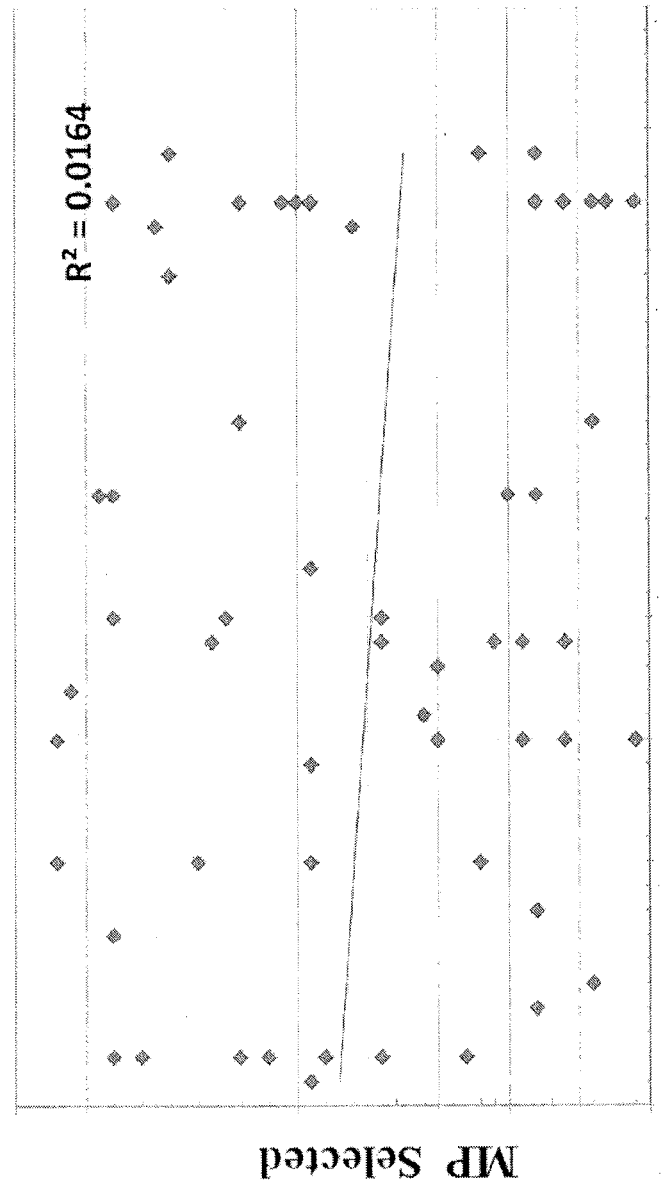
FIG. 37 illustrates the relationship between what clinician selected as what she/he would use to treat the patient before knowing what the molecular profiling results suggested. There were no matches for the 18 patients with PFS ratio ≥1.3.

Other Analyses—Relationship Between What the Clinician Caring for the Patient Would have Selected Versus What the Molecular ProfilingSelected The relationship between what the clinician selected to treat the patient before knowing what molecular profiling results suggested for treatment was also examined. As detailed in FIG. 37, there is no pattern between the two. More specifically, no matches for the 18 patients with PFS ratio ≥1.3 were noted.

Figure 38:
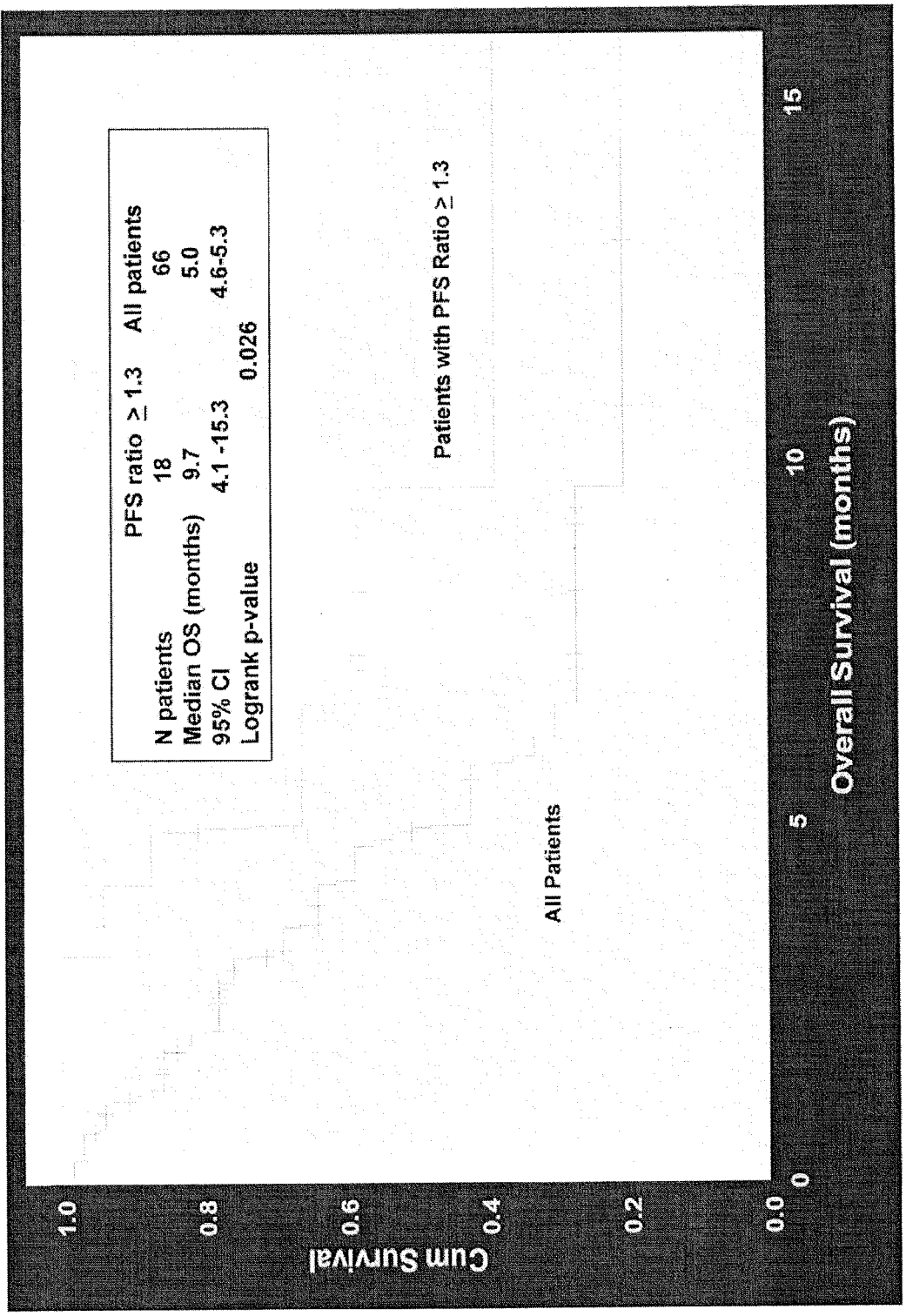
FIG. 38 is a schematic of the overall survival for the 18 patients with PFS ratio ≥1.3 versus all 66 patients.

The overall survival for the 18 patients with a PFS ratio of ≥1.3 versus all 66 patients is shown in FIG. 38. This exploratory analysis was done to help determine if the PFS ratio had some clinical relevance. The overall survival for the 18 patients with the PFS ratio of ≥1.3 is 9.7 months versus 5 months for the whole population–log rank 0.026. This exploratory analysis indicates that the PFS ratio is correlated with yet another clinical parameter.

Conclusions

This prospective multi-center pilot study demonstrates: (a) the feasibility of measuring molecular targets in patients' tumors from 9 different centers across the US with good quality and sufficient tumor collection—and treat patients based on those results; (b) this molecular profiling approach gave a longer PFS for patients on a molecular profiling suggested regimen than on the regimen they had just progressed on for 27% of the patients (confidence interval 17-38%) p=0.007; and (c) this is a promising result demonstrating molecular profiling's use and benefits.

The results also demonstrate that patients with refractory cancer can commonly have simple targets (such as ER) for which therapies are available and can be beneficial to them. Molecular profiling for patients who have exhausted other therapies and who are perhaps candidates for phase I or II trials could have this molecular profiling performed.

Example 5

Molecular Profiling System

A system has several individual components including a gene expression array using the Agilent 44K chip capable of determining the relative expression level of roughly 44,000 different sequences through RT-PCR from RNA extracted from fresh frozen tissue. Because of the practicalities involved in obtaining fresh frozen tissue, only a portion of samples can have the Agilent 44K analysis run. In addition to this gene expression array, the system also performs a subset of 40 different immunohistochemistry assays on formalin fixed paraffin embedded (FFPE) cancer tissue. Finally, gene copy number is determined for a number of genes via FISH (fluorescence in situ hybridization) and mutation analysis is done by DNA sequencing for a several specific mutations. All of this data is stored for each patient case. Microarray results for over 64 genes that have been shown to impact therapeutic options are used to generate a final report. Data is also reported from the IHC, FISH and DNA sequencing analysis. The report is explained by a practicing oncologist. Once the data are reported, the final decisions rest with the treating physician.

Example 6

Illumina Expression Analysis

The Illumina Whole Genome DASL assay (Illumina Inc., San Diego, Calif.) offers a method to simultaneously profile over 24,000 transcripts from minimal RNA input, from both fresh frozen (FF) and formalin-fixed paraffin embedded (FFPE) tissue sources, in a high throughput fashion. The analysis makes use of the Whole-Genome DASL Assay with UDG (Illumina, cat#DA-903-1024/DA-903-1096), the Illumina Hybridization Oven, and the Illumina iScan System.

The Whole Genome DASL assay is performed following the manufacturers instructions. Total RNA isolated from either FF or FFPE sources is converted to cDNA using biotinylated oligo(dT) and random nonamer primers. The use of both oligo(dT) and random nonamer primers helps ensure cDNA synthesis of degraded RNA fragments, such as those obtained from FFPE tissue. The biotinylated cDNA is then annealed to the DASL Assay Pool (DAP) probe groups. Probe groups contain oligonucleotides specifically designed to interrogate each target sequence in the transcripts. The probes span around 50 bases, allowing for the profiling of partially degraded RNA.

The assay probe set consists of an upstream oligonucleotide containing a gene specific sequence and a universal PCR primer sequence (P1) at the 5' end, and a downstream oligonucleotide containing a gene specific sequence and a universal PCR primer sequence (P2) at the 3' end. The upstream oligonucleotide hybridizes to the targeted cDNA site, and then extends and ligates to its corresponding downstream oligonucleotide to create a PCR template that can be amplified with universal PCR primers according to the manufacturer's instructions.

The resulting PCR products are hybridized to the HumanRef-8 Expression BeadChip to determine the presence or absence of specific genes. The HumanRef-8 BeadChip features up-to-date content covering >24,000 annotated transcripts derived from the National Center for Biotechnology Information Reference Sequence (RefSeq) database (Build 36.2, Release 22) (Table 8).

TABLE 8

RefSeq* Content of the HumanRef-8 BeadChip

| Probes | Description | Number |
| --- | --- | --- |
| NM | Coding transcripts, well established annotations | 23,811 |
| XM | Coding transcripts, provisional annotations | 426 |
| NR | Non-coding transcripts, well established annotations | 263 |
| XR | Non-coding transcripts, provisional annotations | 26 |
| Total | | 24,526 |

*Build 36.2, Release 22

After hybridization, HumanRef-8 Expression BeadChips are scanned using the iScan system. This system incorporates high-performance lasers, optics, and detection systems for rapid, quantitative scanning. The system offers a high signal-to-noise ratio, high sensitivity, low limit of detection, and broad dynamic range, leading to exceptional data quality.

Whole genome gene expression analysis using DASL chemistry microarrays allows for an estimate of whether a particular gene is producing more or less mRNA in the tumor than in the cell type from which the tumor was derived. Based on the activity, greater or lesser, of a given gene, may increase the likelihood that a tumor will respond to a particular therapeutic depending on the type of cancer being treated. The differential gene expression of a subject's tumor when compared to normal tissue can provide a useful diagnostic tool for helping an oncologist determine the appropriate treatment route.

The DASL chemistry addresses the limitation of working with degraded FFPE RNA by deviating from the traditional direct hybridization microarray methodologies. However, there is much variability in fixation methods of FFPE tissue, which can lead to higher levels of RNA degradation. The DASL assay can be used for partially degraded RNAs, but not for entirely degraded RNAs. To qualify RNA samples prior to DASL assay analysis, RNA quality is checked using a real-time qPCR method where the highly expressed ribosomal protein gene, RPL13a, is amplified using SYBR green chemistry. If a sample has a cycle threshold value ≤29, then the sample is considered to be intact enough to proceed with the DASL chemistry. See Biotinylated cDNA Pre-Qualification, Illumina, Inc.; Abramovitz, M., et al., Optimization of RNA extraction from FFPE tissues for expression profiling in the DASL assay. Biotechniques, 2008. 44(3): p. 417-23. Any sample that has an A260/A280 ratio <1.5, or a RPL13a Ct value >30 is considered too degraded or too heavily modified to be processed using the Whole Genome DASL gene expression chemistry. Abramovitz, M., et al.

Prior to hybridization on the HumanRef-8 Expression BeadChip, the sample is precipitated. The sample precipitate will be in the form of a blue pellet. If the blue pellet is not visible for that sample, the sample must be re-processed prior to hybridization on the BeadChip.

Although the Whole Genome DASL assay examines the expression of thousands of genes, expression of only the genes of interest need be analyzed.

In order to standardize the reporting of patient data using the Illumina Whole Genome DASL technology, the algorithm below is used. The data is obtained using the Genome Studios Software v2009.1 (Gene Expression Module version 1.1.1).

Step 1:

The detection p-values determined by the Genome Studios software must be less than 0.01. This value is determined by examining the variability of the signals generated by the duplicate copies of the same probe for a particular gene in relation to the variability observed in the negative control probes present on the array. If the detection p-value for either the control or the patient sample is greater than 0.01 for a particular gene the expression for that gene is reported out as "Indeterminate." A cut-off of 0.01 was selected as it indicates that there is less than a one percent chance that the data would be observed given that the null hypothesis of no change in expression is true. The p-value can be corrected for multiple comparisons.

Step 2:

The p-value of the differential expression must be less than 0.001. This p-value is determined by using the following equation: $1/(10^{\wedge}(D/(10*SIGN(PS-CS))))$. In this equation "D" represents the differential expression score that is generated by the Genome Studios. The "PS" and "CS" represents the relative fluorescence units (RFU) obtained on the array of a particular gene for the patient sample (PS) and control sample (CS) respectively. The "SIGN" function converts the sign of the value generated by subtracting the CS RFU from the PS RFU into a numerical value. If PS minus CS is >0 a value of 1 will be generated. If PS minus CS is <0 a value of −1 will be generated. If PS equals CS then a value of 0 will be generated. If the differential expression p-value is greater than 0.001 for any particular gene the expression for that gene is reported out as "No Change." A cut off of 0.001 was chosen because genes passing this threshold can be validated as differentially expressed by alternative methods approximately 95% of the time.

Step 3:

If the expression ratio is less than 0.66 for a particular gene, the expression for that gene will be reported out as "Underexpressed." If the expression ratio is greater than 1.5, the expression for that gene will be reported out as "Overexpressed." If the expression ratio is between 0.66 and 1.5 the expression for a particular gene will be reported out as "No Change." The expression ratio is determined by obtained by dividing the RFUs for a gene from the patient sample by the RFUs for the same gene from the control sample (PS/CS). "No Change" indicates that there is no difference in expression for this gene between tumor and control tissues at a significance level of $p<=0.001$. A significance level of $p<=0.001$ was chosen since genes passing this threshold can be validated as differentially expressed by alternative methods approximately 95% of the time.

"Not Informative (NI)" indicates that the data obtained for either the patient sample or the control sample were not of high enough quality to confidently make a call on the expression level of that particular RNA transcript.

Step 4:

In some where FFPE samples only are used, all genes that are identified as "Under expressed", using the above algorithm, will be reported out as "Indeterminate." This is due to the degraded nature of the RNA obtained from FFPE samples and as such, it may not be possible to determine whether or not the reduced RFUs for a gene in the patient sample relative to the control sample is due to the reduced presence of that particular RNA or if the RNA is highly degraded and impeding the detection of that particular RNA transcript. With improved technologies, some or all genes as "Underexpressed" with FFPE samples are reported.

FIG. 39 shows results obtained from microarray profiling of an FFPE sample. Total RNA was extracted from tumor tissue and was converted to cDNA. The cDNA sample was then subjected to a whole genome (24K) microarray analysis using Illumina cDNA-mediated annealing, selection, extension and ligation (DASL) process. The expression of a subset of 80 genes was then compared to a tissue specific normal control and the relative expression ratios of these 80 target genes indicated in the figure was determined as well as the statistical significance of the differential expression.

Example 7

Molecular Profiling System and Report

A system has several individual components including a gene expression array using the Illumina Whole Genome DASL Assay as described in Example 6. In addition to this gene expression array, the system also performs a subset of immunohistochemistry assays on formalin fixed paraffin embedded (FFPE) cancer tissue. Finally, gene copy number is determined for a number of genes via FISH (fluorescence in situ hybridization) and mutation analysis is done by DNA sequencing for a several specific mutations. All of this data is stored for each patient case. Data is reported from the microarray, IHC, FISH and DNA sequencing analysis. All laboratory experiments are performed according to Standard Operating Procedures (SOPs).

DNA for mutation analysis is extracted from formalin-fixed paraffin-embedded (FFPE) tissues after macrodissection of the fixed slides in an area that % tumor nuclei ≥10% as determined by a pathologist. Extracted DNA is only used for mutation analysis if % tumor nuclei ≥10%. DNA is extracted using the QIAamp DNA FFPE Tissue kit according to the manufacturer's instructions (QIAGEN Inc., Valencia, Calif.). The BRAF Mutector I BRAF Kit (TrimGen, cat#MH1001-04) is used to detect BRAF mutations (TrimGen Corporation, Sparks, Md.). The DxS KRAS Mutation Test Kit (DxS, #KR-03) is used to detect KRAS mutations (QIAGEN Inc., Valencia, Calif.). BRAF and KRAS sequencing of amplified DNA is performed using Applied Biosystem's BigDye® Terminator V1.1 chemistry (Life Technologies Corporation, Carlsbad, Calif.).

IHC is performed according to standard protocols. IHC detection systems vary by marker and include Dako's Autostainer Plus (Dako North America, Inc., Carpinteria, Calif.), Ventana Medical Systems Benchmark® XT (Ventana Medical Systems, Tucson, Ariz.), and the Leica/Vision Biosystems Bond System (Leica Microsystems Inc., Bannockburn, Ill.). All systems are operated according to the manufacturers' instructions.

FISH is performed on formalin-fixed paraffin-embedded (FFPE) tissue. FFPE tissue slides for FISH must be Hematoxylin and Eosion (H & E) stained and given to a pathologist for evaluation. Pathologists will mark areas of tumor to be FISHed for analysis. The pathologist report must show tumor is present and sufficient enough to perform a complete analysis. FISH is performed using the Abbott Molecular VP2000 according to the manufacturer's instructions (Abbott Laboratories, Des Plaines, Iowa).

Figure 40H:
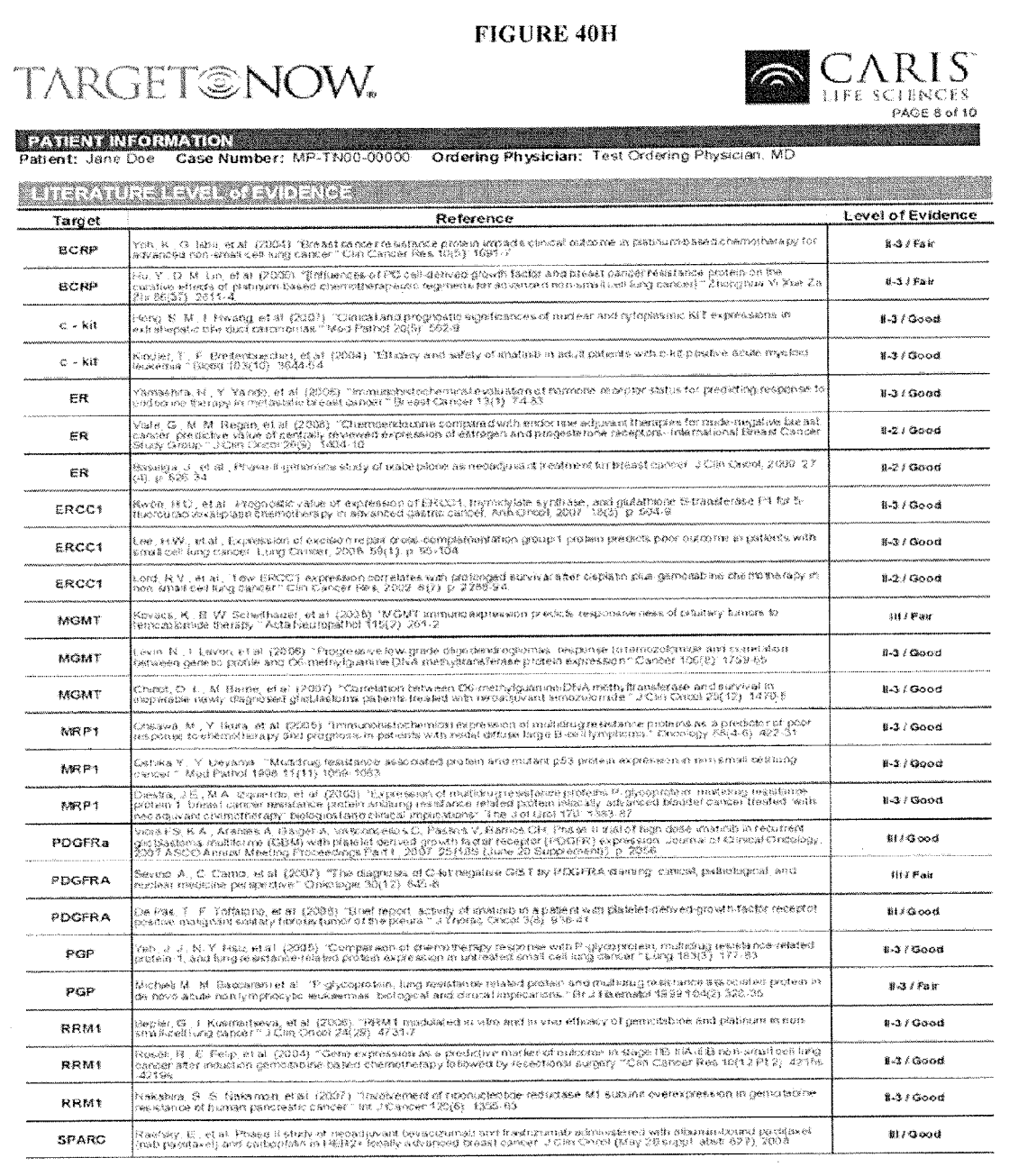

A report generated by the system in shown in FIGS. 40A-40J. FIG. 40A shows that the patient had a primary tumor in the ovary. A paraffin block sample was used. FIGS. 40A-40B illustrate a Summary listing of biomarkers identified as differentially expressed by microarray or IHC analysis. Treatment options corresponding to each differentially expressed biomarker is presented. The subject's physician can decide which candidate treatments to apply. FIG. 40C presents a table of literature evidence linking the candidate treatments to the biomarkers. FIG. 40D presents the results of IHC analysis and FIG. 40E presents the results of microarray analysis. FIGS. 40E-40G present a summary description of the differentially expressed biomarkers. FIGS. 40H-40I present a summary description of literature supporting the candidate therapeutics linked to the differentially expressed biomarkers with a rating for the level of evidence attached to each publication. FIG. 40C presents a chart explaining the codes for level of evidence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for generating a report identifying a therapeutic agent for an individual with mesothelioma comprising:
   a. at least one nucleic acid sequencing device configured to assay a plurality of molecular targets in a biological sample from the individual to determine molecular profile test values for the plurality of molecular targets, wherein the molecular targets comprise BRAF, EGFR, PDGFRA, and PI3K;
   b. at least one computer database comprising:
      i. a reference value for each of the plurality of molecular targets;
      ii. a listing of available therapeutic agents for each of the plurality of molecular targets;
   c. a computer-readable program code comprising instructions to input the molecular profile test values and to compare each of the molecular profile test values with a corresponding reference value from the at least one computer database in (b)(i);
   d. a computer-readable program code comprising instructions to access the at least one computer database and to identify at least one therapeutic agent from the listing of available therapeutic agents for the plurality of molecular targets wherein the comparison to the reference values in (c) indicates a likely benefit of the at least one therapeutic agent; and
   e. a computer-readable program code comprising instructions to generate a report that comprises a listing of all the molecular targets for which the comparison to the reference value indicated a likely benefit of the at least one therapeutic agent in (d) and the at least one therapeutic agent identified in (d).

2. The system of claim 1, wherein the molecular profile test values are input into the system from a location that is remote from the at least one computer database.

3. The system of claim 1, wherein the molecular profile test values are input into the system over an interne connection.

4. The system of claim 1, wherein the report is in electronic or paper format.

5. The system of claim 1, wherein the at least one computer database further comprises data corresponding to at least one clinical trial of a member of the plurality of molecular targets.

6. The system of claim 1, wherein the reference value for each of the plurality of molecular targets comprises a nucleic acid sequence.

7. The system of claim 1, wherein the test values for the plurality of molecular targets are determined after the individual has received a drug therapy for the mesothelioma.

8. The system of claim 1, wherein the molecular profile test values are determined by assessing a cell, a tissue sample, a blood sample or a combination thereof.

9. The system of claim 1, wherein the molecular profile test values are determined by performing a test for a gene and/or protein.

10. The system of claim 1, wherein each reference value is obtained from at least one individual without mesothelioma.

11. The system of claim 1, wherein the individual has been treated by and failed to respond to at least one cancer therapeutic.

12. The system of claim 1, wherein the report further comprises a listing of at least one additional molecular target for which the comparison to the reference value in (c) indicates a likely lack of benefit of at least one additional therapeutic agent and the at least one additional therapeutic agent.

13. The system of claim 1, further comprising a computer-readable program code comprising instructions to prioritize the list of the at least one therapeutic agent.

14. The system of claim 1, wherein the report provides a prioritized list of the at least one therapeutic agent.

15. The system of claim 1, wherein the molecular target EGFR is further assessed by protein testing.

16. The system of claim 1, wherein the plurality of molecular targets further comprises MGMT and/or AR.

17. The system of claim 16, wherein the molecular targets PDGFRA and EGFR are further assessed by protein testing.

18. The system of claim 16, further comprising using immunohistochemistry to determine molecular profile test values for the molecular targets PDGFRA, EGFR, MGMT and AR.

19. The system of claim 1, wherein the at least one nucleic acid sequencing device is configured to perform at least one of polymerase chain reaction (PCR), pyrosequencing, real-time PCR, Sanger sequencing, NextGen sequencing, methylation specific PCR (MSPCR), restriction fragment length polymorphism (RFLP) analysis), a single nucleotide polymorphism (SNP) microarray analysis, in-situ hybridization (ISH), and fluorescent in-situ hybridization (FISH).

20. The system of claim 1, wherein the at least one nucleic acid sequencing device is configured to identify at least one of a mutation, polymorphism, deletion, insertion, substitution, translocation, fusion, break, duplication, amplification or repeat in a nucleic acid sequence corresponding to each of the plurality of molecular targets.

\* \* \* \* \*